(12) United States Patent  
Gangloff et al.

(10) Patent No.: US 7,928,105 B2
(45) Date of Patent: Apr. 19, 2011

(54) SUBSTITUTED 6A,7,8,9-TETRAHYDROPYRIDO[3,2-E]PYRROLO[1,2-A]PYRAZIN-6(5H)-ONES

(75) Inventors: Anthony R. Gangloff, San Diego, CA (US); Andrew John Jennings, San Diego, CA (US); Benjamin Jones, Cardiff-by-the-Sea, CA (US); Andre A. Kiryanov, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/691,668

(22) Filed: Jan. 21, 2010

(65) Prior Publication Data

US 2010/0190763 A1     Jul. 29, 2010

Related U.S. Application Data

(60) Provisional application No. 61/146,740, filed on Jan. 23, 2009, provisional application No. 61/228,879, filed on Jul. 27, 2009.

(51) Int. Cl.
*A61K 31/495* (2006.01)

(52) U.S. Cl. ........ 514/250; 544/180; 544/333; 544/346; 544/361; 546/199; 546/276.7; 548/217; 548/305.1

(58) Field of Classification Search .............. 514/250; 544/180, 333, 346, 361; 546/199, 276.7; 548/217, 305.1
See application file for complete search history.

(56) References Cited

U.S. PATENT DOCUMENTS

| | | | |
|---|---|---|---|
| 4,138,564 | A | 2/1979 | Freed et al. |
| 4,446,323 | A | 5/1984 | Freed et al. |
| 5,055,465 | A | 10/1991 | Davey |
| 5,166,344 | A | 11/1992 | Davey et al. |
| 5,306,819 | A | 4/1994 | Albaugh et al. |
| 5,405,847 | A | 4/1995 | Dieter et al. |
| 5,424,311 | A | 6/1995 | Billhardt-Troughton et al. |
| 6,121,278 | A | 9/2000 | Jackson et al. |
| 6,197,785 | B1 | 3/2001 | Jackson |
| 6,887,996 | B2 | 5/2005 | Ferraris et al. |
| 7,235,557 | B2 | 6/2007 | Ferraris |
| 2006/0003987 | A1 | 1/2006 | Ferraris et al. |
| 2006/0142294 | A1 | 6/2006 | Neamati |
| 2006/0235034 | A1 | 10/2006 | Neamati et al. |
| 2008/0161280 | A1 | 7/2008 | Gandhi et al. |
| 2008/0269234 | A1 | 10/2008 | Gandhi et al. |
| 2009/0093489 | A1 | 4/2009 | Neamati et al. |
| 2009/0163545 | A1 | 6/2009 | Goldfarb et al. |
| 2010/0048556 | A1 | 2/2010 | Okada et al. |
| 2010/0113484 | A1 | 5/2010 | Gotanda et al. |
| 2010/0120781 | A1 | 5/2010 | Neamati |

FOREIGN PATENT DOCUMENTS

| | | |
|---|---|---|
| EP | 0400583 | 12/1990 |
| EP | 2103613 | 9/2009 |
| EP | 2123301 | 11/2009 |
| WO | WO/94/05665 | 3/1994 |
| WO | WO/99/11649 | 3/1999 |
| WO | WO/2005/058843 | 6/2005 |
| WO | WO/2006/009734 | 1/2006 |
| WO | WO/2006/091246 | 8/2006 |
| WO | WO/2006/125179 | 11/2006 |
| WO | WO/2007/130468 | 11/2007 |
| WO | WO/2008/017883 | 2/2008 |
| WO | WO/2010/096426 | 8/2010 |

OTHER PUBLICATIONS

Zaremba, Tomasz et al. "PARP Inhibitors development for systemic Cancer Targeting" Anti-Cancer Agents in Med. Chem., 2007, vol. 7, p. 515-523.

Savelli, Francesco et al. "Heterotricyclic systems. Part I. Synthesis of new dipyridopyrazines [I]" J. Heterocyclic Chem., 1992, vol. 29, p. 529.

Prunier, Herve et al. "Novel and selective partial agonists of 5-HT3 receptors. 2. Synthesis and biological evaluation of piperazinopyridopyrrolopyrazines, piperazinopyrroloquinoxalines, and piperazinopyridopyrroloquinoxalines" J. of Med. Chem., 1997, vol. 40, p. 1808-19.

*Primary Examiner* — James O Wilson
*Assistant Examiner* — Douglas M Willis
(74) *Attorney, Agent, or Firm* — Matthew J. Russo; Mitchell R. Brustein

(57) ABSTRACT

Disclosed are compounds of the following formula:

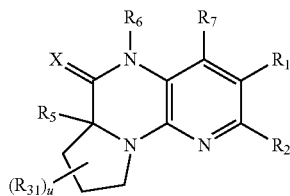

in which $R_1$, $R_2$, $R_5$, $R_6$, $R_7$, $R_{31}$, u, and X are defined in the specification. Also disclosed are pharmaceutical compositions, kits, and articles of manufacture, which contain the compounds, methods and intermediates useful for making the compounds, and methods of using the compounds to treat diseases, disorders, and conditions related to PARP activity.

21 Claims, No Drawings

SUBSTITUTED 6A,7,8,9-TETRAHYDROPYRIDO[3,2-E] PYRROLO[1,2-A]PYRAZIN-6(5H)-ONES

CROSS-REFERENCE TO RELATED APPLICATIONS

This application claims the benefit of U.S. Provisional Applications No. 61/146,740, filed Jan. 23, 2009, and 61,228, 879, filed Jul. 27, 2009, which are incorporated herein by reference.

BACKGROUND OF THE INVENTION

The present invention relates to compounds that may be used to inhibit Poly (ADP-ribose) Polymerase (PARP), as well as compositions of matter, kits and articles of manufacture comprising these compounds. The invention also relates to methods for inhibiting PARP and treatment methods using compounds according to the present invention. In addition, the invention relates to methods of making the compounds of the present invention, as well as intermediates useful in such methods.

The present invention relates to inhibitors of the enzyme poly(ADP-ribose)polymerase (PARP), previously known as poly(ADP-ribose)synthase and poly(ADP-ribosyl)transferase. PARP constitutes a super family of proteins containing PARP catalytic domains. These proteins include PARP-1, PARP-2, PARP-3, vaultPARP and TiPARP. PARP-I consists of an amino (N)-terminal DNA-binding domain (DBD) containing two zinc fingers; an automodification domain; and a carboxy (C)-terminal catalytic domain.

PARP is a nuclear and cytoplasmic enzyme that cleaves NAD+ to nicotinamide and ADP-ribose to form long and branched ADP-ribose polymers on target proteins, including topoisomerases, histones and PARP itself PARP has been implicated in several biological processes, including DNA repair, gene transcription, cell cycle progression (including proliferation and differentiation), cell death, chromatin functions, genomic (e.g., chromosomal) stability and telomere length.

Activation of PARP and the resultant formation of poly (ADP-ribose) can be induced by DNA strand breaks after exposure to chemotherapy, ionizing radiation, oxygen free radicals, or nitric oxide (NO). Because this cellular ADP-ribose transfer process is associated with the repair of DNA strand breakage in response to DNA damage caused by radiotherapy or chemotherapy, it can contribute to the resistance that often develops to various types of cancer therapies. Consequently, inhibition of PARP is expected to retard intracellular DNA repair and enhance the antitumor effects of cancer therapies.

In addition, tankyrases (e.g., tankyrase-1 and tankyrase-2) which bind to the telomeric protein TRF-1, a negative regulator of telomere length maintenance, have a catalytic domain that is homologous to PARP. It has been proposed that telomere function in human cells is regulated by poly(ADP-ribosyl)ation. As a consequence of regulation of telomerase activity by tankyrase, PARP inhibitors are expected to have utility as agents for use in cancer therapy (e.g., to shorten the lifespan of immortal tumor cells) or as anti-aging therapeutics, since telomere length is believed to be associated with cell senescence.

In addition, PARP modulation has been implicated in vascular and cardiovascular diseases, metabolic diseases, inflammatory diseases, reperfusion injuries, ischemic conditions, neurodegenerative diseases and more.

There is a continued need to find new therapeutic agents to treat human diseases. PARP is an especially attractive target for the discovery of new therapeutics due to its important role in cancers, vascular and cardiovascular diseases, metabolic diseases, inflammatory diseases, reperfusion injuries, ischemic conditions, neurodegenerative diseases and other diseases.

SUMMARY OF THE INVENTION

The present invention relates to compounds that have activity for inhibiting PARP. The present invention also provides compositions, articles of manufacture and kits comprising these compounds. In addition, the invention relates to methods of making the compounds of the present invention, as well as intermediates useful in such methods. The compounds of the present invention show in vivo efficacy in animal models, increased cellular potentiation, strong and sustained pharmacodynamic effects in tumours, and longer time-to-tumour progression (TTP).

In one embodiment, a pharmaceutical composition is provided that comprises a PARP inhibitor according to the present invention as an active ingredient. Pharmaceutical compositions according to the invention may optionally comprise 0.001%-100% of one or more inhibitors of this invention. These pharmaceutical compositions may be administered or co-administered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or co-administered in slow release dosage forms.

The invention is also directed to kits and other articles of manufacture for treating disease states associated with PARP.

In one embodiment, a kit is provided that comprises a composition comprising at least one PARP inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one PARP inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit PARP.

In another embodiment, the compounds, compositions, kits and articles of manufacture are used to treat a disease state for which PARP possess activity that contributes to the pathology and/or symptomology of the disease state.

In another embodiment, a compound according to the present invention is administered to a subject wherein PARP activity within the subject is altered, preferably reduced.

In another embodiment, a prodrug of a compound according to the present invention is administered to a subject that is converted to the compound in vivo where it inhibits PARP.

In another embodiment, a method of inhibiting PARP is provided that comprises contacting a PARP with a compound according to the present invention.

In another embodiment, a method of inhibiting PARP is provided that comprises causing a compound according to the present invention to be present in a subject in order to inhibit PARP in vivo.

In another embodiment, a method of inhibiting a PARP is provided that comprises administering a first compound to a subject that is converted in vivo to a second compound wherein the second compound inhibits PARP in vivo. It is noted that the compounds of the present invention may be the first or second compounds.

In another embodiment, a therapeutic method is provided that comprises administering a compound according to the present invention.

In another embodiment, a method is provided for treating a condition in a patient that is known to be mediated by PARP, or which is known to be treated by PARP inhibitors, the method comprising administering to the patient a therapeutically effective amount of a compound according to the present invention.

In another embodiment, a method is provided for treating a disease state for which PARP possess activity that contributes to the pathology and/or symptomology of the disease state, the method comprising: causing a compound according to the present invention to be present in a subject in a therapeutically effective amount for the disease state.

In another embodiment, a method is provided for treating a disease state for which PARP possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which PARP possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by PARP, or that is known to be treated by PARP inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting PARP and thus may themselves be prodrugs for another compound. Such prodrugs of another compound may or may not themselves independently have PARP inhibitory activity.

DEFINITIONS

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY 4$^{TH}$ ED." Vols. A (2000) and B (2001), Plenum Press, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or CR=CR'R", wherein R, R' and R" are each independently hydrogen or further substituents).

Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a $(C_{2-20})$alkenyl, a $(C_{2-15})$alkenyl, a $(C_{2-10})$alkenyl, a $(C_{2-5})$alkenyl or a $(C_{2-3})$alkenyl. Alternatively, "alkenyl," either alone or represented along with another radical, can be a $(C_2)$alkenyl, a $(C_3)$alkenyl or a $(C_4)$alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a $(C_{2-20})$ alkenylene, a $(C_{2-15})$ alkenylene, a $(C_{2-10})$ alkenylene, a $(C_{2-5})$ alkenylene or a $(C_{2-3})$ alkenylene. Alternatively, "alkenylene," either alone or represented along with another radical, can be a $(C_2)$ alkenylene, a $(C_3)$ alkenylene or a $(C_4)$ alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). $(C_X)$alkyl and $(C_{X-Y})$alkyl are typically used where X and Y indicate the number of carbon atoms in the chain. For example, $(C_{1-6})$alkyl includes alkyls that have a chain of between 1 and 6 carbons (e.g., methyl, ethyl, propyl, isopropyl, butyl, sec-butyl, isobutyl, tent-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., $(C_{6-10})$aryl$(C_{1-3})$ alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a $(C_{1-20})$alkyl, a $(C_{1-15})$ alkyl, a $(C_{1-10})$alkyl, a $(C_{1-5})$alkyl or a $(C_{1-3})$alkyl. Alternatively, "alkyl," either alone or represented along with another radical, can be a $(C_1)$alkyl, a $(C_2)$alkyl or a $(C_3)$alkyl.

"Alkylene", unless indicated otherwise, means a straight or branched, saturated or unsaturated, aliphatic, divalent radical. $(C_X)$alkylene and $(C_{X-Y})$alkylene are typically used where X and Y indicate the number of carbon atoms in the chain. For example, $(C_{1-6})$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like. In particular embodiments, "alkylene," either alone or represented along with another radical, can be a $(C_{1-20})$alkylene, a $(C_{1-15})$alkylene, a $(C_{1-10})$alkylene, a $(C_{1-5})$alkylene or a $(C_{1-3})$alkylene. Alternatively, "alkylene," either alone or represented along with another radical, can be a $(C_1)$alkylene, a $(C_2)$alkylene or a $(C_3)$alkylene.

"Alkylidene" means a straight or branched, saturated or unsaturated, aliphatic radical connected to the parent molecule by a double bond. $(C_X)$alkylidene and $(C_{X-Y})$ alkylidene are typically used where X and Y indicate the number of carbon atoms in the chain. For example, $(C_{1-6})$alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like. In particular embodiments, "alkylidene," either alone or represented along with another radical, can be a $(C_{1-20})$alkylidene, a $(C_{1-15})$ alkylidene, a $(C_{1-10})$alkylidene, a $(C_{1-5})$alkylidene or a $(C_{1-3})$alkylidene. Alternatively, "alkylidene," either alone or represented along with another radical, can be a $(C_1)$alkylidene, a $(C_2)$alkylidene or a $(C_3)$alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$ alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$ alkynylene, a $(C_{2-15})$ alkynylene, a $(C_{2-10})$ alkynylene, a $(C_{2-5})$ alkynylene or a $(C_{2-3})$ alkynylene. Alternatively, "alkynylene," either alone or represented along with another radical, can be a $(C_2)$ alkynylene, a $(C_3)$ alkynylene or a $(C_4)$ alkynylene.

"Amido" means the radical —C(=O)—NR—, —C(=O)—NRR', —NR—C(=O)— and/or —NR—C(=O)R', wherein each R and R' are independently hydrogen or a further substituent.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH((C$_{1-10}$)alkyl), —N((C$_{1-10}$)alkyl)$_2$, —NH(aryl), —NH (heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$ aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a $(C_{10})$aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a $(C_{1-10})$azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tent-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene, a $(C_9)$cycloalkylene or a $(C_{10})$cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero$(C_{1-20})$alkyl, a hetero$(C_{1-15})$alkyl, a hetero$(C_{1-10})$alkyl, a hetero$(C_{1-5})$alkyl, a hetero$(C_{1-3})$alkyl or a hetero$(C_{1-2})$alkyl. Alternatively, "heteroalkyl," either alone or represented along with another radical, can be a hetero$(C_1)$alkyl, a hetero$(C_2)$alkyl or a hetero$(C_3)$alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O$^-$)=, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$)bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$)bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-13}$)cycloalkylene, a hetero($C_{1-9}$)cycloalkylene, a hetero($C_{1-6}$)cycloalkylene, a hetero($C_{5-9}$)cycloalkylene or a hetero($C_{2-6}$)cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$)cycloalkylene, hetero($C_7$)cycloalkylene, hetero($C_8$)cycloalkylene or a hetero($C_9$)cycloalkylene.

"Hydroxy" means the radical —OH.

"IC$_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Moiety providing X atom separation" and "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-(L)$_X$-R' where each L is independently selected from the group consisting of CR'R''', NR'''', O, S, CO, CS, C=NR''''', SO, SO$_2$, and the like, where any two or more of R'', R''', R'''' and R''''' can be taken together to form a substituted or unsubstituted ring.

"Nitro" means the radical —NO$_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid, or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" include humans, non-human mammals (e.g., dogs, cats, rabbits, cattle, horses, sheep, goats, swine, deer, and the like) and non-mammals (e.g., birds, and the like).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [($CH_3$)$_3$C—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; $CH_3CH(NH_2)$CO—), Arg (arginine), Asn (asparagine), Asp (aspartic acid), Cys (cysteine), Glu (glutamic acid), His (histidine), Ile (isoleucine), Leu (leucine; ($CH_3$)$_2$CHCH$_2$CH(NH$_2$)CO—), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [($CH_3$)$_3$C—OCO—], and the like. Suitable peptide residues include peptide residues comprising two to five, and optionally two to three, of the aforesaid amino acid residues. Examples of such peptide residues include, but are not limited to, residues of such peptides as Ala-Ala [CH$_3$CH(NH$_2$)CO—NHCH(CH$_3$)CO—], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [(CH$_3$)$_3$C—OCO—], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and halogenoethoxycarbonyl groups (such as β,β,β-trichloroethoxycarbonyl and β-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —CH$_3$. In general, a non-hydrogen substituent may be any substituent that may be bound to an atom of the given moiety that is specified to be substituted. Examples of substituents include, but are not limited to, aldehyde, alicyclic, aliphatic, (C$_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a C$_1$ alkyl indicates that there is one carbon atom but does not indicate what the substituents on the carbon atom are. Hence, a (C$_1$)alkyl comprises methyl (i.e., —CH$_3$) as well as —CRR'R" where R, R', and R" may each independently be hydrogen or a further substituent where the atom attached to the carbon is a heteroatom or cyano. Hence, CF$_3$, CH$_2$OH and CH$_2$CN, for example, are all (C$_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

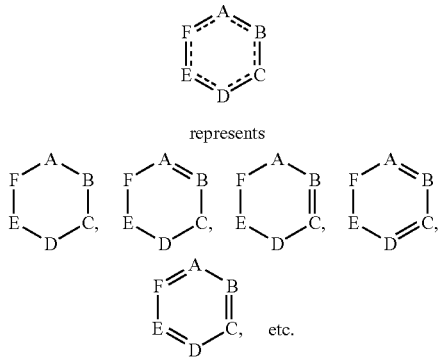

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

DETAILED DESCRIPTION OF THE INVENTION

The present invention relates to compounds that may be used to inhibit PARP. The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other members of the same protein family and thus may be used to address disease states associated with these other family members.

PARP Inhibitors

In one of its aspects, the present invention relates to compounds that are useful as PARP inhibitors. In one embodiment, PARP inhibitors of the present invention comprise:

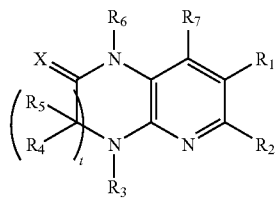

or a polymorph, solvate, ester, tautomer, enantiomer, pharmaceutically acceptable salt or prodrug thereof, wherein t is selected from the group consisting of 1 or 2;

X is selected from the group consisting of O, S and $NR_8$;

$R_1$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, amino$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted; or $R_1$ is $-L_1-R_{13}$;

$L_1$ is absent or a linker providing 1, 2, 3, 4, 5 or 6 atom separation between $R_{13}$ and the ring to which $L_1$ is attached, wherein the atoms of the linker providing the separation are selected from the group consisting of carbon, oxygen, nitrogen, and sulfur;

$R_2$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_3$ is selected from the group consisting of hydrogen, carbonyloxy, $(C_{1-10})$alkoxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; or $R_3$ has the formula $-L_2-R_{18}$;

$L_2$ is absent or a linker providing 1, 2, 3, 4, 5 or 6 atom separation between $R_{18}$ and the ring to which $L_2$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted;

R$_5$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted;

or any two of R$_3$, R$_4$ and R$_5$ are taken together to form a substituted or unsubstituted ring;

R$_6$ is selected from the group consisting of hydrogen, carbonyloxy, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_7$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, imino(C$_{1-10}$)alkyl, (C$_{3-12}$)cyclo alkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted;

R$_8$ is selected from the group consisting of hydrogen, hydroxy, carbonyloxy, (C$_{1-10}$)alkoxy, (C$_{4-12}$)aryloxy, hetero(C$_{1-10}$)aryloxy, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)bicycloalkyl, (C$_{4-12}$)aryl, hetero (C$_{1-10}$)aryl, (C$_{9-12}$)bicycloaryl and hetero(C$_{4-12}$)bicycloaryl, each substituted or unsubstituted;

R$_{13}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted; or R$_{13}$ has the formula:

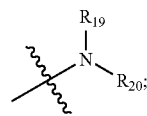

R$_{18}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted; and R$_{19}$ and R$_{20}$ are each independently selected from the group consisting of hydrogen, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero (C$_{8-12}$)bicyclo aryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{19}$ and R$_{20}$ are taken together to form a substituted or unsubstituted ring.

In one variation of the above embodiment, the compound is not: (i) 3-methylpyrido[3,2-e]pyrrolo[1,2-a]pyrazin-6(5H)-one; (ii) 3-methoxypyrido[3,2-e]pyrrolo[1,2-a]pyrazin-6 (5H)-one; (iii) 2-(3-chloro-6-oxo-6a,7,8,9-tetrahydropyrido [3,2-e]pyrrolo[1,2-a]pyrazin-5(6H)-yl)-N-o-tolylacetamide; (iv) 2-(3-chloro-6-oxo-6a,7,8,9-tetrahydropyrido[3,2-e]pyrrolo[1,2-a]pyrazin-5(6H)-yl)-N-(3-(trifluoromethyl)phenyl)

acetamide; (v) 5-Oxo-3-(2-trifluoromethyl-benzyl)-2,3,4,4a,5,6-hexahydro-1H-pyrazino[1,2-a]quinoxaline-8-carboxylic acid isopropylamide; (vi) 3-(5-Fluoro-2-trifluoromethyl-benzoyl)-5-oxo-2,3,4,4a,5,6-hexahydro-1H-pyrazino[1,2-a]quinoxaline-8-carboxylic acid phenylamide; (vii) 5-Oxo-3-(2-trifluoromethyl-benzoyl)-2,3,4,4a,5,6-hexahydro-1H-pyrazino[1,2-a]quinoxaline-8-carboxylic acid pentylamide; or (viii) 3-(5-Fluoro-2-trifluoromethyl-benzoyl)-5-oxo-2,3,4,4a,5,6-hexahydro-1H-pyrazino[1,2-a]quinoxaline-8-carboxylic acid butylamide.

In a further embodiment, PARP inhibitors of the present invention comprise:

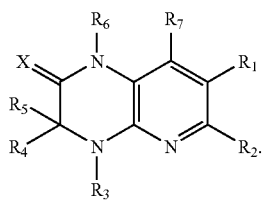

In another embodiment, PARP inhibitors of the present invention comprise:

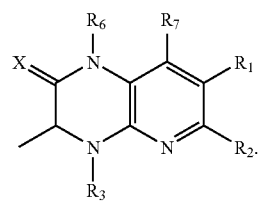

In still another embodiment, PARP inhibitors of the present invention comprise:

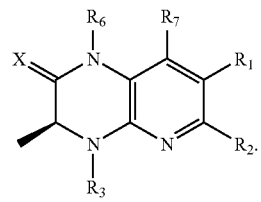

In yet another embodiment, PARP inhibitors of the present invention comprise:

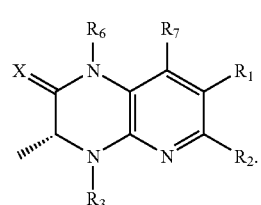

In a further embodiment, PARP inhibitors of the present invention comprise:

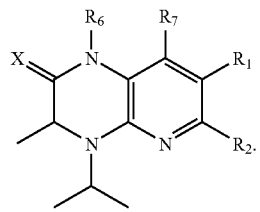

In still a further embodiment, PARP inhibitors of the present invention comprise:

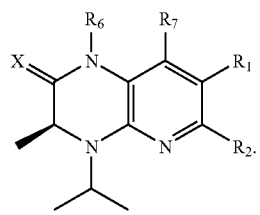

In yet a further embodiment, PARP inhibitors of the present invention comprise:

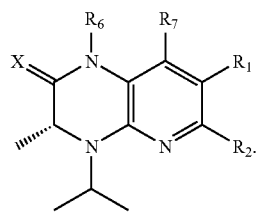

In another embodiment, PARP inhibitors of the present invention comprise:

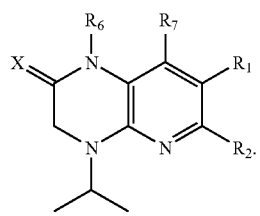

In still another embodiment, PARP inhibitors of the present invention comprise:

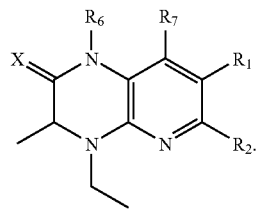

In yet another embodiment, PARP inhibitors of the present invention comprise:

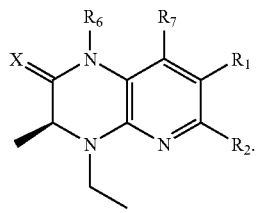

In a further embodiment, PARP inhibitors of the present invention comprise:

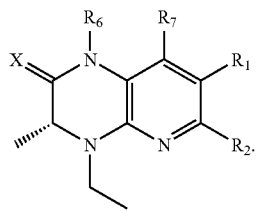

In still a further embodiment, PARP inhibitors of the present invention comprise:

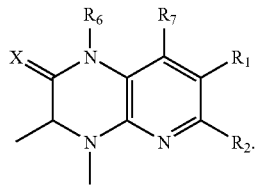

In yet a further embodiment, PARP inhibitors of the present invention comprise:

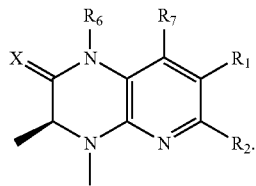

In another embodiment, PARP inhibitors of the present invention comprise:

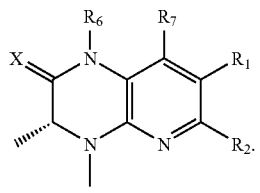

In still another embodiment, PARP inhibitors of the present invention comprise:

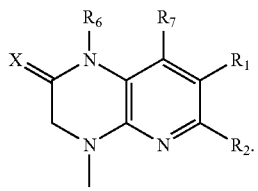

In yet another embodiment, PARP inhibitors of the present invention comprise:

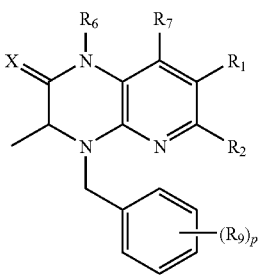

wherein
p is selected from the group consisting of 0, 1, 2, 3, 4 and 5; and $R_9$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cyclo alkyl ($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In a further embodiment, PARP inhibitors of the present invention comprise:

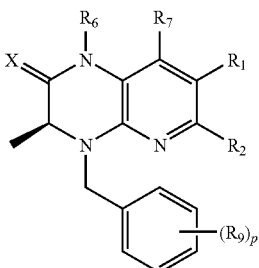

wherein
p is selected from the group consisting of 0, 1, 2, 3, 4 and 5; and

R₉ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further embodiment, PARP inhibitors of the present invention comprise:

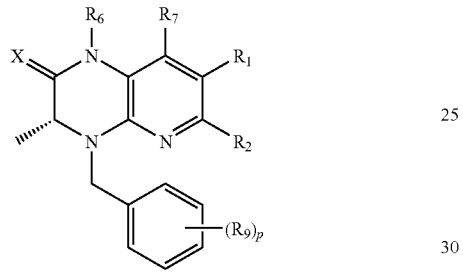

wherein
p is selected from the group consisting of 0, 1, 2, 3, 4 and 5; and

R₉ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet a further embodiment, PARP inhibitors of the present invention comprise:

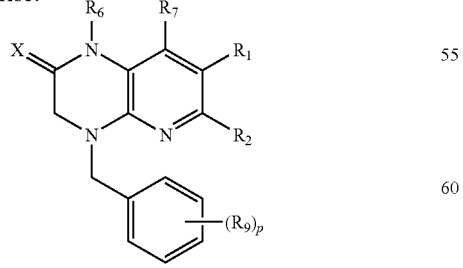

wherein
p is selected from the group consisting of 0, 1, 2, 3, 4 and 5; and

R₉ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further embodiment, PARP inhibitors of the present invention comprise:

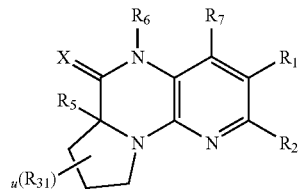

wherein
u is selected from the group consisting of 0, 1, 2, 3, 4, 5 and 6; and

R₃₁ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another embodiment, PARP inhibitors of the present invention comprise:

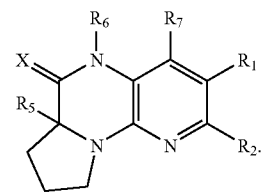

In a further embodiment, PARP inhibitors of the present invention comprise:

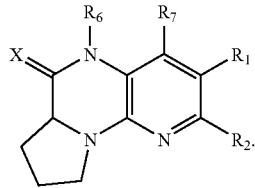

In yet a further embodiment, PARP inhibitors of the present invention comprise:

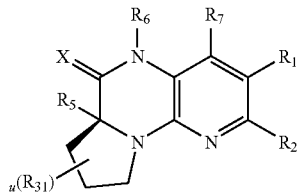

wherein
u is selected from the group consisting of 0, 1, 2, 3, 4, 5 and 6; and
$R_{31}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicyclo aryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still another embodiment, PARP inhibitors of the present invention comprise:

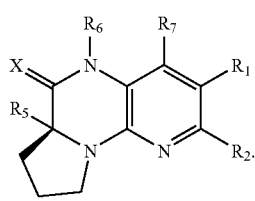

In yet another embodiment, PARP inhibitors of the present invention comprise:

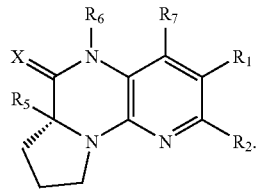

In another embodiment, PARP inhibitors of the present invention comprise:

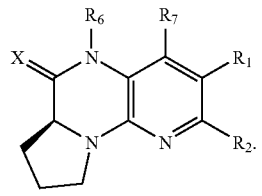

In a further embodiment, PARP inhibitors of the present invention comprise:

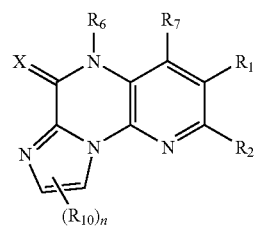

wherein
n is selected from the group consisting of 0, 1 and 2; and
$R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further embodiment, PARP inhibitors of the present invention comprise:

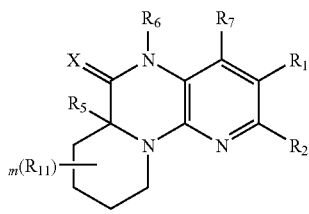

wherein m is selected from the group consisting of 0, 1, 2, 3, 4, 5, 6, 7 and 8; and $R_{11}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another embodiment, PARP inhibitors of the present invention comprise:

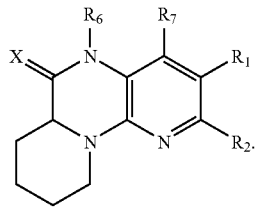

In still another embodiment, PARP inhibitors of the present invention comprise:

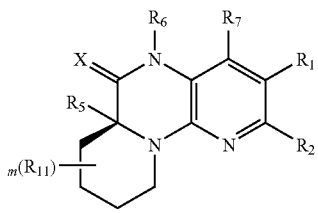

wherein m is selected from the group consisting of 0, 1, 2, 3, 4, 5, 6, 7 and 8; and $R_{11}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet another embodiment, PARP inhibitors of the present invention comprise:

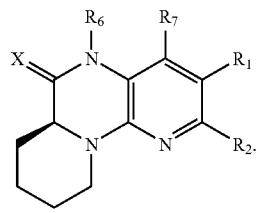

In yet a further embodiment, PARP inhibitors of the present invention comprise:

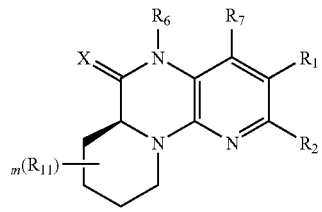

wherein m is selected from the group consisting of 0, 1, 2, 3, 4, 5, 6, 7 and 8; and $R_{11}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another embodiment, PARP inhibitors of the present invention comprise:

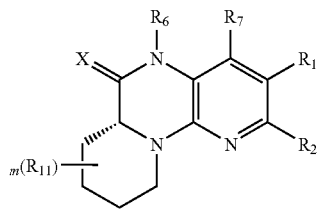

wherein
m is selected from the group consisting of 0, 1, 2, 3, 4, 5, 6, 7 and 8; and
$R_{11}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still another embodiment, PARP inhibitors of the present invention comprise:

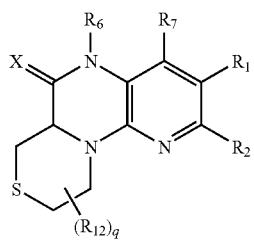

wherein
q is selected from the group consisting of 0, 1, 2, 3, 4, 5 and 6; and
$R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet another embodiment, PARP inhibitors of the present invention comprise:

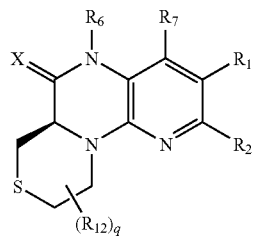

wherein
q is selected from the group consisting of 0, 1, 2, 3, 4, 5 and 6; and
$R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further embodiment, PARP inhibitors of the present invention comprise:

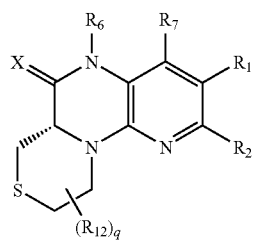

wherein
q is selected from the group consisting of 0, 1, 2, 3, 4, 5 and 6; and
$R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further embodiment, PARP inhibitors of the present invention comprise:

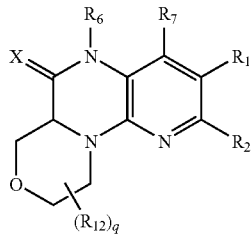

wherein q is selected from the group consisting of 0, 1, 2, 3, 4, 5 and 6; and $R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet a further embodiment, PARP inhibitors of the present invention comprise:

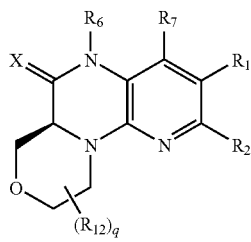

wherein q is selected from the group consisting of 0, 1, 2, 3, 4, 5 and 6; and $R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another embodiment, PARP inhibitors of the present invention comprise:

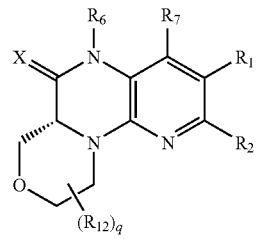

wherein q is selected from the group consisting of 0, 1, 2, 3, 4, 5 and 6; and $R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still another embodiment, PARP inhibitors of the present invention comprise:

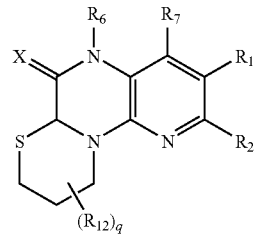

wherein q is selected from the group consisting of 0, 1, 2, 3, 4, 5 and 6; and $R_{12}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In a further embodiment, PARP inhibitors of the present invention comprise:

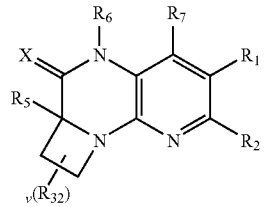

wherein v is selected from the group consisting of 0, 1, 2, 3 and 4; and $R_{32}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cyclo alkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{4-10}$)aryl, ($C_{9-12}$) bicycloaryl and hetero($C_{4-12}$)bicycloaryl, each substituted or unsubstituted.

In one variation of each of the above embodiments and variations, X is O.

In another variation of each of the above embodiments and variations, $R_1$ is -$L_1$-$R_{13}$;

$L_1$ is absent or a linker providing 1, 2, 3, 4, 5 or 6 atom separation between $R_{13}$ and the ring to which $L_1$ is attached, wherein the atoms of the linker providing the separation are selected from the group consisting of carbon, oxygen, nitrogen, and sulfur; and $R_{13}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cyclo alkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{4-10}$)aryl, ($C_{9-12}$) bicycloaryl and hetero($C_{4-12}$)bicycloaryl, each substituted or unsubstituted.

In still another variation of each of the above embodiments and variations, $L_1$ is absent or a linker selected from the group consisting of —($CR_{14}R_{15}$)$_r$—, —CO—, —CS—, —C(=$NR_{16}$)—, —$NR_{17}$—, —O—, —S—, —SO—, —$SO_2$— and combinations thereof;

r is selected from the group consisting of 1, 2 and 3;

$R_{14}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{4-10}$)aryl, ($C_{9-12}$) bicycloaryl and hetero($C_{4-12}$)bicycloaryl, each substituted or unsubstituted;

$R_{15}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxo alkyl, imino($C_{1-10}$)alkyl, ($C_{3-12}$) cyclo alkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicyclo aryl($C_{1-5}$)alkyl, hetero ($C_{8-12}$)bicyclo aryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted;

$R_{16}$ is selected from the group consisting of hydrogen, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cyclo alkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicyclo aryl($C_{1-5}$)alkyl, hetero ($C_{8-12}$)bicyclo aryl($C_{1-5}$)alkyl, hetero($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted; and $R_{17}$ is selected from the group consisting of hydrogen, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cyclo alkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicyclo aryl($C_{1-5}$)alkyl, hetero ($C_{8-12}$)bicyclo aryl($C_{1-5}$)alkyl, hetero($C_{1-10}$)

alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet another variation of each of the above embodiments and variations, $L_1$ is —$CR_{14}R_{15}$—;

$R_{14}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted; and $R_{15}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $L_1$ is —$CH_2$—. In another variation of each of the above embodiments and variations, $L_1$ is —$CF_2$—. In still a further variation of each of the above embodiments and variations, $L_1$ is —$NR_{17}$—. In yet a further variation of each of the above embodiments and variations, $L_1$ is —O—.

In yet another variation of each of the above embodiments and variations, $R_2$ is hydrogen. In a further variation of each of the above embodiments and variations, $R_2$ is halo. In still a further variation of each of the above embodiments and variations, $R_2$ is a substituted or unsubstituted $(C_{1-3})$ alkyl.

In still another variation of each of the above embodiments and variations, $R_3$ is a substituted or unsubstituted $(C_{1-3})$ alkyl. In yet another variation of each of the above embodiments and variations, $R_3$ is methyl. In a further variation of each of the above embodiments and variations, $R_3$ is ethyl. In still a further variation of each of the above embodiments and variations, $R_3$ is propyl. In yet a further variation of each of the above embodiments and variations, $R_3$ is isopropyl. In another variation of each of the above embodiments and variations, $R_3$ is a substituted or unsubstituted aryl$(C_{1-6})$alkyl. In still another variation of each of the above embodiments and variations, $R_3$ is a substituted or unsubstituted benzyl.

In yet another variation of each of the above embodiments and variations, $R_3$ has the formula -$L_2$-$R_{18}$, wherein $L_2$ is absent or a linker providing 1, 2, 3, 4, 5 or 6 atom separation between $R_{18}$ and the ring to which $L_2$ is attached, wherein the atoms of the linker providing the separation are selected from the group consisting of carbon, oxygen, nitrogen, and sulfur; and $R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $L_2$ is absent or a linker selected from the group consisting of —$(CR_{14}R_{15})_r$—, —CO—, —CS—, —C(=$NR_{16}$)—, —$NR_{17}$—, —O—, —S—, —SO—, —$SO_2$— and combinations thereof;

r is selected from the group consisting of 1, 2 and 3;

$R_{14}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_{15}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted;

$R_{16}$ is selected from the group consisting of hydrogen, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl ($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_{17}$ is selected from the group consisting of hydrogen, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In still a further variation of each of the above embodiments and variations, $L_2$ is —$CR_{14}R_{15}$—;

$R_{14}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted; and $R_{15}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In yet a further variation of each of the above embodiments and variations, $L_2$ is —$CH_2$—.

In still another variation of each of the above embodiments and variations, $R_4$ is a substituted or unsubstituted ($C_{1-3}$) alkyl. In yet another variation of each of the above embodiments and variations, $R_4$ is methyl. In a further variation of each of the above embodiments and variations, $R_4$ is hydrogen.

In still a further variation of each of the above embodiments and variations, $R_3$ and $R_4$, together with the atoms to which they are attached, are taken to form a substituted or unsubstituted 3, 4, 5, 6, 7 or 8 membered ring. In yet a further variation of each of the above embodiments and variations, $R_3$ and $R_4$, together with the atoms to which they are attached, are taken to form a substituted or unsubstituted 3, 4, 5, 6, 7 or 8 membered heterocycloalkyl ring. In another variation of each of the above embodiments and variations, $R_3$ and $R_4$, together with the atoms to which they are attached, are taken to form a substituted or unsubstituted 3, 4, 5, 6, 7 or 8 membered heterocycloaryl ring.

In yet another variation of each of the above embodiments and variations, $R_5$ is hydrogen. In a further variation of each of the above embodiments and variations, $R_5$ is halo. In still a further variation of each of the above embodiments and variations, $R_5$ is a substituted or unsubstituted ($C_{1-3}$) alkyl.

In yet another variation of each of the above embodiments and variations, $R_6$ is hydrogen. In still a further variation of each of the above embodiments and variations, $R_6$ is a substituted or unsubstituted ($C_{1-3}$) alkyl.

In yet another variation of each of the above embodiments and variations, $R_7$ is hydrogen. In a further variation of each of the above embodiments and variations, $R_7$ is halo. In still a further variation of each of the above embodiments and variations, $R_7$ is a substituted or unsubstituted ($C_{1-3}$) alkyl.

In still a further variation of each of the above embodiments and variations, $R_8$ is hydrogen. In yet a further variation of each of the above embodiments and variations, $R_8$ is a substituted or unsubstituted ($C_{1-3}$)alkyl.

In yet a further variation of each of the above embodiments and variations, $R_9$ is hydrogen. In another variation of each of the above embodiments and variations, $R_9$ is halo. In still another variation of each of the above embodiments and variations, $R_9$ is a substituted or unsubstituted ($C_{1-3}$)alkyl.

In yet a further variation of each of the above embodiments and variations, $R_{10}$ is hydrogen. In another variation of each of the above embodiments and variations, $R_{10}$ is halo. In still another variation of each of the above embodiments and variations, $R_{10}$ is a substituted or unsubstituted ($C_{1-3}$)alkyl.

In yet a further variation of each of the above embodiments and variations, $R_{11}$ is hydrogen. In another variation of each of the above embodiments and variations, $R_{11}$ is halo. In still another variation of each of the above embodiments and variations, $R_{11}$ is a substituted or unsubstituted ($C_{1-3}$)alkyl.

In yet a further variation of each of the above embodiments and variations, $R_{12}$ is hydrogen. In another variation of each of the above embodiments and variations, $R_{12}$ is halo. In still another variation of each of the above embodiments and variations, $R_{12}$ is a substituted or unsubstituted ($C_{1-3}$)alkyl.

In a further variation of each of the above embodiments and variations, $R_{13}$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted. In another variation of each of the above embodiments and variations, $R_{13}$ is selected from the group consisting of hetero($C_{3-12}$)cycloalkyl, hetero($C_{3-12}$)bicycloalkyl, hetero($C_{1-10}$)aryl and hetero($C_{4-12}$)bicycloaryl, each substituted or unsubstituted.

In still a further variation of each of the above embodiments and variations, $R_{13}$ has the formula:

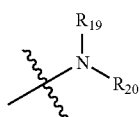

wherein $R_{19}$ and $R_{20}$ are each independently selected from the group consisting of hydrogen, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thio carbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicyclo aryl$(C_{1-5})$alkyl, hetero $(C_{8-12})$bicyclo aryl$(C_{1-5})$alkyl, hetero$(C_{1-10})$alkyl, $(C_{3-12})$cyclo alkyl, hetero $(C_{3-12})$ cyclo alkyl, $(C_{9-12})$bicyclo alkyl, hetero $(C_{3-12})$ bicyclo alkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring.

In yet a further variation of each of the above embodiments and variations, $R_{13}$ is a substituted or unsubstituted piperazinyl.

In another variation of each of the above embodiments and variations, $R_{13}$ has the formula

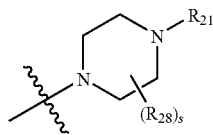

wherein s is selected from the group consisting of 0, 1, 2, 3, 4, 5, 6, 7 and 8;

$R_{21}$ is selected from the group consisting of hydrogen, hydroxy, carbonyloxy, $(C_{1-10})$alkoxy, $(C_{4-12})$aryloxy, hetero $(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero $(C_{4-12})$bicycloaryl, each substituted or unsubstituted; and $R_{28}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In another variation of each of the above embodiments and variations, $R_{13}$ has the formula:

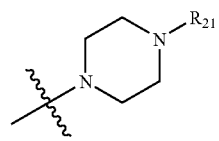

wherein $R_{21}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero $(C_{3-12})$cyclo alkyl, $(C_{9-12})$bicyclo alkyl, hetero $(C_{3-12})$bicyclo alkyl, $(C_{4-12})$aryl, hetero$(C_{1-10})$aryl, $(C_{9-12})$bicycloaryl and hetero$(C_{4-12})$bicycloaryl, each substituted or unsubstituted.

In still another variation of each of the above embodiments and variations, $R_{13}$ has the formula:

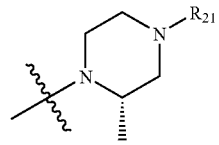

wherein $R_{21}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicyclo aryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted.

In yet another variation of each of the above embodiments and variations, $R_{13}$ has the formula:

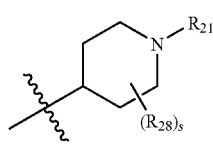

wherein s is selected from the group consisting of 0, 1, 2, 3, 4, 5, 6, 7 and 8;

$R_{21}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_{28}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still another variation of each of the above embodiments and variations, $R_{13}$ is a substituted or unsubstituted piperidinyl.

In yet another variation of each of the above embodiments and variations, $R_{13}$ has the formula:

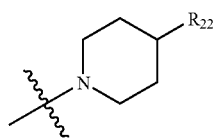

wherein $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $R_{13}$ is a substituted or unsubstituted 1,2,3,6-tetrahydropyridinyl.

In still a further variation of each of the above embodiments and variations, $R_{13}$ has the formula:

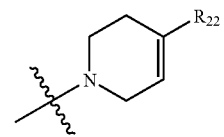

wherein $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet a further variation of each of the above embodiments and variations, $R_{13}$ is a substituted or unsubstituted 3-oxo-piperazinyl.

In another variation of each of the above embodiments and variations, $R_{13}$ has the formula:

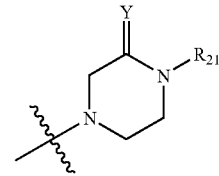

wherein

Y is selected from the group consisting of O and S; and $R_{21}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In still another variation of each of the above embodiments and variations, Y is O.

In yet another variation of each of the above embodiments and variations, $R_{14}$ is hydrogen. In a further variation of each of the above embodiments and variations, $R_{14}$ is halo. In still a further variation of each of the above embodiments and variations, $R_{14}$ is a substituted or unsubstituted ($C_{1-3}$) alkyl.

In yet another variation of each of the above embodiments and variations, $R_{15}$ is hydrogen. In a further variation of each of the above embodiments and variations, $R_{15}$ is halo. In still a further variation of each of the above embodiments and variations, $R_{15}$ is a substituted or unsubstituted ($C_{1-3}$) alkyl.

In yet a further variation of each of the above embodiments and variations, $R_{16}$ is hydrogen. In still another variation of each of the above embodiments and variations, $R_{16}$ is a substituted or unsubstituted ($C_{1-3}$)alkyl.

In another variation of each of the above embodiments and variations, $R_{17}$ is selected from the group consisting of hydrogen, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted. In yet a further variation of each of the above embodiments and variations, $R_{17}$ is hydrogen. In still another variation of each of the above embodiments and variations, $R_{17}$ is a substituted or unsubstituted ($C_{1-3}$)alkyl.

In another variation of each of the above embodiments and variations, $R_{18}$ is a substituted or unsubstituted phenyl.

In a further variation of each of the above embodiments and variations, $R_{19}$ is hydrogen. In still a further variation of each of the above embodiments and variations, $R_{19}$ is a substituted or unsubstituted ($C_{1-3}$)alkyl.

In another variation of each of the above embodiments and variations, $R_{20}$ is hydrogen. In still a further variation of each of the above embodiments and variations, $R_{20}$ is a substituted or unsubstituted ($C_{1-3}$)alkyl.

In a further variation of each of the above embodiments and variations, $R_{19}$ and $R_{20}$ are taken together to form a substituted or unsubstituted ring. In still a further variation of each of the above embodiments and variations, $R_{19}$ and $R_{20}$ are taken together to form a substituted or unsubstituted hetero($C_{3-12}$)cycloalkyl. In yet a further variation of each of the above embodiments and variations, $R_{19}$ and $R_{20}$ are taken together to form a substituted or unsubstituted hetero($C_{3-12}$)bicycloalkyl. In another variation of each of the above embodiments and variations, $R_{19}$ and $R_{20}$ are taken together to form a substituted or unsubstituted hetero($C_{1-10}$)aryl. In still another variation of each of the above embodiments and variations, $R_{19}$ and $R_{20}$ are taken together to form a substituted or unsubstituted hetero($C_{4-12}$)bicycloaryl.

In still another variation of each of the above embodiments and variations, $R_{21}$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted. In yet another variation of each of the above embodiments and variations, $R_{21}$ is a substituted or unsubstituted phenyl. In a further variation of each of the above embodiments and variations, $R_{21}$ is a substituted or unsubstituted 4-chlorophenyl. In still a further variation of each of the above embodiments and variations, $R_{21}$ is a substituted or unsubstituted pyridinyl.

In still another variation of each of the above embodiments and variations, $R_{21}$ has the formula:

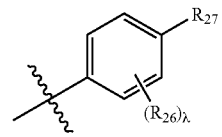

wherein

λ is selected from the group consisting of 0, 1, 2, 3 and 4;

each $R_{26}$ is independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted; and $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In yet another variation of each of the above embodiments and variations, $R_{21}$ has the formula:

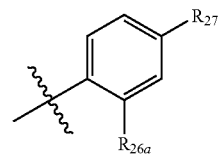

wherein
R$_{26a}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted; and R$_{27}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cyclo alkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In a further variation of each of the above embodiments and variations, R$_{21}$ has the formula:

[Structure: benzene ring with R$_{26b}$ substituent, R$_{27}$ substituent, and wavy-line attachment point]

wherein
R$_{26b}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted; and R$_{27}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxo alkyl, imino(C$_{1-10}$)alkyl, (C$_{3-12}$)cyclo alkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicyclo aryl(C$_{1-5}$)alkyl, hetero (C$_{8-12}$)bicyclo aryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In still a further variation of each of the above embodiments and variations, R$_{21}$ has the formula:

[Structure: benzene ring with R$_{26b}$ substituent, R$_{27}$ substituent, R$_{26a}$ substituent, and wavy-line attachment point]

wherein
R$_{26a}$ and R$_{26b}$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero (C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{4-10}$)aryl, (C$_{9-12}$)bicycloaryl and hetero(C$_{4-12}$)bicycloaryl, each substituted or unsubstituted; and R$_{27}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxo alkyl, imino(C$_{1-10}$)alkyl, (C$_{3-12}$)cyclo alkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicyclo aryl(C$_{1-5}$)alkyl, hetero (C$_{8-12}$)bicyclo aryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl, each substituted or unsubstituted.

In yet a further variation of each of the above embodiments and variations, R$_{21}$ has the formula:

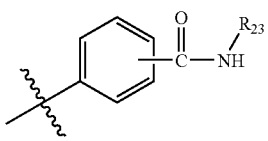

wherein $R_{23}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicyclo aryl$(C_{1-5})$alkyl, hetero $(C_{8-12})$bicyclo aryl$(C_{1-5})$alkyl, hetero$(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero $(C_{4-12})$bicycloaryl, each substituted or unsubstituted.

In another variation of each of the above embodiments and variations, $R_{21}$ has the formula:

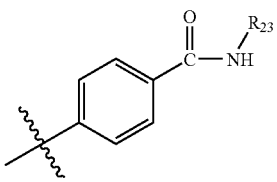

wherein $R_{23}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted.

In still another variation of each of the above embodiments and variations, $R_{21}$ is substituted with a substituent selected from the group consisting of halo, cyano and a substituted or unsubstituted carbonyl. In yet another variation of each of the above embodiments and variations, $R_{21}$ is substituted with a substituent having the formula —C(=O)—$R_{24}$, wherein $R_{24}$ is selected from the group consisting of hydrogen, thio, oxy, hydroxy, carbonyloxy, $(C_{1-10})$alkoxy, $(C_{4-12})$aryloxy, hetero $(C_{1-10})$aryloxy, carbonyl, oxycarbonyl, amido, amino, $(C_{1-10})$ alkylamino, sulfonamido, imino, sulfonyl, sulfinyl, $(C_{1-10})$ alkyl, halo$(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In another variation of each of the above embodiments and variations, $R_{21}$ has the formula:

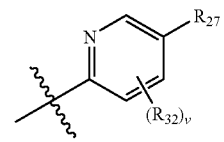

wherein v is selected from the group consisting of 0, 1, 2 and 3;

each $R_{32}$ is independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$ alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{4-10})$aryl, $(C_{9-12})$bicycloaryl and hetero$(C_{4-12})$bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cyclo alkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{4-10})$aryl, $(C_{9-12})$ bicycloaryl and hetero$(C_{4-12})$bicycloaryl, each substituted or unsubstituted.

In still another variation of each of the above embodiments and variations, $R_{21}$ has the formula:

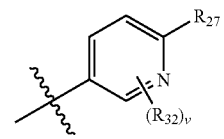

wherein v is selected from the group consisting of 0, 1, 2 and 3;

each $R_{32}$ is independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $R_{22}$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted. In still a further variation of each of the above embodiments and variations, $R_{22}$ is a substituted or unsubstituted phenyl. In yet a further variation of each of the above embodiments and variations, $R_{22}$ is a substituted or unsubstituted 4-chlorophenyl. In another variation of each of the above embodiments and variations, $R_{22}$ is a substituted or unsubstituted pyridinyl.

In still another variation of each of the above embodiments and variations, $R_{22}$ has the formula:

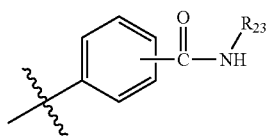

wherein $R_{23}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicyclo aryl$(C_{1-5})$alkyl, hetero $(C_{8-12})$bicyclo aryl$(C_{1-5})$alkyl, hetero$(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$ aryl, hetero$(C_{1-10})$aryl, $(C_{9-12})$bicycloaryl and hetero $(C_{4-12})$bicycloaryl, each substituted or unsubstituted.

In yet another variation of each of the above embodiments and variations, $R_{22}$ has the formula:

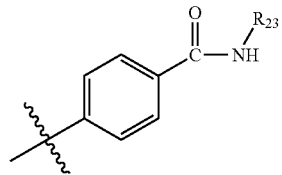

wherein $R_{23}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted.

In a further variation of each of the above embodiments and variations, $R_{22}$ is substituted with a substituent selected from the group consisting of halo, cyano and a substituted or unsubstituted carbonyl. In still a further variation of each of the above embodiments and variations, $R_{22}$ is substituted with a substituent having the formula —C(=O)—$R_{24}$, wherein $R_{24}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In a further variation of each of the above embodiments and variations, $R_{22}$ has the formula:

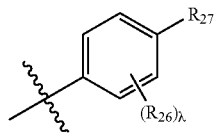

wherein

λ is selected from the group consisting of 0, 1, 2, 3 and 4;

each $R_{26}$ is independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In still a further variation of each of the above embodiments and variations, $R_{22}$ has the formula:

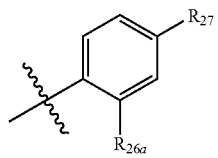

wherein $R_{26a}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet a further variation of each of the above embodiments and variations, $R_{22}$ has the formula:

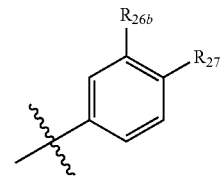

wherein $R_{26b}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{4-10})$aryl, $(C_{9-12})$bicycloaryl and hetero$(C_{4-12})$bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cyclo alkyl$(C_{1-5})$alkyl, hetero$(C_{3-12})$cycloalkyl$(C_{1-10})$ alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In another variation of each of the above embodiments and variations, $R_{22}$ has the formula:

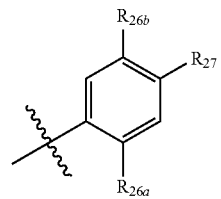

wherein $R_{26a}$ and $R_{26b}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted; and $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In another variation of each of the above embodiments and variations, $R_{22}$ has the formula:

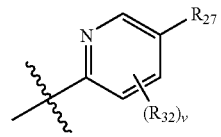

wherein v is selected from the group consisting of 0, 1, 2 and 3;

each $R_{32}$ is independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted; and $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cyclo alkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted.

In still another variation of each of the above embodiments and variations, $R_{22}$ has the formula:

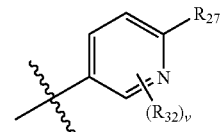

wherein v is selected from the group consisting of 0, 1, 2 and 3;

each $R_{32}$ is independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{4-10}$)aryl, ($C_{9-12}$)bicycloaryl and hetero($C_{4-12}$)bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero $(C_{3-12})$ cyclo alkyl, $(C_{9-12})$bicyclo alkyl, hetero $(C_{3-12})$bicyclo alkyl, $(C_{4-12})$aryl, hetero$(C_{4-10})$aryl, $(C_{9-12})$bicycloaryl and hetero$(C_{4-12})$bicycloaryl, each substituted or unsubstituted.

In yet a further variation of each of the above embodiments and variations, $R_{23}$ is a substituted or unsubstituted $(C_{1-3})$ alkyl. In another variation of each of the above embodiments and variations, $R_{23}$ is a substituted or unsubstituted $(C_{3-6})$ cycloalkyl. In still another variation of each of the above embodiments and variations, $R_{23}$ is methyl, ethyl, propyl, isopropyl or cyclopropyl.

In yet a further variation of each of the above embodiments and variations, $R_{24}$ is hydroxyl. In another variation of each of the above embodiments and variations, $R_{24}$ is a substituted or unsubstituted $(C_{1-3})$alkoxy. In still another variation of each of the above embodiments and variations, $R_{24}$ is a substituted or unsubstituted $(C_{1-3})$alkylamino. In yet another variation of each of the above embodiments and variations, $R_{24}$ is hydrogen. In still a further variation of each of the above embodiments and variations, $R_{24}$ is a substituted or unsubstituted $(C_{1-3})$ alkyl.

In another variation of each of the above embodiments and variations, $R_{26}$ is hydrogen. In still another variation of each of the above embodiments and variations, $R_{26}$ is halo. In yet another variation of each of the above embodiments and variations, $R_{26}$ is a substituted or unsubstituted $(C_{1-3})$ alkyl. In a further variation of each of the above embodiments and variations, $R_{26}$ is a substituted or unsubstituted $(C_{1-3})$alkoxy. In still a further variation of each of the above embodiments and variations, $R_{26}$ is fluoro, chloro, methyl or methoxy.

In another variation of each of the above embodiments and variations, $R_{26a}$ is hydrogen. In still another variation of each of the above embodiments and variations, $R_{26a}$ is halo. In yet another variation of each of the above embodiments and variations, $R_{26a}$ is a substituted or unsubstituted $(C_{1-3})$ alkyl. In a further variation of each of the above embodiments and variations, $R_{26a}$ is a substituted or unsubstituted $(C_{1-3})$alkoxy. In still a further variation of each of the above embodiments and variations, $R_{26a}$ is fluoro, chloro, methyl or methoxy.

In another variation of each of the above embodiments and variations, $R_{26b}$ is hydrogen. In still another variation of each of the above embodiments and variations, $R_{26b}$ is halo. In yet another variation of each of the above embodiments and variations, $R_{26b}$ is a substituted or unsubstituted $(C_{1-3})$ alkyl. In a further variation of each of the above embodiments and variations, $R_{26b}$ is a substituted or unsubstituted $(C_{1-3})$alkoxy. In still a further variation of each of the above embodiments and variations, $R_{26b}$ is fluoro, chloro, methyl or methoxy.

In another variation of each of the above embodiments and variations, $R_{27}$ is —CO—NH—$R_{23}$; and $R_{23}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still another variation of each of the above embodiments and variations, $R_{27}$ is —CO—O—$R_{23}$; and $R_{23}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet another variation of each of the above embodiments and variations, $R_{27}$ is —SO$_2$—O—$R_{23}$; and $R_{23}$ is selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In a further variation of each of the above embodiments and variations, $R_{27}$ is —CO—NR$_{29}$R$_{30}$; and $R_{29}$ and $R_{30}$ are each independently selected from the group consisting of hydrogen, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{29}$ and $R_{30}$ are taken together to form a substituted or unsubstituted ring.

In still a further variation of each of the above embodiments and variations, $R_{27}$ is cyano. In another variation of each of the above embodiments and variations, $R_{27}$ is halo. In yet a further variation of each of the above embodiments and variations, $R_{27}$ is chloro. In another variation of each of the above embodiments and variations, $R_{27}$ is fluoro.

In still another variation of each of the above embodiments and variations, $R_{28}$ is hydrogen. In yet another variation of each of the above embodiments and variations, $R_{28}$ is halo. In a further variation of each of the above embodiments and variations, $R_{28}$ is a substituted or unsubstituted $(C_{1-3})$ alkyl. In a further variation of each of the above embodiments and variations, $R_{28}$ is a substituted or unsubstituted $(C_{1-3})$ alkoxy. In still a further variation of each of the above embodiments and variations, $R_{28}$ is a substituted or unsubstituted amino. In yet a further variation of each of the above embodiments and variations, $R_{28}$ is thio.

In still a further variation of each of the above embodiments and variations, $R_{29}$ is hydrogen. In yet a further variation of each of the above embodiments and variations, $R_{29}$ is a substituted or unsubstituted $(C_{1-3})$ alkyl.

In another variation of each of the above embodiments and variations, $R_{30}$ is hydrogen. In still another variation of each of the above embodiments and variations, $R_{30}$ is a substituted or unsubstituted $(C_{1-3})$ alkyl.

In yet another variation of each of the above embodiments and variations, $R_{31}$ is hydrogen. In a further variation of each of the above embodiments and variations, $R_{31}$ is halo. In still a further variation of each of the above embodiments and variations, $R_{31}$ is a substituted or unsubstituted $(C_{1-3})$ alkyl.

In yet another variation of each of the above embodiments and variations, $R_{32}$ is hydrogen. In a further variation of each of the above embodiments and variations, $R_{32}$ is halo. In still a further variation of each of the above embodiments and variations, $R_{32}$ is a substituted or unsubstituted $(C_{1-3})$ alkyl.

In another variation of each of the above embodiments and variations, $R_1$ is -$L_1$-$R_{13}$;
$L_1$ is —$CH_2$—;
$R_{13}$ has the formula:

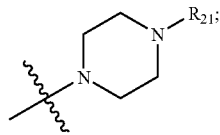

$R_{21}$ has the formula:

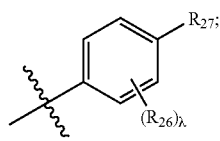

λ is selected from the group consisting of 0, 1 and 2;
each $R_{26}$ is independently selected from the group consisting of hydrogen, halo, $(C_{1-3})$ alkyl and $(C_{1-3})$alkoxy;
$R_{27}$ is —CO—NH—$R_{23}$; and
$R_{23}$ is selected from the group consisting of $(C_{1-3})$alkyl and $(C_{3-6})$cycloalkyl.

In still another variation of each of the above embodiments and variations, n is 0. In yet another variation of each of the above embodiments and variations, n is 1. In a further variation of each of the above embodiments and variations, l is 0. In still a further variation of each of the above embodiments and variations, l is 1. In yet a further variation of each of the above embodiments and variations, l is 2. In a further variation of each of the above embodiments and variations, m is 0. In still a further variation of each of the above embodiments and variations, m is 1. In yet a further variation of each of the above embodiments and variations, p is 0. In another variation of each of the above embodiments and variations, p is 1. In still another variation of each of the above embodiments and variations, q is 0. In yet another variation of each of the above embodiments and variations, q is 1. In still a further variation of each of the above embodiments and variations, r is 1. In yet a further variation of each of the above embodiments and variations, r is 2. In a further variation of each of the above embodiments and variations, s is 0. In still a further variation of each of the above embodiments and variations, s is 1. In yet a further variation of each of the above embodiments and variations, is 2. In another variation of each of the above embodiments and variations, t is 1. In still another variation of each of the above embodiments and variations, u is 0. In yet another variation of each of the above embodiments and variations, u is 1. In a further variation of each of the above embodiments and variations, v is 0. In still a further variation of each of the above embodiments and variations, v is 1.

In another of its aspects, the present invention relates to methods of making compounds that are useful as PARP inhibitors.

In still another of its aspects, the present invention relates to intermediates that are useful in making PARP inhibitors.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as hydrogen.

It is further noted that the compound may be present as a mixture of stereoisomers, or the compound may be present as a single stereoisomer.

In another of its aspects, there is provided a pharmaceutical composition comprising a compound according to any one of the above embodiments and variations; and one or more pharmaceutically acceptable excipients. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

The present invention also provides a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting PARP comprising contacting PARP with a compound of any one of the above embodiments and variations.

In yet another of its aspects, there is provided a method of inhibiting PARP comprising causing a compound of any one of the above embodiments and variations to be present in a subject in order to inhibit PARP in vivo.

In a further of its aspects, there is provided a method of inhibiting PARP comprising administering a first compound to a subject that is converted in vivo to a second compound wherein the second compound inhibits PARP in vivo, the second compound being a compound according to any one of the above embodiments and variations.

In another of its aspects, there is provided a method of treating a disease state for which PARP possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which PARP possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which PARP possesses activity that contributes to the pathology and/or symptomology of the disease state, the method comprising administering a first compound to a subject that is converted in vivo to a second compound wherein the second compound inhibits PARP in vivo, the second compound being a compound according to any one of the above embodiments and variations.

In one variation of each of the above methods the disease state is selected from the group consisting of cancers (including cancers where DNA damaging (e.g., alkylating) agents, cytotoxic drugs, radiation therapy and/or topoisomerase inhibitors are a standard of care (e.g., in combination with chemo- and/or radiosensitizers for cancer treatment); cancers which are deficient in Homologous Recombination (HR) dependent DNA DSB repair; BRCA-I and BRCA-2 deficient tumors; bladder cancer; blood-borne cancers (e.g., acute lymphoblastic leukemia("ALL"), acute lymphoblastic B-cell leukemia, acute lymphoblastic T-cell leukemia, acute myeloblasts leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia("CML"), chronic lymphocytic leukemia("CLL"), hairy cell leukemia and multiple myeloma); bone cancer; breast cancer; carcinomas (e.g., squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, small cell lung carcinoma, bladder carcinoma and epithelial carcinoma); CNS and brain cancers (e.g., glioma (e.g., pilocytic astrocytoma, astrocytoma, anaplastic astrocytoma, or glioblastoma multiforms), pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain cancer, meningioma, spinal tumor and medulloblastoma); cervical cancer; colon cancer; colorectal cancer; esophageal cancer; hepatomas; head and neck cancer; kidney cancer; acute and chronic leukemias (e.g., lymphoblastic, myelogenous, lymphocytic and myelocytic leukemias); liver cancer; lung cancer; lymphomas (e.g., such as Hodgkin's disease, non-Hodgkin's Lymphoma, Multiple myeloma, Waldenstrom's macroglobulinemia, Heavy chain disease and Polycythemia vera); melanomas; nasal cancer; neuroblastomas; oral cancer; ovarian cancer; pancreatic cancer; prostate cancer; retinoblastomas; skin cancer; solid tumors (e.g., such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma and rhabdomyosarcoma); stomach cancer; testicular cancer; throat cancer; uterine cancer and Wilms' tumor); cardiovascular diseases (including chronic heart failure; atherosclerosis; congestive heart failure; circulatory shock; cardiomyopathy; cardiac transplant; myocardialinfarction and cardiac arrhythmia (e.g., atrial fibrillation, supraventricular tachycardia, atrial flutter and paroxysmal atrial tachycardia)); vascular diseases other than cardiovascular diseases (including peripheral arterial occlusion; thromboangitis obliterans; Reynaud's disease and phenomenon; acrocyanosis; erythromelalgia; venous thrombosis; varicose veins; arteriovenous fistula; lymphedema and lipedema); metabolic diseases (including diabetes (e.g., diabetes mellitus (e.g., Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins); and diabetic complications (e.g., diabetic cataract, glaucoma, retinopathy, nephropathy (e.g., microaluminuria and diabetic nephropathy), mononeuropathy, autonomic neuropathy, polyneuropathy, gangrene of the feet, atherosclerotic coronary arterial disease, peripheral arterial disease, non-ketotic hyperglycemic-hyperosmolar coma, mononeuropathies, autonomic neuropathy, foot ulcers, joint problems, skin or mucous membrane complications (e.g., infection, shin spot, candidal infection or necrobiosis lipoidica diabeticorumobesity), hyperlipidemia, hypertension, syndrome of insulin resistance, coronary artery disease, foot ulcers, joint problems, fungal infections, bacterial infections, cardiomyopathy, immune-complex vasculitis and systemic lupus erythematosus (SLE))); inflammatory diseases (including conditions resulting from organ transplant rejection; chronic inflammatory diseases of the joints (e.g., arthritis, rheumatoid arthritis, osteoarthritis and bone diseases associated with increased bone resorption); inflammatory bowel diseases (e.g., ileitis, ulcerative colitis, Barrett's syndrome and Crohn's disease); inflammatory lung diseases (e.g., asthma, adult respiratory distress syndrome and chronic obstructive airway disease); inflammatory diseases of the eye (e.g., corneal dystrophy, trachoma, onchocerciasis, uveitis, sympatheticophthalmitis and endophthalmitis); chronic inflammatory diseases of the gum (e.g., gingivitis and periodontitis); tuberculosis; leprosy; inflammatory diseases of the kidney (e.g., uremic complications, glomerulonephritis and nephrosis); inflammatory diseases of the skin (e.g., sclerodermatitis, psoriasis and eczema); inflammatory diseases of the central nervous system (e.g., chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis and viral or autoimmune encephalitis); inflammatory diseases of the heart (e.g., cardiomyopathy, ischemic heart disease, hypercholesterolemia and atherosclerosis); diseases that can have significant inflammatory components (e.g., preeclampsia, chronic liver failure, brain and spinal cord trauma and multiple organ dysfunction syndrome (MODS) (multiple organ failure (MOF))); systemic inflammation of the body, exemplified by gram-positive or gram negative shock, hemorrhagic or anaphylactic shock, or shock induced by cancer chemotherapy in response to pro-inflammatory cytokines, (e.g., shock associated with pro-inflammatory cytokines; and shock induced, for example, by a chemotherapeutic agent that is administered as a treatment for cancer); reperfusion injuries, including those resulting from naturally occurring episodes and during a surgical procedure (e.g., intestinal reperfusion injury; myocardial reperfusion injury; reperfusion injury resulting from cardiopulmonary bypass surgery, aortic aneurysm repair surgery, carotid endarterectomy surgery, or hemorrhagic shock; and reoxygenation injury resulting from transplantation of organs such as heart, lung, liver, kidney, pancreas, intestine or cornea); ischemic conditions, including those resulting from organ transplantation (e.g., stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemic kidney disease, ischemic liver disease, ischemic retinal disorder, septic shock; and an ischemic disease of the central nervous system (e.g., stroke or cerebral ischemia)); neurodegenerative diseases (e.g., polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS)); tissue injuries; CNS diseases; heart attack; hematolymphoid system disorders; endocrine and neuroendocrine system disorders; urinary tract disorders; respiratory system disorders; female reproductive system disorders; male reproductive system disorders; retroviral infections; retinal damage; skin senescence; UV-induced skin damage; chronic or acute renal disease or failure; age-related cellular dysfunction; and fatty acid synthesis related diseases (e.g., obesity, diabetes and cardiovascular disease).

In another variation of each of the above methods, the PARP is a PARP-1, PARP-2, PARP-3, vaultPARP or TiPARP. It is noted that the compounds of the present invention may also possess inhibitory activity for other PARP family members and thus may be used to address disease states associated with these other family members. Further, the compounds of the present invention may also possess inhibitory activity for tankyrases (e.g., tankyrase-1 and tankyrase-2) and thus may be used to address disease states associated with these target proteins.

Salts, Hydrates, and Prodrugs of PARP Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), Bioorganic and Medicinal Chemistry Letters, Vol. 4, p. 1985.

Protected derivatives of compounds of the present invention can also be made. Examples of techniques applicable to the creation of protecting groups and their removal can be found in T. W. Greene, Protecting Groups in Organic Synthesis, 3$^{rd}$ edition, John Wiley & Sons, Inc. 1999.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Compositions Comprising PARP Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The PARP inhibitors and compositions comprising them may be administered or coadministered in any conventional dosage form. Co-administration in the context of this invention is intended to mean the administration of more than one therapeutic agent, one of which includes a PARP inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an inhibitor of the present invention to reduce PARP activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more PARP inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358, 603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the PARP inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The PARP inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a PARP inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The PARP inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the PARP inhibitor alone or in combination with other pharmaceutically acceptable excipients can also be administered.

Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Kits Comprising PARP Inhibitors

The invention is also directed to kits and other articles of manufacture for treating diseases associated with PARP. It is noted that diseases are intended to cover all conditions for which the PARP possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as PARP inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Combination Therapies

A wide variety therapeutic agents may have a therapeutic additive or synergistic effect with PARP inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with PARP inhibitors include, but are not limited to, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a PARP inhibitor and an alkylating agent may have therapeutic synergistic effects on cancer and reduce sides affects associated with these chemotherapeutic agents.

Antibiotic agents are a group of drugs that are produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a PARP inhibitor and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a PARP inhibitor and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including a PARP inhibitor and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a PARP inhibitor and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a PARP inhibitor and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with PARP inhibitor include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with a PARP inhibitor include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with a PARP inhibitor to reduce chemotherapy-induced myelopoietic toxicity.

Other immuno-modulating agents other than cytokines may also be used in conjunction with a PARP inhibitor to inhibit abnormal cell growth. Examples of such immunomodulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including PARP inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20$^+$ pre-B and mature B cells. RITUXAN® is used as single agent for the treatment of patients with relapsed or refractory low-grade or follicular, CD20+, B cell non-Hodgkin's lymphoma. Combination therapy including PARP inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth cancer. Examples of the tumor suppressor genes include, but are not limited to, DPC-4, NF-1, NF-2, RB, p53, WT1, BRCA1, and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a PARP inhibitor and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/ lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

Further examples of therapeutic agents that may be used in combination with PARP inhibitors include, but are not limited to, P13/Akt signaling inhibitors. Examples of P13/Akt inhibitors that may be used in combination with PARP inhibitors include, but are not limited to, human epidermal growth factor receptor (HER2) inhibitors. Examples of HER2 inhibitors include, but are not limited to, Herceptin® (Trastruzumab) and Tykerb® (Lapatinib). Tykerb®, a small molecule that can be administered orally, inhibits the tyrosine kinase components of ErbB1 and ErbB2 receptors. Stimulation of ErbB1 and ErbB2 is associated with cell proliferation and with multiple processes involved in tumor progression, invasion, and metastasis. Overexpression of these receptors has been reported in a variety of human tumors and is associated with poor prognosis and reduced overall survival.

Still further examples of therapeutic agents that may be used in combination with PARP inhibitors include, but are not limited to, histone deacetylase (HDAC) inhibitors. Examples of HDAC inhibitors that may be used in combination with PARP inhibitors include, but are not limited to, suberoylanilide hydroxamic acid (SAHA).

In addition, the PARP inhibitors of the present invention may be used in combination with aminoglyside antiobiotics, CHK inhibitors, cytotoxic drugs and/or topoisomerase inhibitors.

EXAMPLES

Preparation of PARP Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), Bioorganic and Medicinal Chemistry Letters, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, Protecting Groups in Organic Synthesis, $3^{rd}$ edition, John Wiley & Sons, Inc. 1999.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| µL (microliters) | Ac (acetyl) |
| atm (atmosphere) | ATP (Adenosine Triphophatase) |
| BOC (tert-butyloxycarbonyl) | BOP (bis(2-oxo-3-oxazolidinyl)phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| $Et_2O$ (diethyl ether) | EtOAc (ethyl acetate) |
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | RT (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | |

All references to ether or $Et_2O$ are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60E-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Scheme 1

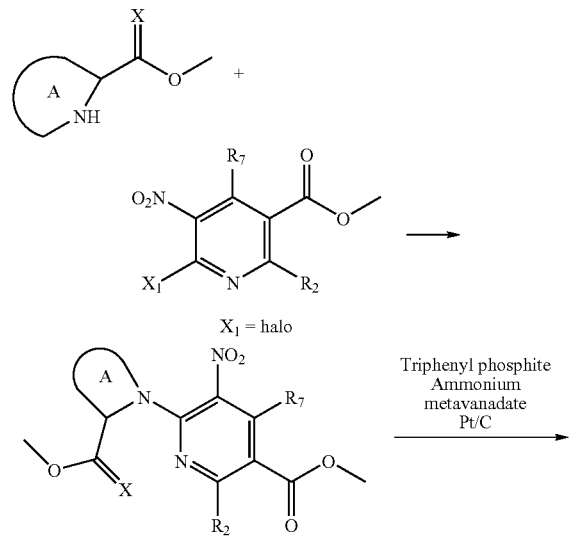

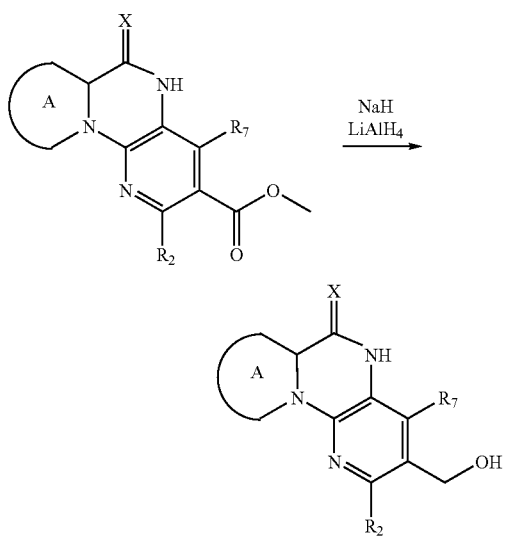

An α-aminoester is condensed with a substituted 2-halo-3-nitropyridine (alternatively with or without solvent or applied heat) followed by reduction of the nitro group and ring closure to give a substituted pyridopyrazine. Alternatively the nitro reduction and cyclization can be carried out with iron dust in AcOH with heating. Reduction of the methyl ester at the 7-position is accomplished with lithium aluminum hydride (or other hydride reducint agents) after deprotonation of the amide N—H to protect the amide.

Scheme 2

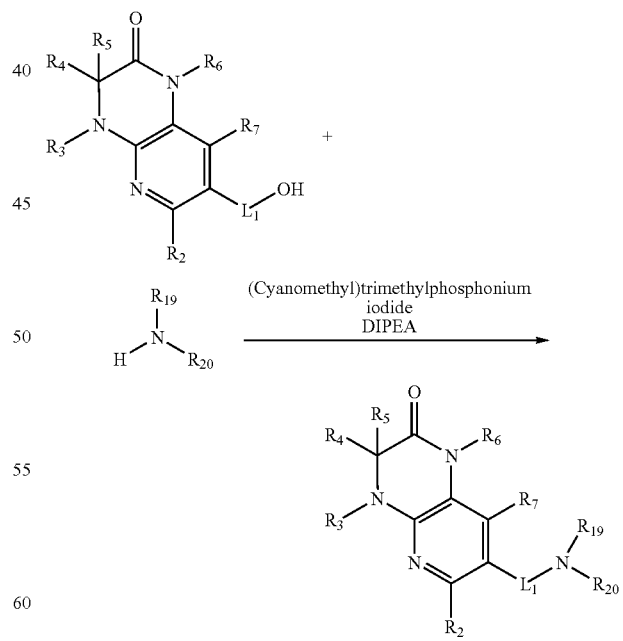

Nucleophilic substitution of the alcohol with amines is accomplished after conversion of the alcohol to the iodide. Other methods of alcohol activation may be utilized including Mitsunobu conditions among others.

Scheme 3

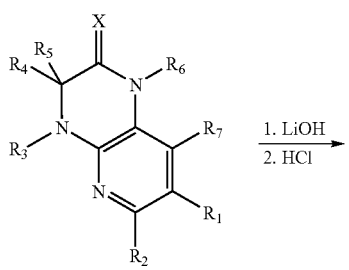

wherein $R_1$ has a terminal ester

1. LiOH
2. HCl

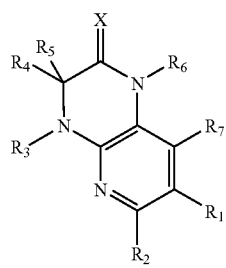

wherein $R_1$ has a terminal carboxylic acid

Hydrolysis of a terminal ester is accomplished with lithium hydroxide followed by treatment with acid to give a terminal carboxylic acid. Alternatively, other hydrolysis conditions can be utilized, both basic and acidic, including sodium hydroxide, potassium hydroxide, hydrochloric acid and others.

Scheme 4

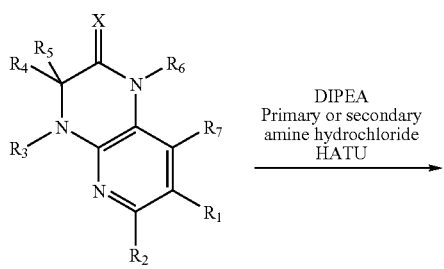

wherein $R_1$ has a terminal ester carboxylic acid

DIPEA
Primary or secondary amine hydrochloride
HATU

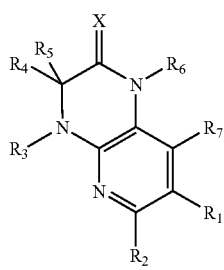

wherein $R_1$ has a terminal carboxamide

Terminal carboxylic acids are converted to terminal carboxamides through activation of the acid with HATU followed by treatment with primary or secondary amines. Alternatively, other methods exist to convert carboxylic acids to carboxamides including conversion to an intermediate acid chloride or use of other activation reagents such as EDC, HOBt, EDAC, PyBOP, TATU and others.

Scheme 5

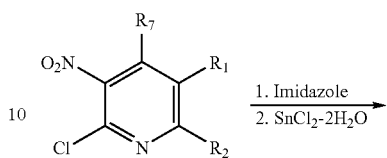

1. Imidazole
2. $SnCl_2 \cdot 2H_2O$

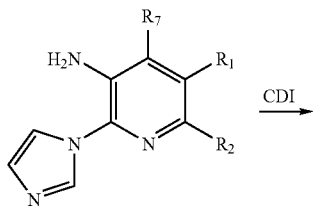

CDI

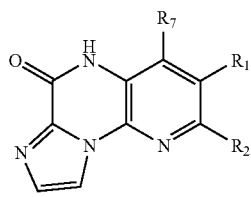

Nucleophilic aromatic substitution of a 2-halo-3-nitropyridine with imidazole is carried out followed by reduction of the nitro group. Treatment with CDI forms the pyrazinone.

Scheme 6

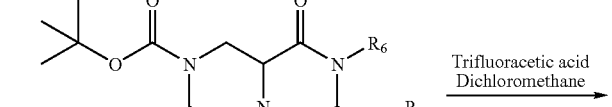

Trifluoroacetic acid
Dichloromethane

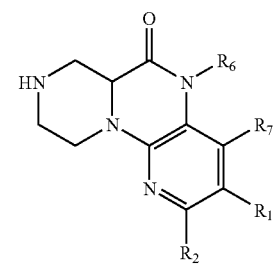

Deprotection of a Boc group is accomplished by stirring with TFA in DCM. Alternatively, other strong acids and solvents may be used including but not limited to HCl in EtOAc.

Scheme 7a: General Procedure for synthesis of substituted 4-piperazinylbenzamides

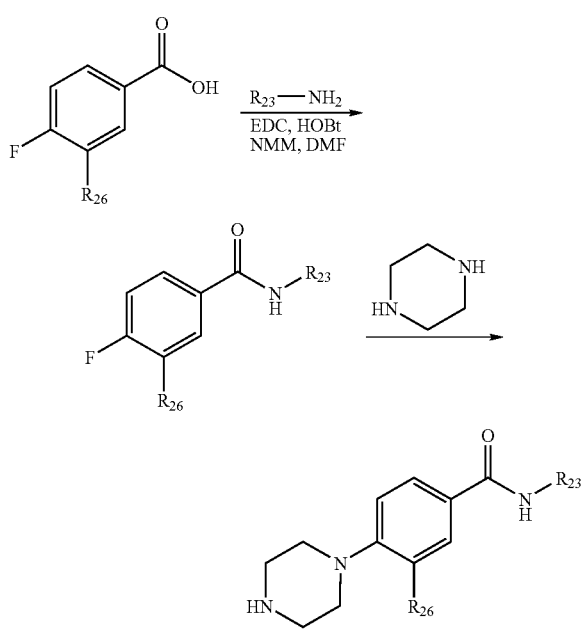

Substituted 4-fluorobenzoic acids are converted to benzamides using various amines and a coupling reagent such as EDC with HOBt. Alternatively, other coupling reagents can be used to form the amide. Subsequent nucleophilic aromatic substitution with piperazine gives the required substituted 4-piperazinylbenzamides.

Scheme 7b: Alternative General Procedure for synthesis of substituted 4-piperazinylbenzamides

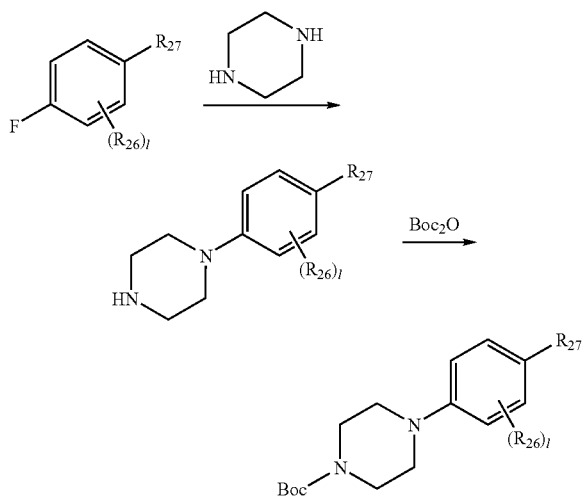

$l = 0, 1, 2, 3$ or $4$

Nucleophilic aromatic substitution of aryl fluorides with piperazine gives N-arylpiperazines which can then be protected with a Boc group to allow further functionalization of the aryl substituents. Alternatively, other protecting groups can be used besides Boc.

Scheme 8

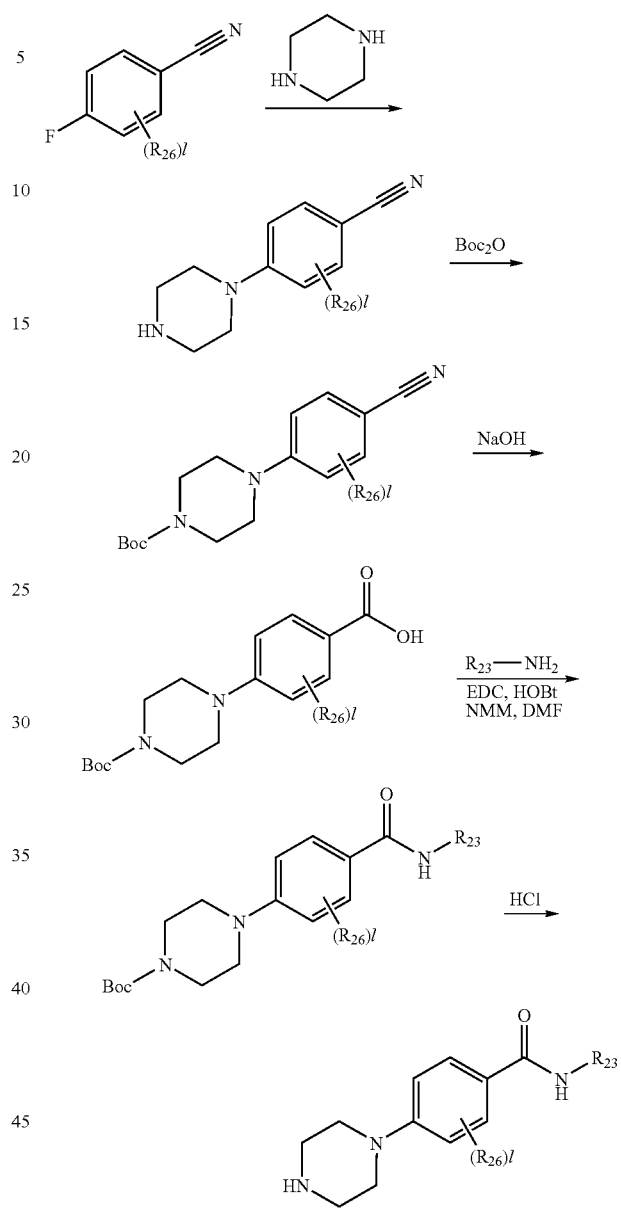

Substituted 4-fluorobenzonitriles are subjected to nucleophilic aromatic substitution with piperazine followed by protection using Boc anhydride. The nitrile is hydrolyzed to the corresponding carboxylic acid which is then coupled with an amine to give the resulting benzamide. Finally the Boc protecting group is removed by treatment with acid to furnish substituted 4-piperazinylbenzamides.

Scheme 9

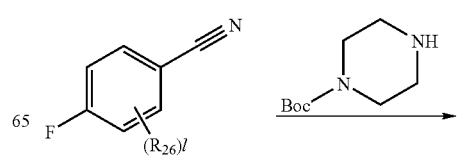

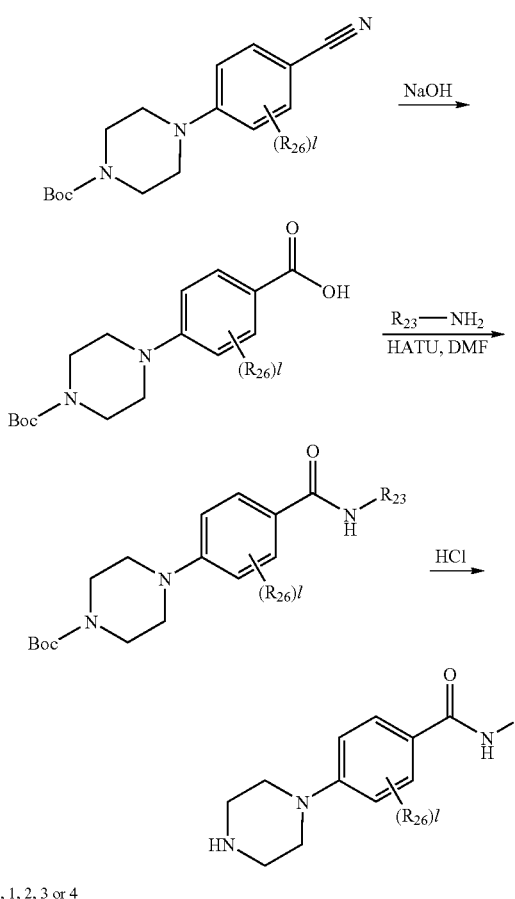

l = 0, 1, 2, 3 or 4

Substituted 4-fluorobenzonitriles are subjected to nucleophilic aromatic substitution with Boc-piperazine. The nitrile is hydrolyzed to the corresponding carboxylic acid which is then coupled with an amine to give the resulting benzamide. Finally the Boc protecting group is removed to furnish substituted 4-piperazinylbenzamides.

Scheme 10

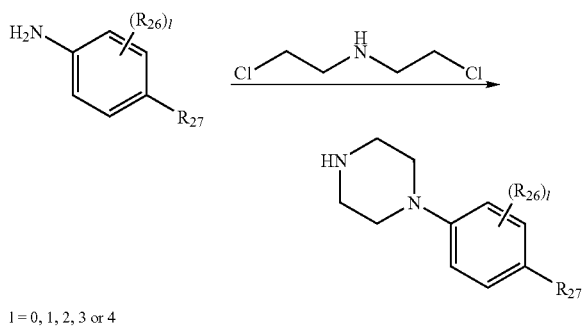

l = 0, 1, 2, 3 or 4

Substituted anilines can be converted to substituted piperazines through alkylation of the aniline with bis(2-chloroethyl) amine. Alternatively, other halogens or leaving groups can be incorporated in the amine such as bis(2-bromoethyl)amine or others.

Scheme 11

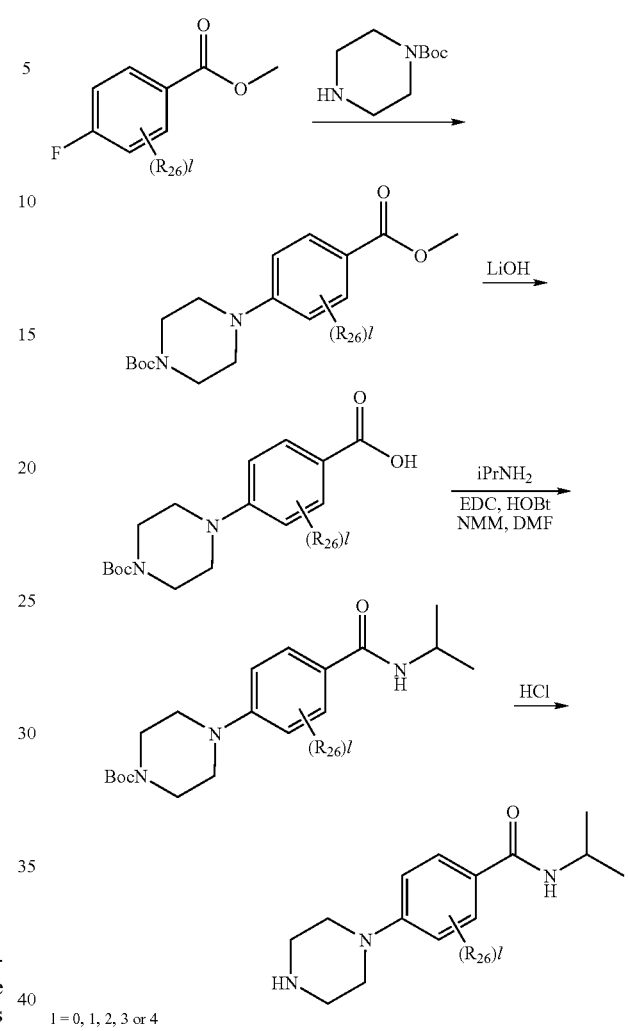

l = 0, 1, 2, 3 or 4

Substituted 4-fluorobenzoates are subjected to nucleophilic aromatic substitution with N-Boc piperazine followed by hydrolysis of the ester with lithium hydroxide to give a protected 4-carboxyphenyl-N-piperazine. Alternatively, other hydrolysis conditions can be utilized, both basic and acidic, including sodium hydroxide, potassium hydroxide, hydrochloric acid and others. Amide formation of the benzoic acid with amines is mediated with coupling reagents such as EDC with HOBt followed by removal of the protecting group with HCl to give the desired substituted 4-benzamidepiperazines. Alternatively, other methods exist to convert carboxylic acids to carboxamides including conversion to an intermediate acid chloride or use of other activation reagents such as EDAC, PyBOP, TATU and others.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Watrers ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10μ in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

In each of the above reaction procedures or schemes, the various substituents may be selected from among the various substituents otherwise taught herein.

Descriptions of the syntheses of particular compounds according to the present invention based on the above reaction scheme are set forth herein.

Examples of PARP Inhibitors

The present invention is further exemplified, but not limited by, the following examples that describe the synthesis of particular compounds according to the invention.

Compound 1: (S)-3-((4-(4-chlorophenyl)piperazin-1-yl)methyl)-6a,7,8,9-tetrahydropyrido[3,2-e]pyrrolo[1,2-a]pyrazin-6(5H)-one

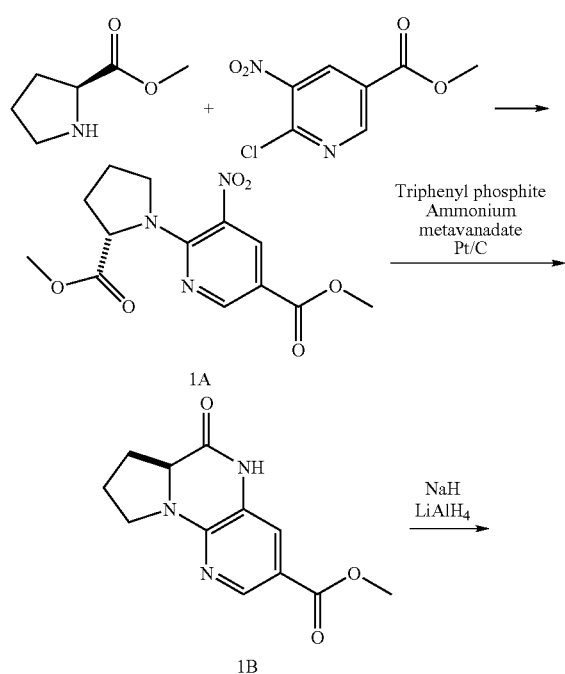

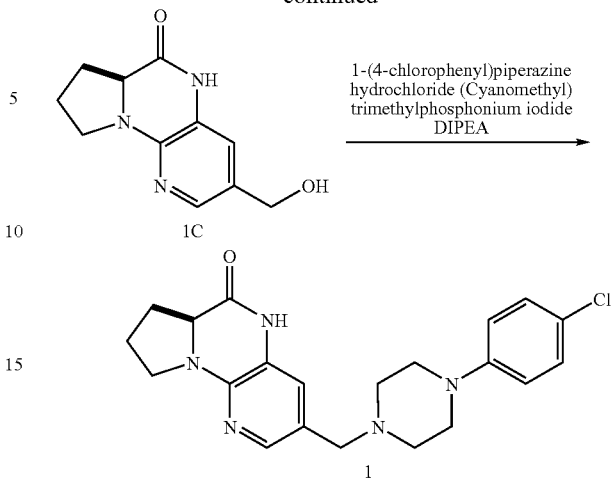

Compound 1A: (S)-Methyl 6-(2-(methoxycarbonyl)pyrrolidin-1-yl)-5-nitronicotinate (S)-Methyl pyrrolidine-2-carboxylate (6.56 g, 50.8 mmol) was added to methyl 6-chloro-5-nitronicotinate (5.00 g, 23.1 mmol) and the reaction mixture was stirred at 90° C. for 10 min (exothermic reaction). It as cooled to room temperature, diluted with EtOAc (10 mL) and purified using flash column chromatography on silica gel (20-30% EtOAc in hexanes) to afford the title compound as a yellow oil (6.70 g, 94%). [M+H] calc'd for $C_{13}H_{15}N_3O_6$, 310; found, 310.

Compound 1B: (S)-methyl 6-oxo-5,6,6a,7,8,9-hexahydropyrido[3,2-e]pyrrolo[1,2-a]pyrazine-3-carboxylate (S)-Methyl 6-(2-(methoxycarbonyl)pyrrolidin-1-yl)-5-nitronicotinate (1.45 g, 46.9 mmol) and triphenyl phosphite (5.00 mg, 0.0161 mmol) were dissolved in dichloromethane (12 mL). Ammonium metavanadate (50 mg, 0.427 mmol) and Pt/C (5% wt., 200 mg) were added and the reaction mixture was stirred under hydrogen (80 psi) for 5 h. The reaction mixture was filtered through a small plug of celite and the precipitate was washed multiple times with hot dichloromethane until it was free from white precipitate. The filtrate was concentrated in vacuo and crystallized with ethyl ether (15 mL). The resulting solid was filtered off and dried in vacuum to afford the title compound as an off-white solid (0.930 g, 80%). [M+H] calc'd for $C_{12}H_{13}N_3O_3$, 248; found, 248.

Compound 1C: (S)-3-(hydroxymethyl)-6a,7,8,9-tetrahydropyrido[3,2-e]pyrrolo[1,2-a]pyrazin-6(5H)-one (S)-methyl 6-oxo-5,6,6a,7,8,9-hexahydropyrido[3,2-e]pyrrolo[1,2-a]pyrazine-3-carboxylate (3.00 g, 10.5 mmol) was suspended in THF and sodium hydride (60% suspension in mineral oil, 0.712 g, 17.8 mmol) was added under nitrogen atmosphere. The reaction mixture was stirred at room temperature for 1 h and cooled to −78° C. LiAlH₄ (2M in THF, 12.5 mL, 25 mmol) was added dropwise over 5 min and the reaction mixture was allowed to warm to −40° C. and kept at −40-(−20)° C. for 3 h. The reaction mixture was cooled to −60° C. and quenched with MeOH, water and TFA until a clear mixture resulted. This was purified using HPLC (1-30% acetonitrile in water, TFA buffered). The fractions containing product were concentrated in vacuo and crystallized with ethyl ether. The solid was filtered and dried in vacuum to afford the title compound as a grey solid (2.60 g, 74%, TFA salt). [M+H] calc'd for $C_{11}H_{13}N_3O_2$, 220; found, 220.

Compound 1: (S)-3-((4-(4-chlorophenyl)piperazin-1-yl)methyl)-6a,7,8,9-tetrahydropyrido[3,2-e]pyrrolo[1,2-a]pyrazin-6(5H)-one (S)-3-(hydroxymethyl)-6a,7,8,9-tetrahydropyrido[3,2-e]pyrrolo[1,2-a]pyrazin-6(5H)-one (200 mg, 0.912 mmol), 1-(4-chlorophenyl)piperazine hydrochloride (200 mg, 0.858 mmol), N,N-diisopropylethylamine (DIPEA; 0.50 mL), and (cyanomethyl)trimethylphosphonium iodide (220 mg, 1.08 mmol) were suspended in propionitrile (2 mL) and heated in a closed vial at 90° C. for 4 h. The reaction mixture was diluted with MeOH (2 mL) and purified using preparative scale HPLC (45-95% acetonitrile in water, buffered with $NH_4HCO_3$). The fractions containing product were concentrated in vacuo and diluted with water (5 mL). The resulting precipitate was filtered and dried in vacuum to afford the title compound as an off-white solid (135 mg, 40%). $^1$H NMR (DMSO-$d_6$) δ (ppm): 10.43 (s, 1H), 7.61 (d, J=1.8 Hz, 1H), 7.21 (d, J=8.8 Hz, 2H), 6.98 (d, J=1.8 Hz, 1H), 6.92 (d, J=9.1 Hz, 2H), 3.91-4.06 (m, 1H), 3.51-3.66 (m, 1H), 3.37-3.47 (m, 1H), 3.10 (br. s., 4H), 2.46 (d, J=4.3 Hz, 4H), 2.09-2.26 (m, 1H), 1.80-2.03 (m, 3H); [M+H] calc'd for $C_{21}H_{24}ClN_3O$, 398; found, 398; melting point 265-268° C.

Compound 2: (S)-3-((4-(4-chlorophenyl)-5,6-dihydropyridin-1(2H)-yl)methyl)-6a,7,8,9-tetrahydropyrido[3,2-e]pyrrolo[1,2-a]pyrazin-6(5H)-one Compound 2 was prepared using a procedure analogous to that described in connection with compound 1, except that 4-(4-chlorophenyl)-1,2,3,6-tetrahydropyridine hydrochloride was used instead of 1-(4-chlorophenyl)piperazine hydrochloride. $^1$H NMR (CHLOROFORM-d) δ (ppm): 7.77 (d, J=2.0 Hz, 1H), 7.52 (s, 1H), 7.29-7.33 (m, 2H), 7.26-7.29 (m, 2H), 7.01 (d, J=1.8 Hz, 1H), 6.01-6.08 (m, 1H), 4.07 (dd, J=9.2, 6.4 Hz, 1H), 3.72-3.83 (m, 1H), 3.57-3.66 (m, 1H), 3.44-3.55 (m, 2H), 3.15 (q, J=2.8 Hz, 2H), 2.65-2.76 (m, 2H), 2.47-2.57 (m, 2H), 2.34-2.46 (m, 1H), 1.94-2.26 (m, 3H): [M+H] calc'd for $C_{22}H_{23}ClN_3O$, 395; found, 395; melting point 234-235° C.

Compound 3: (S)-3-((4-(4-chlorophenyl)piperidin-1-yl)methyl)-6a,7,8,9-tetrahydropyrido[3,2-e]pyrrolo[1,2-a]pyrazin-6(5H)-one Compound 3 was prepared using a procedure analogous to that described in connection with compound 1, except that 4-(4-chlorophenyl)piperidine hydrochloride was used instead of 1-(4-chlorophenyl)piperazine hydrochloride. $^1$H NMR(CHLOROFORM-d) δ (ppm): 7.92 (br. s., 1H), 7.74 (d, J=1.5 Hz, 1H), 7.26 (d, J=8.3 Hz, 2H), 7.15 (d, J=8.3 Hz, 2H), 6.99 (d, J=1.5 Hz, 1H), 4.07 (dd, J=9.5, 6.4 Hz, 1H), 3.69-3.82 (m, 1H), 3.54-3.66 (m, 1H), 3.33-3.49 (m, 2H), 3.00 (d, J=11.4 Hz, 2H), 2.33-2.55 (m, 2H), 1.95-2.25 (m, 5H), 1.74-1.85 (m, 3H); [M+H] calc'd for $C_{22}H_{25}ClN_4O$, 397; found, 397.

Compound 4: (S)-4-(4-((6-oxo-5,6,6a,7,8,9-hexahydropyrido[3,2-e]pyrrolo[1,2-a]pyrazin-3-yl)methyl)piperazin-1-yl)benzonitrile Compound 4 was prepared using a procedure analogous to that described in connection with compound 1, except that 4-(piperazin-1-yl)benzonitrile was used instead of 1-(4-chlorophenyl)piperazine hydrochloride. $^1$H NMR (DMSO-$d_6$) δ (ppm): 10.44 (s, 1H), 7.59 (dd, J=16.9, 5.3 Hz, 3H), 6.99 (dd, J=9.3, 5.3 Hz, 3H), 3.91-4.07 (m, 1H), 3.51-3.65 (m, 1H), 3.31-3.46 (m, 7H), 2.37-2.47 (m, 4H), 2.10-2.25 (m, 1H), 1.82-2.01 (m, 3H); [M+H] calc'd for $C_{22}H_{24}N_6O$, 389; found, 389; melting point 252° C.

Compound 5: (S)-6-(4-(((6-oxo-5,6,6a,7,8,9-hexahydropyrido[3,2-e]pyrrolo[1,2-a]pyrazin-3-yl)methyl)piperazin-1-yl)nicotinonitrile

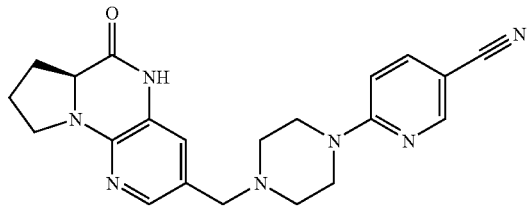

Compound 5 was prepared using a procedure analogous to that described in connection with compound 1, except that 6-(piperazin-1-yl)nicotinonitrile was used instead of 1-(4-chlorophenyl)piperazine hydrochloride. $^1$H NMR (DMSO-$d_6$) δ (ppm): 10.44 (s, 1H), 8.47 (d, J=2.3 Hz, 1H), 7.84 (dd, J=9.1, 2.3 Hz, 1H), 7.60 (d, J=1.5 Hz, 1H), 6.98 (d, J=1.8 Hz, 1H), 6.91 (d, J=9.1 Hz, 1H), 3.92-4.06 (m, 1H), 3.57-3.71 (m, 5H), 3.27-3.48 (m, 3H), 2.40 (t, J=4.5 Hz, 4H), 2.10-2.24 (m, 1H), 1.81-2.01 (m, 3H); [M+H] calc'd for $C_{21}H_{23}N_7O$, 390; found, 390; melting point 252-256° C.

Compound 6: (S)—N-methyl-6-(4-((6-oxo-5,6,6a,7,8,9-hexahydropyrido[3,2-e]pyrrolo[1,2-a]pyrazin-3-yl)methyl)piperazin-1-yl)nicotinamide

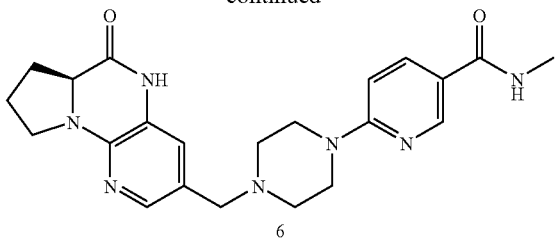

Compound 6A: (S)-ethyl 6-(4-(((6-oxo-5,6,6a,7,8,9-hexahydropyrido[3,2-e]pyrrolo[1,2-a]pyrazin-3-yl)methyl)piperazin-1-yl)nicotinate (S)-3-(hydroxymethyl)-6a,7,8,9-tetrahydropyrido[3,2-e]pyrrolo[1,2-a]pyrazin-6(5H)-one (233 mg, 1.06 mmol), ethyl 6-(piperazin-1-yl)nicotinate (270 mg, 0.1.15 mmol), DIPEA (0.80 mL), and (cyanomethyl)trimethylphosphonium iodide (369 mg, 01.82 mmol) were suspended in propionitrile (3 mL) and heated in a closed vial at 90° C. for 5 h. The mixture was cooled, diluted with a solution of $K_2CO_3$ (2.50 g) in water (15 mL) and extracted with dichloromethane (2×10 mL). The combined organic extracts were dried (MgSO$_4$) and concentrated in vacuo. The resulting oil was crystallized with ethyl ether-ethanol (10:1, 22 mL) to afford the title compounds as a tan solid (0.355 mg, 77%). [M+H] calc'd for $C_{23}H_{28}N_6O_3$, 437; found, 437.

Compound 6B: (S)-6-(4-(((6-oxo-5,6,6a,7,8,9-hexahydropyrido[3,2-e]pyrrolo[1,2-a]pyrazin-3-yl)methyl)piperazin-1-yl)nicotinic acid (S)-ethyl 6-(4-(((6-oxo-5,6,6a,7,8,9-hexahydropyrido[3,2-e]pyrrolo[1,2-a]pyrazin-3-yl)methyl)piperazin-1-yl)nicotinate (0.355 mg, 0.813 mmol) was suspended in dioxane (4 mL) and treated with LiOH (1N, 4.00 mL, 4.00 mmol). The resulting solution was stirred at room temperature for 3 h and concentrated in vacuo until most of the organic solvent was removed. The solution was acidified with HCl (4.5N) to pH=3 and the resulting precipitate was filtered off, washed with ethyl ether (5 mL) and dried in vacuum to afford the title compound as a brown solid (0.260 g, 78%). [M+H] calc'd for $C_{21}H_{24}N_6O_3$, 409; found, 409.

Compound 6: (S)—N-methyl-6-(4-(((6-oxo-5,6,6a,7,8,9-hexahydropyrido[3,2-e]pyrrolo[1,2-a]pyrazin-3-yl)methyl)piperazin-1-yl)nicotinamide (S)-6-(4-(((6-oxo-5,6,6a,7,8,9-hexahydropyrido[3,2-e]pyrrolo[1,2-a]pyrazin-3-yl)methyl)piperazin-1-yl)nicotinic acid (100 mg, 0.245 mmol) was suspended in DMF (1.5 mL) and DIPEA (0.3 mL) was added followed by methylamine hydrochloride (27 mg, 0.400 mmol) and HATU (200 mg, 0.526 mmol). The reaction mixture was stirred at ambient temperature for 4 h and diluted with MeOH (2 mL). The solution was purified using HPCL (25-95% acetonitrile in water, NH$_4$HCO$_3$ buffered). The fractions were concentrated in vacuo and the resulting residue was crystallized with MeOH-water (1:5, 15 mL) to afford the title compound as an off-white solid (52.3 mg, 51%). $^1$H NMR (400 MHz, DMSO-$d_6$) δ (ppm): 1.80-2.03 (m, 3H) 2.09-2.25 (m, 1H) 2.41 (br. s., 4H) 2.74 (d, J=4.29 Hz, 3H) 3.34-3.44 (m, 3H) 3.46-3.64 (m, 5H) 3.92-4.05 (m, 1H) 6.82 (d, J=9.09 Hz, 1H) 6.99 (d, 1H) 6.93-7.04 (m, 1H) 7.61 (s, 1H) 7.91 (dd, J=8.97, 2.15 Hz, 1H)

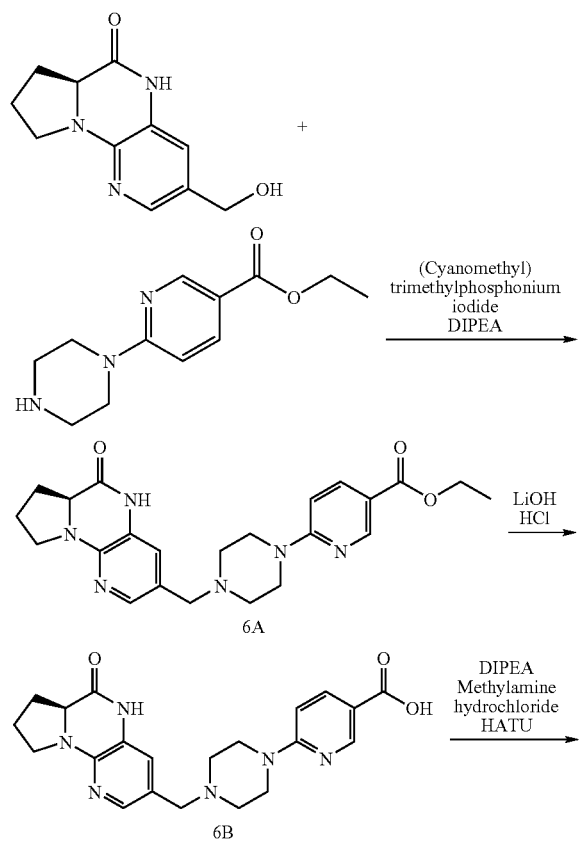

8.17-8.23 (m, 1H) 8.56 (d, J=1.77 Hz, 1H) 10.44 (s, 1H); [M+H] calc'd for $C_{22}H_{27}N_7O_2$, 422; found, 422.

Compound 7: (S)—N-ethyl-6-(4-((6-oxo-5,6,6a,7,8,9-hexahydropyrido[3,2-e]pyrrolo[1,2-a]pyrazin-3-yl)methyl)piperazin-1-yl)nicotinamide

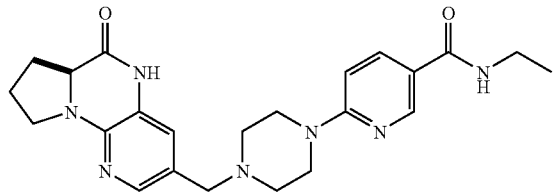

(S)-6-(4-((6-oxo-5,6,6a,7,8,9-hexahydropyrido[3,2-e]pyrrolo[1,2-a]pyrazin-3-yl)methyl)piperazin-1-yl)nicotinic acid (87 mg, 0.213 mmol) and ethanamine hydrochloride (17.4 mg, 0.213 mmol) were suspended in DMF (1.065 mL) and treated with DIPEA (0.186 mL, 1.065 mmol) and 2-(3H-[1,2,3]triazolo[4,5-b]pyridin-3-yl)-1,1,3,3-tetramethylisouronium hexafluorophosphate(V) (162 mg, 0.426 mmol). The reaction mixture was stirred at room temperature for 3 h and purified using HPLC (10-95% acetonitrile in water, $NH_4HCO_3$ buffered) to afford (S)—N-ethyl-6-(4-((6-oxo-5,6,6a,7,8,9-hexahydropyrido[3,2-e]pyrrolo[1,2-a]pyrazin-3-yl)methyl)piperazin-1-yl)nicotinamide (26.4 mg, 0.061 mmol, 28.5% yield) as an off-white solid. $^1H$ NMR (400 MHz, DMSO-$d_6$) δ (ppm): 1.09 (t, J=7.20 Hz, 3H) 1.82-2.02 (m, 3H) 2.18 (d, J=2.27 Hz, 1H) 2.41 (t, J=4.80 Hz, 5H) 3.20-3.29 (m, 2H) 3.34-3.44 (m, 3H) 3.51-3.63 (m, 5H) 3.95-4.03 (m, 1H) 6.82 (d, J=9.09 Hz, 1H) 6.99 (d, J=1.77 Hz, 1H) 7.61 (d, J=1.77 Hz, 1H) 7.93 (dd, J=9.09, 2.53 Hz, 1H) 8.23 (t, J=5.31 Hz, 1H) 8.57 (d, J=2.27 Hz, 1H) 10.44 (s, 1H); [M+H] calc'd for $C_{23}H_{29}N_7O_2$, 422; found, 422.

Compound 8: (S)—N-cyclopropyl-6-(4-((6-oxo-5,6,6a,7,8,9-hexahydropyrido[3,2-e]pyrrolo[1,2-a]pyrazin-3-yl)methyl)piperazin-1-yl)nicotinamide

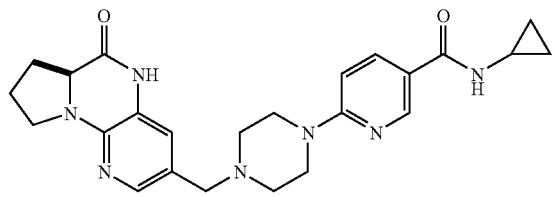

(S)-6-(4-((6-oxo-5,6,6a,7,8,9-hexahydropyrido[3,2-e]pyrrolo[1,2-a]pyrazin-3-yl)methyl)piperazin-1-yl)nicotinic acid (87 mg, 0.213 mmol) and cyclopropanamine (18.24 mg, 0.319 mmol) were suspended in DMF (1 ml) and treated with DIPEA (0.186 ml, 1.065 mmol) and 2-(3H-[1,2,3]triazolo[4,5-b]pyridin-3-yl)-1,1,3,3-tetramethylisouronium hexafluorophosphate(V) (162 mg, 0.426 mmol). The reaction mixture was stirred at room temperature for 3 h and purified using HPLC (10-95% acetonitrile in water, $NH_4HCO_3$ buffered) to afford (S)—N-cyclopropyl-6-(4-((6-oxo-5,6,6a,7,8,9-hexahydropyrido[3,2-e]pyrrolo[1,2-a]pyrazin-3-yl)methyl)piperazin-1-yl)nicotinamide (70.3 mg, 0.157 mmol, 73.7% yield) as an off-white solid. $^1H$ NMR (400 MHz, DMSO-d6) δ (ppm): 0.49-0.56 (m, 2H) 0.62-0.70 (m, 2H) 1.82-2.02 (m, 3H) 2.11-2.22 (m, 1H) 2.40 (t, J=4.93 Hz, 4H) 2.78 (tq, J=7.34, 3.86 Hz, 1H) 3.34 (br. s., 2H) 3.36-3.44 (m, 1H) 3.49-3.64 (m, 5H) 3.94-4.03 (m, 1H) 6.81 (d, J=8.59 Hz, 1H) 6.98 (d, J=1.77 Hz, 1H) 7.61 (d, J=1.77 Hz, 1H) 7.90 (dd, J=9.09, 2.53 Hz, 1H) 8.20 (d, J=4.04 Hz, 1H) 8.54 (d, J=1.77 Hz, 1H) 10.44 (s, 1H); [M+H] calc'd for $C_{24}H_{29}N_7O_2$, 448; found, 448.

Compound 9: (S)—N-isopropyl-6-(4-((6-oxo-5,6,6a,7,8,9-hexahydropyrido[3,2-e]pyrrolo[1,2-a]pyrazin-3-yl)methyl)piperazin-1-yl)nicotinamide

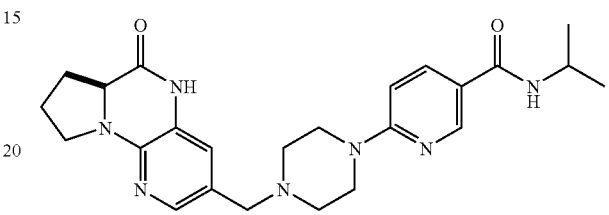

(S)-6-(4-((6-oxo-5,6,6a,7,8,9-hexahydropyrido[3,2-e]pyrrolo[1,2-a]pyrazin-3-yl)methyl)piperazin-1-yl)nicotinic acid (87.0 mg, 0.213 mmol) and propan-2-amine (18.89 mg, 0.319 mmol) were suspended in DMF (1 ml) and treated with DIPEA (0.186 ml, 1.065 mmol) and 2-(3H-[1,2,3]triazolo[4,5-b]pyridin-3-yl)-1,1,3,3-tetramethylisouronium hexafluorophosphate(V) (162 mg, 0.426 mmol). The reaction mixture was stirred at room temperature for 3 h and purified using HPLC (10-95% acetonitrile in water, $NH_4HCO_3$ buffered) to afford (S)—N-isopropyl-6-(4-((6-oxo-5,6,6a,7,8,9-hexahydropyrido[3,2-e]pyrrolo[1,2-a]pyrazin-3-yl)methyl)piperazin-1-yl)nicotinamide (62.1 mg, 0.138 mmol, 64.9% yield) as an off-white solid. $^1H$ NMR (400 MHz, DMSO-d6) δ (ppm): 1.13 (d, J=6.57 Hz, 6H) 1.84-2.01 (m, 3H) 2.12-2.22 (m, 1H) 2.41 (d, J=4.29 Hz, 4H) 3.36-3.47 (m, 1H) 3.49-3.64 (m, 5H) 3.95-4.10 (m, 2H) 6.81 (d, J=8.84 Hz, 1H) 6.99 (d, J=2.02 Hz, 1H) 7.61 (d, J=1.77 Hz, 1H) 7.94 (dd, J=9.09, 2.53 Hz, 1H) 7.97 (d, J=7.83 Hz, 1H) 8.57 (d, J=2.53 Hz, 1H) 10.44 (s, 1H); [M+H] calc'd for $C_{24}H_{31}N_7O_2$, 450; found, 450.

Compound 10: (S)—N-ethyl-4-(4-((6-oxo-5,6,6a,7,8,9-hexahydropyrido[3,2-e]pyrrolo[1,2-a]pyrazin-3-yl)methyl)piperazin-1-yl)benzamide Method A

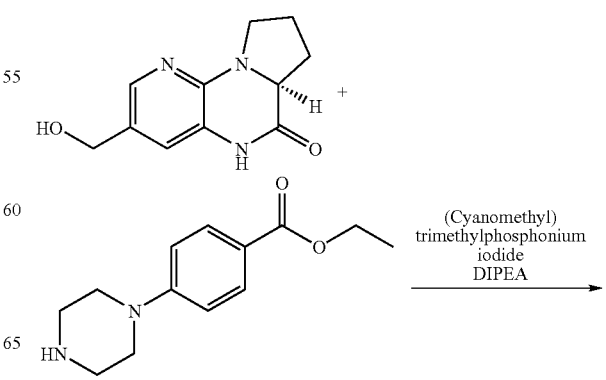

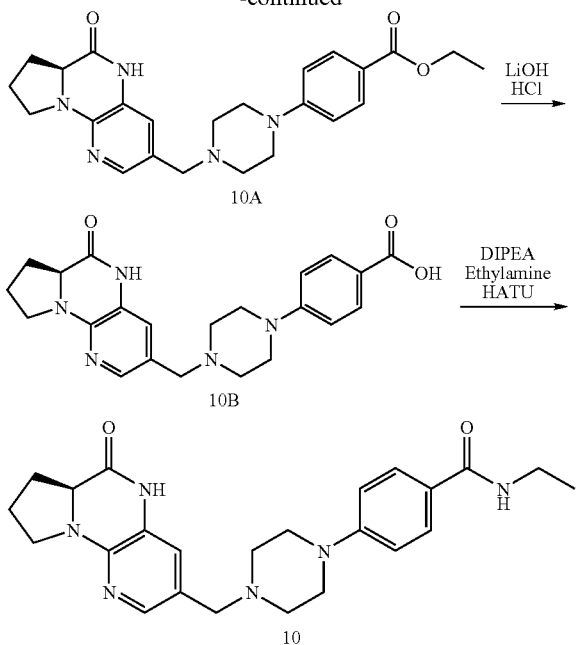

Compound 10A: (S)-ethyl 4-(4-((6-oxo-5,6,6a,7,8,9-hexahydropyrido[3,2-e]pyrrolo[1,2-a]pyrazin-3-yl)methyl)piperazin-1-yl)benzoate (S)-3-(hydroxymethyl)-6a,7,8,9-tetrahydropyrido[3,2-e]pyrrolo[1,2-a]pyrazin-6(5H)-one (187 mg, 0.854 mmol), ethyl 4-(piperazin-1-yl)benzoate (200 mg, 0.854 mmol), (cyanomethyl)trimethylphosphonium iodide (311 mg, 1.280 mmol) and N,N-diisopropylethylamine (0.745 ml, 4.27 mmol) were suspended in propionitrile (2 ml) and heated in a closed vial at 90° C. for 2 h. The reaction mixture became a clear dark brown solution. The mixture was cooled to room temperature, diluted with MeOH (2 mL), filtered, the solids retained, and purified using preparative HPLC. The fractions containing product were concentrated in vacuo and crystallized from water (3 mL). The precipitate was filtered and dried in vacuum to afford the product as a light brown solid (18.3 mg). The solid from the earlier filtration was recrystallized from ether-MeOH (10 mL, 5:1). The combined products were dried in vacuum to afford (S)-ethyl 4-(4-((6-oxo-5,6,6a,7,8,9-hexahydropyrido[3,2-e]pyrrolo[1,2-a]pyrazin-3-yl)methyl)piperazin-1-yl)benzoate (283 mg, 0.650 mmol, 76% yield) as a brownish solid. [M+H] calc'd for $C_{24}H_{29}N_5O_3$, 436; found, 436; melting point 242° C.

Compound 10B: (S)-4-(4-((6-oxo-5,6,6a,7,8,9-hexahydropyrido[3,2-e]pyrrolo[1,2-a]pyrazin-3-yl)methyl)piperazin-1-yl)benzoic acid (S)-ethyl 4-(4-((6-oxo-5,6,6a,7,8,9-hexahydropyrido[3,2-e]pyrrolo[1,2-a]pyrazin-3-yl)methyl)piperazin-1-yl)benzoate (280 mg, 0.643 mmol) was suspended in 1,4-Dioxane (3.22 mL) and treated with 1N LiOH (3.215 mL, 3.22 mmol). The reaction mixture was stirred at room temperature for 23 h. The reaction mixture was concentrated in vacuo until most of the dioxane was gone and acidified with HCl (4.5 N) until a thick precipitate resulted. It was filtered off, washed with water and dried in vacuum to afford (S)-4-(4-((6-oxo-5,6,6a,7,8,9-hexahydropyrido[3,2-e]pyrrolo[1,2-a]pyrazin-3-yl)methyl)piperazin-1-yl)benzoic acid (225 mg, 0.552 mmol, 86% yield) as a brown solid. [M+H] calc'd for $C_{22}H_{25}N_5O_3$, 408; found, 408.

Compound 10: (S)—N-ethyl-4-(4-((6-oxo-5,6,6a,7,8,9-hexahydropyrido[3,2-e]pyrrolo[1,2-a]pyrazin-3-yl)methyl)piperazin-1-yl)benzamide (S)-4-(4-((6-oxo-5,6,6a,7,8,9-hexahydropyrido[3,2-e]pyrrolo[1,2-a]pyrazin-3-yl)methyl)piperazin-1-yl)benzoic acid (75.0 mg, 0.184 mmol) was suspended in DMF (1.0 mL) and DIPEA (0.15 mL) was added followed by ethylamine (30 mg, 0.665 mmol) and HATU (85.0 mg, 0.224 mmol). The reaction mixture was stirred at ambient temperature for 2 h and another portion of HATU (60.0 mg, 0.158 mmol) was added. The reaction mixture was stirred overnight and purified using HPCL (10-75% acetonitrile in water, $NH_4HCO_3$ buffered). The fractions were concentrated in vacuo and the resulting residue was crystallized with MeOH-water (1:10, 5 mL) to afford the title compound as a light green solid (24.0 mg, 30%). $^1$H NMR (400 MHz, DMSO-$d_6$) δ (ppm): 1.09 (t, J=7.20 Hz, 3H) 1.85-2.01 (m, 3H) 2.18 (dt, J=5.37, 2.75 Hz, 1H) 2.43-2.48 (m, 4H) 3.18-3.28 (m, 6H) 3.35 (s, 2H) 3.37-3.45 (m, 1H) 3.54-3.67 (m, 1H) 3.94-4.05 (m, 1H) 6.92 (d, J=9.09 Hz, 2H) 6.99 (d, J=2.02 Hz, 1H) 7.62 (d, J=2.02 Hz, 1H) 7.71 (d, J=9.09 Hz, 2H) 8.17 (t, J=5.56 Hz, 1H) 10.44 (s, 1H); [M+H] calc'd for $C_{24}H_{30}N_6O_2$, 435; found, 435.

Method B

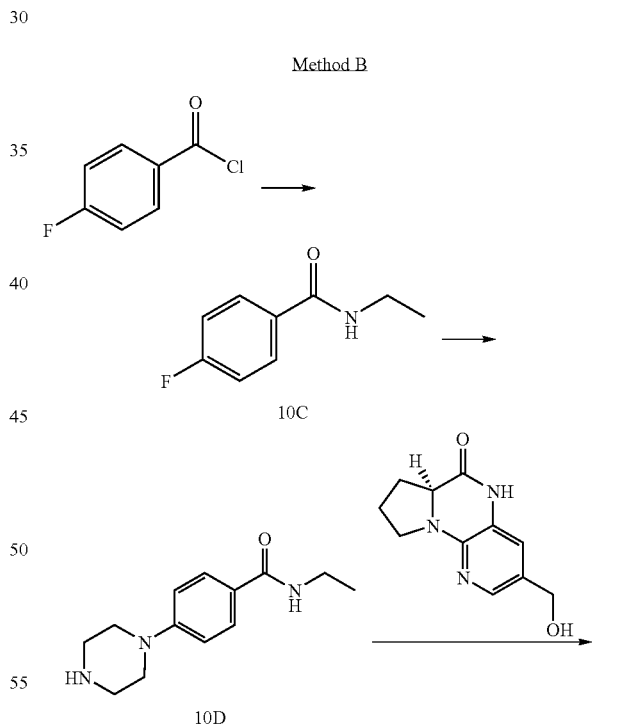

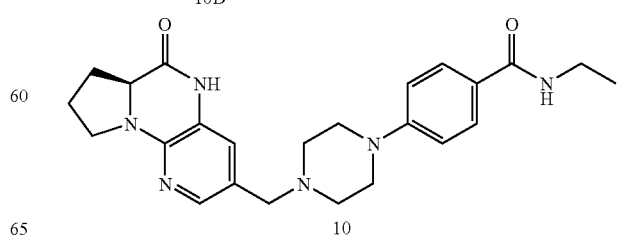

Compound 10C: N-ethyl-4-fluorobenzamide

To a solution of ethylamine (69.4 mL, 139 mmol) and triethylamine (21.10 mL, 151 mmol) in DCM (Volume: 150 mL) was added p-Fluorobenzoyl chloride (15.13 mL, 126 mmol) at 0° C. The reaction was stirred at 0° C. for 1 hr and then warmed slowly to room temperature. The reaction mixture was diluted with water. The layers were separated and the organic layer was washed with brine, dried over MgSO4, filtered, and the organic phase stripped to dryness via rotary evaporation. The organic extract was dried in vacuo to provide N-ethyl-4-fluorobenzamide (21 g, 100% yield) as a tan solid.

Compound 10D: N-ethyl-4-(piperazin-1-yl)benzamide

Using N-ethyl-4-fluorobenzamide in the general procedure for nucleophilic aromatic substitution reactions with piperazine, the title compound was obtained (77% yield) as a white solid. $^1$H NMR (400 MHz, DMSO-$d_6$) δ ppm 1.10 (t, J=7.07 Hz, 3H) 2.25 (br. s., 1H) 2.76-2.86 (m, 4H) 3.09-3.18 (m, 4H) 3.21-3.28 (m, 2H) 6.90 (m, J=8.84 Hz, 2H) 7.67-7.75 (m, 2H) 8.11 (t, J=5.31 Hz, 1H). ESI-MS: m/z 234.2 (M+H)$^+$. mp=131.3-134.4° C.

Compound 10: (S)—N-ethyl-4-(4-((6-oxo-5,6,6a,7,8,9-hexahydropyrido[3,2-e]pyrrolo[1,2-a]pyrazin-3-yl)methyl)piperazin-1-yl)benzamide To a suspension of (S)-3-(hydroxymethyl)-6a,7,8,9-tetrahydropyrido[3,2-e]pyrrolo[1,2-a]pyrazin-6(5H)-one (0.8 g, 3.65 mmol)) in propiononitrile (Volume: 27.4 ml) was added (cyanomethyl)trimethylphosphonium iodide (1.064 g, 4.38 mmol), N-ethyl-4-(piperazin-1-yl)benzamide (0.851 g, 3.65 mmol) and DIEA (1.912 ml, 10.95 mmol). The vial was heated to 90° C. for 16 hours. The crude reaction was cooled to RT, DMSO (1 ml) was added, and the mixture was purified via HPLC (55-90, basic) to give the product as a white solid.

Compound 11: (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzamide

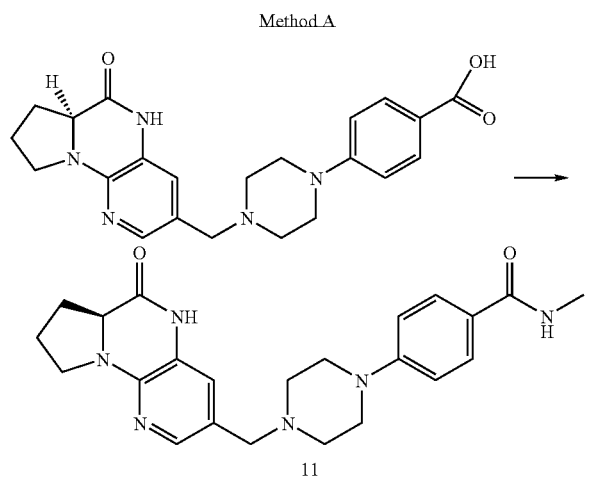

(S)-4-(4-((6-oxo-5,6,6a,7,8,9-hexahydropyrido[3,2-e]pyrrolo[1,2-a]pyrazin-3-yl)methyl)piperazin-1-yl)benzoic acid (87 mg, 0.214 mmol) and methanamine hydrochloride (21.62 mg, 0.320 mmol) were suspended in DMF (1 ml) and treated with DIPEA (0.186 ml, 1.068 mmol) and 2-(3H-[1,2,3]triazolo[4,5-b]pyridin-3-yl)-1,1,3,3-tetramethylisouronium hexafluorophosphate(V) (162 mg, 0.427 mmol). The reaction mixture was stirred at room temperature for 23 h and purified using HPLC (25-95% acetonitrile in water, NH$_4$HCO$_3$ buffered) to afford (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzamide (42.4 mg, 0.101 mmol, 47.2% yield) as a light yellow solid. $^1$H NMR (400 MHz, DMSO-d6) δ (ppm): 1.83-2.01 (m, 3H) 2.11-2.25 (m, 1H) 2.39-2.48 (m, 4H) 2.73 (d, J=4.55 Hz, 3H) 3.13-3.27 (m, 4H) 3.34-3.44 (m, 3H) 3.52-3.64 (m, 1H) 3.96-4.02 (m, 1H) 6.92 (d, J=9.09 Hz, 2H) 6.98 (d, J=2.02 Hz, 1H) 7.62 (d, J=1.77 Hz, 1H) 7.69 (d, J=9.09 Hz, 2H) 8.13 (q, J=4.29 Hz, 1H) 10.44 (s, 1H); [M+H] calc'd for $C_{23}H_{28}N_6O_2$, 421; found, 421.

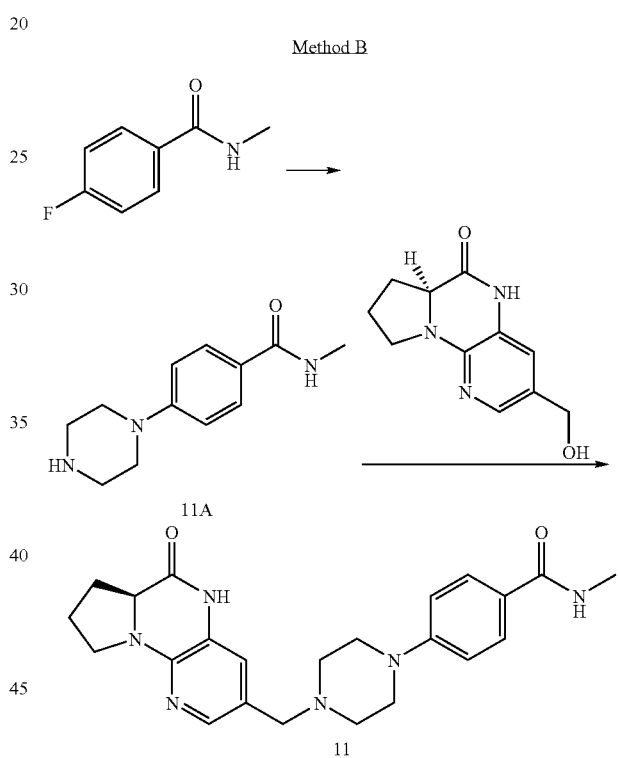

Compound 11A: N-methyl-4-(piperazin-1-yl)benzamide

To a solution of 4-fluoro-N-methylbenzamide (6 g, 39.2 mmol) in DMSO (Volume: 24.0 mL) was added piperazine (16.87 g, 196 mmol) at 23° C. The reaction was stirred at 120° C. for 68 hr. The reaction mixture was poured into ice (261 g) and the reaction vessel was rinsed with H2O (~50 mL). Next, celite (30 g) was added to aid the filtration. The resulting suspension was warmed to 100° C., cooled to ~40° C., filtered, and rinsed with warm H20 (4×50 mL). The resulting solid was dried in vacuo. The filtrate was stirred at room temperature overnight affording a suspension. The suspension was filtered, rinsed with H$_2$O (3×25 mL), and the resulting solid was dried in vacuo. The cloudy filtrate was filtered once again through a medium fitted funnel and rinsed with H2O (3×10 mL). Added NaCl (200.1 g) to the filtrate, cooled on ice, filtered, rinsed with cold H2O (3×25 mL), and dried the resulting solid in vacuo. Re-suspended the purified product in H2O (30 mL), stirred for 30 min at 23° C., filtered, rinsed with H2O (3×5 mL), and dried the resulting solid in vacuo. The purified product was re-suspended in ACN (25 mL), agitated for 10 min, and dried in vacuo. This procedure was repeated three times to provide N-methyl-4-(piperazin-1-yl)benzamide (5.64 g, 25.7 mmol, 65.7% yield) as a white solid. $^1$H NMR (400 MHz, DMSO-$d_6$) δ ppm 2.29 (br. s., 1H) 2.74 (d, J=4.55 Hz, 3H) 2.77-2.86 (m, 4H) 3.08-3.18 (m, 4H) 6.91 (m, 2H) 7.69 (m, 2H) 8.13 (q, J=4.04 Hz, 1H). ESI-MS: m/z 220.2 (M+H)$^+$. mp=153.9-156.5° C.

Compound 11: (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzamide (S)-3-(hydroxymethyl)-6a,7,8,9-tetrahydropyrido[3,2-e]pyrrolo[1,2-a]pyrazin-6(5H)-one (1.500 g, 6.84 mmol), N-methyl-4-(piperazin-1-yl)benzamide (1.500 g, 6.84 mmol), (cyanomethyl)trimethylphosphonium iodide (2.494 g, 10.26 mmol) and N,N-diisopropylethylamine (5.97 ml, 34.2 mmol) were suspended in propiononitrile (Volume: 27.4 ml) and heated in a closed vial at 90° C. The crude reaction was cooled to RT, DMSO (1 ml) was added, and the mixture was purified via HPLC (55-90, basic) to give the product as a white solid.

Compound 12: (S)—N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide

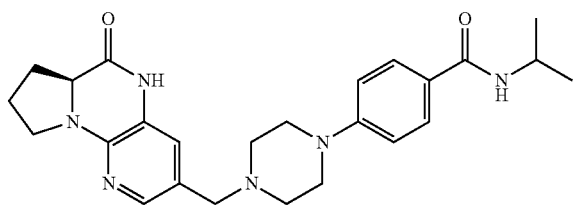

(S)-4-(4-((6-oxo-5,6,6a,7,8,9-hexahydropyrido[3,2-e]pyrrolo[1,2-a]pyrazin-3-yl)methyl)piperazin-1-yl)benzoic acid (87.0 mg, 0.214 mmol) and propan-2-amine (18.93 mg, 0.320 mmol) were suspended in DMF (1 ml) and treated with DIPEA (0.186 ml, 1.068 mmol) and 2-(3H-[1,2,3]triazolo[4,5-b]pyridin-3-yl)-1,1,3,3-tetramethylisouronium hexafluorophosphate(V) (162 mg, 0.427 mmol). The reaction mixture was stirred at room temperature for 3 h and purified using HPLC (25-95% acetonitrile in water, NH$_4$HCO$_3$ buffered) to afford (S)—N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide (39.6 mg, 0.088 mmol, 41.3% yield) as an off-white solid. $^1$H NMR (400 MHz, DMSO-d6) δ (ppm): 1.13 (d, J=6.57 Hz, 6H) 1.85-2.00 (m, 3H) 2.11-2.24 (m, 1H) 2.41-2.48 (m, 4H) 3.17-3.27 (m, 4H) 3.34-3.44 (m, 3H) 3.53-3.65 (m, 1H) 3.93-4.13 (m, 2H) 6.91 (d, J=9.09 Hz, 2H) 6.99 (d, J=2.02 Hz, 1H) 7.62 (d, J=2.02 Hz, 1H) 7.72 (d, J=9.09 Hz, 2H) 7.89 (d, J=7.83 Hz, 1H) 10.44 (s, 1H); [M+H] calc'd for $C_{25}H_{32}N_6O_2$, 449; found, 449.

Compound 13: (S)—N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide Method A

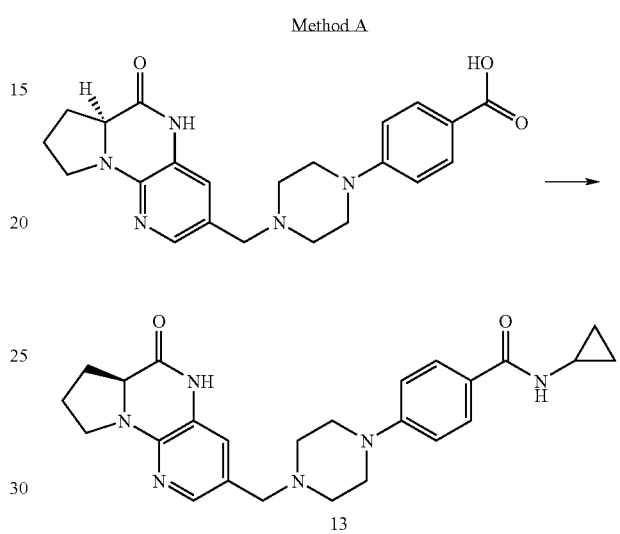

(S)-4-(4-((6-oxo-5,6,6a,7,8,9-hexahydropyrido[3,2-e]pyrrolo[1,2-a]pyrazin-3-yl)methyl)piperazin-1-yl)benzoic acid (87 mg, 0.214 mmol) and cyclopropanamine (18.29 mg, 0.320 mmol) were suspended in DMF (1 ml) and treated with DIPEA (0.186 ml, 1.068 mmol) and 2-(3H-[1,2,3]triazolo[4,5-b]pyridin-3-yl)-1,1,3,3-tetramethylisouronium hexafluorophosphate(V) (162 mg, 0.427 mmol). The reaction mixture was stirred at room temperature for 3 h and purified using HPLC (25-95% acetonitrile in water, NH$_4$HCO$_3$ buffered) to afford (S)—N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide (43.0 mg, 0.096 mmol, 45.1% yield) as an off-white solid. $^1$H NMR (400 MHz, DMSO-d6) δ (ppm): 0.46-0.59 (m, 2H) 0.59-0.71 (m, 2H) 1.82-2.02 (m, 3H) 2.10-2.25 (m, 1H) 2.46 (br. s., 4H) 2.74-2.83 (m, 1H) 3.21 (br. s., 4H) 3.34-3.46 (m, 3H) 3.53-3.64 (m, 1H) 3.94-4.02 (m, 1H) 6.91 (d, J=8.84 Hz, 2H) 6.98 (d, J=1.77 Hz, 1H) 7.61 (d, J=1.26 Hz, 1H) 7.68 (d, J=8.84 Hz, 2H) 8.13 (d, J=4.04 Hz, 1H) 10.44 (s, 1H); [M+H] calc'd for $C_{25}H_{30}N_6O_2$, 447; found, 447; melting point 265-268° C.

Method B

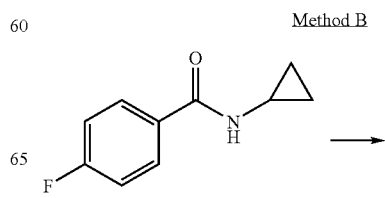

Compound 14: (S)-3-fluoro-4-(4-((6-oxo-5,6,6a,7,8,9-hexahydropyrido[3,2-e]pyrrolo[1,2-a]pyrazin-3-yl)methyl)piperazin-1-yl)benzonitrile

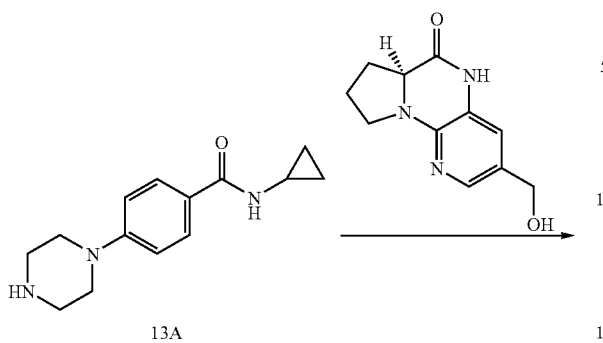

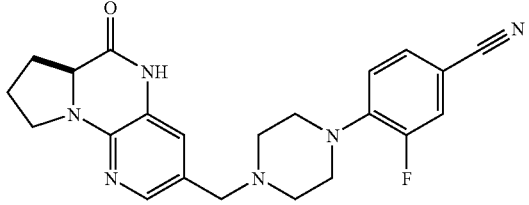

Compound 13A:
N-cyclopropyl-4-(piperazin-1-yl)benzamide

Using N-cyclopropyl-4-fluorobenzamide in the general procedure for nucleophilic aromatic substitution reactions, the title compound was obtained (15% yield) as an off-white solid. $^1$H NMR (400 MHz, DMSO-d$_6$) δ ppm 0.47-0.58 (m, 2H) 0.58-0.73 (m, 2H) 2.28 (br. s., 1H) 2.70-2.88 (m, 5H) 3.04-3.21 (m, 4H) 6.90 (m, J=9.09 Hz, 2H) 7.69 (m, J=8.84 Hz, 2H) 8.12 (d, J=3.79 Hz, 1H). ESI-MS: m/z 246.2 (M+H)$^+$. mp=175.1-177.2° C.

Compound 13: (S)—N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide (S)-3-(hydroxymethyl)-6a,7,8,9-tetrahydropyrido[3,2-e]pyrrolo[1,2-a]pyrazin-6(5H)-one (300 mg, 1.368 mmol), N-cyclopropyl-4-(piperazin-1-yl)benzamide (336 mg, 1.368 mmol), (cyanomethyl)trimethylphosphonium iodide (499 mg, 2.053 mmol) and N,N-diisopropylethylamine (1195 μl, 6.84 mmol) were suspended in propionitrile (Volume: 4109 μl) and heated in a closed vial at 120° C. for 2 h. The reaction mixture became a dark brown solution. It was cooled to room temperature, concentrated in vacuo, dissolved in DMSO (2 mL) and purified using HPLC(NH$_4$HCO$_3$ buffered, 20-70% ACN in water). The fractions were concentrated in vacuo and the resulting solid was recrystallized from water-MeOH (1:1, 15 mL), and then from MeOH:EtOH:water (1:1:1, 10 mL), washed with water (3 mL) and dried in vacuum to give a light green solid.

(S)-3-(hydroxymethyl)-6a,7,8,9-tetrahydropyrido[3,2-e]pyrrolo[1,2-a]pyrazin-6(5H)-one (150 mg, 0.684 mmol), 3-fluoro-4-(piperazin-1-yl)benzonitrile (140 mg, 0.684 mmol), (cyanomethyl)trimethylphosphonium iodide (249 mg, 1.026 mmol) and N,N-diisopropylethylamine (0.597 ml, 3.42 mmol) were suspended in propionitrile (2 ml) and heated in a closed vial at 90° C. for 2 h. The reaction mixture became a clear dark brown solution. It was cooled to room temperature, diluted with DMSO (2 mL) and purified using preparative HPLC (25-95% acetonitrile in water, NH$_4$HCO$_3$ buffered). The fractions containing product were concentrated in vacuo and crystallized with water (3 mL). The precipitate was filtered and dried in vacuum to afford (S)-3-fluoro-4-(4-((6-oxo-5,6,6a,7,8,9-hexahydropyrido[3,2-e]pyrrolo[1,2-a]pyrazin-3-yl)methyl)piperazin-1-yl)benzonitrile (60.2 mg, 0.148 mmol, 21.65% yield) as a light brown solid. $^1$H NMR (400 MHz, DMSO-d6) δ (ppm): 1.83-2.03 (m, 3H) 2.11-2.24 (m, 1H) 2.44-2.49 (m, 4H) 3.07-3.22 (m, 4H) 3.34-3.42 (m, 3H) 3.53-3.65 (m, 1H) 3.93-4.03 (m, 1H) 6.97 (d, J=2.02 Hz, 1H) 7.11 (t, J=8.72 Hz, 1H) 7.56 (dd, J=8.46, 1.64 Hz, 1H) 7.61 (d, J=2.02 Hz, 1H) 7.69 (dd, J=13.39, 2.02 Hz, 1H) 10.44 (s, 1H); [M+H] calc'd for C$_{22}$H$_{23}$FN$_6$O, 407; found, 407; melting point 226° C.

Compound 15: (S)-3-((4-(2,4-difluorophenyl)piperazin-1-yl)methyl)-6a,7,8,9-tetrahydropyrido[3,2-e]pyrrolo[1,2-a]pyrazin-6(5H)-one

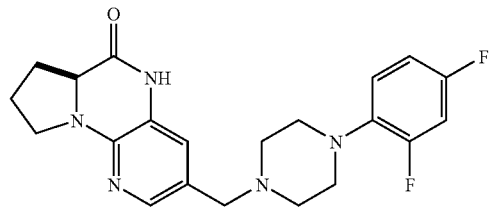

(S)-3-(hydroxymethyl)-6a,7,8,9-tetrahydropyrido[3,2-e]pyrrolo[1,2-a]pyrazin-6(5H)-one (150 mg, 0.684 mmol), 1-(2,4-difluorophenyl)piperazine (136 mg, 0.684 mmol), (cyanomethyl)trimethylphosphonium iodide (249 mg, 1.026 mmol) and N,N-diisopropylethylamine (0.597 ml, 3.42 mmol) were suspended in propionitrile (2 ml) and heated in a closed vial at 90° C. for 2 h. The reaction mixture became a clear dark brown solution. It was cooled to room temperature, diluted with DMSO (2 mL) and purified using preparative HPLC (25-95% acetonitrile in water, NH$_4$HCO$_3$ buffered). The fractions containing product were concentrated in vacuo and crystallized from water (3 mL). The precipitate was filtered and dried in vacuum to afford (S)-3-((4-(2,4-difluorophenyl)piperazin-1-yl)methyl)-6a,7,8,9-tetrahydropyrido [3,2-e]pyrrolo[1,2-a]pyrazin-6(5H)-one (63.2 mg, 0.158 mmol, 23.13% yield) as a light brown solid. $^1$H NMR (400 MHz, DMSO-d6) δ (ppm): 1.84-2.03 (m, 3H) 2.09-2.26 (m, 1H) 2.41-2.49 (m, 4H) 2.88-2.99 (m, 4H) 3.34-3.43 (m, 3H) 3.54-3.63 (m, 1H) 3.94-4.02 (m, 1H) 6.93-7.09 (m, 3H) 7.18 (ddd, J=12.44, 9.16, 2.91 Hz, 1H) 7.61 (d, J=1.77 Hz, 1H) 10.44 (s, 1H); [M+H] calc'd for C$_{21}$H$_{23}$F$_2$N$_5$O, 400; found, 400.

Compound 16: (S)-3-chloro-4-(4-((6-oxo-5,6,6a,7,8, 9-hexahydropyrido[3,2-e]pyrrolo[1,2-a]pyrazin-3-yl) methyl)piperazin-1-yl)benzonitrile

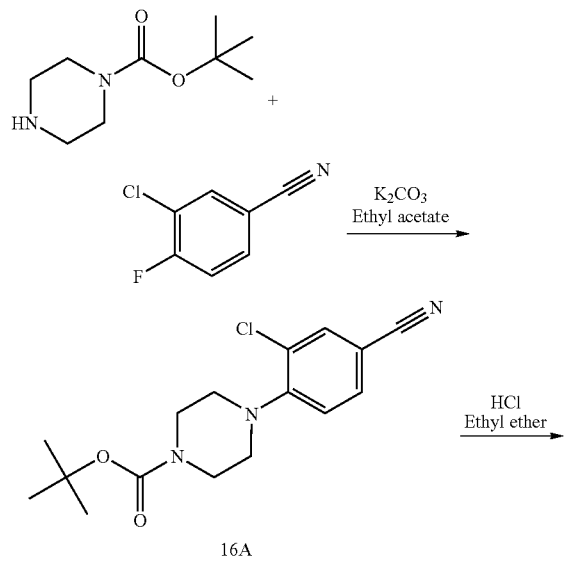

Compound 16A: tert-Butyl 4-(2-chloro-4-cyanophenyl)piperazine-1-carboxylate

Tert-Butyl piperazine-1-carboxylate (0.931 g, 5 mmol) and 3-chloro-4-fluorobenzonitrile (0.785 g, 5.00 mmol) were combined, K$_2$CO$_3$ (0.898 g, 6.50 mmol) was added and the reaction mixture was stirred at 90° C. for 1d. The mixture was triturated with ethyl acetate (3×5 mL) and the combined organic extracts were filtered. This was concentrated down to about 5-10 mL and subjected to flash column chromatograhy on silica gel (120 g SiO2, hexanes:ethyl acetate 1:0 to 4:1) to afford tert-butyl 4-(2-chloro-4-cyanophenyl)piperazine-1-carboxylate (1.264 g, 3.93 mmol, 79% yield) as a white solid. $^1$H NMR (400 MHz, DMSO-d6) δ (ppm): 1.42 (s, 9H) 3.00-3.09 (m, 4H) 3.42-3.53 (m, 4H) 7.25 (d, J=8.59 Hz, 1H) 7.77 (dd, J=8.34, 2.02 Hz, 1H) 7.97 (d, J=2.02 Hz, 1H); [M+H] calc'd for C$_{16}$H$_{20}$ClN$_3$O$_2$, 322; found, 322.

Compound 16B: 3-chloro-4-(piperazin-1-yl)benzonitrile hydrochloride

Tert-Butyl 4-(2-chloro-4-cyanophenyl)piperazine-1-carboxylate (0.322 g, 1 mmol) was diluted with 4.0M HCl in dioxane (3 mL) and stirred for 30 min. The thick white precipitate that formed was diluted with ethyl ether (10 mL) and stirred until a fine suspension resulted. The precipitate was filtered under nitrogen and dried in vacuum to afford 3-chloro-4-(piperazin-1-yl)benzonitrile hydrochloride (0.242 g, 0.937 mmol, 94% yield) as a white solid. $^1$H NMR (400 MHz, DMSO-d6) δ (ppm): 3.14-3.29 (m, 4H) 3.27-3.38 (m, 4H) 7.33 (d, J=8.34 Hz, 1H) 7.80 (dd, J=8.46, 1.89 Hz, 1H) 8.02 (d, J=2.02 Hz, 1H) 9.37 (br. s., 2H); 4H) 7.25 (d, J=8.59 Hz, 1H) 7.77 (dd, J=8.34, 2.02 Hz, 1H) 7.97 (d, J=2.02 Hz, 1H); [M+H] calc'd for C$_{11}$H$_{12}$ClN$_3$, 222; found, 222.

Compound 16: (S)-3-chloro-4-(4-((6-oxo-5,6,6a,7,8, 9-hexahydropyrido[3,2-e]pyrrolo[1,2-a]pyrazin-3-yl) methyl)piperazin-1-yl)benzonitrile

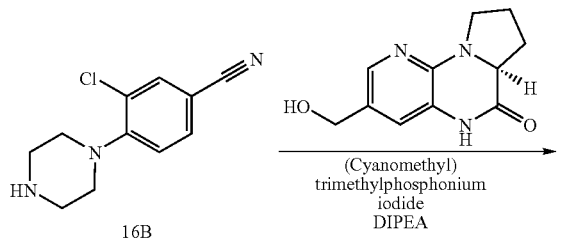

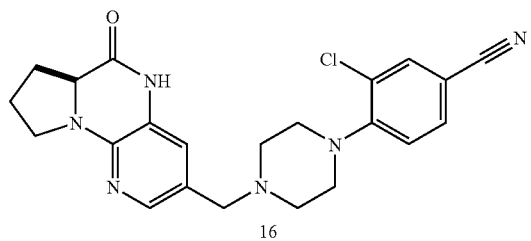

(S)-3-(hydroxymethyl)-6a,7,8,9-tetrahydropyrido[3,2-e] pyrrolo[1,2-a]pyrazin-6(5H)-one (100 mg, 0.456 mmol), 3-chloro-4-(piperazin-1-yl)benzonitrile hydrochloride (118 mg, 0.456 mmol), (cyanomethyl)trimethylphosphonium iodide (166 mg, 0.684 mmol) and N,N-diisopropylethylamine (0.398 ml, 2.281 mmol) were suspended in propionitrile (2 ml) and heated in a closed vial at 90° C. for 2 h. The reaction mixture became a dark brown solution. It was cooled to room temperature, concentrated in vacuo and purified using flash column chromatography on silica gel (80 g SiO$_2$, dichloromethane-methanol 100:0-95:5). The resulting solid was suspended in ether (7 mL), stirred until a fine suspension resulted, filtered and the solid was dried in vacuum to afford (S)-3-chloro-4-(4-((6-oxo-5,6,6a,7,8,9-hexahydropyrido[3, 2-e]pyrrolo[1,2-a]pyrazin-3-yl)methyl)piperazin-1-yl)benzonitrile (135.4 mg, 0.320 mmol, 70.2% yield) as a light brown solid. $^1$H NMR (400 MHz, DMSO-d6) δ (ppm): 1.80-2.03 (m, 3H) 2.10-2.25 (m, 1H) 2.39-2.61 (m, 4H) 2.94-3.19 (m, 4H) 3.35-3.46 (m, 3H) 3.51-3.65 (m, 1H) 3.91-4.05 (m, 1H) 6.97 (d, J=1.77 Hz, 1H) 7.22 (d, J=8.59 Hz, 1H) 7.62 (d, J=1.52 Hz, 1H) 7.74 (dd, J=8.46, 1.89 Hz, 1H) 7.93 (d, J=1.77

Hz, 1H) 10.44 (s, 1H); [M+H] calc'd for $C_{22}H_{23}ClN_6O$, 423; found, 423; melting point 213-215° C.

Compound 17: (S)-2,5-difluoro-4-(4-((6-oxo-5,6,6a, 7,8,9-hexahydropyrido[3,2-e]pyrrolo[1,2-a]pyrazin-3-yl)methyl)piperazin-1-yl)benzonitrile

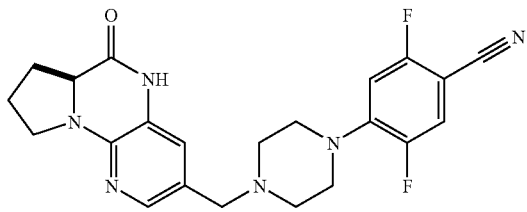

Compound 17 was prepared using a procedure analogous to that described in connection with compound 16, except that 2,4,5-trifluorobenzonitrile was used instead of 3-chloro-4-fluorobenzonitrile. $^1$H NMR (400 MHz, DMSO-d6) δ (ppm): 1.81-2.01 (m, 3H) 2.11-2.25 (m, 1H) 2.47 (br. s., 4H) 3.22 (br. s., 4H) 3.34-3.44 (m, 3H) 3.52-3.65 (m, 1H) 3.92-4.05 (m, 1H) 6.97 (d, J=1.52 Hz, 1H) 7.08 (dd, J=12.00, 7.20 Hz, 1H) 7.61 (d, J=1.52 Hz, 1H) 7.77 (dd, J=13.14, 6.32 Hz, 1H) 10.45 (s, 1H); [M+H] calc'd for $C_{22}H_{22}F_2N_6O$, 425; found, 425; melting point 224-227° C.

Compound 18: (S)-2,3-difluoro-4-(4-((6-oxo-5,6,6a, 7,8,9-hexahydropyrido[3,2-e]pyrrolo[1,2-a]pyrazin-3-yl)methyl)piperazin-1-yl)benzonitrile

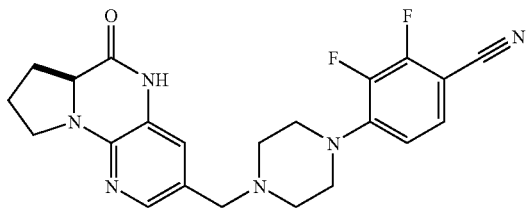

Compound 18 was prepared using a procedure analogous to that described in connection with compound 16, except that 2,3,4-trifluorobenzonitrile was used instead of 3-chloro-4-fluorobenzonitrile. $^1$H NMR (400 MHz, DMSO-d6) δ (ppm): 1.82-2.03 (m, 3H) 2.09-2.28 (m, 1H) 2.38-2.49 (m, 4H) 3.24 (br. s., 4H) 3.34-3.45 (m, 3H) 3.52-3.63 (m, 1H) 3.93-4.03 (m, 1H) 6.88-6.99 (m, 2H) 7.52-7.63 (m, 2H) 10.45 (s, 1H); [M+H] calc'd for $C_{22}H_{22}F_2N_6O$, 425; found, 425.

Compound 19: (S)-2,6-difluoro-4-(4-((6-oxo-5,6,6a, 7,8,9-hexahydropyrido[3,2-e]pyrrolo[1,2-a]pyrazin-3-yl)methyl)piperazin-1-yl)benzonitrile

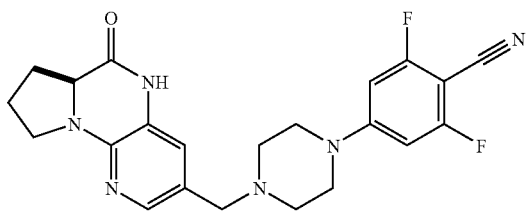

Compound 19 was prepared using a procedure analogous to that described in connection with compound 16, except that 2,4,6-trifluorobenzonitrile was used instead of 3-chloro-4-fluorobenzonitrile. $^1$H NMR (400 MHz, DMSO-d6) δ (ppm): 1.83-2.04 (m, 3H) 2.09-2.26 (m, 1H) 2.33-2.47 (m, 4H) 3.35 (s, 2H) 3.37-3.49 (m, 5H) 3.53-3.66 (m, 1H) 3.94-4.06 (m, 1H) 6.86 (d, J=12.63 Hz, 2H) 6.97 (d, J=1.77 Hz, 1H) 7.61 (d, J=1.52 Hz, 1H) 10.45 (s, 1H); [M+H] calc'd for $C_{22}H_{22}F_2N_6O$, 425; found, 425.

Compound 20: (S)-3,5-difluoro-4-(4-((6-oxo-5,6,6a, 7,8,9-hexahydropyrido[3,2-e]pyrrolo[1,2-a]pyrazin-3-yl)methyl)piperazin-1-yl)benzonitrile

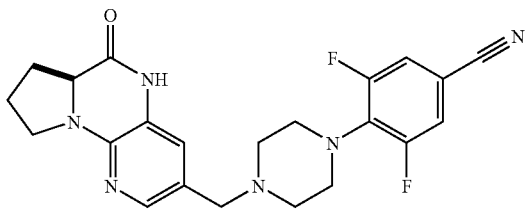

Compound 20 was prepared using a procedure analogous to that described in connection with compound 16, except that 3,4,5-trifluorobenzonitrile was used instead of 3-chloro-4-fluorobenzonitrile. $^1$H NMR (400 MHz, DMSO-d6) δ (ppm): 1.81-2.04 (m, 3H) 2.11-2.25 (m, 1H) 2.43 (br. s., 4H) 3.23 (br. s., 4H) 3.34-3.47 (m, 3H) 3.53-3.64 (m, 1H) 3.94-4.01 (m, 1H) 6.98 (d, J=1.52 Hz, 1H) 7.61 (d, J=1.77 Hz, 1H) 7.62-7.72 (m, 2H) 10.43 (s, 1H); [M+H] calc'd for $C_{22}H_{22}F_2N_6O$, 425; found, 425.

Compound 21: (S)-2-fluoro-4-(4-((6-oxo-5,6,6a,7,8, 9-hexahydropyrido[3,2-e]pyrrolo[1,2-a]pyrazin-3-yl) methyl)piperazin-1-yl)benzonitrile

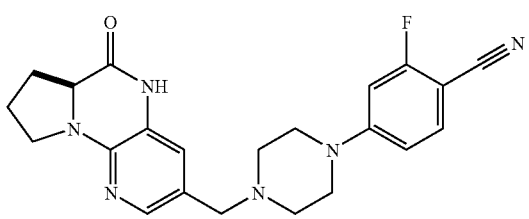

Compound 21 was prepared using a procedure analogous to that described in connection with compound 16, except that 2,4-difluorobenzonitrile was used instead of 3-chloro-4-fluorobenzonitrile. $^1$H NMR (400 MHz, DMSO-d6) δ (ppm): 1.84-2.01 (m, 3H) 2.10-2.23 (m, 1H) 2.36-2.47 (m, 4H) 3.34-3.44 (m, 7H) 3.54-3.63 (m, 1H) 6.83 (dd, J=9.09, 2.53 Hz, 1H) 6.93 (dd, J=14.27, 2.40 Hz, 1H) 6.97 (d, J=2.02 Hz, 1H)

7.55-7.62 (m, 2H) 10.44 (s, 1H); [M+H] calc'd for $C_{22}H_{23}FN_6O$, 407; found, 407; melting point 251-255° C.

Compound 22: (S)-3-fluoro-5-(4-((6-oxo-5,6,6a,7,8,9-hexahydropyrido[3,2-e]pyrrolo[1,2-a]pyrazin-3-yl)methyl)piperazin-1-yl)picolinonitrile

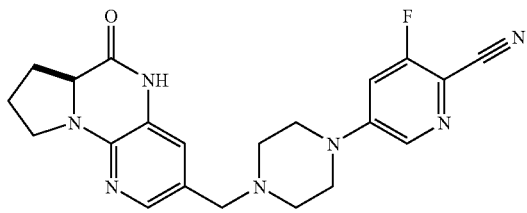

Compound 22 was prepared using a procedure analogous to that described in connection with compound 16, except that 3,5-difluoropicolinonitrile was used instead of 3-chloro-4-fluorobenzonitrile. $^1$H NMR (400 MHz, DMSO-d6) δ (ppm): 1.83-2.02 (m, 3H) 2.10-2.24 (m, 1H) 2.35-2.47 (m, 4H) 3.34-3.51 (m, 7H) 3.52-3.65 (m, 1H) 3.94-4.03 (m, 1H) 6.97 (d, J=1.77 Hz, 1H) 7.38 (dd, J=13.52, 2.15 Hz, 1H) 7.61 (d, J=1.52 Hz, 1H) 8.29 (s, 1H) 10.45 (s, 1H); [M+H] calc'd for $C_{21}H_{22}FN_7O$, 408; found, 408.

Compound 23: (S)-3-((4-phenylpiperazin-1-yl)methyl)-6a,7,8,9-tetrahydropyrido[3,2-e]pyrrolo[1,2-a]pyrazin-6(5H)-one

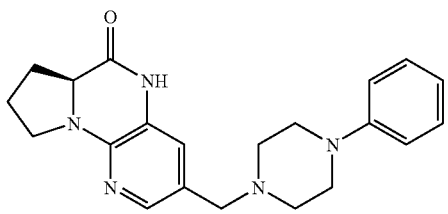

1-Phenylpiperazine hydrochloride (11.9 mg, 0.060 mmol), (cyanomethyl)trimethylphosphonium iodide (0.025 g, 0.102 mmoles), and (S)-3-(hydroxymethyl)-6a,7,8,9-tetrahydropyrido[3,2-e]pyrrolo[1,2-a]pyrazin-6(5H)-one (0.014 g, 0.063 mmoles) were diluted with propionitrile (0.5 ml) and treated with DIPEA (0.017 ml, 0.100 mmol). The reaction mixture was stirred at 90° C. overnight. The reaction mixture was washed with water (1 mL) and concentrated. The residue was dissolved in DMSO (1 mL) and purified using HPLC (acetonitrile-water, $NH_4HCO_3$ buffered). The fractions were concentrated in vacuo, dissolved in dioxane-water (1:1, 2 mL) and lyophilized to yield the title compound as a white solid (5.1 mg, 23%). [M+H] calc'd for $C_{21}H_{25}N_5O$ 364; found, 364.

Compound 24: (S)-3-((4-(4-fluorophenyl)piperazin-1-yl)methyl)-6a,7,8,9-tetrahydropyrido[3,2-e]pyrrolo[1,2-a]pyrazin-6(5H)-one

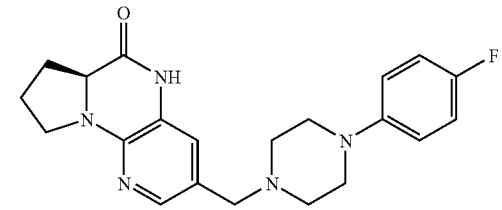

Compound 24 was prepared using a procedure analogous to that described in connection with compound 23. [M+H] calc'd for $C_{21}H_{24}FN_5O$ 382; found, 382.

Compound 25: (S)-3-((4-(4-acetylphenyl)piperazin-1-yl)methyl)-6a,7,8,9-tetrahydropyrido[3,2-e]pyrrolo[1,2-a]pyrazin-6(5H)-one

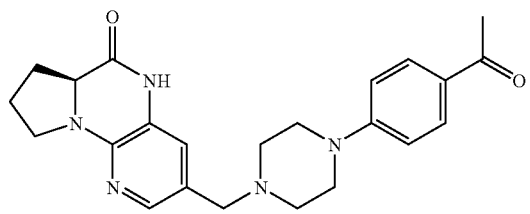

Compound 25 was prepared using a procedure analogous to that described in connection with compound 23. [M+H] calc'd for $C_{23}H_{27}N_5O_2$ 406; found, 406.

Compound 26: (S)-3-((4-(pyridin-2-yl)piperazin-1-yl)methyl)-6a,7,8,9-tetrahydropyrido[3,2-e]pyrrolo[1,2-a]pyrazin-6(5H)-one

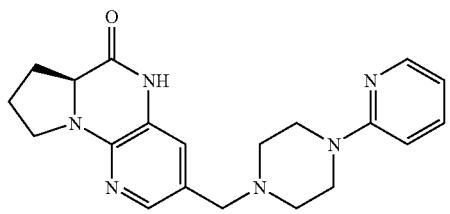

Compound 26 was prepared using a procedure analogous to that described in connection with compound 23. [M+H] calc'd for $C_{20}H_{24}N_6O$ 365; found, 365.

Compound 27: (S)-3-((benzylmethyl)amino)methyl)-6a,7,8,9-tetrahydropyrido[3,2-e]pyrrolo[1,2-a]pyrazin-6(5H)-one

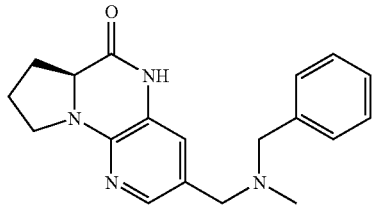

Compound 27 was prepared using a procedure analogous to that described in connection with compound 23. [M+H] calc'd for $C_{19}H_{22}N_4O$ 323; found, 323.

Compound 28: (S)-3-((4-(3-methoxyphenyl)piperazin-1-yl)methyl)-6a,7,8,9-tetrahydropyrido[3,2-e]pyrrolo[1,2-a]pyrazin-6(5H)-one

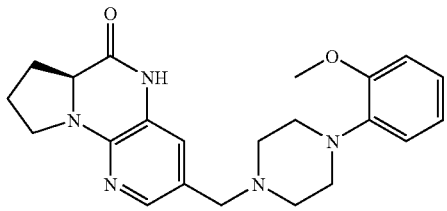

Compound 28 was prepared using a procedure analogous to that described in connection with compound 23. [M+H] calc'd for $C_{22}H_{27}N_5O_2$ 394; found, 394.

Compound 29: (S)-3-((4-m-tolylpiperazin-1-yl)methyl)-6a,7,8,9-tetrahydropyrido[3,2-e]pyrrolo[1,2-a]pyrazin-6(5H)-one

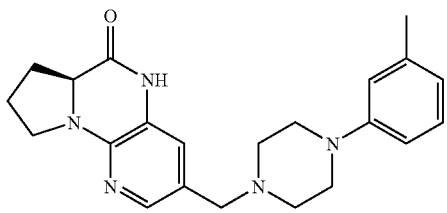

Compound 29 was prepared using a procedure analogous to that described in connection with compound 23. [M+H] calc'd for $C_{22}H_{27}N_5O$ 378; found, 378.

Compound 30: (S)-3-((4-(3-methoxyphenyl)piperazin-1-yl)methyl)-6a,7,8,9-tetrahydropyrido[3,2-e]pyrrolo[1,2-a]pyrazin-6(5H)-one

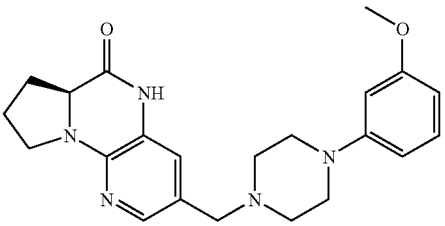

Compound 30 was prepared using a procedure analogous to that described in connection with compound 23. [M+H] calc'd for $C_{22}H_{27}N_5O_2$ 394; found, 394.

Compound 31: (S)-3-((4-(4-methoxyphenyl)piperazin-1-yl)methyl)-6a,7,8,9-tetrahydropyrido[3,2-e]pyrrolo[1,2-a]pyrazin-6(5H)-one

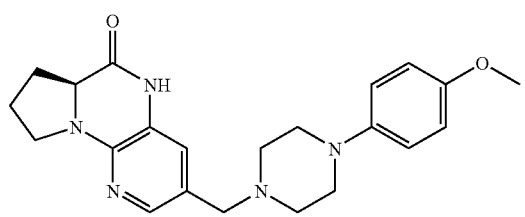

Compound 31 was prepared using a procedure analogous to that described in connection with compound 23. [M+H] calc'd for $C_{22}H_{27}N_5O_2$ 394; found, 394.

Compound 32: (S)-3-((4-p-tolylpiperazin-1-yl)methyl)-6a,7,8,9-tetrahydropyrido[3,2-e]pyrrolo[1,2-a]pyrazin-6(5H)-one

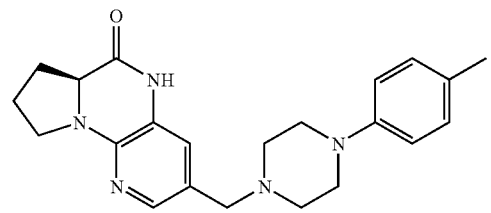

Compound 32 was prepared using a procedure analogous to that described in connection with compound 23. [M+H] calc'd for $C_{22}H_{27}N_5O$ 378; found, 378.

Compound 33: (S)-3-((4-(pyrimidin-2-yl)piperazin-1-yl)methyl)-6a,7,8,9-tetrahydropyrido[3,2-e]pyrrolo[1,2-a]pyrazin-6(5H)-one

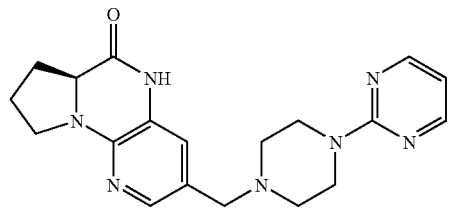

Compound 33 was prepared using a procedure analogous to that described in connection with compound 23. [M+H] calc'd for $C_{19}H_{23}N_7O$ 366; found, 366.

Compound 34: (S)-3-((4-(3-hydroxyphenyl)piperazin-1-yl)methyl)-6a,7,8,9-tetrahydropyrido[3,2-e]pyrrolo[1,2-a]pyrazin-6(5H)-one

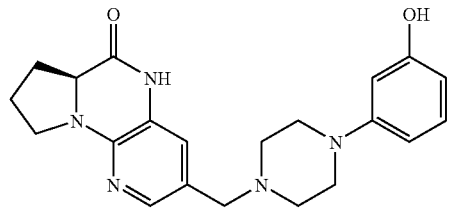

Compound 34 was prepared using a procedure analogous to that described in connection with compound 23. [M+H] calc'd for $C_{21}H_{25}N_5O_2$ 380; found, 380.

Compound 35: (S)-3-((4-(4-hydroxyphenyl)piperazin-1-yl)methyl)-6a,7,8,9-tetrahydropyrido[3,2-e]pyrrolo[1,2-a]pyrazin-6(5H)-one

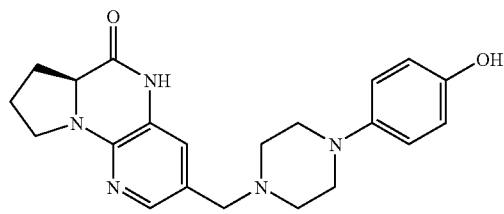

Compound 35 was prepared using a procedure analogous to that described in connection with compound 23. [M+H] calc'd for $C_{21}H_{25}N_5O_2$ 380; found, 380.

Compound 36: (S)-3-((4-(5-(trifluoromethyl)pyridin-2-yl)piperazin-1-yl)methyl)-6a,7,8,9-tetrahydropyrido[3,2-e]pyrrolo[1,2-a]pyrazin-6(5H)-one

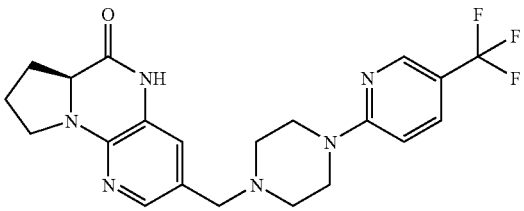

Compound 36 was prepared using a procedure analogous to that described in connection with compound 23. [M+H] calc'd for $C_{21}H_{23}F_3N_6O$ 433; found, 433.

Compound 37: (S)-3-((4-(4-bromophenyl)piperazin-1-yl)methyl)-6a,7,8,9-tetrahydropyrido[3,2-e]pyrrolo[1,2-a]pyrazin-6(5H)-one

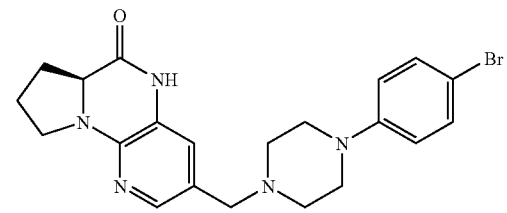

Compound 37 was prepared using a procedure analogous to that described in connection with compound 23. [M+H] calc'd for $C_{21}H_{24}BrN_5O$ 444; found, 444.

Compound 38: (S)-3-((4-(3-fluorophenyl)piperazin-1-yl)methyl)-6a,7,8,9-tetrahydropyrido[3,2-e]pyrrolo[1,2-a]pyrazin-6(5H)-one

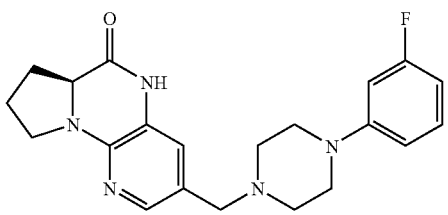

Compound 38 was prepared using a procedure analogous to that described in connection with compound 23. [M+H] calc'd for $C_{21}H_{24}FN_5O$ 382; found, 382.

Compound 39: (S)-3-((4-(1H-benzo[d]imidazol-2-yl)piperazin-1-yl)methyl)-6a,7,8,9-tetrahydropyrido[3,2-e]pyrrolo[1,2-a]pyrazin-6(5H)-one

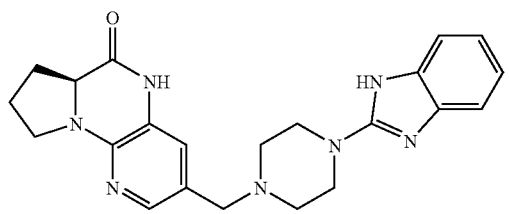

Compound 39 was prepared using a procedure analogous to that described in connection with compound 23. [M+H] calc'd for $C_{22}H_{25}N_7O$ 404; found, 404.

Compound 40: (S)-3-((4-(4-iodophenyl)piperazin-1-yl)methyl)-6a,7,8,9-tetrahydropyrido[3,2-e]pyrrolo[1,2-a]pyrazin-6(5H)-one

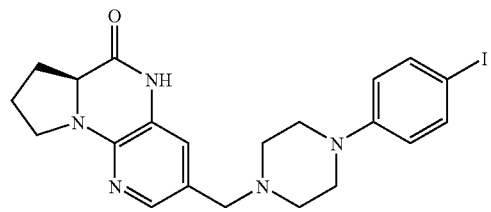

Compound 40 was prepared using a procedure analogous to that described in connection with compound 23. [M+H] calc'd for $C_{21}H_{24}IN_5O$ 490; found, 490.

Compound 41: (S)-3-((4-(benzo[d]oxazol-2-yl)piperazin-1-yl)methyl)-6a,7,8,9-tetrahydropyrido[3,2-e]pyrrolo[1,2-a]pyrazin-6(5H)-one

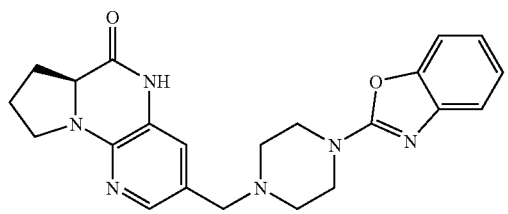

Compound 41 was prepared using a procedure analogous to that described in connection with compound 23. [M+H] calc'd for $C_{22}H_{24}N_6O_2$ 405; found, 405.

Compound 42: (S)-3-((4-(5-chloropyridin-2-yl)piperazin-1-yl)methyl)-6a,7,8,9-tetrahydropyrido[3,2-e]pyrrolo[1,2-a]pyrazin-6(5H)-one

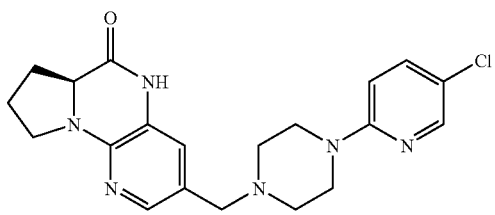

Compound 42 was prepared using a procedure analogous to that described in connection with compound 23. [M+H] calc'd for $C_{20}H_{23}ClN_6O$ 399; found, 399.

Compound 43: (S)-3-(((4-methoxybenzyl)(methyl)amino)methyl)-6a,7,8,9-tetrahydropyrido[3,2-e]pyrrolo[1,2-a]pyrazin-6(5H)-one

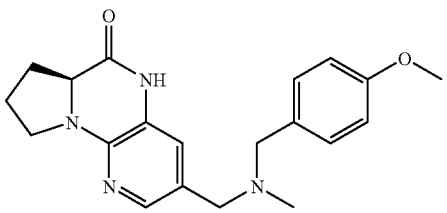

Compound 43 was prepared using a procedure analogous to that described in connection with compound 23. [M+H] calc'd for $C_{20}H_{24}N_4O_2$ 353; found, 353.

Compound 44: (S)-3-((4-(1,3,5-triazin-2-yl)piperazin-1-yl)methyl)-6a,7,8,9-tetrahydropyrido[3,2-e]pyrrolo[1,2-a]pyrazin-6(5H)-one

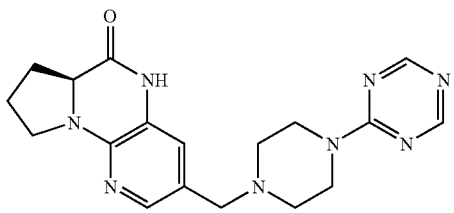

Compound 44 was prepared using a procedure analogous to that described in connection with compound 23. [M+H] calc'd for $C_{18}H_{22}N_8O$ 367; found, 367.

Compound 45: (S)-methyl 4-(4-(((6-oxo-5,6,6a,7,8,9-hexahydropyrido[3,2-e]pyrrolo[1,2-a]pyrazin-3-yl)methyl)piperazin-1-yl)benzoate

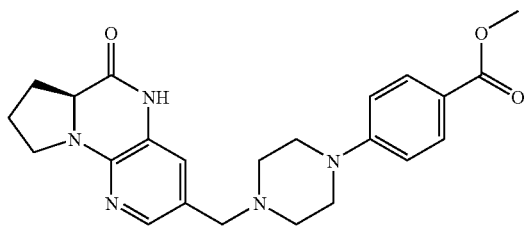

Compound 45 was prepared using a procedure analogous to that described in connection with compound 23. [M+H] calc'd for $C_{23}H_{27}N_5O_3$ 422; found, 422.

Compound 46: (S)-3-((4-(3,5-difluorophenyl)piperazin-1-yl)methyl)-6a,7,8,9-tetrahydropyrido[3,2-e]pyrrolo[1,2-a]pyrazin-6(5H)-one

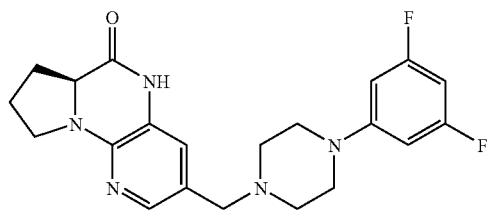

Compound 46 was prepared using a procedure analogous to that described in connection with compound 23. [M+H] calc'd for $C_{21}H_{23}F_2N_5O$ 400; found, 400.

Compound 47: (S)-3-((4-(4-chloro-3-fluorophenyl)piperazin-1-yl)methyl)-6a,7,8,9-tetrahydropyrido[3,2-e]pyrrolo[1,2-a]pyrazin-6(5H)-one

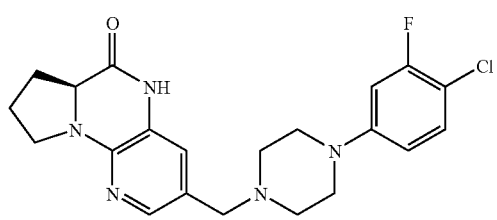

Compound 47 was prepared using a procedure analogous to that described in connection with compound 23. [M+H] calc'd for $C_{21}H_{23}ClFN_5O$ 416; found, 416.

Compound 48: (S)-3-((4-(4-(trifluoromethyl)phenyl)piperazin-1-yl)methyl)-6a,7,8,9-tetrahydropyrido[3,2-e]pyrrolo[1,2-a]pyrazin-6(5H)-one

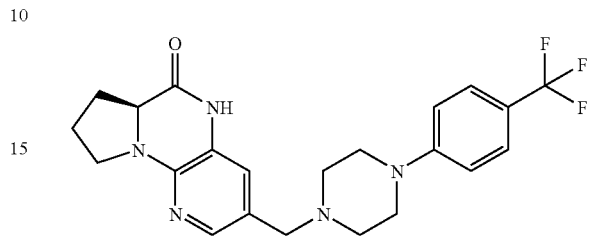

Compound 48 was prepared using a procedure analogous to that described in connection with compound 23. [M+H] calc'd for $C_{22}H_{24}F_3N_5O$ 432; found, 432.

Compound 49: (R)-3-((4-(4-chlorophenyl)-5,6-dihydropyridin-1(2H)-yl)methyl)-6a,7,8,9-tetrahydropyrido[3,2-e]pyrrolo[1,2-a]pyrazin-6(5H)-one

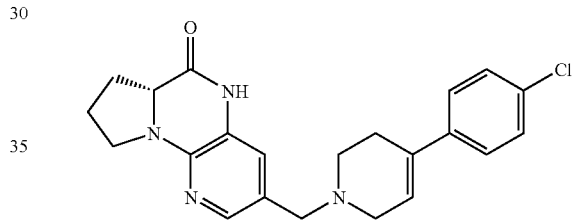

Compound 49 was prepared using a procedure analogous to that described in connection with compound 2, except that (R)-methylpyrrolidine-2-carboxylate was used instead of (S)-methylpyrrolidine-2-carboxylate. $^1$H NMR (DMSO-$d_6$) δ (ppm): 10.43 (s, 1H), 7.62 (d, J=1.8 Hz, 1H), 7.40-7.48 (m, 2H), 7.29-7.40 (m, 2H), 6.99 (d, J=1.8 Hz, 1H), 6.18 (br. s., 1H), 3.91-4.06 (m, 1H), 3.52-3.67 (m, 1H), 3.40-3.49 (m, 3H), 3.01 (d, J=2.3 Hz, 2H), 2.56-2.65 (m, 2H), 2.43 (br. s., 2H), 2.10-2.24 (m, 1H), 1.77-2.01 (m, 3H); [M+H] calc'd for $C_{22}H_{23}ClN_4O$, 395; found, 395.

Compound 50: (R)-3-((4-(4-chlorophenyl)piperazin-1-yl)methyl)-6a,7,8,9-tetrahydropyrido[3,2-e]pyrrolo[1,2-a]pyrazin-6(5H)-one

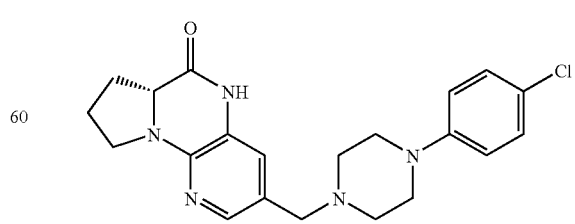

Compound 50 was prepared using a procedure analogous to that described in connection with compound 1, except that (R)-methylpyrrolidine-2-carboxylate was used instead of (S)-methylpyrrolidine-2-carboxylate. $^1$H NMR (DMSO-d$_6$) δ (ppm): 10.43 (s, 1H), 7.61 (d, J=1.5 Hz, 1H), 7.21 (d, J=8.8 Hz, 2H), 6.98 (d, J=1.8 Hz, 1H), 6.92 (d, J=9.1 Hz, 2H), 3.89-4.05 (m, 1H), 3.52-3.66 (m, 1H), 3.37-3.48 (m, 3H), 3.10 (br. s., 4H), 2.46 (d, J=4.5 Hz, 4H), 2.07-2.25 (m, 1H), 1.78-2.04 (m, 3H); [M+H] calc'd for C$_{21}$H$_{24}$ClN$_5$O, 398; found, 398.

Compound 51: (R)-3-((4-(4-chlorophenyl)piperidin-1-yl)methyl)-6a,7,8,9-tetrahydropyrido[3,2-e]pyrrolo[1,2-a]pyrazin-6(5H)-one

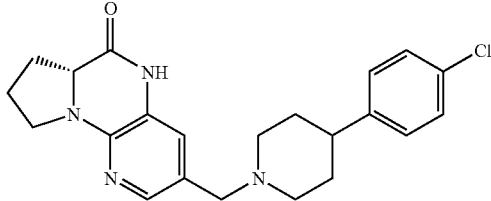

Compound 51 was prepared using a procedure analogous to that described in connection with compound 3, except that (R)-methylpyrrolidine-2-carboxylate was used instead of (S)-methylpyrrolidine-2-carboxylate. $^1$H NMR (DMSO-d$_6$) δ (ppm): 10.42 (s, 1H), 7.60 (d, J=1.8 Hz, 1H), 7.29-7.37 (m, 2H), 7.19-7.29 (m, 2H), 6.97 (d, J=1.8 Hz, 1H), 3.90-4.05 (m, 1H), 3.51-3.65 (m, 1H), 3.35-3.45 (m, 1H), 2.88 (d, J=10.9 Hz, 2H), 2.08-2.25 (m, 1H), 1.82-2.05 (m, 5H), 1.64-1.78 (m, 2H), 1.48-1.64 (m, 2H); [M+H] calc'd for C$_{22}$H$_{25}$ClN$_4$O, 397; found, 397.

Compound 52: (S)-7-((4-(4-chlorophenyl)-5,6-dihydropyridin-1(2H)-yl)methyl)-3,4-dimethyl-3,4-dihydropyrido[3,2-b]pyrazin-2(1H)-one

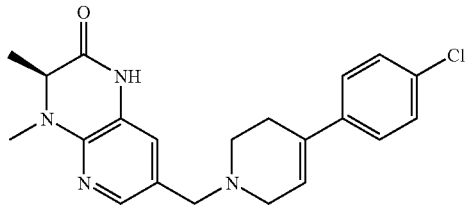

Compound 52 was prepared using a procedure analogous to that described in connection with compound 2, except that (S)-methyl 2-(methylamino)propanoate was used instead of (S)-methylpyrrolidine-2-carboxylate. $^1$H NMR(CHLOROFORM-d) δ (ppm): 7.80 (d, J=1.8 Hz, 1H), 7.60 (br. s., 1H), 7.28-7.33 (m, 4H), 6.96-7.06 (m, 1H), 6.01-6.08 (m, 1H), 4.13 (q, J=6.6 Hz, 1H), 3.47-3.58 (m, J=3.3 Hz, 2H), 3.18 (d, J=2.3 Hz, 2H), 3.08 (s, 3H), 2.69-2.79 (m, 2H), 2.55 (br. s., 2H), 1.36 (d, J=7.1 Hz, 3H); [M+H] calc'd for C$_{21}$H$_{23}$ClN$_4$O, 383; found, 383.

Compound 53: (S)-7-((4-(4-chlorophenyl)piperidin-1-yl)methyl)-3,4-dimethyl-3,4-dihydropyrido[3,2-b]pyrazin-2(1H)-one

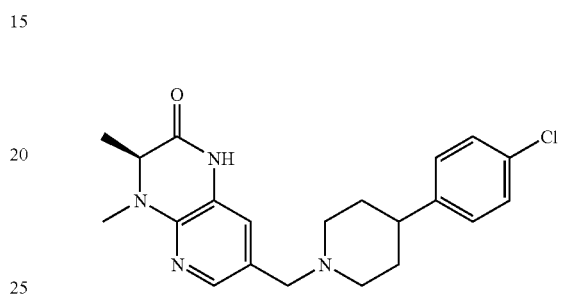

Compound 53 was prepared using a procedure analogous to that described in connection with compound 3, except that (S)-methyl 2-(methylamino)propanoate was used instead of (S)-methylpyrrolidine-2-carboxylate. $^1$H NMR(CHLOROFORM-d) δ (ppm): 7.82-7.94 (m, 1H), 7.78 (d, J=1.8 Hz, 1H), 7.27 (d, J=8.6 Hz, 2H), 7.15 (d, J=8.3 Hz, 2H), 7.00 (br. s., 1H), 4.13 (q, J=7.0 Hz, 1H), 3.48 (br. s., 2H), 3.08 (s, 5H), 2.51 (br. s., 1H), 2.14 (d, J=2.0 Hz, 2H), 1.81 (br. s., 4H), 1.37 (d, J=6.8 Hz, 3H); [M+H] calc'd for C$_{21}$H$_{25}$ClN$_4$O, 385; found, 385.

Compound 54: (S)-3,4-dimethyl-7-((4-phenylpiperidin-1-yl)methyl)-3,4-dihydropyrido[3,2-b]pyrazin-2(1H)-one

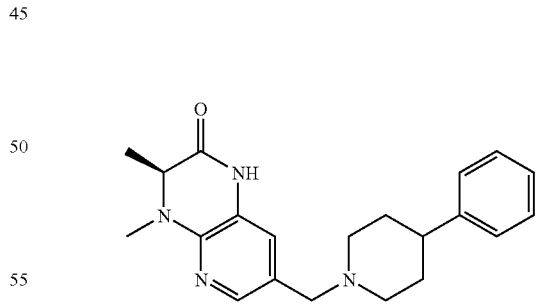

Compound 54 was prepared using a procedure analogous to that described in connection with compound 1, except that (S)-methyl 2-(methylamino)propanoate was used instead of (S)-methylpyrrolidine-2-carboxylate and 4-phenylpiperidine was used instead of 1-(4-chlorophenyl)piperazine. $^1$H NMR (400 MHz, DMSO-d$_6$) δ (ppm): 1.23 (d, J=6.82 Hz, 3H) 1.82 (m, J=13.89 Hz, 2H) 2.00 (d, J=12.88 Hz, 2H) 2.74-2.85 (m, 1H) 2.94-3.11 (m, 5H) 3.47 (t, J=13.77 Hz, 2H) 4.22 (d, J=5.05 Hz, 2H) 7.06 (d, J=2.27 Hz, 1H) 7.18-7.26 (m, 3H)

7.29-7.36 (m, 2H) 7.85 (d, J=2.02 Hz, 1H) 9.30 (br. s., 1H) 10.83 (s, 1H); [M+H] calc'd for $C_{21}H_{26}N_4O$, 351; found, 351.

Compound 55: (S)-3,4-dimethyl-7-((3-oxo-4-phenylpiperazin-1-yl)methyl)-3,4-dihydropyrido[3,2-b]pyrazin-2(1H)-one

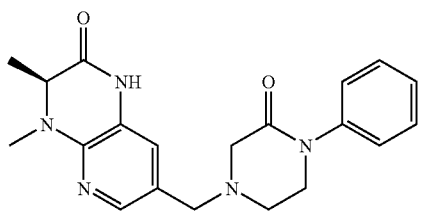

Compound 55 was prepared using a procedure analogous to that described in connection with compound 1, except that (S)-methyl 2-(methylamino)propanoate was used instead of (S)-methylpyrrolidine-2-carboxylate and 1-phenylpiperazin-2-one was used instead of 1-(4-chlorophenyl)piperazine. $^1$H NMR(CHLOROFORM-d) δ (ppm): 7.81 (d, J=1.8 Hz, 1H), 7.68 (s, 1H), 7.37-7.45 (m, 2H), 7.29 (d, J=8.1 Hz, 3H), 6.93 (d, J=1.8 Hz, 1H), 4.14 (q, J=6.8 Hz, 1H), 3.70 (t, J=5.3 Hz, 2H), 3.51 (s, 2H), 3.26-3.38 (m, 2H), 3.08 (s, 3H), 2.83 (t, J=5.4 Hz, 2H), 1.38 (d, J=6.8 Hz, 3H); [M+H] calc'd for $C_{20}H_{23}N_5O_2$, 366; found, 366.

Compound 56: (S)-7-((4-(4-fluorophenyl)-5,6-dihydropyridin-1(2H)-yl)methyl)-3,4-dimethyl-3,4-dihydropyrido[3,2-b]pyrazin-2(1H)-one

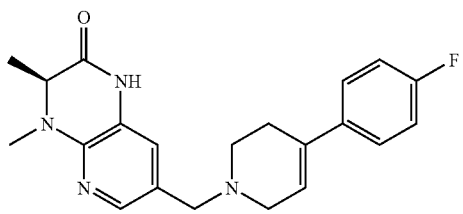

Compound 56 was prepared using a procedure analogous to that described in connection with compound 1, except that (S)-methyl 2-(methylamino)propanoate was used instead of (S)-methylpyrrolidine-2-carboxylate and 4-(4-fluorophenyl)-1,2,3,6-tetrahydropyridine was used instead of 1-(4-chlorophenyl)piperazine. $^1$H NMR (CHLOROFORM-d) δ (ppm): 8.26 (s, 1H), 7.80 (d, J=2.0 Hz, 1H), 7.29-7.38 (m, 2H), 6.93-7.05 (m, 3H), 5.95-6.03 (m, 1H), 4.08-4.17 (m, 1H), 3.46-3.55 (m, 2H), 3.14 (d, J=2.8 Hz, 2H), 3.07 (s, 3H),
2.66-2.75 (m, 2H), 2.48-2.57 (m, 2H), 1.35 (d, J=6.8 Hz, 3H); [M+H] calc'd for $C_{21}H_{23}FN_4O$, 367; found, 367.

Compound 57: (S)-3,4-dimethyl-7-((4-phenyl-5,6-dihydropyridin-1(2H)-yl)methyl)-3,4-dihydropyrido[3,2-b]pyrazin-2(1H)-one

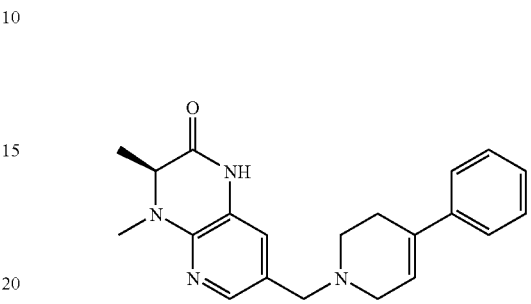

Compound 57 was prepared using a procedure analogous to that described in connection with compound 1, except that (S)-methyl 2-(methylamino)propanoate was used instead of (S)-methylpyrrolidine-2-carboxylate and 4-phenyl-1,2,3,6-tetrahydropyridine was used instead of 1-(4-chlorophenyl)piperazine. $^1$H NMR (DMSO-$d_6$) δ (ppm): 10.49 (s, 1H), 7.68 (d, J=1.5 Hz, 1H), 7.41 (d, J=7.3 Hz, 2H), 7.32 (t, J=7.6 Hz, 2H), 7.17-7.27 (m, 1H), 7.00 (d, J=1.8 Hz, 1H), 6.13 (br. s., 1H), 4.05 (q, J=6.8 Hz, 1H), 3.43 (q, J=12.9 Hz, 2H), 3.02 (d, J=2.5 Hz, 2H), 2.94 (s, 3H), 2.57-2.65 (m, 2H), 2.47 (br. s., 2H), 1.17 (d, J=6.8 Hz, 3H); [M+H] calc'd for $C_{21}H_{24}N_4O$, 349; found, 349.

Compound 58: (S)-7-((4-(3-chlorophenyl)piperazin-1-yl)methyl)-3,4-dimethyl-3,4-dihydropyrido[3,2-b]pyrazin-2(1H)-one

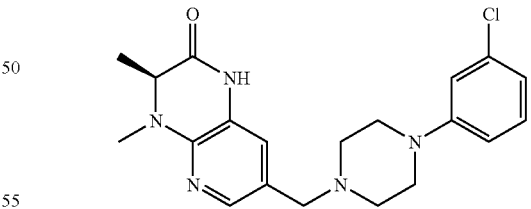

Compound 58 was prepared using a procedure analogous to that described in connection with compound 1, except that (S)-methyl 2-(methylamino)propanoate was used instead of (S)-methylpyrrolidine-2-carboxylate and 1-(3-chlorophenyl)piperazine was used instead of 1-(4-chlorophenyl)piperazine. $^1$H NMR(CHLOROFORM-d) δ (ppm): 7.79 (d, J=1.5 Hz, 1H), 7.68 (br. s., 1H), 7.17 (t, J=8.1 Hz, 1H), 6.89-7.06 (m, 1H), 6.87 (d, J=2.0 Hz, 1H), 6.82 (d, J=7.8 Hz, 1H), 6.78 (dd, J=8.3, 2.0 Hz, 1H), 4.13 (q, J=6.8 Hz, 1H), 3.45 (br. s., 2H), 3.21 (br. s., 4H), 3.08 (s, 3H), 2.60 (br. s., 4H), 1.37 (d, J=6.8 Hz, 3H); [M+H] calc'd for C$_{20}$H$_{24}$ClN$_5$O, 386; found, 386.

Compound 59: (S)-7-((4-(4-chlorophenyl)piperazin-1-yl)methyl)-3,4-dimethyl-3,4-dihydropyrido[3,2-b]pyrazin-2(1H)-one

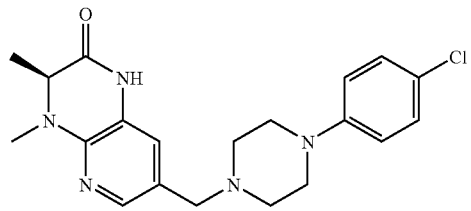

Compound 59 was prepared using a procedure analogous to that described in connection with compound 1, except that (S)-methyl 2-(methylamino)propanoate was used instead of (S)-methylpyrrolidine-2-carboxylate and 1-(4-chlorophenyl)piperazine was used instead of 1-(4-chlorophenyl)piperazine. $^1$H NMR(CHLOROFORM-d) δ (ppm): 7.79 (d, J=1.8 Hz, 1H), 7.72-7.78 (m, 1H), 7.17-7.24 (m, 2H), 6.89-7.02 (m, 1H), 6.79-6.88 (m, 2H), 4.13 (q, J=7.0 Hz, 1H), 3.45 (br. s., 2H), 3.17 (br. s., 4H), 3.08 (s, 3H), 2.60 (br. s., 4H), 1.37 (d, J=6.8 Hz, 3H); [M+H] calc'd for C$_{20}$H$_{24}$ClN$_5$O, 386; found, 386.

Compound 60: (S)-7-((4-(4-chlorophenyl)-5,6-dihydropyridin-1(2H)-yl)methyl)-4-isopropyl-3-methyl-3,4-dihydropyrido[3,2-b]pyrazin-2(1H)-one

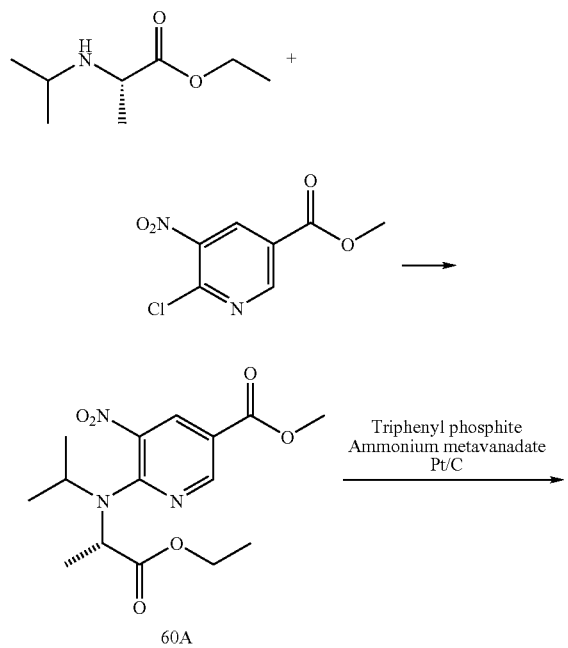

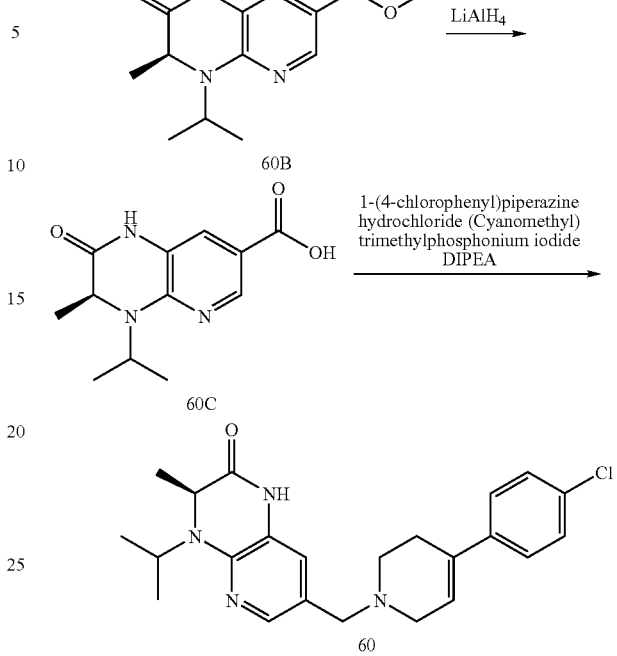

Compound 60A: (S)-methyl 6-((1-ethoxy-1-oxopropan-2-yl)(isopropyl)amino)-5-nitronicotinate (S)-ethyl 2-(isopropylamino)propanoate (2.83 g, 17.8 mmol) was added to methyl 6-chloro-5-nitronicotinate (1.72 g, 7.94 mmol) and the reaction mixture was stirred in a closed vial at 90° C. for 20 h. It was cooled and diluted with EtOAc (25 mL). The resulting precipitate was filtered off, the filtrate was concentrated in vacuo and purified using flash column chromatography on silica gel (220 g SiO2, hexanes:ethyl acetate 4:1) to afford the title compound as yellow oil (1.12 g, 42%). $^1$H NMR (400 MHz, CHLOROFORM-d) δ (ppm): 1.18 (t, J=7.07 Hz, 3H) 1.30 (d, J=6.32 Hz, 3H) 1.36 (d, J=6.57 Hz, 3H) 1.66 (d, J=6.82 Hz, 3H) 3.48-3.62 (m, 1H) 3.90 (s, 3H) 4.03 (q, J=6.65 Hz, 1H) 4.06-4.21 (m, 2H) 8.54 (d, J=2.02 Hz, 1H) 8.70 (d, J=2.02 Hz, 1H); [M+H] calc'd for C$_{15}$H$_{21}$N$_3$O$_6$, 340; found, 340.

Compound 60B: (S)-methyl 4-isopropyl-3-methyl-2-oxo-1,2,3,4-tetrahydropyrido[3,2-b]pyrazine-7-carboxylate (S)-methyl 6-((1-ethoxy-1-oxopropan-2-yl)(isopropyl)amino)-5-nitronicotinate (0.900 g, 2.65 mmol) was dissolved in dichloromethane (10 mL). To this solution was added triphenyl phosphite (3.0 mg, 9.7 umol), ammonium metavanadate (30 mg, 0.265 mmol) and Pt/C (5% wt., 0.120 g). The reaction mixture was hydrogenated at 80 psi at 25° C. for 6 h. The mixture was filtered through a small pad of celite and the pad was washed with dichloromethane (20 mL). The combined filtrates were concentrated in vacuo and crystallized with ethyl ether to afford the title compounds as a white solid (0.658 g, 94%). $^1$H NMR (400 MHz, CHLOROFORM-d) δ (ppm): 1.33 (d, J=6.82 Hz, 3H) 1.36-1.41 (m, 6H) 3.90 (s, 3H) 4.34 (q, J=6.65 Hz, 1H) 4.86 (m, 1H) 7.52 (d, J=1.77 Hz, 1H) 8.59 (d, J=1.77 Hz, 1H) 8.73 (br. s., 1H); [M+H] calc'd for $C_{13}H_{17}N_3O_3$, 264; found, 264.

Compound 60C: (S)-7-(hydroxymethyl)-4-isopropyl-3-methyl-3,4-dihydropyrido[3,2-b]pyrazin-2(1H)-one (S)-methyl 4-isopropyl-3-methyl-2-oxo-1,2,3,4-tetrahydropyrido[3,2-b]pyrazine-7-carboxylate (0.649 g, 2.46 mmol) was dissolved in THF (8 mL) and cooled to 0° C. under nitrogen atmosphere. Sodium hydride (60% susp. in mineral oil, 0.112 g, 2.80 mmol) was added in one portion. The reaction mixture was allowed to warm to room temperature and stirred for 30 min. It was then cooled to −50° C. and LiAlH$_4$ (1M in THF, 9.80 mL, 9.80 mmol) was added dropwise over 10 min. The reaction mixture was kept at −30-(−20)° C. for 1 h, cooled to below −50° C. and slowly quenched with MeOH (5 mL). The resulting solution was warmed to room temperature and subjected to preparative HPLC (1-30% acetonitrile in water, TFA buffered) to afford the title compound as a grey solid (TFA salt, 450 mg, 52%). [M+H] calc'd for $C_{12}H_{17}N_3O_2$, 236; found, 236.

Compound 60: (S)-7-((4-(4-chlorophenyl)-5,6-dihydropyridin-1(2H)-yl)methyl)-4-isopropyl-3-methyl-3,4-dihydropyrido[3,2-b]pyrazin-2(1H)-one Compound 60 was prepared using a procedure analogous to that described in connection with compound 1D, except that (S)-7-(hydroxymethyl)-4-isopropyl-3-methyl-3,4-dihydropyrido[3,2-b]pyrazin-2(1H)-one was used instead of (S)-3-(hydroxymethyl)-6a,7,8,9-tetrahydropyrido[3,2-e]pyrrolo[1,2-a]pyrazin-6(5H)-one and 4-(4-chlorophenyl)-1,2,3,6-tetrahydropyridine was used instead of 1-(4-chlorophenyl)piperazine. $^1$H NMR(CHLOROFORM-d) δ (ppm): 8.33 (s, 1H), 7.84 (d, J=1.8 Hz, 1H), 7.21-7.36 (m, 4H), 7.04 (d, J=1.5 Hz, 1H), 6.06 (br. s., 1H), 4.64-4.84 (m, 1H), 4.28 (q, J=6.7 Hz, 1H), 3.52 (s, 2H), 3.05-3.27 (m, 2H), 2.65-2.79 (m, 2H), 2.54 (br. s., 2H), 1.37 (d, J=6.8 Hz, 3H), 1.25-1.33 (m, 6H); [M+H] calc'd for $C_{23}H_{27}ClN_4O$, 411; found, 411.

Compound 61: (S)-7-((4-(4-chlorophenyl)piperazin-1-yl)methyl)-4-isopropyl-3-methyl-3,4-dihydropyrido[3,2-b]pyrazin-2(1H)-one

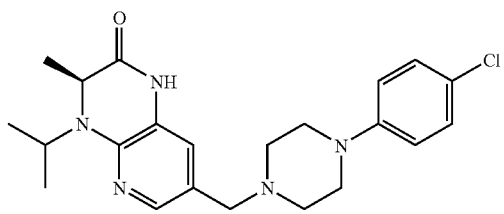

Compound 61 was prepared using a procedure analogous to that described in connection with compound 60, except that 1-(4-chlorophenyl)piperazine was used instead of 4-(4-chlorophenyl)-1,2,3,6-tetrahydropyridine. $^1$H NMR(CHLOROFORM-d) δ (ppm): 8.58 (s, 1H), 7.83 (d, J=2.0 Hz, 1H), 7.17-7.23 (m, 2H), 7.00 (d, J=2.0 Hz, 1H), 6.80-6.86 (m, 2H), 4.67-4.81 (m, 1H), 4.28 (q, J=6.7 Hz, 1H), 3.45 (s, 2H), 3.12-3.21 (m, 4H), 2.54-2.66 (m, 4H), 1.37 (d, J=6.8 Hz, 3H), 1.32 (d, J=6.8 Hz, 3H), 1.29 (d, J=7.1 Hz, 3H); [M+H] calc'd for $C_{22}H_{28}ClN_4O$, 414; found, 414.

Compound 62: (S)-7-((4-(4-chlorophenyl)piperidin-1-yl)methyl)-4-isopropyl-3-methyl-3,4-dihydropyrido[3,2-b]pyrazin-2(1H)-one

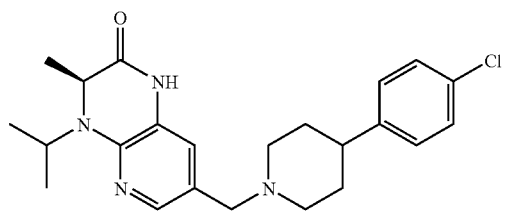

Compound 62 was prepared using a procedure analogous to that described in connection with compound 60, except that 4-(4-chlorophenyl)piperidine was used instead of 4-(4-chlorophenyl)-1,2,3,6-tetrahydropyridine. $^1$H NMR(CHLOROFORM-d) δ (ppm): 8.15 (s, 1H), 7.82 (d, J=2.0 Hz, 1H), 7.22-7.30 (m, 2H), 7.13-7.19 (m, 2H), 7.00 (s, 1H), 4.66-4.82 (m, 1H), 4.28 (q, J=6.8 Hz, 1H), 3.43 (s, 2H), 3.01 (br. s., 2H), 2.41-2.56 (m, 1H), 2.08 (t, J=11.4 Hz, 2H), 1.57-1.87 (m, 4H), 1.36 (d, J=6.8 Hz, 3H), 1.31 (d, J=6.8 Hz, 3H), 1.29 (d, J=6.8 Hz, 3H); [M+H] calc'd for $C_{23}H_{29}ClN_4O$, 413; found, 413.

Compound 63: (S)-7-((4-(4-chlorophenyl)-5,6-dihydropyridin-1(2H)-yl)methyl)-4-ethyl-3-methyl-3,4-dihydropyrido[3,2-b]pyrazin-2(1H)-one

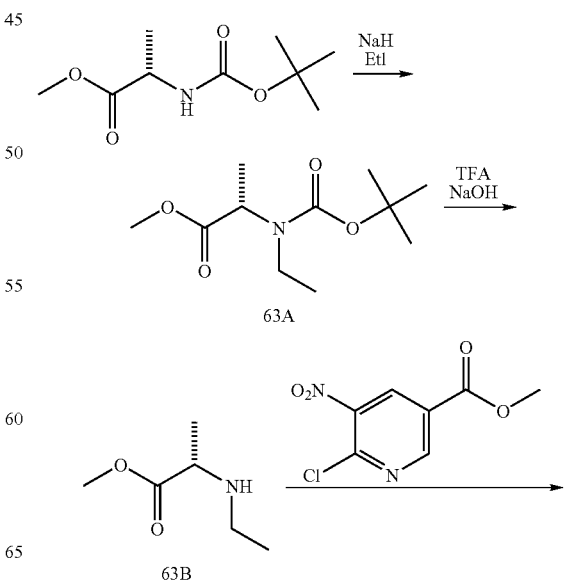

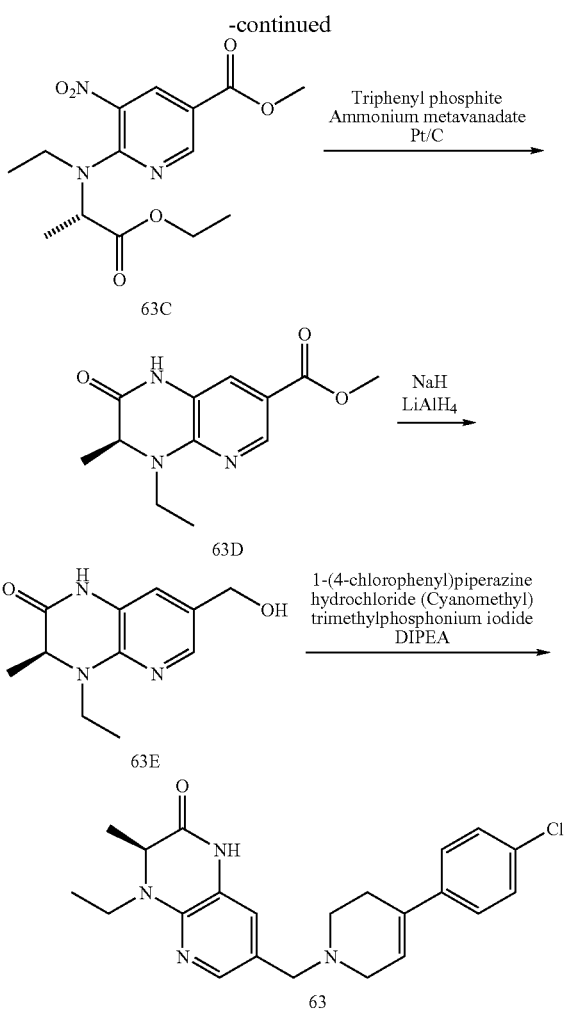

Compound 63A (S)-methyl 2-(tert-butoxycarbonyl(ethyl)amino)propanoate (S)-methyl 2-(tert-butoxycarbonylamino)propanoate (10.0 g, 49.2 mmol) was dissolved in THF (100 mL) and cooled to 0° C. under nitrogen. Sodium hydride (60% susp. in mineral oil, 3.00 g, 75.1 mmol) was added in portions over 2 min. The reaction mixture was stirred for 5 min at 0° C. and EtI (4.80 mL, 59.5 mmol) was added. It was allowed to warm to room temperature over the period of 1 h, stirred at room temperature overnight and at 70° C. for 7 d. The reaction mixture was cooled, filtered and concentrated in vacuo. The solid was triturated with hexanes (2×70 mL), the triturates were concentrated in vacuo and the residue was purified using flash column chromatography on silica gel (330 g SiO$_2$, hexanes:ethyl acetate 19:1-9:1) to afford the title compounds as an oil (4.40 g, 39%). [M+H] calc'd for $C_{11}H_{21}NO_4$, 232; found, 232.

Compound 63B: (S)-methyl 2-(ethylamino)propanoate (S)-methyl 2-(tert-butoxycarbonyl(ethyl)amino)propanoate (4.40 g, 19.0 mmol) was dissolved in dichloromethane and treated with TFA (10 mL). The reaction mixture was stirred for 2 h at room temperature and concentrated in vacuo. The residue was diluted with brine and NaOH (aq. 50%) was added dropwise until pH=12.5. This was extracted with EtOAc (3×30 mL). The combined organic extracts were dried (MgSO4), filtered and concentrated in vacuo to afford the title compound as an opaque liquid (1.85 g, 74%). [M+H] calc'd for $C_6H_{13}NO_2$, 132; found, 132.

Compound 63C: (S)-methyl 6-((1-ethoxy-1-oxopropan-2-yl)(ethyl)amino)-5-nitronicotinate (S)-methyl 2-(ethylamino)propanoate (1.83 g, 14.0 mmol) was added to methyl 6-chloro-5-nitronicotinate (1.30 g, 6.00 mmol) and the reaction mixture was stirred in a closed vial at 90° C. for 1 h. It was cooled and diluted with EtOAc (25 mL). The resulting precipitate was filtered off, the filtrate was concentrated in vacuo and purified using flash column chromatography on silica gel (220 g SiO$_2$, ethyl acetate in hexanes 0-50%) to afford the title compound as a yellow oil (1.23 g, 66%). [M+H] calc'd for $C_{14}H_{19}N_3O_6$, 326; found, 326.

Compound 63D: (S)-methyl 4-ethyl-3-methyl-2-oxo-1,2,3,4-tetrahydropyrido[2,3-b]pyrazine-7-carboxylate (S)-methyl 6-((1-ethoxy-1-oxopropan-2-yl)(ethyl)amino)-5-nitronicotinate (1.22 g, 3.92 mmol) was dissolved in dichloromethane (12 mL). To this solution were added triphenyl phosphite (5.0 mg, 16 umol), ammonium metavanadate (50.0 mg, 0.427 mmol) and Pt/C (5% wt., 0.200 g). The reaction mixture was hydrogenated at 100 psi at 25° C. for 18 h. The mixture was filtered through a small pad of celite and the pad was washed with dichloromethane (20 mL). The combined filtrates were concentrated in vacuo and crystallized with ethyl ether (50 mL) to afford the title compound as a white solid (0.560 g, 57%). [M+H] calc'd for $C_{12}H_5N_3O_3$, 250; found, 250.

Compound 63E: (S)-4-ethyl-7-(hydroxymethyl)-3-methyl-3,4-dihydropyrido[2,3-b]pyrazin-2(1H)-one (S)-methyl 4-ethyl-3-methyl-2-oxo-1,2,3,4-tetrahydropyrido[2,3-b]pyrazine-7-carboxylate (0.560 g, 2.25 mmol) was dissolved in THF (5 mL) and cooled to 0° C. under nitrogen atmosphere. Sodium hydride (60% susp. in mineral oil, 0.135 g, 3.38 mmol) was added in one portion. The reaction mixture was allowed to warm to room temperature and stirred for 30 min. It was then cooled to −50° C. and LiAlH$_4$ (2M in THF, 3.40 mL, 6.80 mmol) was added dropwise over 10 min. The reaction mixture was kept at −30-(−20)° C. for 1 h, cooled to below −50° C. and slowly quenched with MeOH (5 mL). The resulting solution was warmed to room temperature and subjected to preparative HPLC (1-30% acetonitrile in water, TFA buffered) to afford the title compound as a dark oil (TFA salt, 0.587 mg, 78%). [M+H] calc'd for $C_{11}H_{15}N_3O_2$, 222; found, 222.

Compound 63: (S)-7-((4-(4-chlorophenyl)-5,6-dihydropyridin-1(2H)-yl)methyl)-4-ethyl-3-methyl-3,4-dihydropyrido[3,2-b]pyrazin-2(1H)-one Compound 63 was prepared using a procedure analogous to that described in connection with compound 1D, except that (S)-4-ethyl-7-(hydroxymethyl)-3-methyl-3,4-dihydropyrido[3,2-b]pyrazin-2(1H)-one was used instead of (S)-3-(hydroxymethyl)-6a,7,8,9-tetrahydropyrido[3,2-e]pyrrolo[1,2-a]pyrazin-6(5H)-one and 4-(4-chlorophenyl)-1,2,3,6-tetrahydropyridine was used instead of 1-(4-chlorophenyl)

piperazine. ¹H NMR(CHLOROFORM-d) δ (ppm): 7.79 (d, J=1.5 Hz, 1H), 7.68 (br. s., 1H), 7.27-7.34 (m, 4H), 7.02 (s, 1H), 6.06 (br. s., 1H), 4.21 (q, J=6.8 Hz, 1H), 3.98-4.12 (m, 1H), 3.44-3.61 (m, 2H), 3.07-3.26 (m, 3H), 2.75 (t, J=5.2 Hz, 2H), 2.55 (br. s., 2H), 1.36 (d, J=6.8 Hz, 3H), 1.26 (t, J=7.2 Hz, 3H); [M+H] calc'd for C$_{22}$H$_{25}$ClN$_4$O, 397; found, 397.

Compounds 64a and 64b: 3-((4-(4-chlorophenyl)-5,6-dihydropyridin-1(2H)-yl)methyl)imidazo[1,2-a]pyrido[3,2-e]pyrazin-6(5H)-one and 3-((4-(4-chlorophenyl)-5,6-dihydropyridin-1(2H)-yl)methyl)imidazo[1,5-a]pyrido[3,2-e]pyrazin-6(5H)-one

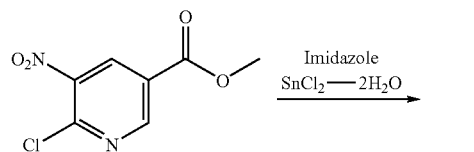

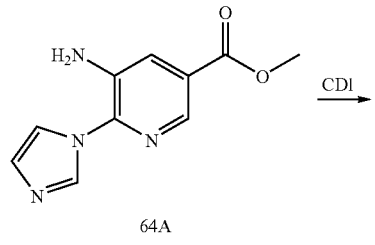

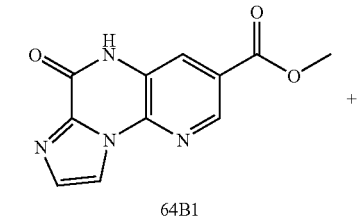

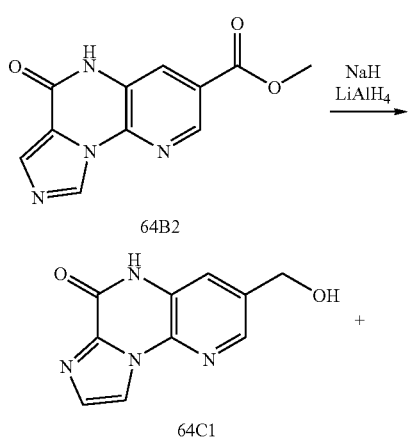

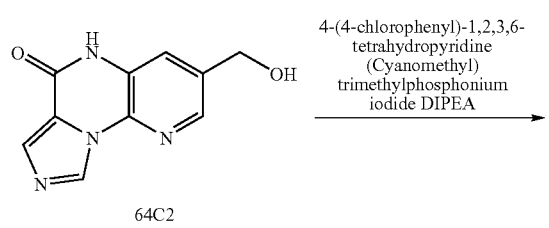

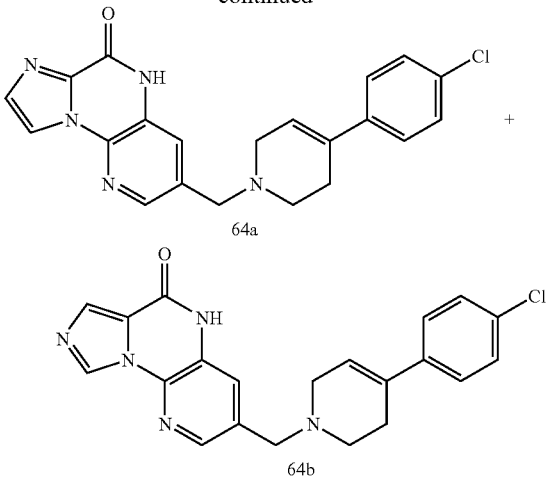

Compound 64A: Methyl 5-amino-6-(1H-imidazol-1-yl)nicotinate

Methyl 6-chloro-5-nitronicotinate (2.17 g, 10.0 mmol) was dissolved in ethyl acetate (55 mL) and imidazole (4.09 g, 60 mmol) was added. The reaction mixture was stirred at room temperature for 2 h and treated with 5 nCl$_2$-2H$_2$O (13.5 g, 60.0 mmol). It was heated to 70° C. for 2 h, diluted with potassium carbonate (sat. aq.) and extracted with ethyl acetate (5×20 mL). The combined organic extracts were dried (MgSO4), filtered and concentrated in vacuo to afford the title compound as a crude yellow solid, which was used in the next step without further purification. [M+H] calc'd for C$_{10}$H$_{10}$N$_4$O$_2$, 219; found, 219.

Compounds 64B1 and 64B2: Methyl 6-oxo-5,6-dihydroimidazo[1,2-a]pyrido[3,2-e]pyrazine-3-carboxylate and Methyl 6-oxo-5,6-dihydroimidazo[1,5-a]pyrido[3,2-e]pyrazine-3-carboxylate Crude methyl 5-amino-6-(1H-imidazol-1-yl)nicotinate from the step above (max 10.0 mmol) was suspended in 1,2-dichlorobenzene 90 mL and N,N'-carbonyl diimidazole (CDI; 2.43 g, 15.0 mmol) was added. The reaction mixture was heated in a closed vial at 170° C. for 2 h. The reaction mixture was cooled, poured into ethyl ether:hexanes (1:1, 300 mL) and the resulting solid was filtered and subjected to flash column chromatography on silica gel (330 g SiO2, dichloromethane:methanol 19:1-6:1). The solid was suspended in ethyl ether (30 mL), filtered off and dried in vacuum to afford the title compound as a yellow solid (0.467 g, 19%, ~2:1 mixture of imidazole regioisomers). [M+H] calc'd for C$_{11}$H$_8$N$_4$O$_3$, 245; found, 245.

Compounds 64C1 and 64C2: 3-(Hydroxymethyl)imidazo[1,2-a]pyrido[3,2-e]pyrazin-6(5H)-one and 3-(Hydroxymethyl)imidazo[1,5-a]pyrido[3,2-e]pyrazin-6(5H)-one Methyl 6-oxo-5,6-dihydroimidazo[1,2-a]pyrido[3,2-e]pyrazine-3-carboxylate (0.410 g, 1.68 mmol) was suspended in THF (20 mL) and sodium hydride (60% susp. in mineral oil, 0.112 g, 2.80 mmol) was added in one portion. The reaction mixture was stirred at room temperature for 1 h, cooled to −50° C. and LiAlH$_4$ (2M in THF, 1.7 mL, 3.4 mmol)

was added dropwise over 2 min. The reaction mixture was kept at −30-(−10)° C. for 3 h and more LiAlH₄ (2M in THF, 0.7 mL and 1.0 mL, 3.4 mmol combined) was added. The reaction mixture was cooled to −60° C. and slowly quenched with MeOH, warmed to room temperature and TFA and water were added until a clear solution resulted. The solution was subjected to preparative HPLC (1-30% acetonitrile in water, TFA buffered) to afford the title compound as a grey solid (147 mg, 40%; ~2:1 mixture of imidazole regioisomers). [M+H] calc'd for $C_{10}H_8N_4O_2$, 217; found, 217.

Compounds 64a and 64b: 3-((4-(4-chlorophenyl)-5, 6-dihydropyridin-1(2H)-yl)methyl)imidazo[1,2-a] pyrido[3,2-e]pyrazin-6(5H)-one and 3-((4-(4-chlorophenyl)-5,6-dihydropyridin-1(2H)-yl)methyl) imidazo[1,5-a]pyrido[3,2-e]pyrazin-6(5H)-one Compound 64 was prepared as a mixture using a procedure analogous to that described in connection with compound 1D, except that a mixture of 3-(hydroxymethyl)imidazo[1,2-a] pyrido[3,2-e]pyrazin-6(5H)-one and 3-(hydroxymethyl)imidazo[1,5-a]pyrido[3,2-e]pyrazin-6(5H)-one was used instead of (S)-3-(hydroxymethyl)-6a,7,8,9-tetrahydropyrido [3,2-e]pyrrolo[1,2-a]pyrazin-6(5H)-one and 4-(4-chlorophenyl)-1,2,3,6-tetrahydropyridine was used instead of 1-(4-chlorophenyl)piperazine. ¹H NMR (400 MHz, DMSO-d₆) δ (ppm): 2.51-2.53 (m, 2H) 2.63-2.76 (m, 2H) 3.12 (br. s., 2H) 3.72 (br. s., 2H) 6.20-6.23 (m, 1H) 7.37-7.40 (m, 2H) 7.45-7.48 (m, 2H) 7.61 (d, J=1.26 Hz, 1H) 7.76 (d, J=2.02 Hz, 1H) 7.91 (s, 1H) 8.27 (d, J=1.77 Hz, 1H) 8.38 (d, J=1.26 Hz, 1H); [M+H] calc'd for $C_{21}H_{18}ClN_5O$, 392; found, 392. Minor regioisomer: ¹H NMR (400 MHz, DMSO-d₆) δ (ppm): 2.50-2.53 (m, 2H) 2.63-2.76 (m, 2H) 3.12 (br. s., 2H) 3.70 (br. s., 2H) 6.20-6.23 (m, 1H) 7.37-7.40 (m, 2H) 7.45-7.48 (m, 2H) 7.70 (d, J=1.77 Hz, 1H) 7.91 (d, J=0.76 Hz, 1H) 8.21 (d, J=1.77 Hz, 1H) 8.91 (d, J=0.76 Hz, 1H); [M+H] calc'd for $C_{21}H_{18}ClN_5O$, 392; found, 392.

Compound 65: 3-((4-(4-chlorophenyl)-5,6-dihydropyridin-1(2H)-yl)methyl)-7,8,9,10-tetrahydro-5H-dipyrido[1,2-a:3',2'-e]pyrazin-6(6aH)-one

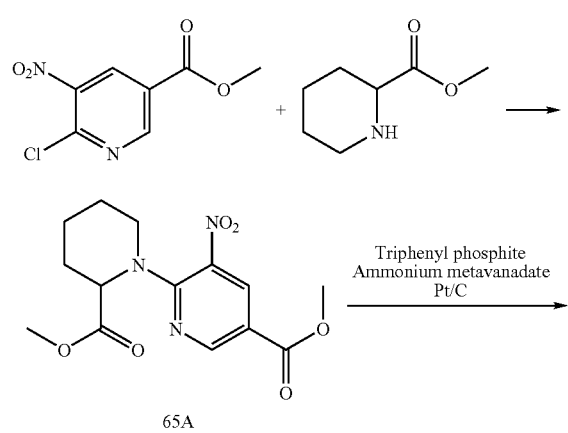

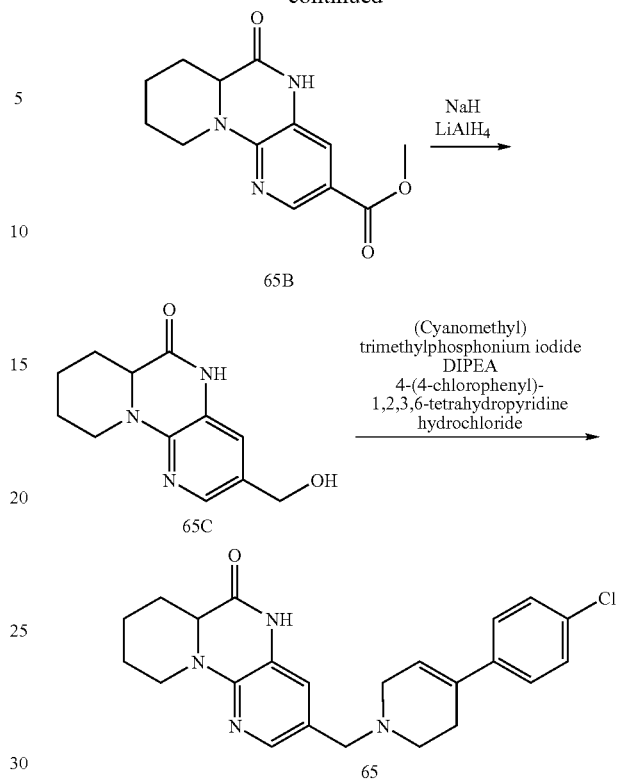

Compound 65A: Methyl 6-(2-(methoxycarbonyl) piperidin-1-yl)-5-nitronicotinate

Methyl 6-chloro-5-nitronicotinate (2.0 g, 9.23 mmol) was added to methyl piperidine-2-carboxylate (5.2 g, 36.92 mmol) while stirring at room temperature. The viscous yellow reaction was heated to 90° C. for one h and then allowed to cool back to room temperature. The reaction was diluted with dichloromethane (20 mL) and purified via column chromatography (220 g SiO2, 20-30% gradient, ethyl acetate in hexanes) to yield the title compound (2.95 g, 99% yield) as a yellow oil. [M+H] calc'd for C14H17N3O6, 324; found, 324.

Compound 65B: Methyl 6-oxo-6,6a,7,8,9,10-hexahydro-5H-dipyrido[1,2-a:3',2'-e]pyrazine-3-carboxylate Methyl 6-oxo-6,6a,7,8,9,10-hexahydro-5H-dipyrido[1,2-a:3',2'-e]pyrazine-3-carboxylate (2.95 g, 9.12 mmol) was dissolved in dichloromethane (20 mL). To the yellow solution was added ammonium metavanadate (20.0 mg, 0.171 mmol), triphenyl phosphite (aprox 30 ul, 0.097 mmol), and Pt/C (300 mg, 5% w/w). The reaction mixture was pressurized with hydrogen gas (110 psi) and stirred at room temperature for 16 h. The reaction was then depressurized and diluted with dichloromethane (100 mL) which was then refluxed for 30 min. The hot solution was filtered through a pad of celite and washed with hot dichloromethane (3×20 mL). The filtrate was concentrated to yield the title compound (1.91 g, 80%) as a white solid. [M+H] calc'd for C13H15N3O3, 262; found, 262.

Compound 65C: 3-(hydroxymethyl)-7,8,9,10-tetrahydro-5H-dipyrido[1,2-a:3',2'-e]pyrazin-6(6aH)-one Methyl 6-oxo-6,6a,7,8,9,10-hexahydro-5H-dipyrido[1,2-a:3',2'-e]pyrazine-3-carboxylate (500 mg, 1.91 mmol) was taken up in tetrahydrofuran (23 mL) in an inert environment. To the stirred suspension at room temperature was added NaH (60% dispersion in mineral oil, 114.7 mg, 2.87 mmol) and stirred 30 min. The reaction was then cooled to −45° C. and lithium aluminum hydride (2M in THF, 1.91 mL, 3.82 mmol) was added. The reaction was stirred at a temperature between −20 and −10° C. for 1 h. The reaction was then cooled back to −60° C. and MeOH (1 mL) followed by water (1 mL) was added. The reaction was allowed to stir at ambient temperature for 2 h and then poured into ethyl acetate (300 mL) and water (200 mL). The biphasic mixture was stirred vigorously and then filtered through a medium frit. The layers were separated and the aqueous phase was extracted with ethyl acetate (3×100 mL). The organic layers were combined, washed with brine (100 mL), dried with sodium sulfate and concentrated to yield the title compound (429.4 mg, 96%) as a white solid. [M+H] calc'd for C12H15N3O2, 234; found, 234.

Compound 65: 3-((4-(4-chlorophenyl)-5,6-dihydropyridin-1(2H)-yl)methyl)-7,8,9,10-tetrahydro-5H-dipyrido[1,2-a:3',2'-e]pyrazin-6(6aH)-one 3-(hydroxymethyl)-7,8,9,10-tetrahydro-5H-dipyrido[1,2-a:3',2'-e]pyrazin-6(6aH)-one (100 mg, 0.43 mmol) was suspended in propionitrile (1 mL) and (cyanomethyl)trimethylphosphonium iodide (103 mg, 0.41 mmol) was added followed by N-ethyl-N-isopropylpropan-2-amine (180 ul, 1.03 mmol). To the stirred mixture was then added 4-(4-chlorophenyl)-1,2,3,6-tetrahydropyridine hydrochloride (94.0 mg, 0.41 mmol). The reaction was heated to 90° C. with stirring 2 h. The reaction was then cooled to room temperature and diluted with water (3 mL) and filtered. The solids were collected and refluxed in ethanol (5 mL) for 1 h. The suspension was cooled back to room temperature and filtered. The precipitate was filtered off and dried in vacuum to afford the title compound (31.8 mg, 18%) as a white solid. $^1$H NMR (DMSO-d$_6$) δ (ppm): 10.47 (s, 1H), 7.66 (d, J=2.0 Hz, 1H), 7.41-7.48 (m, 2H), 7.33-7.40 (m, 2H), 6.98 (d, J=2.0 Hz, 1H), 6.18 (s, 1H), 4.43-4.57 (m, 1H), 3.84 (d, J=11.4 Hz, 1H), 3.42 (s, 2H), 3.01 (d, J=2.8 Hz, 2H), 2.55-2.66 (m, 3H), 2.44 (br. s., 2H), 1.98-2.09 (m, 1H), 1.78-1.92 (m, 1H), 1.57-1.70 (m, 1H), 1.33-1.56 (m, 3H). [M+H] calc'd for C23H25ClN4O, 409; found, 409.

Compound 66: 3-((4-(4-chlorophenyl)piperazin-1-yl)methyl)-7,8,9,10-tetrahydro-5H-dipyrido[1,2-a:3',2'-e]pyrazin-6(6aH)-one

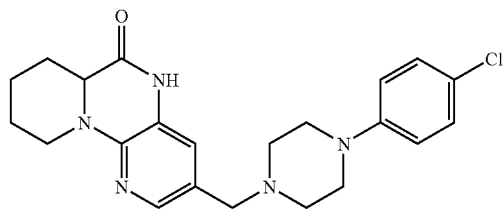

3-(hydroxymethyl)-7,8,9,10-tetrahydro-5H-dipyrido[1,2-a:3',2'-e]pyrazin-6(6aH)-one (100 mg, 0.43 mmol) was suspended in propionitrile (1 mL) and (cyanomethyl)trimethylphosphonium iodide (103 mg, 0.41 mmol) was added followed by N-ethyl-N-isopropylpropan-2-amine (180 ul, 1.03 mmol). To the stirred mixture was then added 1-(4-chlorophenyl)piperazine hydrochloride (94.0 mg, 0.41 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The solids were collected to afford the title compound (69.9 mg, 39%) as a white solid. $^1$H NMR (DMSO-d$_6$) δ (ppm): 10.47 (s, 1H), 7.65 (d, J=1.8 Hz, 1H), 7.21 (d, J=9.1 Hz, 2H), 6.97 (d, J=1.8 Hz, 1H), 6.92 (d, J=9.1 Hz, 2H), 4.50 (d, J=12.9 Hz, 1H), 3.83 (dd, J=11.2, 2.7 Hz, 1H), 3.34 (d, J=5.6 Hz, 2H), 3.01-3.17 (m, 4H), 2.55-2.65 (m, 1H), 2.37-2.48 (m, 4H), 1.98-2.08 (m, 1H), 1.85 (d, J=12.4 Hz, 1H), 1.63 (d, J=12.6 Hz, 1H), 1.32-1.56 (m, 3H). [M+H] calc'd for C22H26ClN5O, 412; found, 412.

Compound 67: 3-((4-(4-chlorophenyl)piperidin-1-yl)methyl)-7,8,9,10-tetrahydro-5H-dipyrido[1,2-a:3',2'-e]pyrazin-6(6aH)-one

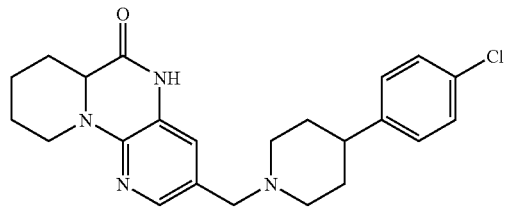

3-(hydroxymethyl)-7,8,9,10-tetrahydro-5H-dipyrido[1,2-a:3',2'-e]pyrazin-6(6aH)-one (100 mg, 0.43 mmol) was suspended in propionitrile (1 mL) and (cyanomethyl)trimethylphosphonium iodide (103 mg, 0.41 mmol) was added followed by N-ethyl-N-isopropylpropan-2-amine (180 ul, 1.03 mmol). To the stirred mixture was then added 4-(4-chlorophenyl)piperidine hydrochloride (95.0 mg, 0.41 mmol). The reaction was heated to 90° C. with stirring for 2 h. The reaction was cooled to room temperature and purified via HPLC (10-80 MeCN/H$_2$O, TFA buffered). The fractions were collected and lyophilized to yield the title compound (57.3 mg, 32%) as a white solid. $^1$H NMR (DMSO-d$_6$) δ: 13.44 (br. s., 1H), 10.82 (s, 1H), 9.52 (br. s., 1H), 7.84 (d, J=2.0 Hz, 1H), 7.36-7.42 (m, 2H), 7.24 (d, J=8.3 Hz, 2H), 7.06 (d, J=2.0 Hz, 1H), 4.58 (d, J=13.1 Hz, 1H), 4.21 (d, J=4.5 Hz, 2H), 3.97 (dd, J=11.6, 2.8 Hz, 1H), 3.46 (d, J=11.6 Hz, 2H), 2.96-3.07 (m, 2H), 2.79-2.85 (m, 1H), 2.67 (td, J=12.8, 2.7 Hz, 1H), 2.06-2.10 (m, 1H), 1.95-2.02 (m, 2H), 1.72-1.91 (m, 3H), 1.64-1.67 (m, 1H), 1.33-1.58 (m, 3H). [M+H] calc'd for C23H27ClN4O, 411; found, 411.

Compound 68: (S)-3-((4-(4-chlorophenyl)-5,6-dihydropyridin-1(2H)-yl)methyl)-7,8,9,10-tetrahydro-5H-dipyrido[1,2-a:3',2'-e]pyrazin-6(6aH)-one

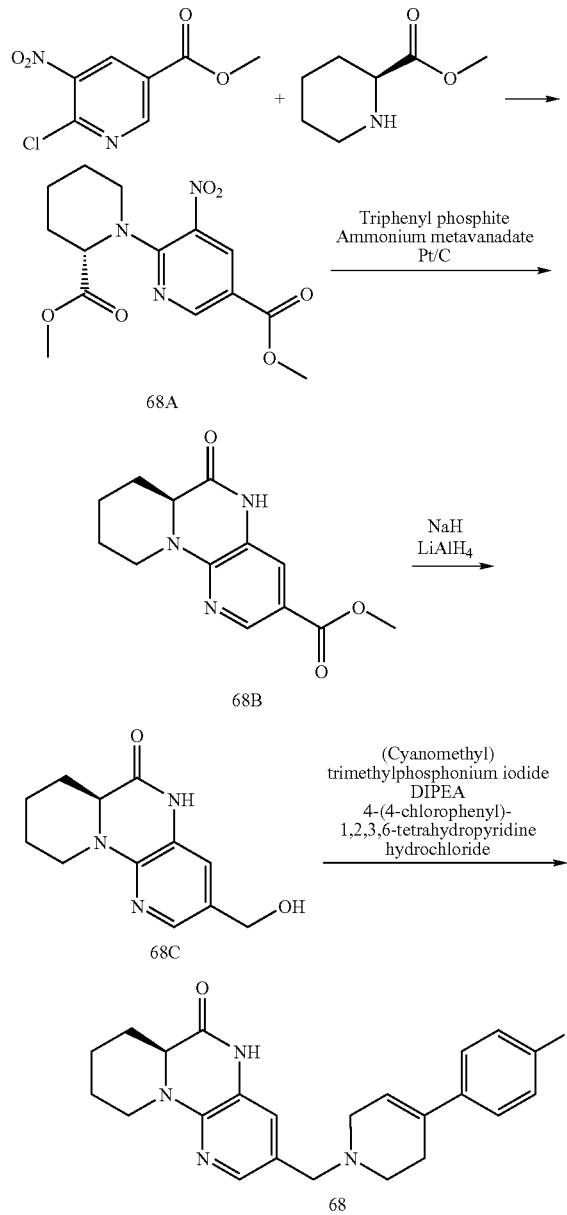

Compound 68A: (S)-methyl 6-(2-(methoxycarbonyl)piperidin-1-yl)-5-nitronicotinate Methyl 6-chloro-5-nitronicotinate (2.333 g, 10.77 mmol) was added to (S)-methyl piperidine-2-carboxylate (2.93 g, 20.46 mmol) neat while stirring. The reaction was stirred 1 h at 90° C., cooled to room temperature and taken up in ethyl acetate (10 mL). The mixture was purified by SiO$_2$ (330 g, 20-30% EA in Hexanes) to yield 3.4 g (98%) of the title compound as a yellow oil. [M+H] calc'd for C14H17N3O6, 324; found, 324.

Compound 68B: (S)-methyl 6-oxo-6,6a,7,8,9,10-hexahydro-5H-dipyrido[1,2-a:3',2'-e]pyrazine-3-carboxylate In a bomb hydroginator, (S)-methyl 6-(2-(methoxycarbonyl)piperidin-1-yl)-5-nitronicotinate (1.95 g, 6.03 mmol), triphenyl phosphite (0.019 ml, 0.060 mmol), ammonium vanadate (0.056 g, 0.483 mmol) and platinum (5% on carbon, 0.235 g, 0.060 mmol) were mixed in dichloromethane (Volume: 30.2 ml) to give a suspension. The bomb was sealed and pressurized to 110 psi with hydrogen gas. The reaction was stirred at 110 psi 16 h, depressurized, diluted with DCM (100 mL) and refluxed 10 minutes. The hot mixture was filtered through celite and washed with DCM (50 mL). The filtrate was concentrated in vacuo to yield 1.4 g (89%) of the product as a white solid and used without further purification. [M+H] calc'd for C13H15N3O3, 262; found, 262.

Compound 68C: (S)-3-(hydroxymethyl)-7,8,9,10-tetrahydro-5H-dipyrido[1,2-a:3',2'-e]pyrazin-6(6aH)-one In round-bottomed flask, (S)-methyl 6-oxo-6,6a,7,8,9,10-hexahydro-5H-dipyrido[1,2-a:3',2'-e]pyrazine-3-carboxylate (860 mg, 3.29 mmol) was dissolved in Tetrahydrofuran (Volume: 41 mL) to give a clear solution. The solution was cooled to 0° C. and NaH (197 mg, 4.94 mmol) was added. The reaction was allowed to stir at RT for 0.5 hour. The translucent solution was then cooled to −78° C. and LAH was added over two minutes. The reaction temperature was maintained between −30° C. and −20° C. for 3 hours while stirring, then cooled to −78° C. Methanol (3 ml, gas evolution) and water (1 ml) were added. The reaction was stirred at room temperature for 30 minutes. The crude product was added to 400 ml ethyl acetate. Water (100 ml) was added and the mixture stirred for 1 hr. The mixture was filtered through medium frit to remove tan solids which were discarded. The aqueous layer was extracted with ethyl acetate (1×100 mL). The organic fractions were combined, washed once with brine and dried with sodium sulfate and concentrated to yield 743 mg (97%) of the product as a white residue. [M+H] calc'd for C12H15N3O2, 234; found, 234.

Compound 68: (S)-3-((4-(4-chlorophenyl)-5,6-dihydropyridin-1(2H)-yl)methyl)-7,8,9,10-tetrahydro-5H-dipyrido[1,2-a:3',2'-e]pyrazin-6(6aH)-on (S)-3-(hydroxymethyl)-7,8,9,10-tetrahydro-5H-dipyrido[1,2-a:3',2'-e]pyrazin-6(6aH)-one (100 mg, 0.429 mmol) was suspended in propionitrile (1 mL) and (cyanomethyl)trimethylphosphonium iodide (125.0 mg, 0.51 mmol) was added followed by N-ethyl-N-isopropylpropan-2-amine (225 ul, 1.3 mmol). To the stirred mixture was then added 4-(4-chlorophenyl)-1,2,3,6-tetrahydropyridine hydrochloride (109 mg, 0.472 mmol). The reaction was heated to 90° C. with stirring for 16 h. The reaction was then cooled to room temperature, diluted with EtOH (3 ml) and water (~300 ul), then filtered. The solids were collected and refluxed in ethanol (5 mL) for 2 h. The suspension was cooled back to room temperature and filtered. The precipitate was filtered off and dried in vacuum to afford the title compound (75.1 mg, 43%) as a white solid. $^1$H NMR (DMSO-d$_6$) δ (ppm): 10.47 (s, 1H), 7.66 (d, J=1.8 Hz, 1H), 7.40-7.48 (m, 2H), 7.34-7.40 (m, 2H), 6.98 (d, J=2.0 Hz, 1H), 6.18 (s, 1H), 4.45-4.55 (m, 1H), 3.84 (d, J=11.4 Hz, 1H), 3.42 (s, 2H), 3.01 (d, J=2.8 Hz, 2H), 2.56-2.66 (m, 3H), 2.44 (br. s., 2H), 1.98-2.08 (m, 1H), 1.80-1.89 (m, 1H), 1.59-

1.68 (m, 1H), 1.34-1.57 (m, 3H). [M+H] calc'd for C23H25ClN4O, 409; found, 409. MP: 201.6° C.

Compound 69: (S)-3-((4-(4-chlorophenyl)piperazin-1-yl)methyl)-7,8,9,10-tetrahydro-5H-dipyrido[1,2-a:3',2'-e]pyrazin-6(6aH)-one

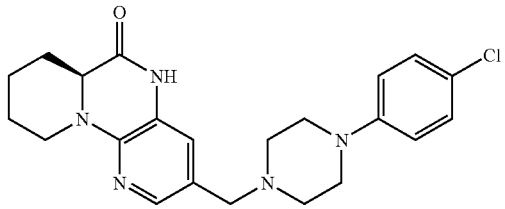

(S)-3-(hydroxymethyl)-7,8,9,10-tetrahydro-5H-dipyrido[1,2-a:3',2'-e]pyrazin-6(6aH)-one (100 mg, 0.429 mmol) was suspended in propionitrile (1 mL) and (cyanomethyl)trimethylphosphonium iodide (125.0 mg, 0.51 mmol) was added followed by N-ethyl-N-isopropylpropan-2-amine (225 ul, 1.3 mmol). To the stirred mixture was then added 1-(4-chlorophenyl)piperazine hydrochloride (110 mg, 0.472 mmol). The reaction was heated to 90° C. with stirring for 16 h. The reaction was then cooled to room temperature, diluted with EtOH (3 ml) and water (~300 ul), then filtered. The solids were collected and refluxed in ethanol (5 mL) for 2 h. The suspension was cooled back to room temperature and filtered. The precipitate was filtered off and dried in vacuum to afford the title compound (67.3 mg, 43%) as a white solid. $^1$H NMR (DMSO-d$_6$) δ (ppm): 10.47 (s, 1H), 7.65 (d, J=2.0 Hz, 1H), 7.21 (d, J=9.1 Hz, 2H), 6.97 (d, J=2.0 Hz, 1H), 6.88-6.95 (m, 2H), 4.45-4.55 (m, 1H), 3.83 (dd, J=11.4, 2.8 Hz, 1H), 3.35 (s, 2H), 3.05-3.16 (m, 5H), 2.60 (td, J=12.6, 2.5 Hz, 1H), 2.38-2.48 (m, 3H), 2.03 (d, J=12.6 Hz, 1H), 1.77-1.91 (m, 1H), 1.63 (d, J=12.6 Hz, 1H), 1.33-1.56 (m, 3H). [M+H] calc'd for C22H26ClN5O, 412; found, 412.

Compound 70: (S)-3-((4-(4-chlorophenyl)piperidin-1-yl)methyl)-7,8,9,10-tetrahydro-5H-dipyrido[1,2-a:3',2'-e]pyrazin-6(6aH)-one

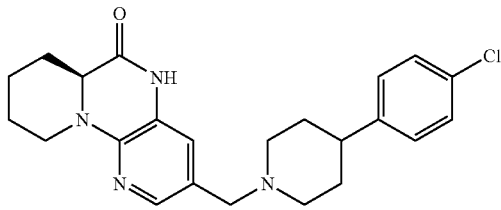

(S)-3-(hydroxymethyl)-7,8,9,10-tetrahydro-5H-dipyrido[1,2-a:3',2'-e]pyrazin-6(6aH)-one (100 mg, 0.429 mmol) was suspended in propionitrile (1 mL) and (cyanomethyl)trimethylphosphonium iodide (125.0 mg, 0.51 mmol) was added followed by N-ethyl-N-isopropylpropan-2-amine (225 ul, 1.3 mmol). To the stirred mixture was then added 4-(4-chlorophenyl)piperidine hydrochloride (109 mg, 0.472 mmol). The reaction was heated to 90° C. with stirring for 16 h. The crude reaction was cooled to room temperature and concentrated to a residue, then taken up in 3 mL DMSO and purified via HPLC (55-90% acetonitrile in water, ammonium bicarbonate buffer). The fractions were combined and concentrated until a white solid precipitated. The precipitate was filtered off and dried in vacuum to afford the title compound (22.1 mg, 12.5%) as a white solid. $^1$H NMR (DMSO-d$_6$) δ (ppm): 10.46 (s, 1H), 7.64 (d, J=2.0 Hz, 1H), 7.29-7.37 (m, 2H), 7.21-7.28 (m, 2H), 6.96 (d, J=2.0 Hz, 1H), 4.42-4.58 (m, 1H), 3.83 (dd, J=11.4, 2.8 Hz, 1H), 3.32 (s, 2H), 2.80-2.95 (m, 2H), 2.54-2.66 (m, 1H), 1.92-2.08 (m, 3H), 1.83 (br. s., 1H), 1.66-1.77 (m, 2H), 1.33-1.66 (m, 6H). [M+H] calc'd for C23H27ClN4O, 411; found, 411.

Compound 71: (S)-4-(4-((6-oxo-6,6a,7,8,9,10-hexahydro-5H-dipyrido[1,2-a:3',2'-e]pyrazin-3-yl)methyl)piperazin-1-yl)benzonitrile

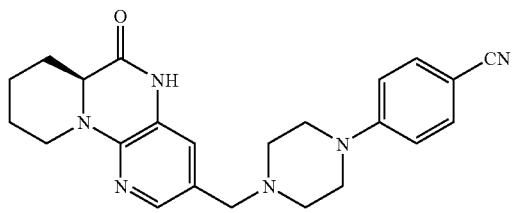

(S)-3-(hydroxymethyl)-7,8,9,10-tetrahydro-5H-dipyrido[1,2-a:3',2'-e]pyrazin-6(6aH)-one (86.0 mg, 0.369 mmol) was suspended in propionitrile (1 mL) and (cyanomethyl)trimethylphosphonium iodide (108.0 mg, 0.442 mmol) was added followed by N-ethyl-N-isopropylpropan-2-amine (193 ul, 1.1 mmol). To the stirred mixture was then added 4-(piperazin-1-yl)benzonitrile (76 mg, 0.406 mmol). The reaction was heated to 90° C. with stirring for 16 h. The crude reaction was cooled to room temperature and concentrated to a residue, then taken up in 3 mL DMSO and purified via HPLC (55-90% acetonitrile in water, ammonium bicarbonate buffer). The fractions were combined and concentrated until a white solid precipitated. The precipitate was filtered off and dried in vacuum to afford the title compound (29.7 mg, 20.0%) as a white solid. $^1$H NMR (DMSO-d$_6$) δ (ppm): 10.48 (s, 1H), 7.65 (s, 1H), 7.57 (d, J=8.8 Hz, 2H), 6.94-7.04 (m, 3H), 4.44-4.55 (m, 1H), 3.79-3.88 (m, 1H), 3.35 (br. s., 2H), 3.30 (br. s., 4H), 2.54-2.69 (m, 1H), 2.45 (br. s., 4H), 1.97-2.09 (m, 1H), 1.80-1.90 (m, 1H), 1.57-1.69 (m, 1H), 1.32-1.56 (m, 3H). [M+H] calc'd for C23H26N6O, 403; found, 403. MP: 212.2° C.

Compound 72: (S)-6-(4-((6-oxo-6,6a,7,8,9,10-hexahydro-5H-dipyrido[1,2-a:3',2'-e]pyrazin-3-yl)methyl)piperazin-1-yl)nicotinonitrile

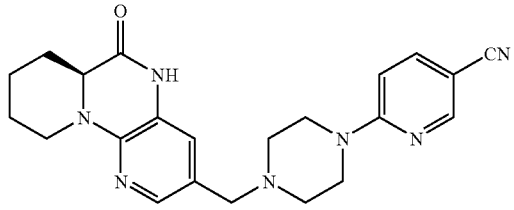

(S)-3-(hydroxymethyl)-7,8,9,10-tetrahydro-5H-dipyrido[1,2-a:3',2'-e]pyrazin-6(6aH)-one (89.0 mg, 0.382 mmol) was suspended in propionitrile (1 mL) and (cyanomethyl)

trimethylphosphonium iodide (111.0 mg, 0.458 mmol) was added followed by N-ethyl-N-isopropylpropan-2-amine (200 ul, 1.1 mmol). To the stirred mixture was then added 6-(piperazin-1-yl)nicotinonitrile (79 mg, 0.420 mmol). The reaction was heated to 90° C. with stirring for 16 h. The crude reaction was cooled to room temperature and concentrated to a residue, then taken up in 3 mL DMSO and purified via HPLC (55-90% acetonitrile in water, ammonium bicarbonate buffer). The fractions were combined and concentrated until a white solid precipitated. The precipitate was filtered off and dried in vacuum to afford the title compound (54.2 mg, 35.2%) as a white solid. $^1$H NMR (DMSO-d$_6$) δ (ppm): 10.48 (br. s., 1H), 8.46 (d, J=2.3 Hz, 1H), 7.83 (dd, J=9.1, 2.5 Hz, 1H), 7.64 (d, J=2.0 Hz, 1H), 6.97 (d, J=1.8 Hz, 1H), 6.90 (d, J=9.1 Hz, 1H), 4.50 (d, J=12.9 Hz, 1H), 3.83 (dd, J=11.4, 2.8 Hz, 1H), 3.55-3.70 (m, 4H), 3.34 (s, 2H), 2.59 (td, J=12.6, 2.4 Hz, 1H), 2.40 (t, J=4.8 Hz, 4H), 2.03 (d, J=12.6 Hz, 1H), 1.84 (d, J=12.1 Hz, 1H), 1.63 (d, J=13.6 Hz, 1H), 1.29-1.56 (m, 3H). [M+H] calc'd for C22H25N7O, 404; found, 404.

Compound 73: (S)—N-ethyl-4-(4-((6-oxo-6,6a,7,8,9,10-hexahydro-5H-dipyrido[1,2-a:3',2'-e]pyrazin-3-yl)methyl)piperazin-1-yl)benzamide Compound 73A: (S)-ethyl 4-(4-((6-oxo-6,6a,7,8,9,10-hexahydro-5H-dipyrido[1,2-a:3',2'-e]pyrazin-3-yl)methyl)piperazin-1-yl)benzoate (S)-3-(hydroxymethyl)-7,8,9,10-tetrahydro-5H-dipyrido[1,2-a:3',2'-e]pyrazin-6(6aH)-one (400 mg, 1.715 mmol) was suspended in propionitrile (4.3 mL) and (cyanomethyl)trimethylphosphonium iodide (500.0 mg, 2.06 mmol) was added followed by N-ethyl-N-isopropylpropan-2-amine (898 ul, 5.1 mmol). To the stirred mixture was then added ethyl ethyl 4-(piperazin-1-yl)benzoate (402 mg, 1.715 mmol). The reaction was heated to 90° C. with stirring for 16 h. The reaction was then cooled to room temperature, diluted with EtOH (8 ml) and water (1 mL), then filtered. The precipitate was filtered off and dried in vacuum to afford the title compound (508 mg, 65.9%) as a brown solid. $^1$H NMR (DMSO-d$_6$) δ (ppm): 10.48 (s, 1H), 7.77 (d, J=9.1 Hz, 2H), 7.65 (d, J=2.0 Hz, 1H), 6.90-7.01 (m, 3H), 4.50 (d, J=12.9 Hz, 1H), 4.23 (q, J=7.1 Hz, 2H), 3.84 (dd, J=11.4, 2.8 Hz, 1H), 3.35 (s, 2H), 3.28 (br. s., 4H), 2.60 (td, J=12.6, 2.5 Hz, 1H), 2.40-2.47 (m, 4H), 2.03 (d, J=12.9 Hz, 1H), 1.80-1.89 (m, 1H), 1.64 (d, J=12.6 Hz, 1H), 1.33-1.57 (m, 3H), 1.28 (t, J=7.1 Hz, 3H). [M+H] calc'd for C25H31N5O3, 450; found, 450.

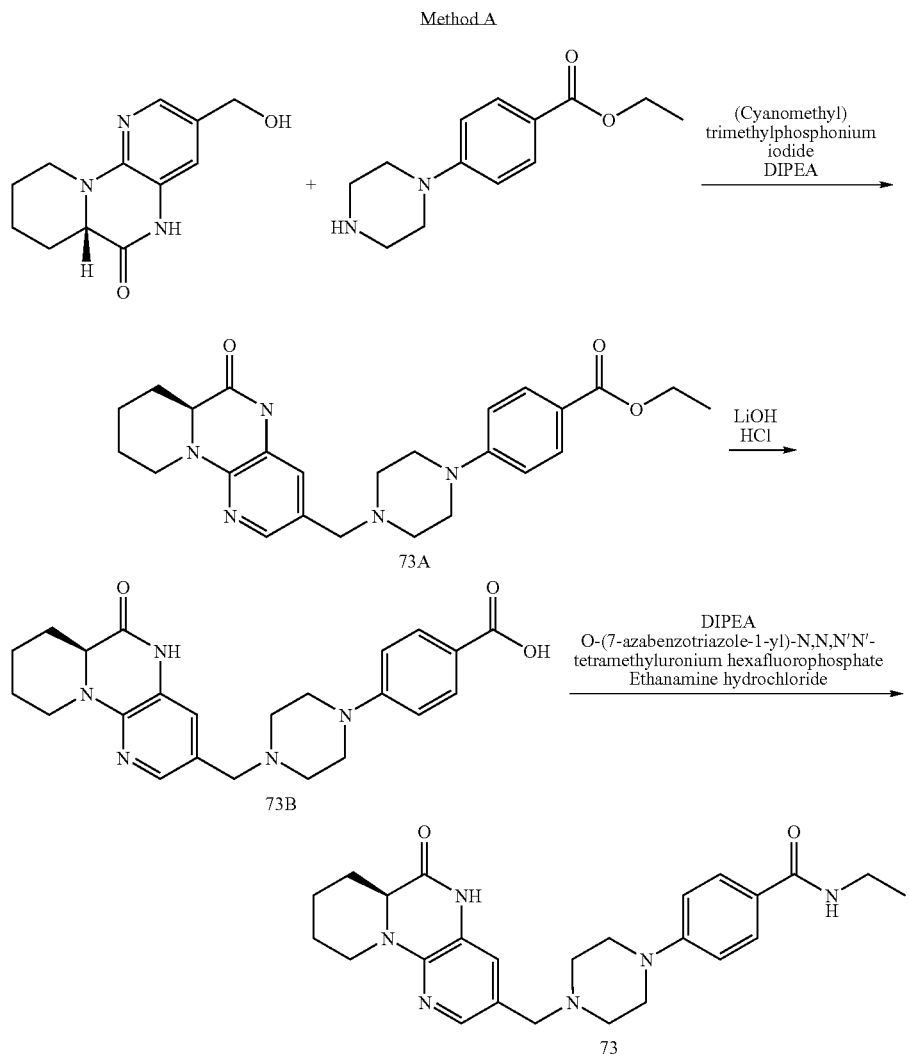

Compound 73B: (S)-4-(4-((6-oxo-6,6a,7,8,9,10-hexahydro-5H-dipyrido[1,2-a:3',2'-e]pyrazin-3-yl)methyl)piperazin-1-yl)benzoic acid (S)-methyl 4-(4-((6-oxo-6,6a,7,8,9,10-hexahydro-5H-dipyrido[1,2-a:3',2'-e]pyrazin-3-yl)methyl)piperazin-1-yl)benzoate (152 mg, 0.349 mmol) was taken up in dioxane (2 ml) and LiOH (1N, 2 ml, 2.000 mmol) was added. The reaction was stirred 16 h at room temperature. The reaction was concentrated in-vacuo and the residue was taken up in water (5 mL) and acidified (4.5N HCl) to pH 4. A white precipitate formed. The precipitate was filtered off and dried in vacuum to afford the title compound (122.8 mg, 83%) as a white solid. [M+H] calc'd for C23H27N5O3, 422; found, 422.

Compound 73: (S)—N-ethyl-4-(4-((6-oxo-6,6a,7,8,9,10-hexahydro-5H-dipyrido[1,2-a:3',2'-e]pyrazin-3-yl)methyl)piperazin-1-yl)benzamide (S)-4-(4-((6-oxo-6,6a,7,8,9,10-hexahydro-5H-dipyrido[1,2-a:3',2'-e]pyrazin-3-yl)methyl)piperazin-1-yl)benzoic acid (122 mg, 0.29 mmol) was taken up in DMF (2.9 mL). To the mixture was added N-ethyl-N-isopropylpropan-2-amine (152 ul, 0.87 mmol), O-(7-azabenzotriazole-1-yl)-N,N,N'N'-tetramethyluronium hexafluorophosphate (165 mg, 0.434 mmol), and ethanamine hydrochloride (26.0 mg, 0.318 mmol). The reaction was stirred at room temperature overnight. The reaction was purified via HPLC (10-80 MeCN/H2O, TFA buffered). The fractions were collected and lyophilized to yield 135 mg (85%) of the product as a white solid. $^1$H NMR (DMSO-d$_6$) δ (ppm): 10.82 (s, 1H), 9.83 (br. s., 1H), 8.25 (t, J=5.6 Hz, 1H), 7.84 (d, J=2.0 Hz, 1H), 7.77 (d, J=8.8 Hz, 2H), 6.94-7.12 (m, 3H), 4.59 (d, J=13.1 Hz, 1H), 4.27 (br. s., 2H), 3.85-4.10 (m, 3H), 3.43 (d, J=10.4 Hz, 2H), 3.21-3.30 (m, 2H), 2.95-3.19 (m, 4H), 2.61-2.72 (m, 1H), 2.05 (d, J=11.8 Hz, 1H), 1.87 (d, J=12.4 Hz, 1H), 1.66 (d, J=12.1 Hz, 1H), 1.31-1.62 (m, 3H), 1.09 (t, J=7.2 Hz, 3H). [M+H] calc'd for C23H27N5O3, 449; found, 449. MP: 232.6° C.

Method B

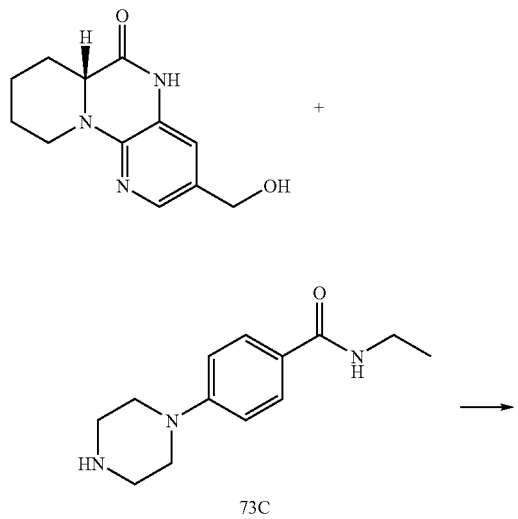

-continued

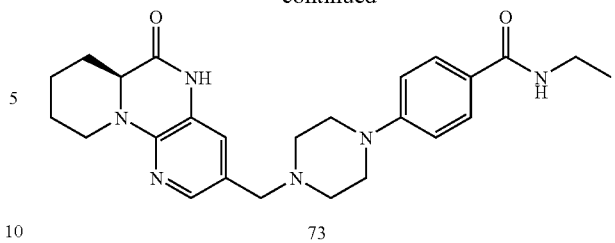

73

Compound 73: (S)—N-ethyl-4-(4-((6-oxo-6,6a,7,8,9,10-hexahydro-5H-dipyrido[1,2-a:3',2'-e]pyrazin-3-yl)methyl)piperazin-1-yl)benzamide To a suspension of (S)-3-(hydroxymethyl)-7,8,9,10-tetrahydro-5H-dipyrido[1,2-a:3',2'-e]pyrazin-6(6aH)-one (800 mg, 3.43 mmol) was added (cyanomethyl)trimethylphosphonium iodide (1000 mg, 4.12 mmol) and DIEA (1797 µl, 10.29 mmol) and N-ethyl-4-(piperazin-1-yl)benzamide (800 mg, 3.43 mmol)). The vial was heated to 90° C. for 16 hours. The crude reaction was cooled to RT and filtered. The resulting solid were collected and suspended in EtOH (24 mL), heated to reflux, then cooled to RT and filtered. The resulting material was rinsed with EtOH to give a white solid.

Compound 74: (S)—N-methyl-4-(4-((6-oxo-6,6a,7,8,9,10-hexahydro-5H-dipyrido[1,2-a:3',2'-e]pyrazin-3-yl)methyl)piperazin-1-yl)benzamide

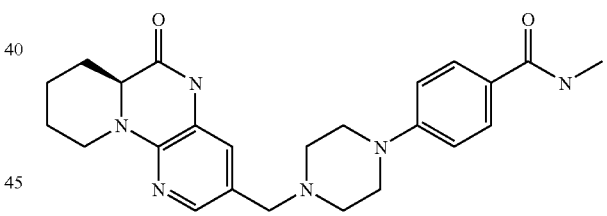

(S)-4-(4-((6-oxo-6,6a,7,8,9,10-hexahydro-5H-dipyrido[1,2-a:3',2'-e]pyrazin-3-yl)methyl)piperazin-1-yl)benzoic acid (50 mg, 0.119 mmol) was taken up in DMF (0.5 mL). To the mixture was added N1-((ethylimino)methylene)-N3,N3-dimethylpropane-1,3-diamine hydrochloride (34.1 mg, 0.178 mmol), 1H-benzo[d][1,2,3]triazol-1-ol hydrate (27.2 mg, 0.178 mmol), 4-methylmorpholine (0.065 mL, 0.593 mmol) and methanamine hydrochloride (8.01 mg, 0.119 mmol). The reaction was stirred at room temperature overnight. To the stirred solution was added water (2 mL) and the precipitate was filtered, collected, and dried in vacuum to afford the title compound (23.8 mg, 46.2%) as a white solid. $^1$H NMR (DMSO-d$_6$) δ (ppm): 10.49 (s, 1H), 8.14 (q, J=4.5 Hz, 1H), 7.58-7.80 (m, 3H), 6.82-7.04 (m, 3H), 4.51 (d, J=12.9 Hz, 1H), 3.84 (dd, J=11.2, 2.7 Hz, 1H), 3.30-3.51 (m, 3H), 3.23 (br. s., 4H), 2.74 (d, J=4.5 Hz, 3H), 2.61 (td, J=12.7, 2.7 Hz, 1H), 2.49 (br. s., 3H), 2.04 (d, J=12.6 Hz, 1H), 1.85 (d, J=12.1

Hz, 1H), 1.64 (d, J=12.6 Hz, 1H), 1.33-1.59 (m, 3H). [M+H] calc'd for C24H30N6O2, 435; found, 435.

Compound 75: (S)—N-cyclopropyl-4-(4-((6-oxo-6,6a,7,8,9,10-hexahydro-5H-dipyrido[1,2-a:3',2'-e]pyrazin-3-yl)methyl)piperazin-1-yl)benzamide

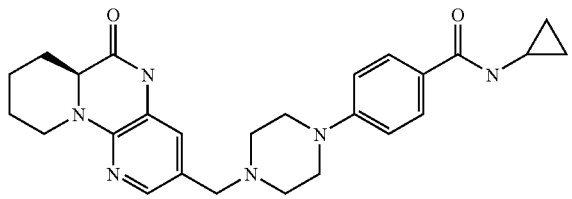

(S)-4-(4-((6-oxo-6,6a,7,8,9,10-hexahydro-5H-dipyrido[1,2-a:3',2'-e]pyrazin-3-yl)methyl)piperazin-1-yl)benzoic acid (50 mg, 0.119 mmol) was taken up in DMF (0.5 mL). To the mixture was added N1-((ethylimino)methylene)-N3,N3-dimethylpropane-1,3-diamine hydrochloride (34.1 mg, 0.178 mmol), 1H-benzo[d][1,2,3]triazol-1-ol hydrate (27.2 mg, 0.178 mmol), 4-methylmorpholine (0.065 mL, 0.593 mmol) and cyclopropanamine (6.77 mg, 0.119 mmol). The reaction was stirred at room temperature overnight. To the stirred solution was added water (2 mL) and the precipitate was filtered, collected, and dried in vacuum to afford the title compound (41.2 mg, 75.0%) as a white solid. $^1$H NMR (DMSO-d$_6$) δ (ppm): 10.48 (s, 1H), 8.13 (d, J=4.0 Hz, 1H), 7.57-7.76 (m, 3H), 6.80-7.02 (m, 3H), 4.50 (d, J=13.1 Hz, 1H), 3.84 (dd, J=11.4, 2.8 Hz, 1H), 3.35 (br. s., 2H), 3.22 (br. s., 4H), 2.79 (td, J=7.3, 3.9 Hz, 1H), 2.60 (td, J=12.6, 2.7 Hz, 1H), 2.46 (br. s., 4H), 2.03 (d, J=12.9 Hz, 1H), 1.83 (br. s., 1H), 1.64 (d, J=12.9 Hz, 1H), 1.31-1.57 (m, 3H), 0.61-0.69 (m, 2H), 0.48-0.56 (m, 2H). [M+H] calc'd for C26H32N6O2, 461; found, 461.

Compound 76: (S)—N-isopropyl-6-(4-((6-oxo-6,6a,7,8,9,10-hexahydro-5H-dipyrido[1,2-a:3',2'-e]pyrazin-3-yl)methyl)piperazin-1-yl)nicotinamide

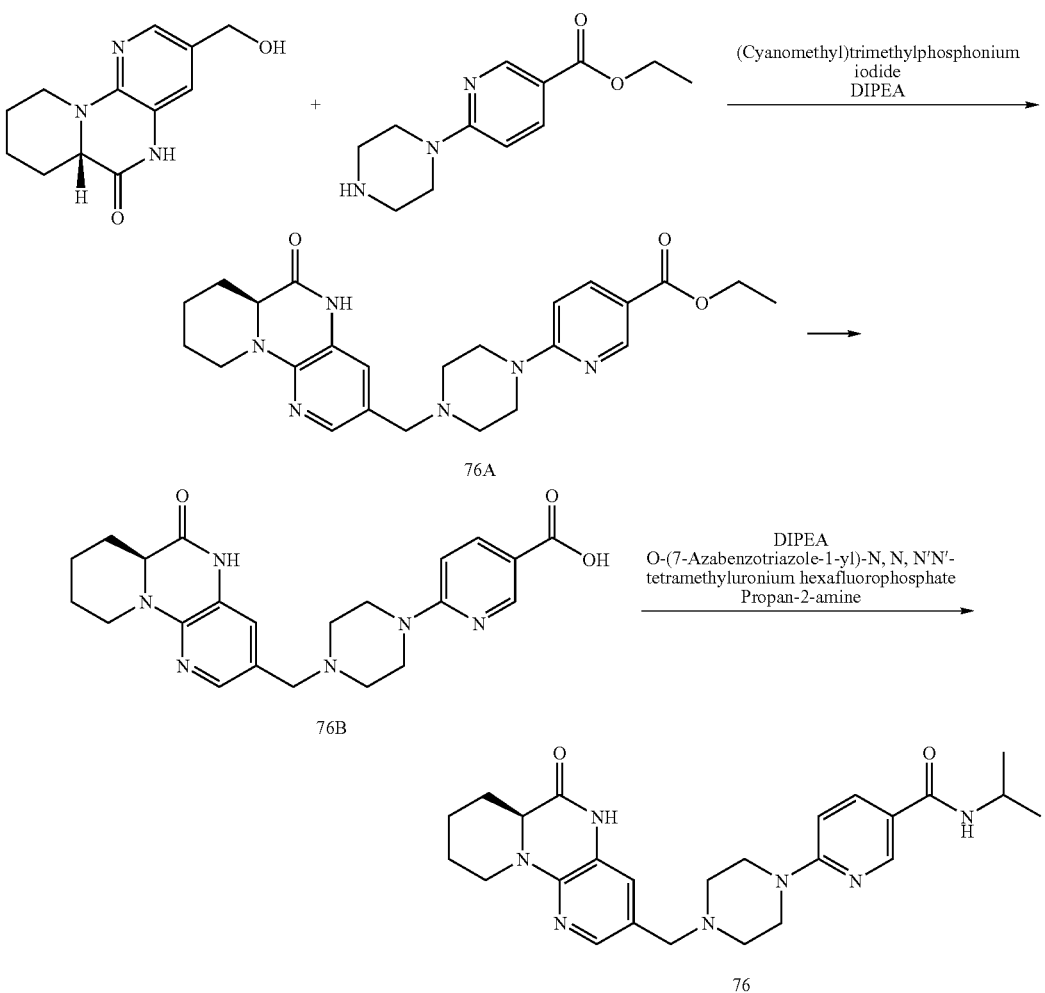

Compound 76A (S)-ethyl 6-(4-((6-oxo-6,6a,7,8,9,10-hexahydro-5H-dipyrido[1,2-a:3',2'-e]pyrazin-3-yl)methyl)piperazin-1-yl)nicotinate (S)-3-(hydroxymethyl)-7,8,9,10-tetrahydro-5H-dipyrido[1,2-a:3',2'-e]pyrazin-6(6aH)-one (330 mg, 1.415 mmol) was suspended in propionitrile (3.5 mL) and (cyanomethyl)trimethylphosphonium iodide (413.0 mg, 1.70 mmol) was added followed by N-ethyl-N-isopropylpropan-2-amine (741 ul, 4.2 mmol). To the stirred mixture was then added ethyl 6-(piperazin-1-yl)nicotinate (366 mg, 1.56 mmol). The reaction was heated to 90° C. with stirring for 16 h. The reaction was then cooled to room temperature, diluted with EtOH (8 ml) and water (1 mL), then filtered. The precipitate was filtered off and dried in vacuum to afford the title compound (567 mg, 89%) as a brown solid. $^1$H NMR (DMSO-d$_6$) δ (ppm): 10.48 (s, 1H), 8.63 (d, J=2.0 Hz, 1H), 7.93 (dd, J=9.1, 2.3 Hz, 1H), 7.65 (d, J=1.8 Hz, 1H), 6.97 (d, J=2.0 Hz, 1H), 6.85 (d, J=9.1 Hz, 1H), 4.44-4.56 (m, 1H), 4.24 (q, J=7.1 Hz, 2H), 3.84 (dd, J=11.4, 2.8 Hz, 1H), 3.53-3.73 (m, 4H), 3.35 (s, 2H), 2.60 (td, J=12.6, 2.5 Hz, 1H), 2.41 (t, J=4.8 Hz, 4H), 2.05 (br. s., 1H), 1.85 (d, J=12.4 Hz, 1H), 1.64 (d, J=12.4 Hz, 1H), 1.34-1.57 (m, 3H), 1.28 (t, 3H) [M+H] calc'd for C24H30N6O3, 451; found, 451.

Compound 76B: (S)-6-(4-(((6-oxo-6,6a,7,8,9,10-hexahydro-5H-dipyrido[1,2-a:3',2'-e]pyrazin-3-yl)methyl)piperazin-1-yl)nicotinic acid Compound 76B was prepared using a procedure analogous to that described in connection with Compound 73B except that (S)-ethyl 6-(4-(((6-oxo-6,6a,7,8,9,10-hexahydro-5H-dipyrido[1,2-a:3',2'-e]pyrazin-3-yl)methyl)piperazin-1-yl)nicotinate was used instead of (S)-ethyl 4-(4-(((6-oxo-6,6a,7,8,9,10-hexahydro-5H-dipyrido[1,2-a:3',2'-e]pyrazin-3-yl)methyl)piperazin-1-yl)benzoate to yield the title compound as a white solid. [M+H] calc'd for C22H26N6O3, 423; found, 423.

Compound 76: (S)—N-isopropyl-6-(4-(((6-oxo-6,6a,7,8,9,10-hexahydro-5H-dipyrido[1,2-a:3',2'-e]pyrazin-3-yl)methyl)piperazin-1-yl)nicotinamide (S)-6-(4-(((6-oxo-6,6a,7,8,9,10-hexahydro-5H-dipyrido[1,2-a:3',2'-e]pyrazin-3-yl)methyl)piperazin-1-yl)nicotinic acid (75 mg, 0.178 mmol) was taken up in DMF (0.9 mL). To the mixture was added N-ethyl-N-isopropylpropan-2-amine (93 μl, 0.53 mmol), O-(7-Azabenzotriazole-1-yl)-N,N,N'N'-tetramethyluronium hexafluorophosphate (101 mg, 0.266 mmol), and propan-2-amine (11.5 mg, 0.195 mmol). The reaction was stirred at room temperature overnight. The reaction was purified via HPLC (10-80 MeCN/H$_2$O, TFA buffered). The fractions were collected and lyophilized to yield 64.8 mg (65%) of the product as a white solid. $^1$H NMR (DMSO-d$_6$) δ (ppm): 10.84 (s, 1H), 9.93 (br. s., 1H), 8.64 (d, J=2.0 Hz, 1H), 8.02-8.11 (m, 2H), 7.82 (d, J=2.0 Hz, 1H), 7.05 (d, J=2.0 Hz, 1H), 6.96 (d, J=9.1 Hz, 1H), 4.43-4.63 (m, 3H), 4.25 (s, 2H), 4.07 (dd, J=14.1, 6.6 Hz, 1H), 3.93-4.02 (m, 1H), 3.37-3.55 (m, 1H), 2.96-3.25 (m, 4H), 2.68 (td, J=12.9, 2.5 Hz, 1H), 2.02-2.11 (m, 1H), 1.87 (d, J=12.4 Hz, 1H), 1.33-1.72 (m, 4H), 1.14 (d, J=6.8 Hz, 6H). [M+H] calc'd for C25H33N7O2, 464; found, 464.

Compound 77: (S)—N-methyl-6-(4-(((6-oxo-6,6a,7,8,9,10-hexahydro-5H-dipyrido[1,2-a:3',2'-e]pyrazin-3-yl)methyl)piperazin-1-yl)nicotinamide

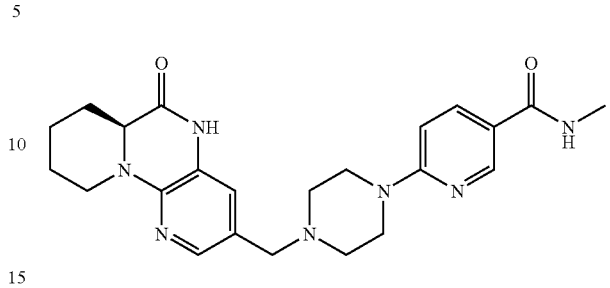

(S)-6-(4-(((6-oxo-6,6a,7,8,9,10-hexahydro-5H-dipyrido[1,2-a:3',2'-e]pyrazin-3-yl)methyl)piperazin-1-yl)nicotinic acid (75 mg, 0.178 mmol) was taken up in DMF (0.9 mL). To the mixture was added N-ethyl-N-isopropylpropan-2-amine (93 μl, 0.53 mmol), O-(7-Azabenzotriazole-1-yl)-N,N,N'N'-tetramethyluronium hexafluorophosphate (101 mg, 0.266 mmol), and methanamine hydrochloride (13.2 mg, 0.195 mmol). The reaction was stirred at room temperature overnight. The reaction was purified via HPLC (10-80 MeCN/H$_2$O, TFA buffered). The fractions were collected and lyophilized to yield 23.8 mg (30%) of the product as a white solid. $^1$H NMR (DMSO-d$_6$) δ (ppm): 10.48 (s, 1H), 8.56 (d, J=2.3 Hz, 1H), 8.20 (d, J=4.5 Hz, 1H), 7.92 (dd, J=9.0, 2.1 Hz, 1H), 7.65 (s, 1H), 6.98 (d, J=1.5 Hz, 1H), 6.82 (d, J=8.8 Hz, 1H), 4.50 (d, J=12.9 Hz, 1H), 3.77-3.94 (m, 1H), 3.56 (d, J=2.3 Hz, 4H), 3.34 (s, 2H), 2.74 (d, J=4.5 Hz, 3H), 2.53-2.69 (m, 1H), 2.41 (br. s., 4H), 1.99-2.08 (m, 1H), 1.84 (br. s., 1H), 1.59-1.69 (m, 1H), 1.31-1.57 (m, 3H). [M+H] calc'd for C25H33N7O2, 436; found, 436.

Compound 78: (S)—N-ethyl-6-(4-(((6-oxo-6,6a,7,8,9,10-hexahydro-5H-dipyrido[1,2-a:3',2'-e]pyrazin-3-yl)methyl)piperazin-1-yl)nicotinamide

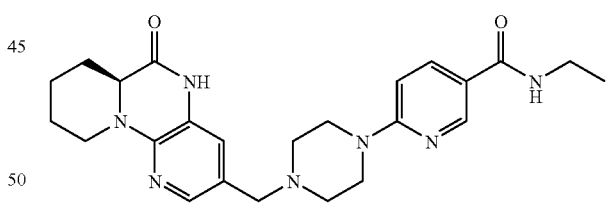

(S)-6-(4-(((6-oxo-6,6a,7,8,9,10-hexahydro-5H-dipyrido[1,2-a:3',2'-e]pyrazin-3-yl)methyl)piperazin-1-yl)nicotinic acid (75 mg, 0.178 mmol) was taken up in DMF (0.9 mL). To the mixture was added N-ethyl-N-isopropylpropan-2-amine (93 μl, 0.53 mmol), O-(7-Azabenzotriazole-1-yl)-N,N,N'N'-tetramethyluronium hexafluorophosphate (101 mg, 0.266 mmol), and ethanamine hydrochloride (15.9 mg, 0.195 mmol). The reaction was stirred at room temperature overnight. The reaction was purified via HPLC (10-80 MeCN/H$_2$O, TFA buffered). The fractions were collected and lyophilized to yield 27.4 mg (34%) of the title compound as a white solid. $^1$H NMR (DMSO-d$_6$) δ (ppm): 10.84 (s, 1H), 10.03 (br. s., 1H), 8.64 (s, 1H), 8.35 (t, J=5.2 Hz, 1H), 8.04 (d, J=9.1 Hz, 1H), 7.83 (s, 1H), 6.90-7.11 (m, 2H), 4.40-4.71 (m, 3H), 4.26 (s, 2H), 3.98 (d, J=11.1 Hz, 1H), 2.96-3.57 (m, 8H), 2.61-2.74 (m, 1H), 2.08 (d, J=11.9 Hz, 1H), 1.87 (d, J=12.4 Hz, 1H), 1.33-1.73 (m, 4H), 1.11 (t, 3H). [M+H] calc'd for C24H31N7O2, 450; found, 450.

Compound 79: (S)—N-cyclopropyl-6-(4-((6-oxo-6,6a,7,8,9,10-hexahydro-5H-dipyrido[1,2-a:3',2'-e]pyrazin-3-yl)methyl)piperazin-1-yl)nicotinamide

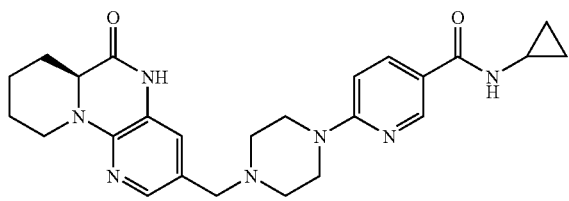

(S)-6-(4-((6-oxo-6,6a,7,8,9,10-hexahydro-5H-dipyrido[1,2-a:3',2'-e]pyrazin-3-yl)methyl)piperazin-1-yl)nicotinic acid (75 mg, 0.178 mmol) was taken up in DMF (0.9 mL). To the mixture was added N-ethyl-N-isopropylpropan-2-amine (93 μl, 0.53 mmol), O-(7-Azabenzotriazole-1-yl)-N,N,N'N'-tetramethyluronium hexafluorophosphate (101 mg, 0.266 mmol), and cyclopropanamine (11.15 mg, 0.195 mmol). The reaction was stirred at room temperature overnight. The reaction was purified via HPLC (10-80 MeCN/H2O, TFA buffered). The fractions were collected and lyophilized to yield 41.2 mg (50%) of the product as a white solid. $^1$H NMR (DMSO-d$_6$) δ (ppm): 10.81 (s, 1H), 9.85 (br. s., 1H), 8.61 (d, J=2.3 Hz, 1H), 8.30 (d, J=4.0 Hz, 1H), 8.01 (dd, J=9.0, 2.4 Hz, 1H), 7.82 (d, J=2.0 Hz, 1H), 7.04 (d, J=2.0 Hz, 1H), 6.95 (d, J=8.8 Hz, 1H), 4.42-4.64 (m, 3H), 4.24 (br. s., 2H), 3.92-4.01 (m, 1H), 3.42 (br. s., 2H), 2.94-3.26 (m, 4H), 2.75-2.86 (m, 1H), 2.58-2.73 (m, 1H), 2.03-2.12 (m, 1H), 1.87 (d, J=12.4 Hz, 1H), 1.66 (d, J=12.6 Hz, 1H), 1.31-1.61 (m, 3H), 0.62-0.73 (m, 2H), 0.46-0.57 (m, 2H). [M+H] calc'd for C25H31N7O2, 462; found, 462.

Compound 80: 7-((4-(4-chlorophenyl)-5,6-dihydropyridin-1(2H)-yl)methyl)-4-methyl-3,4-dihydropyrido[2,3-b]pyrazin-2(1H)-one

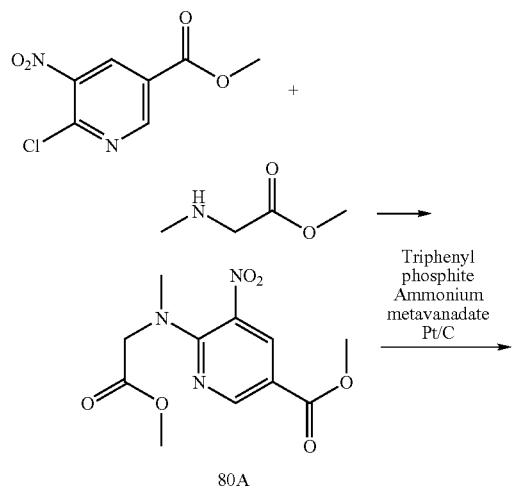

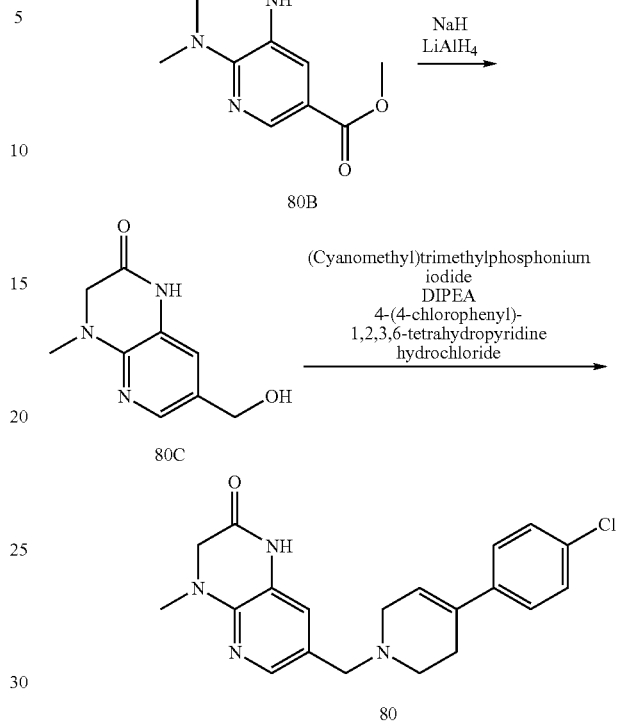

Compound 80A: Methyl 6-((2-methoxy-2-oxoethyl)(methyl)amino)-5-nitronicotinate

Methyl 6-chloro-5-nitronicotinate (2.0 g, 9.23 mmol) was added to methyl 2-(methylamino)acetate (1.9 g, 18.47 mmol) neat while stirring at room temperature. The viscous yellow reaction was heated to 90° C. for one hour and then allowed to cool back to room temperature. The reaction was diluted with dichloromethane (20 mL) and purified using flash column chromatography (220 g SiO2, 20-30% gradient, ethyl acetate in hexanes) to yield 2.60 g (99% yield) of the title compound as a yellow oil. [M+H] calc'd for C11H13N3O6, 284; found, 284.

Compound 80B: Methyl 4-methyl-2-oxo-1,2,3,4-tetrahydropyrido[2,3-b]pyrazine-7-carboxylate Methyl 6-((2-methoxy-2-oxoethyl)(methyl)amino)-5-nitronicotinate (2.7 g, 9.53 mmol) was dissolved in dichloromethane (10 mL). To the yellow solution was added ammonium metavanadate (30.0 mg, 0.256 mmol), triphenyl phosphite (aprox 30 ul, 0.097 mmol), and Pt/C (300 mg, 5% w/w). The reaction mixture was pressurized with hydrogen gas (110 psi) and stirred at room temperature for 16 h. The reaction was then depressurized and diluted with dichloromethane (100 mL) which was then refluxed for 30 min. The hot solution was filtered through a pad of celite and washed with hot dichloromethane (3×20 mL). The filtrate was concentrated in vacuo to yield the title compound (1.45 g, 68%) as a white solid. [M+H] calc'd for C10H11N3O3, 222; found, 222.

Compound 80C: 7-(hydroxymethyl)-4-methyl-3,4-dihydropyrido[2,3-b]pyrazin-2(1H)-one Methyl 4-methyl-2-oxo-1,2,3,4-tetrahydropyrido[2,3-b]pyrazine-7-carboxylate (500 mg, 2.25 mmol) was taken up in tetrahydrofuran (25 mL) in an inert environment. To the stirred suspension at room temperature was added NaH (60% dispersion in mineral oil, 136 mg, 3.40 mmol) and stirred 30 min. The reaction was then cooled to −45° C. and lithium aluminum hydride (2M in THF, 3.3 mL, 6.6 mmol) was added. The reaction was stirred at a temperature between −20 and −10° C. for 1 h. The reaction was then cooled back to −60° C. and MeOH (1 mL) followed by water (1 mL) was added. The reaction was allowed to stir at ambient temperature for 2 h and then poured into ethyl acetate (300 mL) and water (200 mL). The biphasic mixture was stirred vigorously and then filtered through a medium frit. The layers were separated and the aqueous phase was extracted with ethyl acetate (3×100 mL). The organic layers were combined, washed with brine (100 mL), dried with sodium sulfate and concentrated to yield the title compound (415 mg, 95%) as a white solid. [M+H] calc'd for C9H11N4O2, 194; found, 194.

Compound 80: 7-((4-(4-chlorophenyl)-5,6-dihydropyridin-1(2H)-yl)methyl)-4-methyl-3,4-dihydropyrido[2,3-b]pyrazin-2(1H)-one 7-(hydroxymethyl)-4-methyl-3,4-dihydropyrido[2,3-b]pyrazin-2(1H)-one (85.0 mg, 0.44 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 4-(4-chlorophenyl)-1,2,3,6-tetrahydropyridine hydrochloride (103.5 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The precipitate was filtered off and dried in vacuum to afford the title compound (30.2 mg, 19%) as a white solid. $^1$H NMR (DMSO-d$_6$) δ (ppm): 10.51 (s, 1H), 7.64 (s, 1H), 7.41-7.47 (m, 2H), 7.34-7.40 (m, 2H), 6.97 (d, J=1.8 Hz, 1H), 6.18 (s, 1H), 3.93 (s, 2H), 3.41 (s, 2H), 3.01 (br. s., 2H), 2.91 (s, 3H), 2.60 (br. s., 2H), 2.39-2.47 (m, J=7.3 Hz, 2H). [M+H] calc'd for C20H21ClN4O, 369; found, 369.

Compound 81: 7-((4-(4-chlorophenyl)piperazin-1-yl)methyl)-4-methyl-3,4-dihydropyrido[2,3-b]pyrazin-2(1H)-one

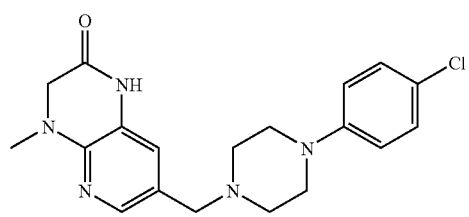

7-(hydroxymethyl)-4-methyl-3,4-dihydropyrido[2,3-b]pyrazin-2(1H)-one (85.0 mg, 0.44 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 1-(4-chlorophenyl)piperazine hydrochloride (104.8 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The precipitate was filtered off and dried in vacuum to afford the title compound (14.7 mg, 8%) as a white solid. $^1$H NMR (DMSO-d$_6$) δ (ppm): 10.50 (s, 1H), 7.63 (d, J=1.8 Hz, 1H), 7.21 (d, J=9.1 Hz, 2H), 6.96 (d, J=2.0 Hz, 1H), 6.92 (d, J=9.1 Hz, 2H), 3.93 (s, 2H), 3.34 (s, 2H), 3.10 (br. s., 4H), 2.91 (s, 3H), 2.46 (br. s., 4H). [M+H] calc'd for C19H22ClN5O, 372; found, 372.

Compound 82: 7-((4-(4-chlorophenyl)piperidin-1-yl)methyl)-4-methyl-3,4-dihydropyrido[2,3-b]pyrazin-2(1H)-one

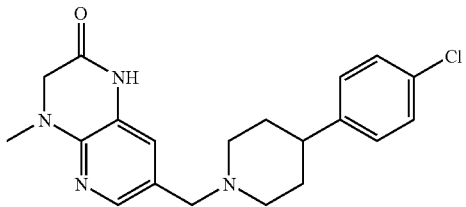

7-(hydroxymethyl)-4-methyl-3,4-dihydropyrido[2,3-b]pyrazin-2(1H)-one (85.0 mg, 0.44 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 4-(4-chlorophenyl)piperidine hydrochloride (104.5 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The precipitate was filtered off and dried in vacuum to afford the title compound (18.1 mg, 11%) as a white solid. $^1$H NMR (DMSO-d$_6$) δ (ppm): 10.49 (s, 1H), 7.61 (d, J=2.0 Hz, 1H), 7.30-7.36 (m, 2H), 7.23-7.29 (m, 2H), 6.95 (d, J=2.0 Hz, 1H), 3.92 (s, 2H), 3.32 (s, 3H), 2.84-2.92 (m, 5H), 1.98 (t, J=10.7 Hz, 2H), 1.66-1.75 (m, 2H), 1.50-1.64 (m, 2H). [M+H] calc'd for C20H23ClN4O, 371; found, 371.

Compound 83: 4-benzyl-7-((4-(4-chlorophenyl)-5,6-dihydropyridin-1(2H)-yl)methyl)-3,4-dihydropyrido[2,3-b]pyrazin-2(1H)-one

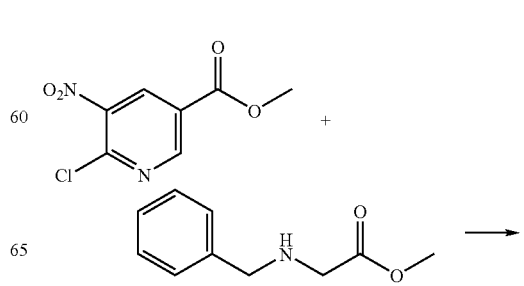

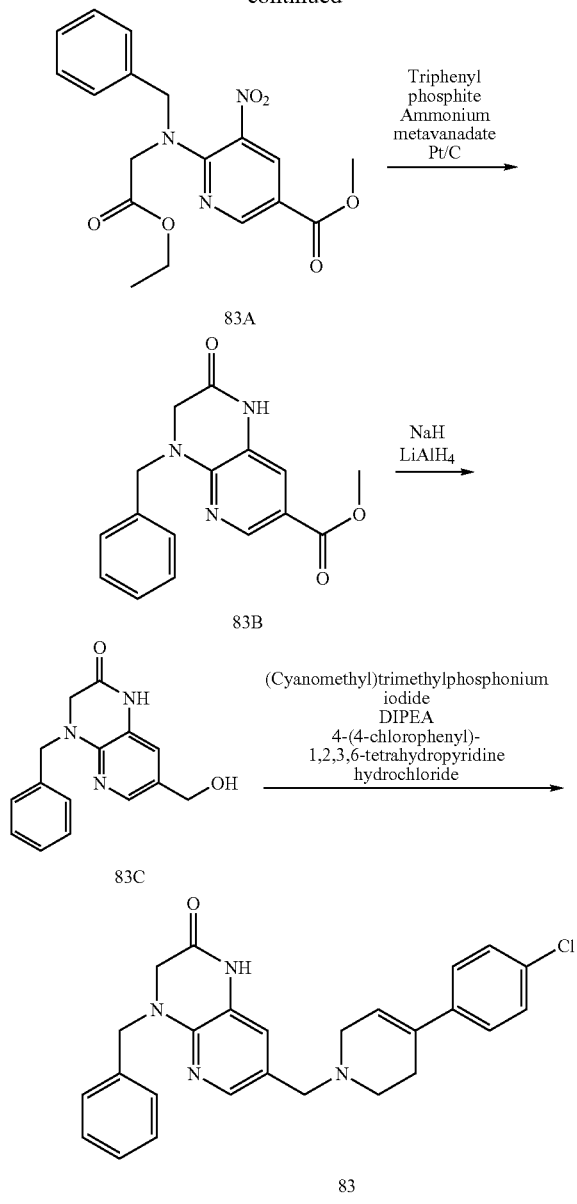

Compound 83A: Methyl 6-(benzyl(2-ethoxy-2-oxo-ethyl)amino)-5-nitronicotinate

Methyl 6-chloro-5-nitronicotinate (2.0 g, 9.23 mmol) was added to methyl 2-(benzylamino)acetate (6.0 g, 31.05 mmol) neat while stirring at room temperature. The viscous yellow reaction was heated to 90° C. for one h and then allowed to cool back to room temperature. The reaction was diluted with dichloromethane (20 mL) and purified via column chromatography (220 g SiO2, 20-30% gradient, ethyl acetate in hexanes) to yield the title compound (3.10 g, 90% yield) as a yellow oil. [M+H] calc'd for C18H19N3O6, 374; found, 374.

Compound 83B: Methyl 4-benzyl-2-oxo-1,2,3,4-tetrahydropyrido[2,3-b]pyrazine-7-carboxylate Methyl 6-(benzyl(2-ethoxy-2-oxoethyl)amino)-5-nitronicotinate (445 mg g, 1.19 mmol) was dissolved in dichloromethane (5 mL). To the yellow solution was added ammonium metavanadate (10.0 mg, 0.085 mmol), triphenyl phosphite (aprox 10 ul, 0.032 mmol), and Pt/C (50 mg, 5% w/w). The reaction mixture was pressurized with hydrogen gas (75 psi) and stirred at room temperature for 48 h. The reaction was then depressurized and diluted with dichloromethane (20 mL) which was then refluxed for 30 min. The hot solution was filtered through a pad of celite and washed with hot dichloromethane (3×10 mL). The filtrate was concentrated to yield the title compound (250 mg, 71%) as a white solid. [M+H] calc'd for C16H15N3O3, 298; found, 298.

Compound 83C: 4-benzyl-7-(hydroxymethyl)-3,4-dihydropyrido[2,3-b]pyrazin-2(1H)-one Methyl 4-benzyl-2-oxo-1,2,3,4-tetrahydropyrido[2,3-b]pyrazine-7-carboxylate (600 mg, 2.02 mmol) was taken up in tetrahydrofuran (25 mL) in an inert environment. To the stirred suspension at room temperature was added NaH (60% dispersion in mineral oil, 121 mg, 3.03 mmol) and stirred 30 min. The reaction was then cooled to −78° C. and lithium aluminum hydride (3 mL, 2M in THF) was added. The reaction was stirred at a temperature between −20 and −10° C. for 2 h. The reaction was then cooled back to −78° C. and MeOH (1 mL) followed by water (1 mL) was added. The reaction was allowed to stir at ambient temperature for 2 h and then poured into ethyl acetate (200 mL) and water (100 mL). The biphasic mixture was stirred vigorously and then filtered through a medium frit. The layers were separated and the aqueous phase was extracted with ethyl acetate (2×50 mL). The organic layers were combined, washed with brine (100 mL), dried with sodium sulfate and concentrated to afford the title compound (540 mg, 99%) as a white solid. [M+H] calc'd for C15H15N3O2, 270; found, 270.

Compound 83: 4-benzyl-7-((4-(4-chlorophenyl)-5,6-dihydropyridin-1(2H)-yl)methyl)-3,4-dihydropyrido[2,3-b]pyrazin-2(1H)-one 4-benzyl-7-(hydroxymethyl)-3,4-dihydropyrido[2,3-b]pyrazin-2(1H)-one (100 mg, 0.37 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 4-(4-chlorophenyl)-1,2,3,6-tetrahydropyridine hydrochloride (104.5 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The precipitate was filtered off and dried in vacuum to afford the title compound (45.3 mg, 27%) as a white solid. $^1$H NMR (DMSO-$d_6$) δ (ppm): 10.57 (s, 1H), 7.66 (d, J=2.0 Hz, 1H), 7.41-7.48 (m, 2H), 7.23-7.41 (m, 7H), 7.03 (d, J=2.0 Hz, 1H), 6.19 (s, 1H), 4.72 (s, 2H), 3.86 (s, 2H), 3.43 (s, 2H), 3.03 (d, J=2.8 Hz, 2H), 2.58-2.65 (m, 2H), 2.44 (br. s., 2H). [M+H] calc'd for C26H25ClN4O, 445; found, 445.

Compound 84: 4-benzyl-7-((4-(4-chlorophenyl)piperazin-1-yl)methyl)-3,4-dihydropyrido[2,3-b]pyrazin-2(1H)-one

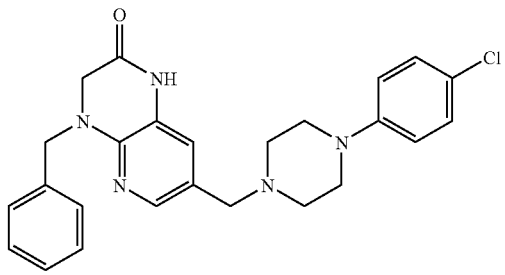

4-benzyl-7-(hydroxymethyl)-3,4-dihydropyrido[2,3-b]pyrazin-2(1H)-one (100 mg, 0.37 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 1-(4-chlorophenyl)piperazine hydrochloride (104.5 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The precipitate was filtered off and dried in vacuum to afford the title compound (66.6 mg, 40%) as a white solid. $^1$H NMR (DMSO-$d_6$) δ (ppm): 10.57 (s, 1H), 7.64 (d, J=1.8 Hz, 1H), 7.33 (d, J=4.5 Hz, 4H), 7.25-7.30 (m, 1H), 7.19-7.24 (m, 2H), 7.01 (d, J=1.8 Hz, 1H), 6.92 (d, J=9.1 Hz, 2H), 4.72 (s, 2H), 3.86 (s, 2H), 3.36 (s, 2H), 3.07-3.15 (m, 4H), 2.44-2.49 (m, 4H). [M+H] calc'd for C25H26ClN5O, 448; found, 448.

Compound 85: 4-benzyl-7-((4-(4-chlorophenyl)piperidin-1-yl)methyl)-3,4-dihydropyrido[2,3-b]pyrazin-2(1H)-one

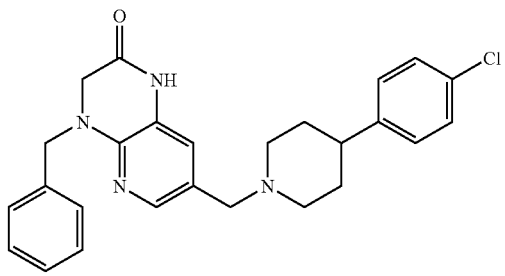

4-benzyl-7-(hydroxymethyl)-3,4-dihydropyrido[2,3-b]pyrazin-2(1H)-one (100 mg, 0.37 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 4-(4-chlorophenyl)piperidine hydrochloride (104.5 mg, 0.45 mmol). The reaction was heated to 90° C. with stirring for 2 h. The reaction was then cooled to room temperature and purified via HPLC (55-90% acetonitrile in water, ammonium bicarbonate buffer). The fractions were combined and concentrated until a white solid precipitated. The precipitate was filtered and dried in vacuum to afford the title compound (69.9 mg, 42%) as a white solid. $^1$H NMR (DMSO-$d_6$) δ (ppm): 10.56 (s, 1H), 7.63 (d, J=2.0 Hz, 1H), 7.30-7.37 (m, 6H), 7.23-7.30 (m, 3H), 7.00 (d, J=2.0 Hz, 1H), 4.71 (s, 2H), 3.85 (s, 2H), 3.33 (s, 3H), 2.89 (d, J=11.4 Hz, 2H), 1.99 (t, J=10.6 Hz, 2H), 1.67-1.78 (m, 2H), 1.48-1.66 (m, 2H). [M+H] calc'd for C11H15Cl2N, 447; found, 447.

Compound 86: 3-((4-(4-chlorophenyl)-5,6-dihydropyridin-1(2H)-yl)methyl)-6a,7,9,10-tetrahydropyrido[3,2-e][1,4]thiazino[4,3-a]pyrazin-6(5H)-one

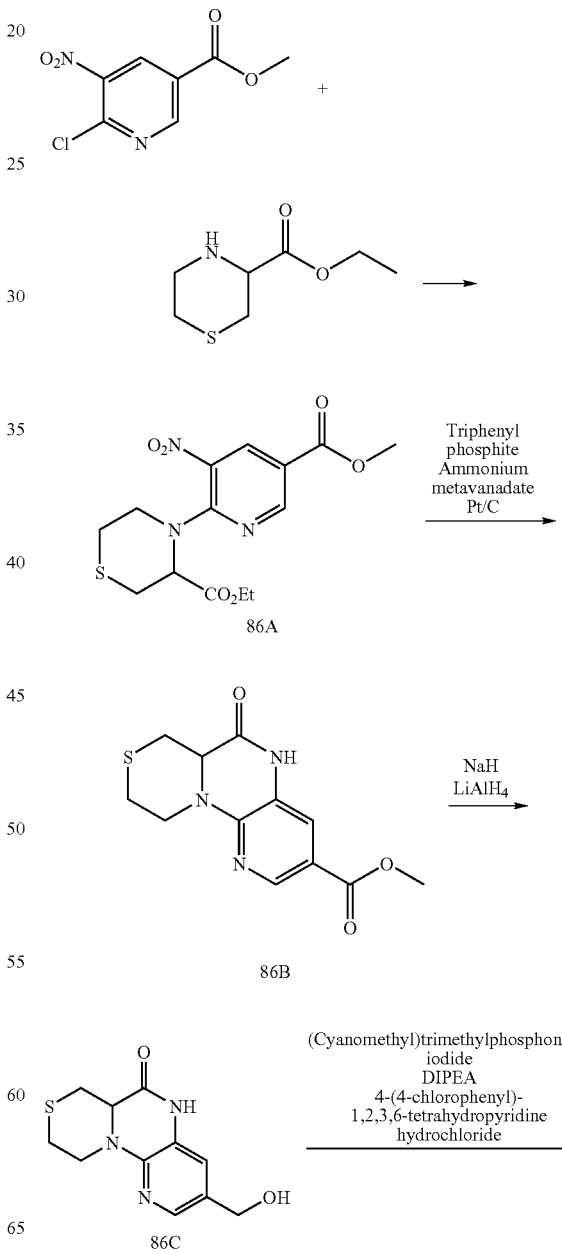

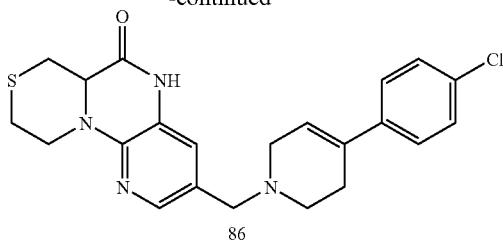

Compound 86A: Ethyl 4-(5-(methoxycarbonyl)-3-nitropyridin-2-yl)thiomorpholine-3-carboxylate Methyl 6-chloro-5-nitronicotinate (1.1 g, 5.10 mmol) was added to ethyl thiomorpholine-3-carboxylate (2.0 g, 11.41 mmol) neat while stirring at room temperature. The viscous yellow reaction was heated to 90° C. for one hour and then allowed to cool back to room temperature. The reaction was diluted with dichloromethane (20 mL) and purified via column chromatography (220 g SiO2, 20-30% gradient, ethyl acetate in hexanes) to yield the title compound (1.71 g, 95%) as a yellow oil. [M+H] calc'd for C15H18N2O6S, 356; found, 356.

Compound 86B: methyl 6-oxo-5,6,6a,7,9,10-hexahydropyrido[3,2-e][1,4]thiazino[4,3-a]pyrazine-3-carboxylate Ethyl 4-(5-(methoxycarbonyl)-3-nitropyridin-2-yl)thiomorpholine-3-carboxylate (600 mg g, 1.69 mmol) was dissolved in dichloromethane (5 mL). To the yellow solution was added ammonium metavanadate (10.0 mg, 0.085 mmol), triphenyl phosphite (aprox 10 ul, 0.032 mmol), and Pt/C (50 mg, 5% w/w). The reaction mixture was pressurized with hydrogen gas (110 psi) and stirred at room temperature for 16 h. The reaction was then depressurized and diluted with dichloromethane (20 mL) which was refluxed for 30 min. The hot solution was filtered through a pad of celite and washed with hot dichloromethane (3×10 mL). The filtrate was concentrated to yield the title compound (452 mg, 96%) as a white solid. [M+H] calc'd for C12H13N3O3S, 280; found, 280.

Compound 86C: 3-(hydroxymethyl)-6a,7,9,10-tetrahydropyrido[3,2-e][1,4]thiazino[4,3-a]pyrazin-6 (5H)-one Methyl 6-oxo-5,6,6a,7,9,10-hexahydropyrido[3,2-e][1,4] thiazino[4,3-a]pyrazine-3-carboxylate (386 mg, 1.38 mmol) was taken up in tetrahydrofuran (25 mL) in an inert environment. To the stirred suspension at room temperature was added NaH (60% dispersion in mineral oil, 121 mg, 3.03 mmol) and stirred 30 min. The reaction was cooled to –78° C. and lithium aluminum hydride (3 mL, 2M in THF) was added. The reaction was stirred at a temperature between –20 and –10° C. for 3 h. The reaction was cooled back to –78° C. and MeOH (1 mL) followed by water (1 mL) was added. The reaction was allowed to stir at ambient temperature for 2 h and then poured into ethyl acetate (200 mL) and water (100 mL). The biphasic mixture was stirred vigorously and then filtered through a medium frit. The layers were separated and the aqueous phase was extracted with ethyl acetate (2×50 mL). The organic layers were combined, washed with brine (100 mL), dried with sodium sulfate and concentrated to afford the title compound (497 mg, 98%) as a white solid. [M+H] calc'd for C11H13N3O2S, 252; found, 252.

Compound 86: 3-((4-(4-chlorophenyl)-5,6-dihydropyridin-1(2H)-yl)methyl)-6a,7,9,10-tetrahydropyrido[3,2-e][1,4]thiazino[4,3-a]pyrazin-6(5H)-one 3-(hydroxymethyl)-6a,7,9,10-tetrahydropyrido[3,2-e][1,4]thiazino[4,3-a]pyrazin-6(5H)-one (100 mg, 0.36 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 4-(4-chlorophenyl)-1,2,3,6-tetrahydropyridine hydrochloride (104.5 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The solids were collected to afford the title compound (79.5 mg, 19%) as a white solid. $^1$H NMR (DMSO-d$_6$) δ (ppm): 10.66 (s, 1H), 7.70 (d, J=2.0 Hz, 1H), 7.41-7.47 (m, 2H), 7.33-7.40 (m, 2H), 7.02 (d, J=2.0 Hz, 1H), 6.18 (br. s., 1H), 4.88 (dt, J=13.6, 2.7 Hz, 1H), 4.27 (dd, J=10.6, 3.0 Hz, 1H), 3.43 (d, J=3.5 Hz, 2H), 2.98-3.07 (m, 3H), 2.66-2.83 (m, 3H), 2.58-2.65 (m, 2H), 2.39-2.48 (m, 3H). [M+H] calc'd for C22H23ClN4OS, 427; found, 427.

Compound 87: 3-((4-(4-chlorophenyl)piperazin-1-yl) methyl)-6a,7,9,10-tetrahydropyrido[3,2-e][1,4]thiazino[4,3-a]pyrazin-6(5H)-one

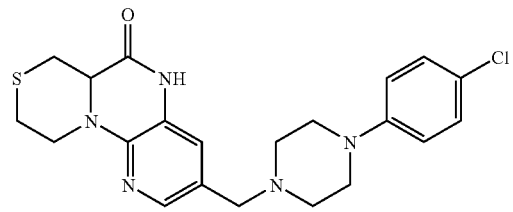

3-(hydroxymethyl)-6a,7,9,10-tetrahydropyrido[3,2-e][1,4]thiazino[4,3-a]pyrazin-6(5H)-one (Compound 86C; 100 mg, 0.36 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 1-(4-chlorophenyl)piperazine hydrochloride (104.9 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The solids were collected to afford the title compound (86.1 mg, 56%) as a white solid. $^1$H NMR (DMSO-d$_6$) δ: 10.66 (s, 1H), 7.69 (d, J=2.0 Hz, 1H), 7.16-7.26 (m, 2H), 7.00 (d, J=2.0 Hz, 1H), 6.86-6.96 (m, 2H), 4.88 (dt, J=13.6, 2.7 Hz, 1H), 4.26 (dd, J=10.7, 2.9 Hz, 1H), 3.34-3.42 (m, 2H), 3.07-3.16

(m, 4H), 3.02 (td, J=12.8, 2.3 Hz, 1H), 2.65-2.83 (m, 3H), 2.43-2.48 (m, 5H). [M+H] calc'd for C21H24ClN5OS, 430; found, 430.

Compound 88: 3-((4-(4-chlorophenyl)piperidin-1-yl)methyl)-6a,7,9,10-tetrahydropyrido[3,2-e][1,4]thiazino[4,3-a]pyrazin-6(5H)-one

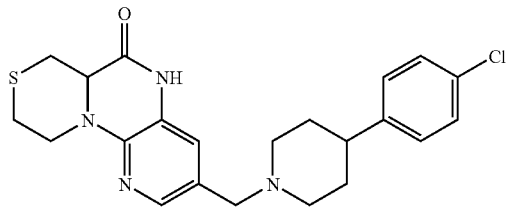

3-(hydroxymethyl)-6a,7,9,10-tetrahydropyrido[3,2-e][1,4]thiazino[4,3-a]pyrazin-6(5H)-one (Compound 86C; 100 mg, 0.36 mmol) was suspended in propionitrile (1 mL) and (cyanomethyl)trimethylphosphonium iodide (123.0 mg, 0.51 mmol) was added followed by N-ethyl-N-isopropylpropan-2-amine (180 ul, 1.03 mmol). To the stirred mixture was then added 4-(4-chlorophenyl)piperidine hydrochloride (104.5 mg, 0.45 mmol). The reaction was heated to 90° C. with stirring for 2 h. The reaction was then cooled to room temperature and diluted with water (3 mL) and filtered. The solids were collected and refluxed in ethanol (5 mL) for 1 h. The suspension was cooled back to room temperature and filtered. The precipitate was filtered off and dried in vacuum to afford the title compound (86.1 mg, 56%) as a white solid. $^1$H NMR (DMSO-d$_6$) δ (ppm): 10.44-10.83 (m, 1H), 7.68 (d, J=1.8 Hz, 1H), 7.30-7.38 (m, 2H), 7.23-7.29 (m, 2H), 6.99 (d, J=2.0 Hz, 1H), 4.83-4.91 (m, 1H), 4.22-4.29 (m, 1H), 3.33 (s, 3H), 2.96-3.07 (m, 1H), 2.83-2.94 (m, 2H), 2.65-2.83 (m, 3H), 2.39-2.48 (m, 1H), 1.91-2.06 (m, 2H), 1.66-1.78 (m, 2H), 1.49-1.66 (m, 2H) [M+H] calc'd for C22H25ClN4OS, 429; found, 429.

Compound 89: (R)-6-(4-((6-oxo-5,6,6a,7,9,10-hexahydropyrido[3,2-e][1,4]thiazino[4,3-a]pyrazin-3-yl)methyl)piperazin-1-yl)nicotinonitrile

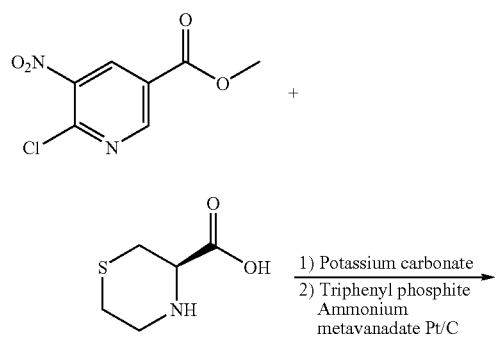

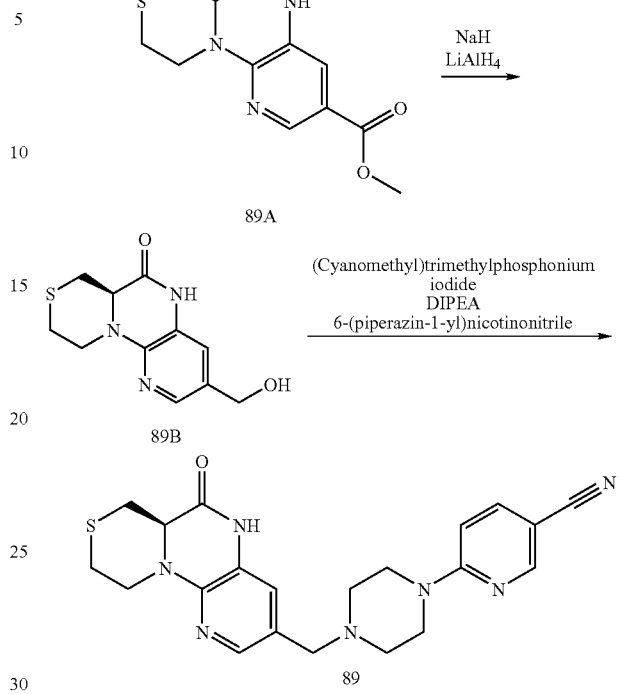

Compound 89A: (R)-methyl 6-oxo-5,6,6a,7,9,10-hexahydropyrido[3,2-e][1,4]thiazino[4,3-a]pyrazine-3-carboxylate To a suspension of (R)-thiomorpholine-3-carboxylic acid (1.009 g, 6.86 mmol) in THF was added methyl 6-chloro-5-nitronicotinate (1.35 g, 6.23 mmol) and potassium carbonate (2.58 g, 18.70 mmol). The suspension was heated to reflux for 3 hours. The crude orange solution was allowed to cool to RT and filtered through a pad of celite which was washed with DCM (50 mL), and transferred to a bomb hydroginator. To the solution was added triphenyl phosphite (0.019 ml, 0.061 mmol), platinum (0.238 g, 0.061 mmol), and ammonium metavanadate. The vessel was sealed and pressurized to 140 psi with stirring for 24 h at room temperature. The vessel was depressurized and the mixture was diluted with DCM (100 mL) and refluxed for 30 minutes. The hot mixture was filtered through celite and concentrated to yield 887 mg (52%) of the product as a white solid. [M+H] calc'd for C12H13N3O3S, 280; found, 280.

Compound 89B: (R)-3-(hydroxymethyl)-6a,7,9,10-tetrahydropyrido[3,2-e][1,4]thiazino[4,3-a]pyrazin-6(5H)-one (R)-methyl 6-oxo-5,6,6a,7,9,10-hexahydropyrido[3,2-e][1,4]thiazino[4,3-a]pyrazine-3-carboxylate (887 mg, 3.18 mmol) was taken up in tetrahydrofuran (40 mL) in an inert environment. To the stirred suspension at room temperature was added NaH (191 mg, 4.76 mmol, 60% dispersion in mineral oil) and stirred 30 minutes. The reaction was then cooled to −45° C. and lithium aluminum hydride (4.76 mL, 2M in THF) was added. The reaction was stirred at a temperature between −20 and −10° C. for 1 hour. The reaction was then cooled back to −78° C. and methanol (5 ml) followed by water (1 ml) was added. The reaction was allowed to stir at ambient temperature for 2 hours and then poured into ethyl acetate (400 ml) and water (100 ml). The biphasic mixture was stirred vigorously and then filtered through a medium frit. The filtrate was collected. The layers were separated and the aqueous phase was extracted with ethyl acetate (1×100 ml). The organic layers were combined, washed with brine (100 ml), and concentrated to yield 710.8 mg (89%) of the title compound as a white solid. [M+H] calc'd for C11H13N3O2S, 252; found, 252.

Compound 89: (R)-6-(4-((6-oxo-5,6,6a,7,9,10-hexahydropyrido[3,2-e][1,4]thiazino[4,3-a]pyrazin-3-yl)methyl)piperazin-1-yl)nicotinonitrile (R)-3-(hydroxymethyl)-6a,7,9,10-tetrahydropyrido[3,2-e][1,4]thiazino[4,3-a]pyrazin-6(5H)-one (80.0 mg, 0.318 mmol) was suspended in propionitrile (0.8 mL) and (cyanomethyl)trimethylphosphonium iodide (93.0 mg, 0.382 mmol) was added followed by N-ethyl-N-isopropylpropan-2-amine (167 ul, 0.955 mmol). To the stirred mixture was then added 6-(piperazin-1-yl)nicotinonitrile (59.9 mg, 0.318 mmol). The reaction was heated to 90° C. with stirring for 16 h. The reaction was cooled to room temperature and left to sit 48 h. The precipitate was filtered off, washed with ethanol (5 mL) and dried in vacuum to afford the title compound (53.9 mg, 40.2%) as a white solid. $^1$H NMR(CHLOROFORM-d) δ (ppm): 8.41 (d, J=1.8 Hz, 1H), 7.78 (d, J=1.8 Hz, 2H), 7.62 (dd, J=8.8, 2.3 Hz, 1H), 6.95 (br. s., 1H), 6.60 (d, J=8.8 Hz, 1H), 5.06 (dt, J=13.6, 2.8 Hz, 1H), 4.43 (dd, J=10.4, 3.3 Hz, 1H), 3.70 (br. s., 4H), 3.45 (br. s., 2H), 3.15 (td, J=12.9, 2.3 Hz, 1H), 3.00 (td, J=12.8, 2.8 Hz, 1H), 2.78-2.94 (m, 2H), 2.54 (br. s., 4H), 2.40 (dd, J=13.6, 1.5 Hz, 1H). [M+H] calc'd for C21H23N7OS, 422; found, 422.

Compound 90: (R)-4-(4-((6-oxo-5,6,6a,7,9,10-hexahydropyrido[3,2-e][1,4]thiazino[4,3-a]pyrazin-3-yl)methyl)piperazin-1-yl)benzonitrile

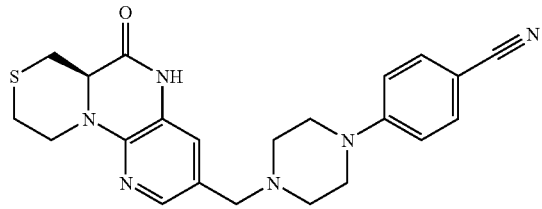

(R)-3-(hydroxymethyl)-6a,7,9,10-tetrahydropyrido[3,2-e][1,4]thiazino[4,3-a]pyrazin-6(5H)-one (80.0 mg, 0.318 mmol) was suspended in propionitrile (0.8 mL) and (cyanomethyl)trimethylphosphonium iodide (93.0 mg, 0.382 mmol) was added followed by N-ethyl-N-isopropylpropan-2-amine (167 ul, 0.955 mmol). To the stirred mixture was then added 4-(piperazin-1-yl)benzonitrile (59.6 mg, 0.318 mmol). The reaction was heated to 90° C. with stirring for 16 h. The reaction was cooled to room temperature and left to sit 48 h. The precipitate was filtered off, washed with ethanol (5 mL) and dried in vacuum to afford the title compound (36.0 mg, 26.9%) as a white solid. $^1$H NMR(CHLOROFORM-d) δ (ppm): 8.26 (br. s., 1H), 7.79 (d, J=1.8 Hz, 1H), 7.44-7.60 (m, 2H), 6.96 (br. s., 1H), 6.76-6.91 (m, 2H), 5.05 (dt, J=13.6, 2.7 Hz, 1H), 4.43 (dd, J=10.7, 3.2 Hz, 1H), 3.27-3.63 (m, 6H), 3.15 (td, J=12.8, 2.3 Hz, 1H), 3.00 (td, J=12.8, 2.7 Hz, 1H), 2.77-2.93 (m, 2H), 2.59 (br. s., 4H), 2.34-2.45 (m, 1H). [M+H] calc'd for C22H24N6OS, 421; found, 421.

Compound 91: (R)-3-((4-(4-chlorophenyl)-5,6-dihydropyridin-1(2H)-yl)methyl)-6a,7,9,10-tetrahydropyrido[3,2-e][1,4]thiazino[4,3-a]pyrazin-6(5H)-one

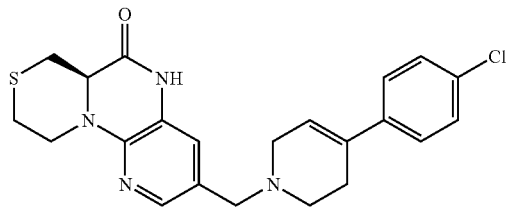

To a suspension of (R)-3-(hydroxymethyl)-6a,7,9,10-tetrahydropyrido[3,2-e][1,4]thiazino[4,3-a]pyrazin-6(5H)-one (70 mg, 0.279 mmol) in propiononitrile (Volume: 696 µl) was added (cyanomethyl)trimethylphosphonium iodide (81 mg, 0.334 mmol), DIEA (146 µl, 0.836 mmol) and finally 4-(4-chlorophenyl)-1,2,3,6-tetrahydropyridine hydrochloride (64.1 mg, 0.279 mmol). The vial was heated to 90° C. for 12 hours. Cooled to rt and concentrated to a brown residue which was treated with MeOH (5 mL). The precipitate was filtered, the solids were collected, taken up in EtOH (15 mL) and refluxed 2 hours. Let sit at RT ON. Filtered, dried in vacuum and retrieved 75.6 mg (63.6%) of the title compound as a white solid. $^1$H NMR (CHLOROFORM-d) δ (ppm): 7.80 (d, J=1.8 Hz, 1H), 7.66 (br. s., 1H), 7.30 (d, J=3.8 Hz, 5H), 7.04 (br. s., 1H), 6.02-6.09 (m, 1H), 5.06 (ddd, J=13.5, 2.8, 2.7 Hz, 1H), 4.42 (dd, J=10.5, 3.2 Hz, 1H), 3.54 (br. s., 2H), 3.10-3.26 (m, 3H), 3.00 (td, J=12.8, 2.7 Hz, 1H), 2.85-2.92 (m, 1H), 2.75 (br. s., 2H), 2.56 (br. s., 2H), 2.35-2.44 (m, 1H). [M+H] calc'd for C22H23ClN4OS, 427; found, 427.

Compound 92: (R)—N-ethyl-4-(4-((6-oxo-5,6,6a,7,9,10-hexahydropyrido[3,2-e][1,4]thiazino[4,3-a]pyrazin-3-yl)methyl)piperazin-1-yl)benzamide

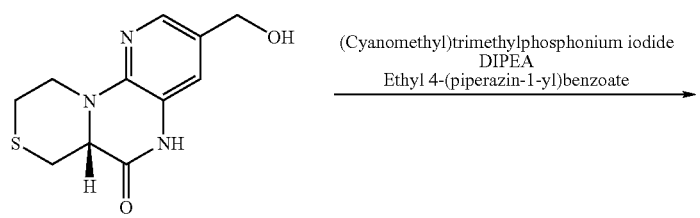

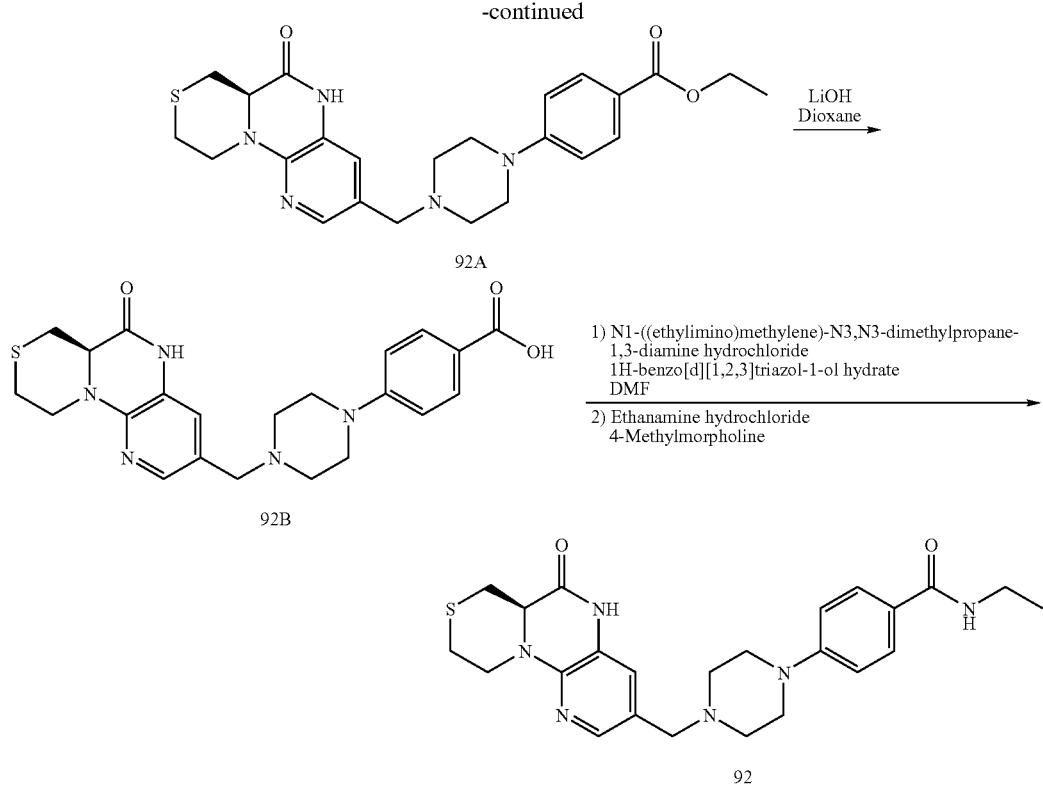

Compound 92A: (R)-ethyl 4-(4-((6-oxo-5,6,6a,7,9,10-hexahydropyrido[3,2-e][1,4]thiazino[4,3-a]pyrazin-3-yl)methyl)piperazin-1-yl)benzoate To a suspension of (R)-3-(hydroxymethyl)-6a,7,9,10-tetrahydropyrido[3,2-e][1,4]thiazino[4,3-a]pyrazin-6(5H)-one (333 mg, 1.325 mmol) in propiononitrile (3313 µl) was added (cyanomethyl)trimethylphosphonium iodide (386 mg, 1.590 mmol) and DIPEA (694 µl, 3.98 mmol) and finally ethyl 4-(piperazin-1-yl)benzoate (310 mg, 1.325 mmol). The vial was heated to 90° C. for 12 hours. The reaction was then cooled to room temperature, diluted with EtOH (8 ml) and water (1 mL), then filtered. The precipitate was filtered off and dried in vacuum to afford the title compound 508 mg, 82%) as a white solid. [M+H] calc'd for C24H29N5O3S, 468; found, 468.

Compound 92B: (R)-4-(4-((6-oxo-5,6,6a,7,9,10-hexahydropyrido[3,2-e][1,4]thiazino[4,3-a]pyrazin-3-yl)methyl)piperazin-1-yl)benzoic acid (R)-ethyl 4-(4-((6-oxo-5,6,6a,7,9,10-hexahydropyrido[3,2-e][1,4]thiazino[4,3-a]pyrazin-3-yl)methyl)piperazin-1-yl)benzoate (180 mg, 0.385 mmol) was taken up in dioxane (2081 µl) and LiOH (1N, 2310 µl, 2.310 mmol) was added. The reaction was stirred 16 h at room temperature. The reaction was concentrated in-vacuo and the residue was taken up in water (5 mL) and acidified (4.5N HCl) to pH 4. A tan precipitate formed which was filtered and the solids were collected, dried and determined to be the product (166 mg, 98%) as a tan solid. [M+H] calc'd for C22H25N5O3S, 440; found, 440.

Compound 92: (R)—N-ethyl-4-(4-((6-oxo-5,6,6a,7,9,10-hexahydropyrido[3,2-e][1,4]thiazino[4,3-a]pyrazin-3-yl)methyl)piperazin-1-yl)benzamide (R)-4-(4-((6-oxo-5,6,6a,7,9,10-hexahydropyrido[3,2-e][1,4]thiazino[4,3-a]pyrazin-3-yl)methyl)piperazin-1-yl)benzoic acid (50 mg, 0.114 mmol), N1-((ethylimino)methylene)-N3,N3-dimethylpropane-1,3-diamine hydrochloride (32.7 mg, 0.171 mmol), 1H-benzo[d][1,2,3]triazol-1-ol hydrate (26.1 mg, 0.171 mmol), and DMF (Volume: 0.5 mL) were stirred together to give a yellow solution. Ethanamine hydrochloride (9.28 mg, 0.114 mmol) and 4-methylmorpholine (0.065 mL, 0.593 mmol) were added. The reaction was stirred at room temperature for 4 hours. The crude reaction was purified via HPLC (55-90% acetonitrile in water, ammonium bicarbonate buffer). The fractions were combined and concentrated until a white solid precipitated. The precipitate was filtered off and dried in vacuum to afford the title compound (12.0 mg, 22.6%) as a white solid. $^1$H NMR(CHLOROFORM-d) δ (ppm): 7.79 (s, 1H), 7.68 (d, J=8.8 Hz, 2H), 7.53 (s, 1H), 6.85-7.00 (m, 3H), 5.96 (br. s., 1H), 5.06 (d, J=13.4 Hz, 1H), 4.43 (dd, J=10.5, 3.4 Hz, 1H), 3.39-3.54 (m, 4H), 3.30 (br. s., 4H), 3.15 (td, J=12.9, 2.3 Hz, 1H), 3.00 (br. s., 1H), 2.87 (d, J=10.4 Hz, 2H), 2.60 (br. s., 4H), 2.42 (d, J=1.5 Hz, 1H), 1.25 (t, J=7.2 Hz, 3H). [M+H] calc'd for C24H30N6O2S, 467; found, 467. MP: 288.9° C.

Compound 93: 3-((4-(4-chlorophenyl)piperazin-1-yl) methyl)-6a,7,9,10-tetrahydro-[1,4]oxazino[4,3-a] pyrido[3,2-e]pyrazin-6(5H)-one

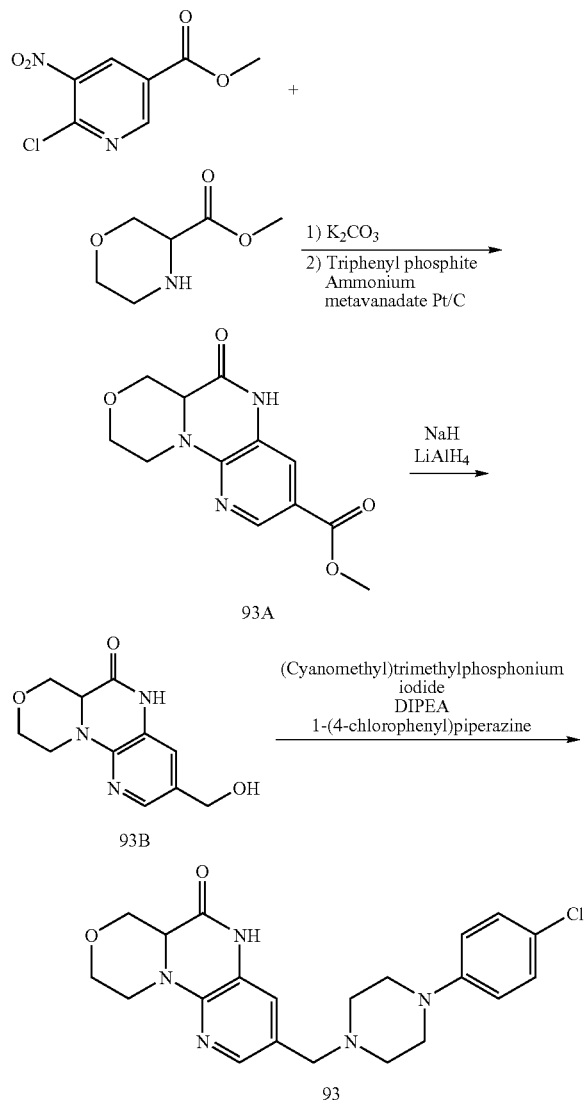

Compound 93A: methyl 6-oxo-5,6,6a,7,9,10-hexahydro-[1,4]oxazino[4,3-a]pyrido[3,2-e]pyrazine-3-carboxylate To a suspension of methyl morpholine-3-carboxylate (2.0 g, 13.78 mmol) in THF was added methyl methyl 6-chloro-5-nitronicotinate (2.71 g, 12.53 mmol) and potassium carbonate (5.19 g, 37.6 mmol). The suspension was heated to reflux for 3 hours. The crude orange solution was allowed to cool to RT and filtered through a pad of celite which was washed with DCM (50 mL) and transferred to a bomb hydroginator. To the solution was added triphenyl phosphite (0.039 ml, 0.125 mmol), platinum (5%, 0.489 g, 0.125 mmol), and ammonium metavanadate (0.117 g, 1.0 mmol). The vessel was sealed and pressurized to 140 psi with stirring for 24 h at room temperature. The vessel was depressurized and the mixture was diluted with DCM (100 mL) and refluxed for 30 minutes. The hot mixture was filtered through celite and concentrated to yield 1.98 g (60%) of the product as a white solid. [M+H] calc'd for C12H13N3O4, 264; found, 264.

Compound 93B: 3-(hydroxymethyl)-6a,7,9,10-tetrahydro-[1,4]oxazino[4,3-a]pyrido[3,2-e]pyrazin-6(5H)-one Methyl 6-oxo-5,6,6a,7,9,10-hexahydro-[1,4]oxazino[4,3-a]pyrido[3,2-e]pyrazine-3-carboxylate (1000 mg, 3.80 mmol) was taken up in tetrahydrofuran (47 mL) in an inert environment. To the stirred suspension at room temperature was added NaH (228 mg, 5.70 mmol, 60% dispersion in mineral oil) and stirred 30 minutes. The reaction was then cooled to −45° C. and lithium aluminum hydride (11.4 mL, 1M in THF) was added. The reaction was stirred at a temperature between −20 and −10° C. for 1 hour. The reaction was then cooled back to −78° C. and methanol (3 ml) followed by water (1 ml) was added. The reaction was allowed to stir at ambient temperature for 2 hours and then poured into ethyl acetate (400 ml) and water (100 ml). The biphasic mixture was stirred vigorously and then filtered through a medium frit. The filtrate was collected. The layers were separated and the aqueous phase was extracted with ethyl acetate (1×100 ml). The organic layers were combined, washed with brine (100 ml), and concentrated to yield 657 mg (73.5%) of the title compound as a white solid. [M+H] calc'd for C11H13N3O3, 236; found, 236.

Compound 93: 3-((4-(4-chlorophenyl)piperazin-1-yl) methyl)-6a,7,9,10-tetrahydro-[1,4]oxazino[4,3-a] pyrido[3,2-e]pyrazin-6(5H)-one To a suspension of 3-(hydroxymethyl)-6a,7,9,10-tetrahydro-[1,4]oxazino[4,3-a]pyrido[3,2-e]pyrazin-6(5H)-one (73.2 mg, 0.311 mmol) in propiononitrile (778 μl) was added (cyanomethyl)trimethylphosphonium iodide (91 mg, 0.373 mmol) and DIPEA (163 μl, 0.934 mmol) and finally 1-(4-chlorophenyl)piperazine (61.2 mg, 0.311 mmol). The mixture was heated to 90° C. for 4 hours. The crude product was cooled to RT and left to sit 16 hours, then treated with MeOH (5 mL). The precipitate was collected and refluxed in EtOH (15 mL) 2 hours. The suspension was cooled to room temperature and filtered to retrieve the title compound (75.6 mg, 58.7%) as a white solid. $^1$H NMR(CHLOROFORM-d) δ (ppm): 7.82 (d, J=1.8 Hz, 1H), 7.72 (br. s., 1H), 7.16-7.24 (m, 2H), 6.99 (br. s., 1H), 6.77-6.89 (m, 2H), 4.41 (dd, J=11.5, 3.7 Hz, 1H), 4.26 (dd, J=13.3, 1.6 Hz, 1H), 3.95-4.12 (m, 2H), 3.59-3.75 (m, 2H), 3.46 (br. s., 2H), 3.16 (br. s., 4H), 2.94-3.06 (m, 1H), 2.60 (br. s., 4H). [M+H] calc'd for C21H24ClN5O2, 414; found, 414.

Compound 94: 7-((4-(4-chlorophenyl)-5,6-dihydropyridin-1(2H)-yl)methyl)-4-isopropyl-3,4-dihydropyrido[2,3-b]pyrazin-2(1H)-one

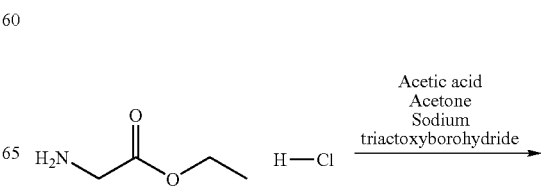

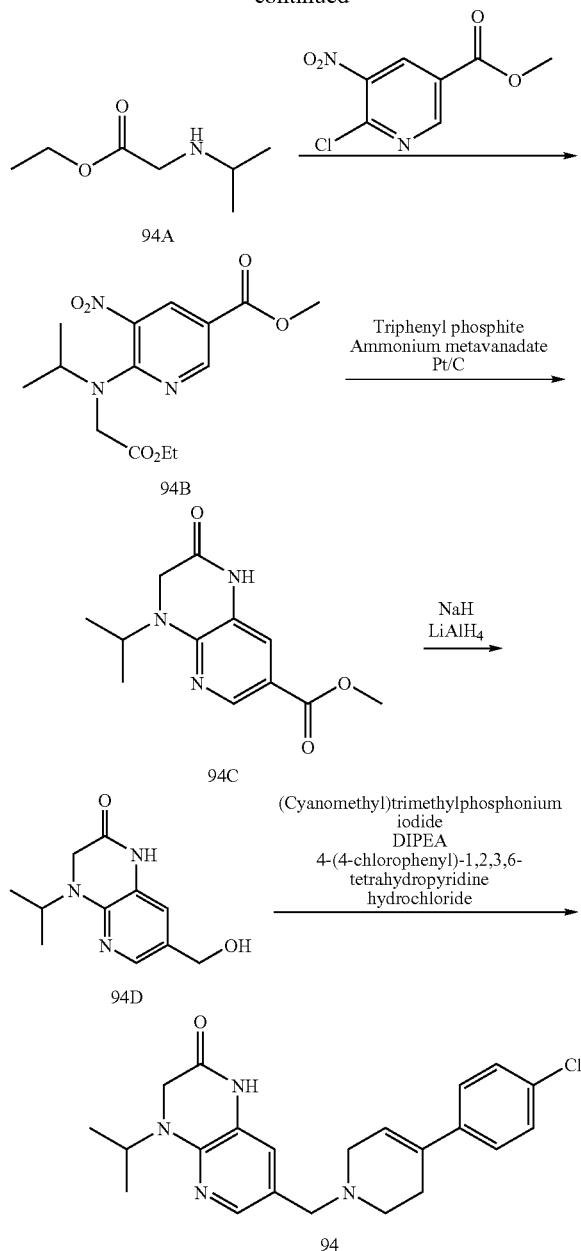

Compound 94A: Ethyl 2-(isopropylamino)acetate

To a suspension of ethyl 2-aminoacetate hydrochloride (20 g, 143.28 mmol) in THF (400 mL) was added glacial acetic acid (20 mL) followed by acetone (11.59 mL, 151.62 mmol). The reaction was stirred 30 min at room temperature. Sodium triacetoxyborohydride (60.73 g, 286.56 mmol) was added over the course of one hour. The reaction was poured slowly into a vigorously stirred biphasic mixture of water (300 mL) and ethyl acetate (800 mL). The aqueous layer was adjusted to pH 13 using a solution of 50% (weight) NaOH. The mixture was stirred 30 min and poured into a separatory funnel. The organic layer was collected and the aqueous layer was back extracted with ethyl acetate (3×200 mL). The organic layers were combined, washed with brine (300 mL), dried with sodium sulfate, and concentrated to yield the title compound (17.6 g, 85%) as a translucent oil which was used in the next step without further purification. [M+H] calc'd for C7H15NO2, 146; found, 146.

Compound 94B: Methyl 6-((2-ethoxy-2-oxoethyl)(isopropyl)amino)-5-nitronicotinate Methyl 6-chloro-5-nitronicotinate (2 g, 9.23 mmol) was added to ethyl 2-(isopropylamino) acetate (5.0 g, 34.5 mmol) neat while stirring at room temperature. The viscous yellow reaction was heated to 90° C. for one h and then allowed to cool back to room temperature. The reaction was diluted with dichloromethane (20 mL) and purified via column chromatography (220 g SiO2, 20-30% gradient, ethyl acetate in hexanes) to yield the title compound (2.39 g, 83%) as a yellow oil. [M+H] calc'd for C14H19N3O6, 326; found, 326.

Compound 94C: Methyl 4-isopropyl-2-oxo-1,2,3,4-tetrahydropyrido[2,3-b]pyrazine-7-carboxylate Methyl 6-((2-ethoxy-2-oxoethyl)(isopropyl)amino)-5-nitronicotinate (2.39 g, 7.35 mmol) was dissolved in dichloromethane (10 mL). To the yellow solution was added ammonium metavanadate (15.0 mg, 1.13 mmol), triphenyl phosphite (aprox 10 ul, 0.032 mmol), and Pt/C (240 mg, 5% w/w). The reaction mixture was pressurized with hydrogen gas (110 psi) and stirred at room temperature for 16 h. The reaction was then depressurized and diluted with dichloromethane (80 mL) which was then refluxed for 30 min. The hot solution was filtered through a pad of celite and washed with hot dichloromethane (3×20 mL). The filtrate was concentrated to yield the title compound (1.70 g, 93%) as a white solid. [M+H] calc'd for C12H15N3O3, 250; found, 250.

Compound 94D: 7-(hydroxymethyl)-4-isopropyl-3,4-dihydropyrido[2,3-b]pyrazin-2(1H)-one Methyl 4-isopropyl-2-oxo-1,2,3,4-tetrahydropyrido[2,3-b]pyrazine-7-carboxylate (1.3 g, 5.45 mmol) was suspended in tetrahydrofuran (68 mL). The white suspension was cooled to 0° C. and NaH (60% dispersion in mineral oil, 0.327 g, 8.17 mmol) was added. The reaction was removed from the ice bath and allowed to stir at RT for 0.5 h. The solution was then cooled to −78° C. and LiAlH4 was added over two min. A temperature between −30 and −20° C. was maintained. The reaction was cooled to −78° C. and MeOH (2 mL) was added. The reaction was stirred at room temperature 30 min. The reaction was poured into ethyl acetate (400 mL) and water (100 mL), and stirred for 1 hr. The mixture was filtered through medium frit to remove tan solids. The aqueous layer was extracted with ethyl acetate (1×100 mL). The organic fractions were combined, washed once with brine (100 mL), dried with sodium sulfate and concentrated to the title compound (1.10 g, 91%) as a white solid. [M+H] calc'd for C11H15N3O2, 222; found, 222.

Compound 94:4(4-(4-chlorophenyl)-5,6-dihydropyridin-1(2H)-yl)methyl)-4-isopropyl-3,4-dihydropyrido[2,3-b]pyrazin-2(1H)-one 7-(hydroxymethyl)-4-isopropyl-3,4-dihydropyrido[2,3-b]pyrazin-2(1H)-one (100 mg, 0.452 mmol) was taken up as a suspension in propiononitrile (1 mL). Next was added (cyanomethyl)trimethylphosphonium iodide (132 mg, 0.542 mmol) followed by DIPEA (0.237 mL, 1.356 mmol). To the stirred white suspension was then added the 4-(4-chlorophenyl)-1,2,3,6-tetrahydropyridine hydrochloride (114 mg, 0.50 mmol). The reaction was heated to 90° C. and stirred overnight. The crude reaction was cooled to room temperature and concentrated to a residue, then taken up in 3 mL DMSO and purified via HPLC (55-90% acetonitrile in water, ammonium bicarbonate buffer). The fractions were combined and concentrated until a white solid precipitated. The precipitate was filtered off and dried in vacuum to afford the title compound (46.9 mg, 26%) as a white solid. $^1$H NMR (DMSO-d$_6$) δ (ppm): 10.50 (s, 1H), 7.65 (d, J=1.8 Hz, 1H), 7.40-7.46 (m, 2H), 7.34-7.39 (m, 2H), 6.98 (d, J=2.0 Hz, 1H), 6.18 (br. s., 1H), 4.76-4.87 (m, 1H), 3.81 (s, 2H), 3.40 (s, 2H), 3.01 (d, J=2.8 Hz, 2H), 2.60 (t, J=5.6 Hz, 2H), 2.43 (br. s., 2H), 1.12 (d, J=6.8 Hz, 6H). [M+H] calc'd for C22H25ClN4O, 397; found, 397.

Compound 95: 7-((4-(4-chlorophenyl)piperazin-1-yl)methyl)-4-isopropyl-3,4-dihydropyrido[2,3-b]pyrazin-2(1H)-one

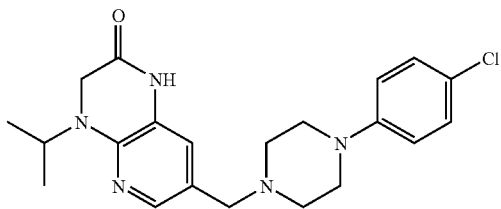

The 7-(hydroxymethyl)-4-isopropyl-3,4-dihydropyrido[2,3-b]pyrazin-2(1H)-one (100 mg, 0.452 mmol) was weighed into a vial and taken up as a suspension in propiononitrile (1 mL). Next was added (cyanomethyl)trimethylphosphonium iodide (132 mg, 0.542 mmol) followed by DIEA (0.237 mL, 1.356 mmol). To the stirred white suspension was then added the 1-(4-chlorophenyl)piperazine hydrochloride (116 mg, 0.50 mmol). The reaction was stirred overnight at 90° C. The crude reaction was cooled to room temperature and concentrated to a residue, then taken up in DMSO (3 mL) and purified via HPLC (55-90% acetonitrile in water, ammonium bicarbonate buffer). The fractions were combined and concentrated until a white solid precipitated. The precipitate was filtered off and dried in vacuum to afford the title compound (46.6 mg, 26%) as a white solid. $^1$H NMR (DMSO-d$_6$) δ (ppm): 10.49 (s, 1H), 7.63 (d, J=2.0 Hz, 1H), 7.21 (d, J=9.1 Hz, 2H), 6.97 (d, J=1.8 Hz, 1H), 6.92 (d, J=9.1 Hz, 2H), 4.74-4.87 (m, 1H), 3.81 (s, 2H), 3.33 (d, J=2.0 Hz, 2H), 3.01-3.15 (m, 4H), 2.41-2.48 (m, 4H), 1.12 (d, J=6.8 Hz, 6H). [M+H] calc'd for C21H26ClN5O, 400; found, 400.

Compound 96: 7-((4-(4-chlorophenyl)piperidin-1-yl)methyl)-4-isopropyl-3,4-dihydropyrido[2,3-b]pyrazin-2(1H)-one

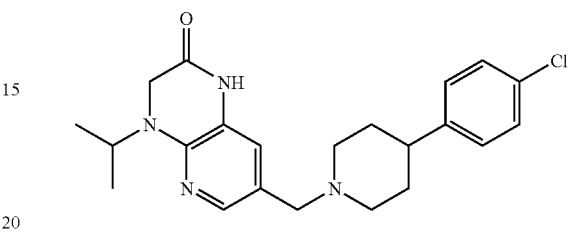

The 7-(hydroxymethyl)-4-isopropyl-3,4-dihydropyrido[2,3-b]pyrazin-2(1H)-one (100 mg, 0.452 mmol) suspended in propionitrile (1 mL). To this was added (cyanomethyl)trimethylphosphonium iodide (132 mg, 0.542 mmol) followed by DIEA (0.237 mL, 1.356 mmol) and 4-(4-chlorophenyl)piperidine hydrochloride (115 mg, 0.50 mmol). The reaction was stirred at 90° C. overnight. The crude reaction was cooled to room temperature and concentrated to a residue, then taken up in DMSO (3 mL) and purified via HPLC (55-90% acetonitrile in water, ammonium bicarbonate buffer). The fractions were combined and concentrated until a white solid precipitated. The precipitate was filtered and dried in vacuum to afford the title compound (28.3 mg, 16%) as a white solid. $^1$H NMR (DMSO-d$_6$) δ (ppm): 10.49 (s, 1H), 7.62 (d, J=2.0 Hz, 1H), 7.29-7.37 (m, 2H), 7.18-7.29 (m, 2H), 6.96 (d, J=2.0 Hz, 1H), 4.75-4.87 (m, 1H), 3.81 (s, 2H), 3.32 (d, J=12.9 Hz, 3H), 2.88 (d, J=11.1 Hz, 2H), 1.87-2.07 (m, 2H), 1.65-1.77 (m, 2H), 1.57 (dd, J=12.4, 3.3 Hz, 2H), 1.10 (d, 6H). [M+H] calc'd for C22H27ClN4O, 399; found, 399.

Compound 97: 7-[4-(4-Chloro-phenyl)-piperazin-1-ylmethyl]-2-methyl-1,3,4,10a-tetrahydro-2H,9H-2,4-a,5,9-tetraaza-phenanthren-10-one

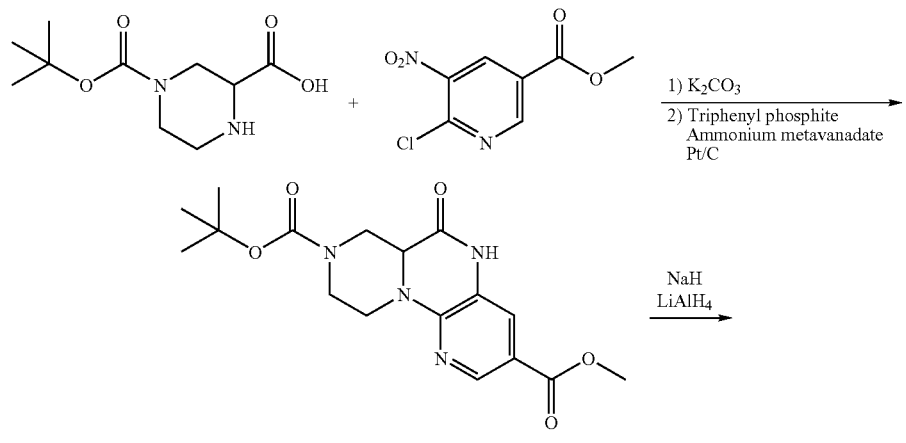

97A

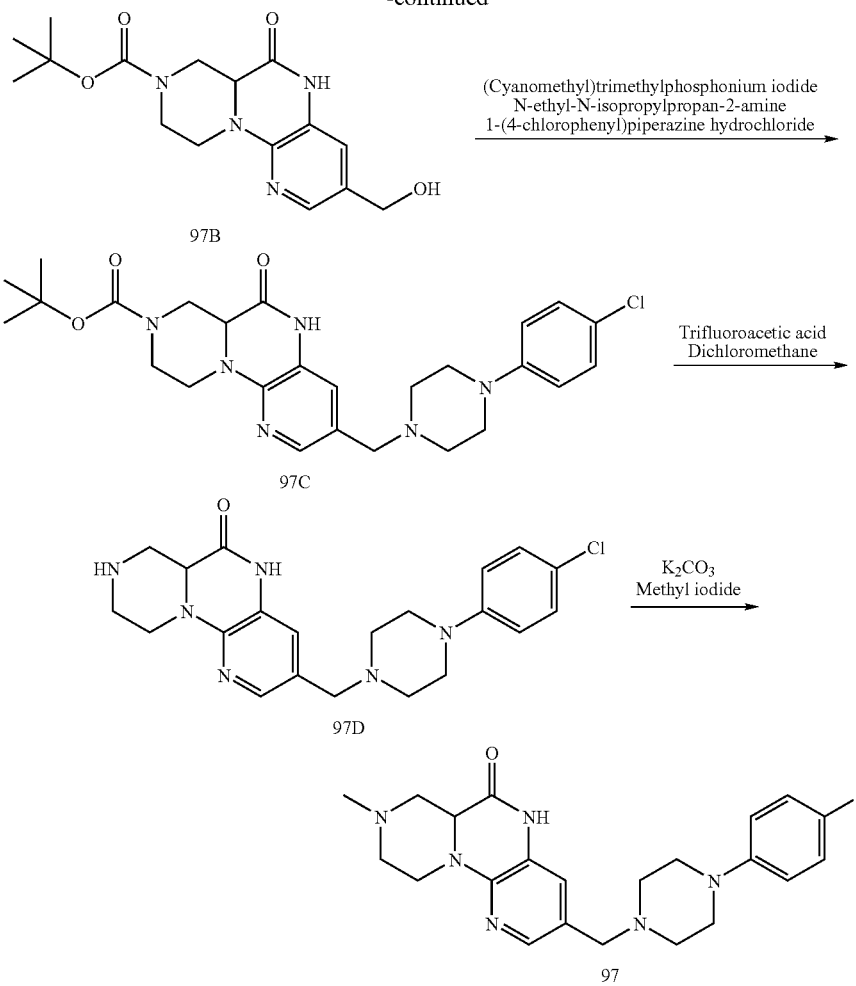

Compound 97A: 10-Oxo-1,3,4,9,10,10a-hexahydro-2,4-a,5,9-tetraaza-phenanthrene-2,7-dicarboxylic acid 2-tert-butyl ester 7-methyl ester To a suspension of 4-(tert-butoxycarbonyl)piperazine-2-carboxylic acid (1169 mg, 5.08 mmol) in THF (46 mL) was added methyl 6-chloro-5-nitronicotinate (1000 mg, 4.62 mmol) and $K_2CO_3$ (638 mg, 4.62 mmol). The suspension was heated to reflux for 2 hours, cooled to room temperature, and filtered through a pad of celite. The celite was washed with DCM (50 mL) and the organic portions were combined. The solution was charged into a bomb hydroginator, then treated with triphenyl phosphite (0.015 ml, 0.048 mmol), ammonium vanadate (44 mg, 0.380 mmol), and platinum (1.853 g, 0.475 mmol). The reaction was sealed and pressurized with hydrogen gas (150 psi) overnight. The reaction was then diluted with DCM (100 mL) and heated to reflux for 1 hr. The hot mixture was filtered through celite, washed with DCM (50 mL), and concentrated to 1.65 g (96%) of the title compound as an off-white solid. [M+H] calc'd for $C_{17}H_{22}N_4O_5$, 363; found, 363.

Compound 97B: 7-Hydroxymethyl-10-oxo-1,3,4,9,10,10a-hexahydro-2,4-a,5,9-tetraaza-phenanthrene-2-carboxylic acid tert-butyl ester 10-Oxo-1,3,4,9,10,10a-hexahydro-2,4-a,5,9-tetraaza-phenanthrene-2,7-dicarboxylic acid 2-tert-butyl ester 7-methyl ester (545 mg, 1.504 mmol) was taken up in tetrahydrofuran (18 mL) in an inert environment. To the stirred suspension at room temperature was added NaH (90 mg, 2.26 mmol, 60% dispersion in mineral oil) and stirred 30 minutes. The reaction was then cooled to −45° C. and lithium aluminum hydride (2.26 ml, 2M in THF) was added. The reaction was stirred at a temperature between −20 and −10° C. for 1 hour. The reaction was then cooled back to −60° C. and MeOH (5 ml) followed by water (1 ml) was added. The reaction was allowed to stir at ambient temperature for 2 hours and then poured into ethyl acetate (400 ml) and water (100 ml). The biphasic mixture was stirred vigorously and then filtered through a medium frit. The filtrate was collected. The layers were separated and the aqueous phase was extracted with ethyl acetate (1×100 ml). The organic layers were combined, washed with brine (100 ml), and concentrated to 429.4 mg (96%) of the title compound as an off-white solid. [M+H] calc'd for $C_{16}H_{22}N_4O_4$, 335; found, 335

Compound 97C: 7-[4-(4-Chloro-phenyl)-piperazin-1-ylmethyl]-10-oxo-1,3,4,9,10,10a-hexahydro-2,4-a,5,9-tetraaza-phenanthrene-2-carboxylic acid tert-butyl ester 7-Hydroxymethyl-10-oxo-1,3,4,9,10,10a-hexahydro-2,4-a,5,9-tetraaza-phenanthrene-2-carboxylic acid tert-butyl ester (22.0 mg, 0.598 mmol) was suspended in propionitrile (1.5 mL) and (cyanomethyl)trimethylphosphonium iodide (174.0 mg, 0.718 mmol) was added followed by N-ethyl-N-isopropylpropan-2-amine (313 ul, 1.794 mmol). To the stirred mixture was then added 1-(4-chlorophenyl)piperazine hydrochloride (139 mg, 0.598 mmol). The reaction was heated to 90° C. with stirring for 16 h. The crude reaction was cooled to room temperature and purified on silica column (24 g, 25% THF in ethyl acetate). The fractions were combined and concentrated to afford 250.9 mg (82%) of the title compound as a brown solid in 80% purity. [M+H] calc'd for C26H33ClN6O3, 513; found, 513.

Compound 97D: 7-[4-(4-Chloro-phenyl)-piperazin-1-ylmethyl]-1,3,4,10a-tetrahydro-2H,9H-2,4-a,5,9-tetraaza-phenanthren-10-one 7-[4-(4-Chloro-phenyl)-piperazin-1-ylmethyl]-10-oxo-1,3,4,9,10,10a-hexahydro-2H-2,4-a,5,9-tetraaza-phenanthrene-2-carboxylic acid tert-butyl ester (250 mg, 0.487 mmol) was dissolved in dichloromethane (5 mL) and trifluoroacetic acid (3 mL) was added while stirring at room temperature. The reaction was stirred for 16 h and concentrated to a residue. The residue was dissolved in DMF and purified via HPLC (55-90% acetonitrile in water, ammonium bicarbonate buffer). The fractions were combined and concentrated until a white solid precipitated. The precipitate was filtered off and dried in vacuum to afford the title compound (17.8 mg, 8.8%) as a white solid. ¹H NMR (DMSO-d₆) δ (ppm): 10.68 (s, 1H), 7.70 (d, J=2.0 Hz, 1H), 7.14-7.30 (m, 2H), 7.03 (d, J=2.0 Hz, 1H), 6.92 (d, J=9.1 Hz, 2H), 4.33 (d, J=11.4 Hz, 1H), 3.97 (dd, J=11.0, 3.4 Hz, 1H), 3.45 (dd, J=12.5, 2.9 Hz, 4H), 3.32-3.36 (m, 4H), 3.16 (d, J=9.6 Hz, 1H), 3.06-3.13 (m, 4H), 2.72-2.87 (m, 3H). [M+H] calc'd for C26H33ClN6O3, 413; found, 413.

Compound 97: 7-[4-(4-Chloro-phenyl)-piperazin-1-ylmethyl]-2-methyl-1,3,4,10a-tetrahydro-2H,9H-2,4-a,5,9-tetraaza-phenanthren-10-one To a solution of 7-[4-(4-Chloro-phenyl)-piperazin-1-ylmethyl]-1,3,4,10a-tetrahydro-2H,9H-2,4-a,5,9-tetraaza-phenanthren-10-one (139 mg, 0.337 mmol) in DMF (3.4 mL) cooled to 0° C. was added potassium carbonate (233 mg, 1.683 mmol) and methyl iodide (2 M in THF, 0.168 mL). The reaction was stirred 1 h at 0° C. and filtered through celite. The filtrate was purified via HPLC (55-90% acetonitrile in water, ammonium bicarbonate buffer). The fractions were combined and concentrated until a white solid precipitated. The precipitate was filtered off and dried in vacuum to afford the title compound (4.6 mg, 3.2%) as a white solid. ¹H NMR (DMSO-d₆) δ (ppm): 10.59 (s, 1H), 7.68 (d, J=1.8 Hz, 1H), 7.15-7.28 (m, 2H), 7.01 (d, J=2.0 Hz, 1H), 6.85-6.97 (m, 2H), 4.17-4.30 (m, 1H), 3.88 (dd, J=10.6, 3.3 Hz, 1H), 3.37 (s, 2H), 3.14-3.20 (m, 1H), 3.06-3.14 (m, 4H), 2.84 (d, J=11.6 Hz, 1H), 2.74 (td, J=12.4, 3.0 Hz, 1H), 2.44-2.48 (m, 4H), 2.26 (s, 3H), 1.91-2.02 (m, 2H). [M+H] calc'd for C22H27ClN6O, 427; found, 427.

Compound 98: (R)—N-methyl-4-(4-((6-oxo-5,6,6a,7,9,10-hexahydropyrido[3,2-e][1,4]thiazino[4,3-a]pyrazin-3-yl)methyl)piperazin-1-yl)benzamide

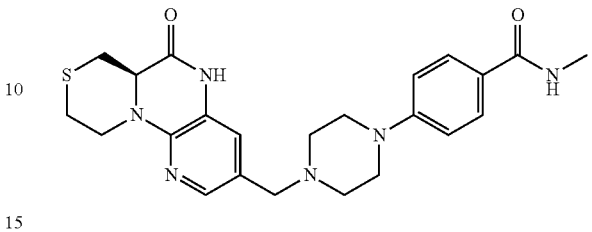

In a vial equipped with a stir bar was charged (R)-4-(4-((6-oxo-5,6,6a,7,9,10-hexahydropyrido[3,2-e][1,4]thiazino[4,3-a]pyrazin-3-yl)methyl)piperazin-1-yl)benzoic acid (50 mg, 0.114 mmol) was taken up in DMF (1.14 mL). To the mixture was added N-ethyl-N-isopropylpropan-2-amine (59 µl, 0.34 mmol), O-(7-Azabenzotriazole-1-yl)-N,N,N'N'-tetramethyluronium hexafluorophosphate (64.9 mg, 0.171 mmol), and methanamine hydrochloride (8.45 mg, 0.125 mmol). The reaction was stirred at room temperature overnight. The reaction was purified via HPLC (55-90% acetonitrile in water, ammonium bicarbonate buffer). The fractions were collected and lyophilized to yield 25.1 mg (49%) of the product as a white solid. ¹H NMR(CHLOROFORM-d) δ: 8.37 (br. s., 1H), 7.58-7.89 (m, 3H), 7.15 (br. s., 1H), 6.87 (d, J=8.8 Hz, 2H), 6.07 (d, J=4.5 Hz, 1H), 5.06 (dt, J=13.6, 2.5 Hz, 1H), 4.42 (dd, J=10.1, 3.8 Hz, 1H), 3.55 (br. s., 2H), 3.36 (br. s., 4H), 3.08-3.24 (m, 1H), 2.56-3.08 (m, 8H), 2.40 (dd, J=13.5, 1.1 Hz, 1H), 1.74 (br. s., 2H). [M+H] calc'd for C23H28N6O2S, 453; found, 453.

Compound 99: (R)—N-cyclopropyl-4-(4-((6-oxo-5,6,6a,7,9,10-hexahydropyrido[3,2-e][1,4]thiazino[4,3-a]pyrazin-3-yl)methyl)piperazin-1-yl)benzamide

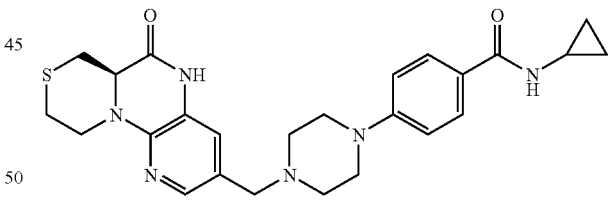

In a vial equipped with a stir bar was charged (R)-4-(4-((6-oxo-5,6,6a,7,9,10-hexahydropyrido[3,2-e][1,4]thiazino[4,3-a]pyrazin-3-yl)methyl)piperazin-1-yl)benzoic acid (50 mg, 0.114 mmol) was taken up in DMF (1.14 mL). To the mixture was added N-ethyl-N-isopropylpropan-2-amine (59 µl, 0.34 mmol), O-(7-Azabenzotriazole-1-yl)-N,N,N'N'-tetramethyluronium hexafluorophosphate (64.9 mg, 0.171 mmol), and cyclopropanamine (9.16 uL, 0.125 mmol). The reaction was stirred at room temperature overnight. The reaction was purified via HPLC (55-90% acetonitrile in water, ammonium bicarbonate buffer). The fractions were collected and lyophilized to yield 25.1 mg (49%) of the product as a white solid ¹H NMR (CHLOROFORM-d) δ: 8.42 (br. s., 1H), 7.78 (d, J=1.5 Hz, 1H), 7.65 (d, J=8.8 Hz, 2H), 7.13 (br. s., 1H), 6.85 (d, J=9.1 Hz, 2H), 6.17 (d, J=2.3 Hz, 1H), 5.05 (ddd, J=13.5, 2.7, 2.5 Hz, 1H), 4.42 (dd, J=10.4, 3.5 Hz, 1H), 3.53 (br. s., 2H), 3.34 (br. s., 4H), 3.14 (td, J=12.9, 2.3 Hz, 1H), 2.99 (td, J=12.8, 2.7 Hz, 1H), 2.78-2.93 (m, 3H), 2.68 (br. s., 4H), 2.39 (dd, J=13.6, 1.3 Hz, 1H), 0.80-0.90 (m, 2H), 0.54-0.67 (m, 2H). [M+H] calc'd for C23H28N6O2S, 479; found, 479.

Compound 100: 6-(4-(((6-oxo-5,6,6a,7,9,10-hexahydro-[1,4]oxazino[4,3-a]pyrido[3,2-e]pyrazin-3-yl)methyl)piperazin-1-yl)nicotinonitrile

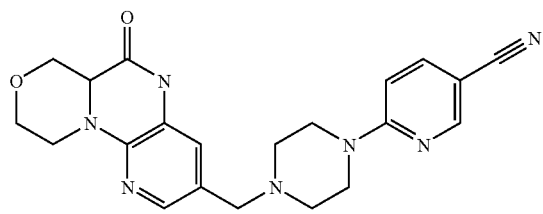

3-(hydroxymethyl)-6a,7,9,10-tetrahydro-[1,4]oxazino[4,3-a]pyrido[3,2-e]pyrazin-6(5H)-one (70.0 mg, 0.298 mmol) was suspended in propionitrile (0.74 mL) and (cyanomethyl)trimethylphosphonium iodide (87.0 mg, 0.357 mmol) was added followed by N-ethyl-N-isopropylpropan-2-amine (115 ul, 0.893 mmol). To the stirred mixture was then added 6-(piperazin-1-yl)nicotinonitrile (56.0 mg, 0.298 mmol). The reaction was heated to 90° C. with stirring for 16 h. The reaction was cooled to room temperature and left to sit 48 h. The precipitate was filtered off, washed with methanol (5 mL) and dried in vacuum to afford the title compound (72.5 mg, 60.1%) as a white solid. $^1$H NMR(CHLOROFORM-d) δ: 8.41 (d, J=1.8 Hz, 1H), 8.20 (br. s., 1H), 7.80 (d, J=2.0 Hz, 1H), 7.61 (dd, J=9.0, 2.4 Hz, 1H), 6.99 (br. s., 1H), 6.59 (d, J=9.1 Hz, 1H), 4.42 (dd, J=11.5, 3.7 Hz, 1H), 4.26 (dd, J=13.3, 1.6 Hz, 1H), 3.95-4.12 (m, 2H), 3.58-3.80 (m, 6H), 3.45 (s, 2H), 2.92-3.08 (m, 1H), 2.53 (br. s., 4H). [M+H] calc'd for C21H23N7O2, 406; found, 406.

Compound 101: (S)-ethyl 4-(4-(((6-oxo-5,6,6a,7,8,9-hexahydropyrido[3,2-e]pyrrolo[1,2-a]pyrazin-3-yl)methyl)piperazin-1-yl)benzoate

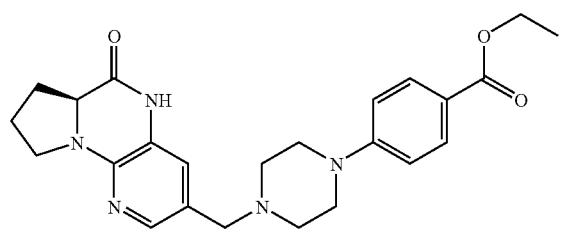

Compound 101 was prepared using a procedure analogous to that described in connection with compound 23. [M+H] calc'd for C24H29N5O3 436; found, 436.1.

Compound 102: (S)-4-(4-(((6-oxo-6,6a,7,8-tetrahydro-5H-azeto[1,2-a]pyrido[3,2-e]pyrazin-3-yl)methyl)piperazin-1-yl)benzonitrile

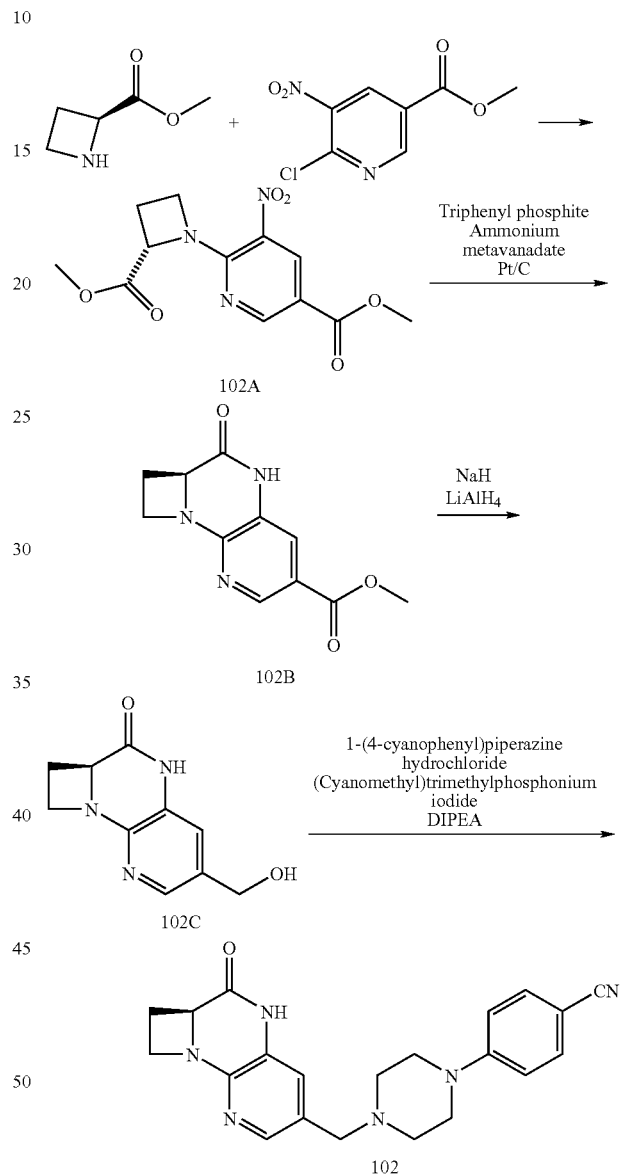

Compound 102A: (S)-methyl 6-(2-(methoxycarbonyl)azetidin-1-yl)-5-nitronicotinate (S)-methyl azetidine-2-carboxylate hydrochloride (1 g, 6.60 mmol) was diluted with Tetrahydrofuran (Volume: 20 ml) and treated with TRIETHYLAMINE (0.919 ml, 6.60 mmol). The reaction mixture was stirred vigorously and sonicated periodically, until a fine suspension resulted. This was stirred for 1 h and filtered through a small plug of celite. The plug was washed well with THF (20 mL) and the combined filtrate and washes were treated with methyl 6-chloro-5-nitronicotinate (0.714 g, 3.30 mmol). The reaction mixture was concentrated in vacuo and heated briefly (5 min) to 80° C. LCMS showed complete conversion. The reaction mixture was diluted with DCM (10 mL) and purified using flash column chromatography on silica gel (80 g SiO2, 20-30% ethyl acetate in hexanes) to afford the title compound (S)-methyl 6-(2-(methoxycarbonyl)azetidin-1-yl)-5-nitronicotinate (0.90 g, 3.05 mmol, 92% yield) as a yellow oil. [M+H] calc'd for $C_{12}H_{13}N_3O_6$, 295; found, 295.

Compound 102B: (S)-methyl 6-oxo-6,6a,7,8-tetrahydro-5H-azeto[1,2-a]pyrido[3,2-e]pyrazine-3-carboxylate (S)-methyl 6-(2-(methoxycarbonyl)azetidin-1-yl)-5-nitronicotinate (0.90 g, 3.05 mmol) was dissolved in dichloromethane (Volume: 15.24 ml) and to this solution was added triphenyl phosphite (9.46 mg, 0.030 mmol), ammonium metavanadate (0.021 g, 0.183 mmol) and Pt/C (5% wt.) (0.119 g, 0.030 mmol). The reaction mixture was hydrogenated at 100 psi at 25° C. for 2 h. LCMS showed complete conversion of the starting material to the corresponding amine, but no cyclization product was observed. The reaction mixture was filtered through a short plug of celite and the plug and precipitate were washed well with dichloromethane (30 mL) and methanol (20 mL). The combined filtrates were concentrated in vacuo (LC: CR1) and dissolved in AcOH (5 mL) (LC: AA-rt). This solution was heated to 80° C. for 5 min (LCMS-AA-90C-5 min—complete conversion to the desired product) and concentrated in vacuo. The residue was crystallized with ethyl ether (20 mL) and sonicated until a fine suspension was obtained The precipitate was filtered off and dried in vacuum to afford (S)-methyl 6-oxo-6,6a,7,8-tetrahydro-5H-azeto[1,2-a]pyrido[3,2-e]pyrazine-3-carboxylate (0.5840, 2.504 mmol, 82% yield) as a light pink solid. [M+H] calc'd for $C_{11}H_{11}N_3O_3$, 234; found, 234.

Compound 102C: (S)-3-(hydroxymethyl)-7,8-dihydro-5H-azeto[1,2-a]pyrido[3,2-e]pyrazin-6(6aH)-one (S)-methyl 6-oxo-6,6a,7,8-tetrahydro-5H-azeto[1,2-a]pyrido[3,2-e]pyrazine-3-carboxylate (0.570 g, 2.444 mmol) was suspended in Tetrahydrofuran (Volume: 8.15 ml) under nitrogen atmosphere and NaH (196 mg, 4.9 mmol) was added in several portions over 2 min. The reaction mixture was stirred at room temperature for 10 min and cooled to below −50° C. lithium aluminum hydride (2.200 ml, 4.40 mmol) was added over the period of 5 min and the reaction was kept at a temperature between −30 and −20° C. for 1 h (LCMS: >95% conversion). The mixture was cooled to below −50° C. and MeOH (4 mL) was added. Water (1 mL) was added and the reaction mixture was stirred at rt for 10 min. Rochelle salt (20% solution) was added (10 mL) and the mixture was extracted with EtOAc (3×30 mL) and THF (3×100 mL). The combined organic extracts were dried (Na2SO4 and MgSO4), filtered and concentrated in vacuo. The residue was suspended in THF/Ethyl ether (1:1, 20 mL), filtered off and dried in vacuum to afford (S)-3-(hydroxymethyl)-7,8-dihydro-5H-azeto[1,2-a]pyrido[3,2-e]pyrazin-6(6aH)-one (0.332 g, 1.618 mmol, 66.2% yield) as a light tan solid. [M+H] calc'd for $C_{10}H_{11}N_3O_2$, 205; found, 205.

Compound 102: (S)-4-(4-((6-oxo-6,6a,7,8-tetrahydro-5H-azeto[1,2-a]pyrido[3,2-e]pyrazin-3-yl)methyl)piperazin-1-yl)benzonitrile (S)-3-(hydroxymethyl)-7,8-dihydro-5H-azeto[1,2-a]pyrido[3,2-e]pyrazin-6(6aH)-one (103 mg, 0.5 mmol), 4-(piperazin-1-yl)benzonitrile (108 mg, 0.575 mmol), (cyanomethyl)trimethylphosphonium iodide (207 mg, 0.850 mmol) and N,N-diisopropylethylamine (0.437 ml, 2.500 mmol) were suspended in Propiononitrile (Volume: 1.502 ml) and heated in a closed vial at 90° C. for 23 h. The reaction mixture was cooled, diluted with MeOH (2 mL) and purified using preparative HPLC (basic phase). The fractions containing product were concentrated in vacuo and crystallized from water-methanol (3 mL, ~5:1) The precipitate was filtered and dried in vacuum to afford (S)-4-(4-((6-oxo-6,6a,7,8-tetrahydro-5H-azeto[1,2-a]pyrido[3,2-e]pyrazin-3-yl)methyl)piperazin-1-yl)benzonitrile (11.7 mg, 0.031 mmol, 6.25% yield) as a light brown solid. $^1$H NMR (400 MHz, DMSO-d6) δ ppm 2.37-2.47 (m, 4H) 2.68-2.80 (m, 1H) 2.94 (tt, J=10.67, 7.26 Hz, 1H) 3.30 (d, J=4.80 Hz, 4H) 3.36 (s, 2H) 3.87-4.00 (m, 1H) 4.21 (q, J=7.66 Hz, 1H) 4.93 (t, 1H) 6.98 (d, J=1.77 Hz, 1H) 7.00 (d, J=9.09 Hz, 2H) 7.57 (d, J=9.09 Hz, 2H) 7.65 (d, J=1.77 Hz, 1H) 10.34 (s, 1H). [M+H] calc'd for $C_{21}H_{22}N_6O$, 374; found, 374.

Compound 103: 4-(4-((6-oxo-6,7,7a,8,9,10-hexahydro-5H-pyrido[3,2-b]pyrrolo[1,2-d][1,4]diazepin-3-yl)methyl)piperazin-1-yl)benzonitrile

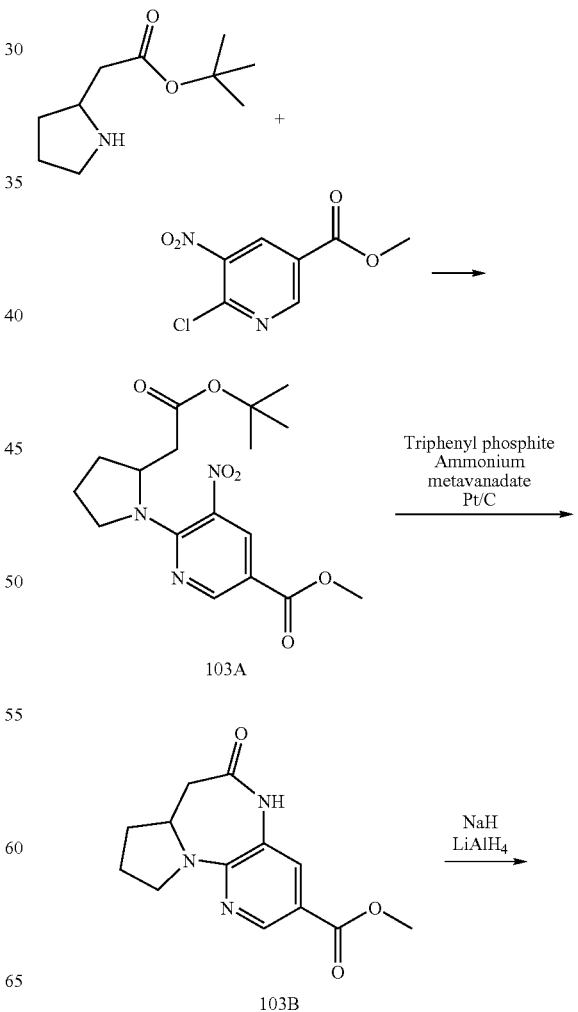

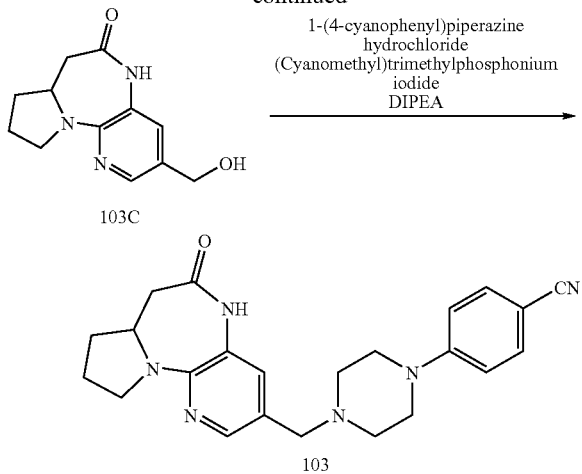

Compound 103A: Methyl 6-(2-(2-tert-butoxy-2-oxo-ethyl)pyrrolidin-1-yl)-5-nitronicotinate Tert-butyl 2-(pyrrolidin-2-yl)acetate (1.00 g, 5.40 mmol) was added to a solution of methyl 6-chloro-5-nitronicotinate (1.169 g, 5.40 mmol) in THF (Volume: 10 ml). The reaction mixture was stirred at rt for 1 h and K₂CO₃ (0.760 g, 5.50 mmol) was added. The reaction mixture was stirred for 2 h and triethylamine (0.379 ml, 2.70 mmol) was added. The mixture was stirred for 1 h, filtered and concentrated in vacuo. Flash column chromatography on silica gel (120 g SiO2, hexanes:ethyl acetate 9:1) afforded methyl 6-(2-(2-tert-butoxy-2-oxoethyl)pyrrolidin-1-yl)-5-nitronicotinate (1.79 g, 4.90 mmol, 91% yield) as a yellow oil. [M+H] calc'd for C₁₇H₂₃N₃O₆, 365; found, 365.

Compound 103B: Methyl 6-oxo-6,7,7a,8,9,10-hexahydro-5H-pyrido[3,2-b]pyrrolo[1,2-d][1,4]diazepine-3-carboxylate Methyl 6-(2-(2-tert-butoxy-2-oxoethyl)pyrrolidin-1-yl)-5-nitronicotinate (1.79 g, 4.90 mmol) was dissolved in dichloromethane (Volume: 24.49 ml) and to this solution was added triphenyl phosphite (0.015 g, 0.049 mmol), ammonium metavanadate (0.034 g, 0.294 mmol) and Pt/C (5% wt.) (0.191 g, 0.049 mmol). The reaction mixture was hydrogenated at 100 psi at 25° C. for 3 h. The reaction mixture was filtered through a short plug of celite and the plug and precipitate were washed well with dichloromethane (30 mL). The combined filtrates were concentrated in vacuo and dissolved in AcOH (7 mL). This solution was heated to 90° C. for 10 min and concentrated in vacuo. The residue was crystallized with ethyl ether (20 mL) and sonicated until a fine suspension was obtained The precipitate was filtered off and dried in vacuum to afford methyl 6-oxo-6,7,7a,8,9,10-hexahydro-5H-pyrido[3,2-b]pyrrolo[1,2-d][1,4]diazepine-3-carboxylate (0.927 g, 3.55 mmol, 72.4% yield) as a light pink solid. ¹H NMR (400 MHz, DMSO-d6) δ ppm 1.55-1.71 (m, 1H) 1.74-1.89 (m, 1H) 1.89-1.99 (m, 1H) 2.19 (d, J=5.81 Hz, 1H) 2.59 (dd, J=14.78, 1.64 Hz, 1H) 2.77 (dd, J=14.78, 9.98 Hz, 1H) 3.56-3.67 (m, 1H) 3.67-3.76 (m, 1H) 3.78 (s, 3H) 3.99 (td, J=9.85, 5.56 Hz, 1H) 7.64 (d, J=2.02 Hz, 1H) 8.40 (d, J=2.02 Hz, 1H) 9.73 (d, 1H) [M+H] calc'd for C₁₃H₁₅N₃O₃, 261; found, 261.

Compound 103C: 3-(Hydroxymethyl)-7a,8,9,10-tetrahydro-5H-pyrido[3,2-b]pyrrolo[1,2-d][1,4]diazepin-6(7H)-one Methyl 6-oxo-6,7,7a,8,9,10-hexahydro-5H-pyrido[3,2-b]pyrrolo[1,2-d][1,4]diazepine-3-carboxylate (0.900 g, 3.44 mmol) was suspended in THF (Volume: 11.48 ml) under nitrogen atmosphere and NaH (276 mg, 6.9 mmol) was added in several portions over 2 min. The reaction mixture was stirred at room temperature for 10 min and cooled to below −50° C. aluminum(III) lithium hydride (3.10 ml, 6.20 mmol) was added over the period of 5 min and the reaction was kept at a temperature between −30 and −20° C. for 1 h (LCMS: >95% conversion). The mixture was cooled to below −50° C. and MeOH (4 mL) was added. Water (1 mL) was added and the reaction mixture was stirred at rt for 10 min. Rochelle salt (20% solution) was added (10 mL) and the mixture was extracted with THF (4×10 mL). The combined organic extracts were dried (Na2SO4 and MgSO4), filtered and concentrated in vacuo. The residue was recrystallized from THF/Ethyl ether (1:1, 20 mL). The solid was filtered off and dried in vacuum to afford 3-(hydroxymethyl)-7a,8,9,10-tetrahydro-5H-pyrido[3,2-b]pyrrolo[1,2-d][1,4]diazepin-6(7H)-one (0.654 g, 2.80 mmol, 81% yield) as a white solid. ¹H NMR (400 MHz, DMSO-d6) δ ppm 1.58 (m, J=11.62, 11.62, 9.73, 6.69 Hz, 1H) 1.74-1.85 (m, 1H) 1.86-1.96 (m, 1H) 2.14 (m, J=11.91, 5.98, 5.98, 1.89 Hz, 1H) 2.52-2.58 (m, 1H) 2.58-2.67 (m, 1H) 3.49 (ddd, J=10.93, 8.15, 2.15 Hz, 1H) 3.66 (td, J=10.61, 6.82 Hz, 1H) 3.81-3.93 (m, 1H) 4.31 (d, J=5.31 Hz, 2H) 5.01 (t, J=5.43 Hz, 1H) 7.14 (d, J=2.02 Hz, 1H) 7.77 (d, J=2.02 Hz, 1H) 9.60 (d, 1H). [M+H] calc'd for C₁₂H₁₅N₃O₂, 233; found, 233.

Compound 103: 4-(4-((6-oxo-6,7,7a,8,9,10-hexahydro-5H-pyrido[3,2-b]pyrrolo[1,2-d][1,4]diazepin-3-yl)methyl)piperazin-1-yl)benzonitrile 4-(4-((6-oxo-6,7,7a,8,9,10-hexahydro-5H-pyrido[3,2-b]pyrrolo[1,2-d][1,4]diazepin-3-yl)methyl)piperazin-1-yl)benzonitrile: 3-(hydroxymethyl)-7a,8,9,10-tetrahydro-5H-pyrido[3,2-b]pyrrolo[1,2-d][1,4]diazepin-6(7H)-one (100 mg, 0.429 mmol), 4-(piperazin-1-yl)benzonitrile (96 mg, 0.514 mmol), (cyanomethyl)trimethylphosphonium iodide (167 mg, 0.685 mmol) and N,N-diisopropylethylamine (0.374 mL, 2.141 mmol) were suspended in propiononitrile (Volume: 2 mL) and heated in a closed vial at 90° C. for 5 h. The reaction mixture was cooled, diluted with DMSO (2 mL) and purified using preparative HPLC (basic phase, 25-95% ACN). The fractions containing product were concentrated in vacuo and crystallized from water (5 mL). The precipitate was filtered and dried in vacuum to afford 4-(4-((6-oxo-6,7,7a,8,9,10-hexahydro-5H-pyrido[3,2-b]pyrrolo[1,2-d][1,4]diazepin-3-yl)methyl)piperazin-1-yl)benzonitrile (124.2 mg, 0.309 mmol, 72.1% yield) as a light brown solid. ¹H NMR (400 MHz, DMSO-d6) δ ppm 1.51-1.65 (m, 1H) 1.72-1.86 (m, 1H) 1.87-1.97 (m, 1H) 2.14 (qd, J=5.81, 4.04 Hz, 1H) 2.40-2.48 (m, 4H) 2.52-2.59 (m, 1H) 2.66 (dd, 1H) 3.30 (br. s., 4H) 3.33-3.40 (m, 2H) 3.45-3.54 (m, 1H) 3.66 (td, J=10.61, 6.82 Hz, 1H) 3.88 (td, J=9.47, 6.06 Hz, 1H) 7.00 (d, J=9.35 Hz, 2H) 7.14 (d, J=2.02 Hz, 1H) 7.57 (d, J=9.09 Hz, 2H) 7.75 (d, J=2.02 Hz, 1H) 9.56 (d, 1H). [M+H] calc'd for $C_{23}H_{26}N_6O$, 402; found, 402.

Compound 104: 3-((4-(4-chlorophenyl)piperazin-1-yl)methyl)-7a,8,9,10-tetrahydro-5H-pyrido[3,2-b]pyrrolo[1,2-d][1,4]diazepin-6(7H)-one

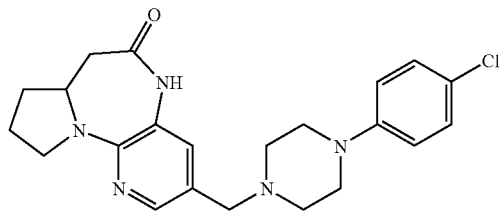

Compound 104 was prepared using a procedure analogous to that described in connection with compound 103, except that 1-(4-chlorophenyl)piperazine hydrochloride was used instead of 1-(4-cyanophenyl)piperazine hydrochloride. $^1$H NMR (400 MHz, DMSO-d6) δ ppm 1.51-1.65 (m, 1H) 1.70-1.87 (m, 1H) 1.87-1.98 (m, 1H) 2.09-2.21 (m, 1H) 2.40-2.48 (m, 4H) 2.55 (d, 1H) 2.66 (dd, 1H) 3.04-3.15 (m, 4H) 3.34 (dd, 2H) 3.46-3.55 (m, 1H) 3.66 (td, J=10.55, 6.69 Hz, 1H) 3.88 (td, J=9.35, 6.06 Hz, 1H) 6.92 (d, J=9.09 Hz, 2H) 7.14 (d, J=1.77 Hz, 1H) 7.21 (d, J=9.09 Hz, 2H) 7.76 (d, J=1.77 Hz, 1H) 9.55 (br. s., 1H). [M+H] calc'd for $C_{23}H_{26}ClN_5O$, 411; found, 411.

Compound 105: 44(S)-3-methyl-4-(((R)-6-oxo-5,6,6a,7,9,10-hexahydropyrido[3,2-e][1,4]thiazino[4,3-a]pyrazin-3-yl)methyl)piperazin-1-yl)benzonitrile

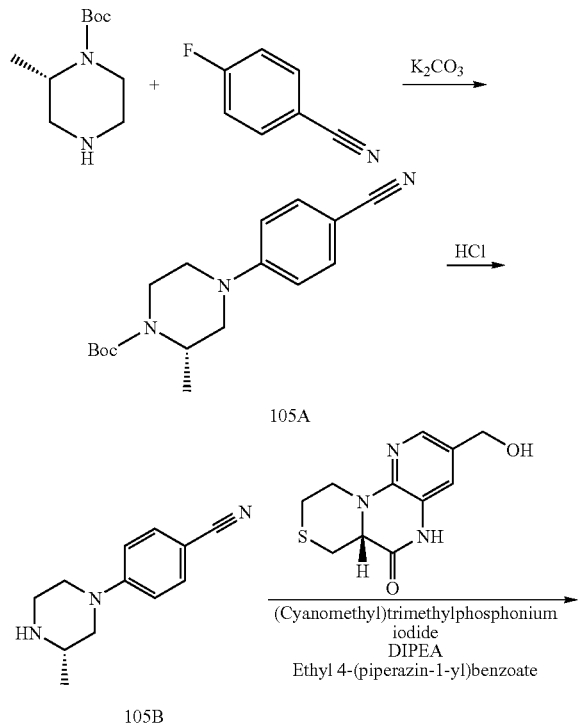

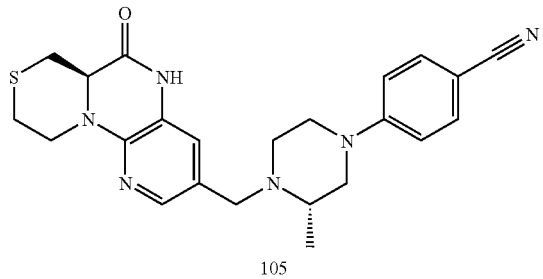

Compound 105A: (S)-tert-butyl 4-(4-cyanophenyl)-2-methylpiperazine-1-carboxylate (S)-tert-butyl 2-methylpiperazine-1-carboxylate (1 g, 4.99 mmol), 4-fluorobenzonitrile (0.605 g, 4.99 mmol), and $K_2CO_3$ (0.897 g, 6.49 mmol) were combined into a vial equipped with a stir bar. The reaction was heated to 110° C. for 48 h. Cooled to RT, diluted with EA and filtered. Concentrated to a clear oil and purified on silica gel (80 g, 10-20% EA in Hex) to give a clear oil (450 mg, 30% yield) which became a crystalline solid upon sitting. [M+H] calc'd for $C_{17}H_{23}N_3O_2$, 301; found, 301.

Compound 105B: (S)-4-(3-methylpiperazin-1-yl)benzonitrile hydrochloride (S)-tert-butyl 4-(4-cyanophenyl)-2-methylpiperazine-1-carboxylate (0.404 g, 1.340 mmol) was diluted with 4.0M HCl in dioxane (3 mL) and stirred for 30 min. The thick white precipitate that formed was diluted with ethyl ether (10 mL) and stirred until a fine suspension resulted. The precipitate was filtered under nitrogen and dried in vacuum to afford a white solid (300 mg, 94%). [M+H] calc'd for $C_{12}H_{15}N_3$, 201; found, 201.

Compound 105: 4-((S)-3-methyl-4-0(R)-6-oxo-5,6,6a,7,9,10-hexahydropyrido[3,2-e][1,4]thiazino[4,3-a]pyrazin-3-yl)methyl)piperazin-1-yl)benzonitrile To a suspension of (R)-3-(hydroxymethyl)-6a,7,9,10-tetrahydropyrido[3,2-e][1,4]thiazino[4,3-a]pyrazin-6(5H)-one (100 mg, 0.617 mmol) in propiononitrile (1.2 mL) was added (cyanomethyl)trimethylphosphonium iodide (180 mg, 0.74 mmol) and DIEA (0.323 ml, 1.80 mmol) and finally (S)-4-(3-methylpiperazin-1-yl)benzonitrile hydrochloride (0.147 g, 0.617 mmol). The vial was heated to 90° C. for 16 hours. The crude rxn was cooled to RT, DMSO (1 ml) was added, and purified via HPLC (55-90, basic) to give the product as a tan solid (58 mg, 22% yield). $^1$H NMR (400 MHz, DMSO-d6) δ ppm 10.62 (s, 1H), 7.69 (d, J=2.0 Hz, 1H), 7.56 (d, J=9.1 Hz, 2H), 6.92-7.11 (m, 3H), 4.87 (dt, J=13.6, 2.7 Hz, 1H), 4.25 (dd, J=10.9, 3.0 Hz, 1H), 3.84 (d, J=13.4 Hz, 1H), 3.66 (d, J=10.6 Hz, 1H), 3.58 (d, J=12.6 Hz, 1H), 2.87-3.12 (m, 3H), 2.64-2.83 (m, 5H), 2.39-2.48 (m, 2H), 2.06-2.19 (m, 1H), 1.14 (d, J=6.1 Hz, 3H). [M+H] calc'd for $C_{23}H_{26}N_6OS$, 434; found, 434.

Compound 106: (R)—N-ethyl-3-fluoro-4-(4-((6-oxo-5,6,6a,7,9,10-hexahydropyrido[3,2-e][1,4]thiazino[4,3-a]pyrazin-3-yl)methyl)piperazin-1-yl)benzamide

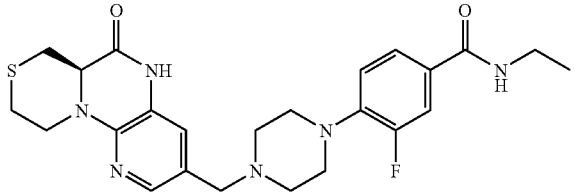

To a suspension of (R)-3-(hydroxymethyl)-6a,7,9,10-tetrahydropyrido[3,2-e][1,4]thiazino[4,3-a]pyrazin-6(5H)-one (146 mg, 0.581 mmol) in propiononitrile (1.2 mL) was added (cyanomethyl)trimethylphosphonium iodide (169 mg, 0.697 mmol) and N-ethyl-3-fluoro-4-(piperazin-1-yl)benzamide hydrochloride (167 mg, 0.581 mmol) and DIEA (304 µl, 1.743 mmol)). The vial was heated to 90° C. for 16 hours. The crude rxn was cooled to RT, DMSO (1 ml) was added, and purified via HPLC (55-90, basic). The fractions were collected, concentrated until a precipitate was visible and filtered. The solids were washed with water and collected to retrieve the product as a white solid (97 mg, 34% yield). $^1$H NMR (400 MHz, DMSO-d6) δ ppm 10.66 (s, 1H), 8.35 (t, J=5.6 Hz, 1H), 7.69 (d, J=1.8 Hz, 1H), 7.55-7.65 (m, 2H), 6.97-7.08 (m, 2H), 4.88 (dt, J=13.6, 2.7 Hz, 1H), 4.27 (dd, J=10.9, 3.0 Hz, 1H), 3.38 (d, J=2.0 Hz, 2H), 3.20-3.30 (m, 2H), 2.95-3.15 (m, 5H), 2.65-2.87 (m, 3H), 2.51 (br. s., 4H), 2.45 (dd, J=13.4, 1.8 Hz, 1H), 1.09 (t, J=7.2 Hz, 3H). [M+H] calc'd for $C_{24}H_{29}FN_6O_2S$, 484; found, 484.

Compound 107: (R)-3-chloro-N-ethyl-4-(4-((6-oxo-5,6,6a,7,9,10-hexahydropyrido[3,2-e][1,4]thiazino[4,3-a]pyrazin-3-yl)methyl)piperazin-1-yl)benzamide

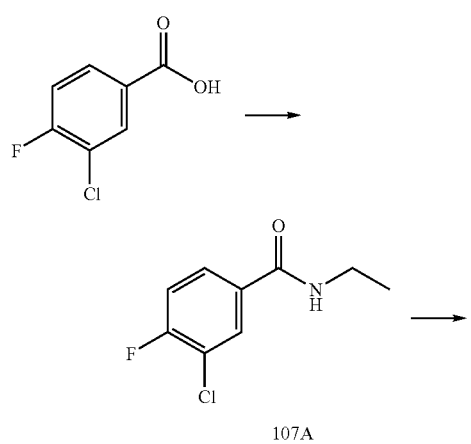

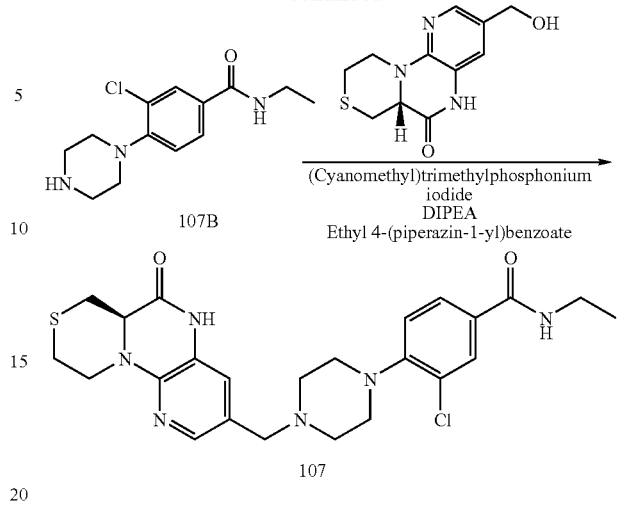

Compound 107A:
3-chloro-4-fluoro-N-ethylbenzamide

Using ethanamine hydrochloride and 3-chloro-4-fluorobenzoic acid in the general procedure for coupling of amines to carboxylic acids, the title compound was obtained (77% yield) as an off-white solid. $^1$H NMR (400 MHz, DMSO-d$_6$) δ ppm 1.12 (t, J=7.20 Hz, 3H) 3.28 (qd, J=7.16, 5.56 Hz, 2H) 7.53 (t, J=8.84 Hz, 1H) 7.87 (ddd, J=8.72, 4.80, 2.15 Hz, 1H) 8.06 (dd, J=7.33, 2.27 Hz, 1H) 8.61 (t, J=4.67 Hz, 1H). ESI-MS: m/z 202.0 (M+H)$^+$. mp=101.7-101.8° C.

Compound 107B:
3-chloro-N-ethyl-4-(piperazin-1-yl)benzamide

Using 3-chloro-4-fluoro-N-ethylbenzamide in the general procedure for nucleophilic aromatic substitution reactions, the title compound was obtained (74% yield) as an off-white solid. $^1$H NMR (400 MHz, DMSO-d$_6$) δ ppm 1.10 (t, J=7.20 Hz, 3H) 2.24 (br. s., 1H) 2.81-2.87 (m, 4H) 2.90-2.98 (m, 4H) 3.26 (qd, J=7.24, 5.56 Hz, 2H) 7.15 (d, J=8.59 Hz, 1H) 7.77 (dd, J=8.34, 2.02 Hz, 1H) 7.87 (d, J=2.27 Hz, 1H) 8.43 (t, J=5.56 Hz, 1H). ESI-MS: m/z 268.2 (M+H)$^+$. mp=117.3-118.7° C.

Compound 107: (R)-3-chloro-N-ethyl-4-(4-((6-oxo-5,6,6a,7,9,10-hexahydropyrido[3,2-e][1,4]thiazino[4,3-a]pyrazin-3-yl)methyl)piperazin-1-yl)benzamide To a suspension of (R)-3-(hydroxymethyl)-6a,7,9,10-tetrahydropyrido[3,2-e][1,4]thiazino[4,3-a]pyrazin-6(5H)-one (154 mg, 0.613 mmol) in propiononitrile (1.2 mL) was added (cyanomethyl)trimethylphosphonium iodide (179 mg, 0.735 mmol) and 3-chloro-N-ethyl-4-(piperazin-1-yl)benzamide hydrochloride (186 mg, 0.613 mmol) and DIEA (321 µl, 1.838 mmol). The vial was heated to 90° C. for 16 hours. The crude rxn was cooled to RT, DMSO (1 ml) was added, and purified via HPLC (55-90, basic). The fractions were collected, concentrated until a precipitate was visible and filtered. The solids were washed with water and collected to retrieve the product as a white solid (80 mg, 26% yield). $^1$H NMR (400 MHz, DMSO-d6) δ ppm 10.67 (s, 1H), 8.43 (t, J=5.6 Hz, 1H), 7.87 (d, J=2.0 Hz, 1H), 7.76 (dd, J=8.6, 2.0 Hz, 1H), 7.70 (d, J=2.0 Hz, 1H), 7.17 (d, J=8.3 Hz, 1H), 7.01 (d, J=2.0 Hz, 1H), 4.88 (dt, J=13.6, 2.7 Hz, 1H), 4.27 (dd, J=10.7, 3.2 Hz, 1H), 3.40 (s, 2H), 3.18-3.30 (m, 2H), 2.90-3.16 (m, 5H), 2.67-2.85 (m, 3H), 2.52 (br. s., 4H), 2.45 (dd, J=13.5, 1.6 Hz, 1H), 1.10 (t, J=7.2 Hz, 3H). [M+H] calc'd for $C_{24}H_{29}ClN_6O_2S$, 501; found, 501.

Compound 108: (R)-3-chloro-N-methyl-4-(4-((6-oxo-5,6,6a,7,9,10-hexahydropyrido[3,2-e][1,4]thiazino[4,3-a]pyrazin-3-yl)methyl)piperazin-1-yl)benzamide

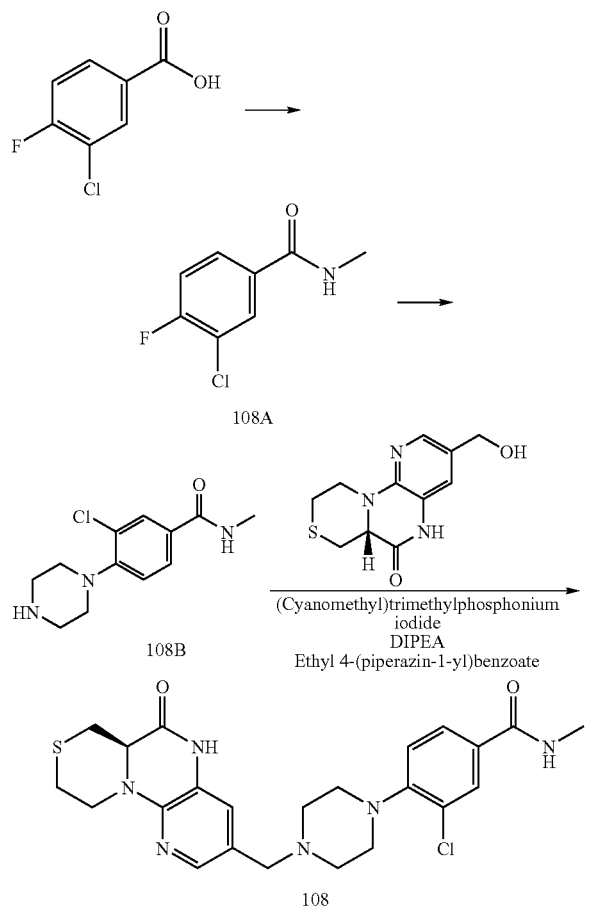

Compound 108A: 3-chloro-4-fluoro-N-methylbenzamide

To a suspension of 3-chloro-4-fluorobenzoic acid (25.0 g, 143 mmol), Methylamine hydrochloride (11.60 g, 172 mmol), N1-((ethylimino)methylene)-N3,N3-dimethylpropane-1,3-diamine hydrochloride (41.2 g, 215 mmol), and 1H-benzo[d][1,2,3]triazol-1-ol hydrate (32.9 g, 215 mmol) in DMF (Volume: 150 mL) was added 4-methylmorpholine (79 mL, 716 mmol) at 23° C. The reaction was stirred at 23° C. for 3 hr. The reaction mixture was diluted with water (500 mL) to furnish a yellow-orange solution. The solution was stirred overnight at 23° C. affording a suspension. The suspension was filtered, washed with H2O (3×100 mL), and the resulting solid was dried in vacuo at 30° C. to provide 3-chloro-4-fluoro-N-methylbenzamide (14.24 g, 76 mmol, 53.0% yield) as an off-white solid. $^1$H NMR (400 MHz, DMSO-d$_6$) δ ppm 2.78 (d, J=4.55 Hz, 3H) 7.53 (t, J=8.97 Hz, 1H) 7.86 (ddd, J=8.59, 4.80, 2.27 Hz, 1H) 8.04 (dd, J=7.20, 2.15 Hz, 1H) 8.51-8.65 (m, 1H). ESI-MS: m/z 188.0 (M+H)$^+$. Mp=108.3-110.0° C.

Compound 108B: 3-chloro-N-methyl-4-(piperazin-1-yl)benzamide

Using 3-chloro-4-fluoro-N-methylbenzamide in the general procedure for nucleophilic aromatic substitution reactions, the title compound was obtained (29% yield) as a white solid. $^1$H NMR (400 MHz, DMSO-d$_6$) δ ppm 2.59-2.70 (m, 2H) 2.73-2.79 (m, 3H) 2.87-2.93 (m, 2H) 2.95-3.01 (m, 2H) 3.03-3.11 (m, 2H) 3.23-4.03 (m, 1H) 7.14-7.23 (m, 1H) 7.77 (dd, J=8.46, 2.15 Hz, 1H) 7.85-7.90 (m, 1H) 8.38-8.48 (m, 1H). ESI-MS: m/z 254.2 (M+H)$^+$. mp=176.4-189.1° C.

Compound 108: (R)-3-chloro-N-methyl-4-(4-((6-oxo-5,6,6a,7,9,10-hexahydropyrido[3,2-e][1,4]thiazino[4,3-a]pyrazin-3-yl)methyl)piperazin-1-yl)benzamide To a suspension of (R)-3-(hydroxymethyl)-6a,7,9,10-tetrahydropyrido[3,2-e][1,4]thiazino[4,3-a]pyrazin-6(5H)-one (97 mg, 0.386 mmol) in propiononitrile (1.2 mL) was added (cyanomethyl)trimethylphosphonium iodide (113 mg, 0.463 mmol) and 3-chloro-N-methyl-4-(piperazin-1-yl)benzamide hydrochloride (112 mg, 0.386 mmol) and DIEA (202 µl, 1.158 mmol). The vial was heated to 90° C. for 16 hours. The crude rxn was cooled to RT, DMSO (1 ml) was added, and purified via HPLC (55-90, basic). The fractions were collected, concentrated until a precipitate was visible and filtered. The solids were washed with water and collected to retrieve the product as a white solid (21 mg, 11% yield). $^1$H NMR (400 MHz, DMSO-d6) δ ppm 10.67 (s, 1H), 8.41 (d, J=4.5 Hz, 1H), 7.86 (d, J=2.0 Hz, 1H), 7.75 (dd, J=8.6, 2.0 Hz, 1H), 7.70 (d, J=1.8 Hz, 1H), 7.17 (d, J=8.6 Hz, 1H), 7.00 (d, J=2.0 Hz, 1H), 4.88 (ddd, J=13.5, 2.7, 2.5 Hz, 1H), 4.27 (dd, J=10.6, 3.0 Hz, 1H), 3.40 (s, 2H), 2.92-3.14 (m, 5H), 2.64-2.85 (m, 6H), 2.51-2.64 (m, 3H), 2.45 (dd, J=13.4, 1.5 Hz, 2H). [M+H] calc'd for $C_{23}H_{27}ClN_6O_2S$, 487; found, 487.

Compound 109: (S)—N-ethyl-3-fluoro-4-(4-((6-oxo-6,6a,7,8,9,10-hexahydro-5H-dipyrido[1,2-a:3',2'-e]pyrazin-3-yl)methyl)piperazin-1-yl)benzamide

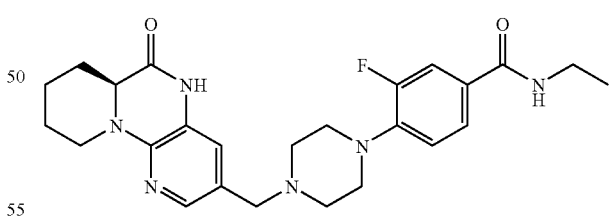

To a suspension of(S)-3-(hydroxymethyl)-7,8,9,10-tetrahydro-5H-dipyrido[1,2-a:3',2'-e]pyrazin-6(6aH)-one (83 mg, 0.355 mmol) in propiononitrile (1.2 mL) was added (cyanomethyl)trimethylphosphonium iodide (104 mg, 0.426 mmol) and DIEA (0.186 ml, 1.066 mmol) and finally N-ethyl-3-fluoro-4-(piperazin-1-yl)benzamide (102 mg, 0.355 mmol). The vial was heated to 90° C. for 16 hours. The crude rxn was cooled to RT, DMSO (1 ml) was added, and purified via HPLC (55-90, basic). The fractions were collected, concentrated until a precipitate was visible and filtered. The solids were washed with water and collected to retrieve the product as a white solid (50 mg, 30% yield). $^1$H NMR (400 MHz, DMSO-d6) δ ppm 10.48 (s, 1H), 8.35 (t, J=5.4 Hz, 1H), 7.49-7.72 (m, 3H), 6.87-7.15 (m, 2H), 4.50 (d, J=12.9 Hz, 1H), 3.84 (dd, J=11.4, 2.8 Hz, 1H), 3.40 (d, J=2.8 Hz, 2H), 3.18-3.30 (m, 2H), 3.08 (br. s., 4H), 2.60 (td, J=12.6, 2.5 Hz, 1H), 2.49 (br. s., 4H), 2.03 (d, J=12.9 Hz, 1H), 1.77-1.91 (m, 1H), 1.64 (d, J=12.9 Hz, 1H), 1.32-1.57 (m, 3H), 1.09 (t, J=7.2 Hz, 3H). [M+H] calc'd for $C_{25}H_{31}FN_6O_2$, 467; found, 467.

Compound 110: (S)-3-chloro-N-ethyl-4-(4-((6-oxo-6,6a,7,8,9,10-hexahydro-5H-dipyrido[1,2-a:3',2'-e]pyrazin-3-yl)methyl)piperazin-1-yl)benzamide

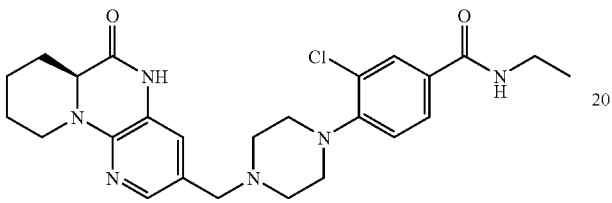

To a suspension of (S)-3-(hydroxymethyl)-7,8,9,10-tetrahydro-5H-dipyrido[1,2-a:3',2'-e]pyrazin-6(6aH)-one (81 mg, 0.347 mmol) in propiononitrile (1.2 mL) was added (cyanomethyl)trimethylphosphonium iodide (101 mg, 0.417 mmol) and DIEA (182 μl, 1.042 mmol) and finally 3-chloro-N-ethyl-4-(piperazin-1-yl)benzamide hydrochloride (106 mg, 0.347 mmol). The vial was heated to 90° C. for 16 hours. The crude rxn was cooled to RT, DMSO (1 ml) was added, and purified via HPLC (55-90, basic). The fractions were collected, concentrated until a precipitate was visible and filtered. The solids were washed with water and collected to retrieve the product as a white solid (70 mg, 20% yield). $^1$H NMR (400 MHz, DMSO-d6) δ ppm 10.48 (s, 1H), 8.43 (t, J=5.4 Hz, 1H), 7.87 (d, J=2.3 Hz, 1H), 7.76 (dd, J=8.3, 2.0 Hz, 1H), 7.66 (d, J=1.8 Hz, 1H), 7.17 (d, J=8.6 Hz, 1H), 6.97 (d, J=2.0 Hz, 1H), 4.50 (d, J=12.9 Hz, 1H), 3.84 (dd, J=11.4, 2.8 Hz, 1H), 3.38 (s, 2H), 3.18-3.31 (m, 2H), 3.03 (br. s., 4H), 2.60 (td, J=12.7, 2.7 Hz, 1H), 2.51 (br. s., 4H), 2.04 (d, J=12.9 Hz, 1H), 1.85 (d, J=12.1 Hz, 1H), 1.64 (d, J=12.6 Hz, 1H), 1.32-1.58 (m, 3H), 1.10 (t, J=7.1 Hz, 3H). [M+H] calc'd for $C_{25}H_{31}ClN_6O_2$, 483; found, 483.

Compound 111: (S)-3-chloro-N-methyl-4-(4-((6-oxo-6,6a,7,8,9,10-hexahydro-5H-dipyrido[1,2-a:3',2'-e]pyrazin-3-yl)methyl)piperazin-1-yl)benzamide

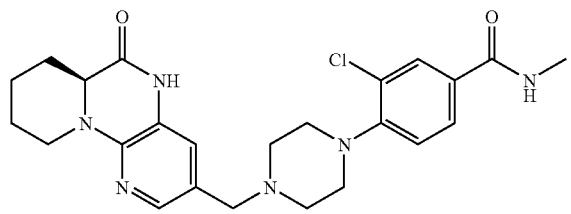

To a suspension of (S)-34(S)-3-(hydroxymethyl)-7,8,9,10-tetrahydro-5H-dipyrido[1,2-a:3',2'-e]pyrazin-6(6aH)-one (111 mg, 0.476 mmol) in propiononitrile (1.2 mL) was added (cyanomethyl)trimethylphosphonium iodide (139 mg, 0.571 mmol) and DIEA (249 μl, 1.428 mmol) and finally 3-chloro-N-methyl-4-(piperazin-1-yl)benzamide hydrochloride (138 mg, 0.476 mmol). The vial was heated to 90° C. for 16 hours. The crude rxn was cooled to RT, DMSO (1 ml) was added, and purified via HPLC (55-90, basic). The fractions were collected, concentrated until a precipitate was visible and filtered. The solids were washed with water and collected to retrieve the product as a white solid (64 mg, 29% yield). $^1$H NMR (400 MHz, DMSO-d6) δ ppm 10.52 (br. s., 1H), 8.43 (d, J=4.3 Hz, 1H), 7.87 (s, 1H), 7.76 (dd, J=8.3, 1.5 Hz, 1H), 7.66 (d, J=2.0 Hz, 1H), 7.54-7.74 (m, 1H), 7.19 (d, J=8.1 Hz, 1H), 6.99 (br. s., 1H), 4.52 (d, J=12.6 Hz, 1H), 3.85 (br. s., 1H), 3.44 (br. s., 2H), 2.92 (d, J=4.5 Hz, 4H), 2.75 (d, J=4.5 Hz, 4H), 2.52-2.69 (m, 3H), 1.99-2.09 (m, 1H), 1.85 (d, J=12.4 Hz, 1H), 1.64 (d, J=12.4 Hz, 1H), 1.32-1.58 (m, 3H). [M+H] calc'd for $C_{24}H_{29}ClN_6O_2$, 469; found, 469.

Compound 112: (S)-3-fluoro-N-methyl-4-(4-((6-oxo-6,6a,7,8,9,10-hexahydro-5H-dipyrido[1,2-a:3',2'-e]pyrazin-3-yl)methyl)piperazin-1-yl)benzamide

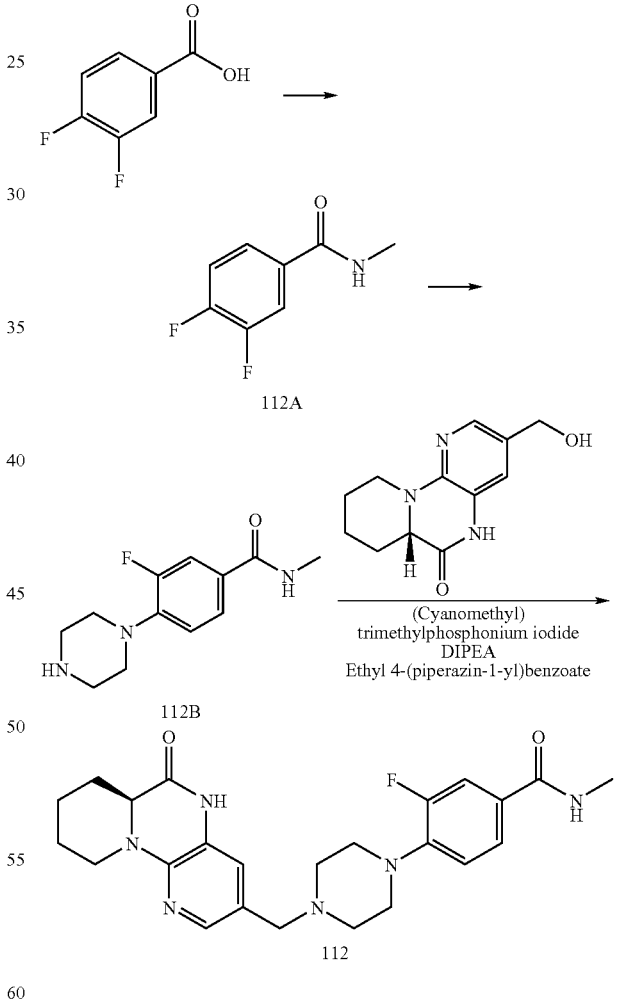

Compound 112A: 3,4-difluoro-N-methylbenzamide

Using methanamine hydrochloride and 3,4-difluorobenzoic acid in the general procedure for coupling of amines to carboxylic acids, the title compound was obtained (75% yield) as an off-white solid. $^1$H NMR (400 MHz, DMSO-$d_6$)

δ ppm 2.78 (d, J=4.55 Hz, 3H) 7.55 (dt, J=10.61, 8.34 Hz, 1H) 7.72 (dddd, J=8.59, 4.55, 2.15, 1.39 Hz, 1H) 7.86 (ddd, J=11.68, 7.89, 2.15 Hz, 1H) 8.48-8.59 (m, 1H). ESI-MS: m/z 172.1 (M+H)⁺. mp=142.7-145.0° C.

Compound 112B: 3-fluoro-N-methyl-4-(piperazin-1-yl)benzamide

Using 3,4-difluoro-N-methylbenzamide in the general procedure for nucleophilic aromatic substitution reactions, the title compound was obtained (43% yield) as white solid. ¹H NMR (400 MHz, DMSO-d₆) δ ppm 2.34 (br. s., 1H) 2.57-2.66 (m, 1H) 2.72-2.79 (m, 3H) 2.80-2.88 (m, 3H) 2.95-3.04 (m, 3H) 3.07-3.16 (m, 1H) 6.99-7.11 (m, 1H) 7.52-7.65 (m, 2H) 8.29-8.38 (m, 1H). ESI-MS: m/z 238.2 (M+H)⁺. mp=174.1-192.9° C.

Compound 112: (S)-3-fluoro-N-methyl-4-(4-((6-oxo-6,6a,7,8,9,10-hexahydro-5H-dipyrido[1,2-a:3',2'-e]pyrazin-3-yl)methyl)piperazin-1-yl)benzamide To a suspension of (S)-3-(hydroxymethyl)-7,8,9,10-tetrahydro-5H-dipyrido[1,2-a:3',2'-e]pyrazin-6(6aH)-one (129 mg, 0.553 mmol) in propiononitrile (1.2 mL) was added ((cyanomethyl)trimethylphosphonium iodide (161 mg, 0.664 mmol)) and 3-fluoro-N-methyl-4-(piperazin-1-yl)benzamide hydrochloride (151 mg, 0.553 mmol) and DIEA (290 μl, 1.659 mmol)). The vial was heated to 90° C. for 16 hours. The crude rxn was cooled to RT, DMSO (1 ml) was added, and purified via HPLC (55-90, basic). The fractions were collected, concentrated until a precipitate was visible and filtered. The solids were washed with water and collected to retrieve the product as a white solid (83 mg, 33% yield). ¹H NMR (400 MHz, DMSO-d6) δ ppm 10.48 (s, 1H), 8.33 (d, J=4.5 Hz, 1H), 7.45-7.70 (m, 3H), 6.88-7.10 (m, 2H), 4.50 (d, J=12.9 Hz, 1H), 3.83 (dd, J=11.1, 2.5 Hz, 1H), 3.36 (s, 2H), 3.08 (br. s., 4H), 2.75 (d, J=4.5 Hz, 3H), 2.56-2.64 (m, 1H), 2.50 (br. s., 4H), 1.97-2.12 (m, 1H), 1.85 (d, J=11.1 Hz, 1H), 1.63 (d, J=11.9 Hz, 1H), 1.29-1.57 (m, 3H). [M+H] calc'd for C₂₄H₂₉FN₆O₂, 453; found, 453.

Compound 113: (S)—N,3-dimethyl-4-(4-((6-oxo-6,6a,7,8,9,10-hexahydro-5H-dipyrido[1,2-a:3',2'-e]pyrazin-3-yl)methyl)piperazin-1-yl)benzamide

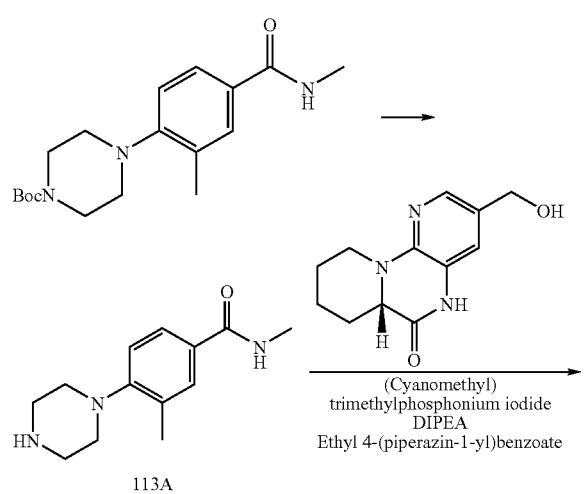

113A

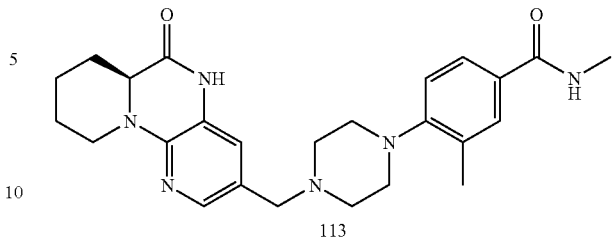

113

Compound 113: N,3-dimethyl-4-(piperazin-1-yl)benzamide

To tert-butyl 4-(2-methyl-4-(methylcarbamoyl)phenyl)piperazine-1-carboxylate (1.90 g, 5.70 mmol) was added Hydrochloric acid solution (17.10 ml, 68.4 mmol) in dioxane at 23° C. The reaction was stirred at 23° C. for 30 min. The resulting suspension was diluted with Et₂O (20 mL), filtered, rinsed with Et₂O (3×10 mL), and the resulting solid was dried in vacuo to provide N,3-dimethyl-4-(piperazin-1-yl)benzamide dihydrochloride (1.70 g, 5.55 mmol, 97% yield) as an off-white, hygroscopic solid. ¹H NMR (400 MHz, DMSO-d₆) δ ppm 2.28 (s, 3H) 2.72-2.79 (m, 3H) 3.05-3.14 (m, 4H) 3.17-3.28 (m, 4H) 7.06 (d, J=8.34 Hz, 1H) 7.64-7.68 (m, 1H) 7.68-7.70 (m, 1H) 8.29-8.39 (m, 1H) 9.36 (br. s., 2H). ESI-MS: m/z 234.2 (M+H)⁺.

Compound 113: (S)—N,3-dimethyl-4-(4-((6-oxo-6,6a,7,8,9,10-hexahydro-5H-dipyrido[1,2-a:3',2'-e]pyrazin-3-yl)methyl)piperazin-1-yl)benzamide (S)-3-(hydroxymethyl)-7,8,9,10-tetrahydro-5H-dipyrido[1,2-a:3',2'-e]pyrazin-6(6aH)-one (100 mg, 0.429 mmol), N,3-dimethyl-4-(piperazin-1-yl)benzamide dihydrochloride (131 mg, 0.429 mmol), (cyanomethyl)trimethylphosphonium iodide (167 mg, 0.686 mmol) and N,N-diisopropylethylamine (374 μl, 2.143 mmol) were suspended in propiononitrile (Volume: 1287 μl) and heated in a closed vial at 90° C. for 4 h. The reaction mixture became a dark brown solution. It was cooled to room temperature and purified using HPLC (NH4HCO3 buffered, 20-70% ACN in water). The fractions were concentrated in vacuo and the resulting solid was recrystallized from MeCN (5 mL), filtered off, washed with water (2 mL) and dried in vacuum to afford (S)—N,3-dimethyl-4-(4-((6-oxo-6,6a,7,8,9,10-hexahydro-5H-dipyrido[1,2-a:3',2'-e]pyrazin-3-yl)methyl)piperazin-1-yl)benzamide (27.4 mg, 0.061 mmol, 14.25% yield) as a light beige solid. ¹H NMR (400 MHz, DMSO-d₆) δ ppm 1.31-1.57 (m, 3H) 1.64 (d, J=11.87 Hz, 1H) 1.85 (d, J=11.37 Hz, 1H) 2.04 (d, J=11.87 Hz, 1H) 2.25 (s, 3H) 2.51-2.70 (m, 5H) 2.56-2.70 (m, 2H) 2.74 (d, J=4.29 Hz, 3H) 2.87 (br. s., 4H) 3.37-3.45 (m, 2H) 3.84 (dd, J=11.24, 2.40 Hz, 1H) 4.50 (d, J=13.14 Hz, 1H) 6.98 (d, J=1.77 Hz, 1H) 7.01 (d, J=8.34 Hz, 1H) 7.61 (dd, J=8.46, 1.64 Hz, 1H) 7.65 (dd, J=12.25, 1.64 Hz, 2H) 8.23 (q, J=4.13 Hz, 1H) 10.48 (s, 1H); [M+H] calc'd for $C_{25}H_{32}N_6O_2$, 449; found, 449.

Compound 114: (S)—N-ethyl-3-methyl-4-(4-((6-oxo-6,6a,7,8,9,10-hexahydro-5H-dipyrido[1,2-a:3',2'-e]pyrazin-3-yl)methyl)piperazin-1-yl)benzamide

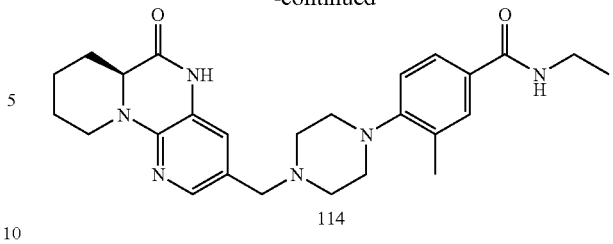

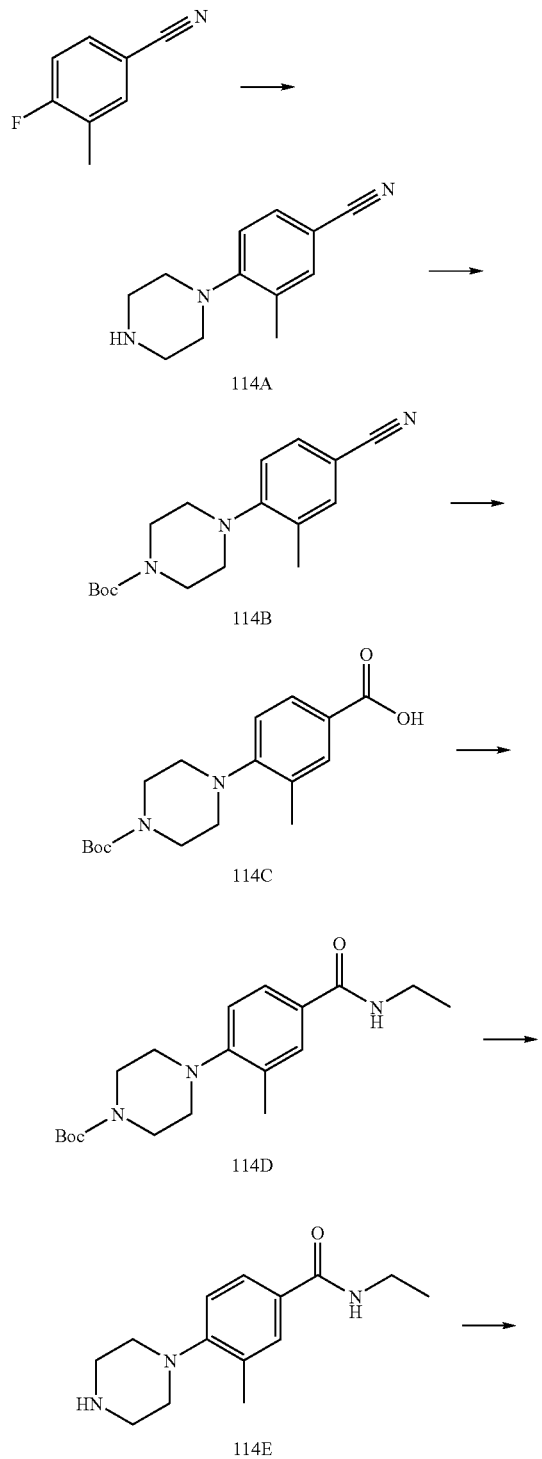

Compound 114A: 3-methyl-4-(piperazin-1-yl)benzonitrile

To a solution of 4-fluoro-3-methylbenzonitrile (2.5 g, 18.50 mmol) in DMSO (Volume: 10.0 mL) was added piperazine (7.97 g, 92 mmol) at 23° C. The reaction was stirred at 140° C. for 16 hr. The reaction mixture was poured into H2O (100 mL) and the reaction vessel was rinsed with H2O (~50 mL). The resulting suspension was filtered, rinsed with H2O (3×10 mL) and the resulting solid was dried in vacuo to provide 3-methyl-4-(piperazin-1-yl)benzonitrile (2.593 g, 12.88 mmol, 69.6% yield) as a white solid. $^1$H NMR (400 MHz, DMSO-$d_6$) δ ppm 2.21-2.30 (m, 3H) 2.57-2.70 (m, 1H) 2.83 (s, 8H) 7.03-7.09 (m, 1H) 7.55-7.62 (m, 2H). ESI-MS: m/z 202.1 (M+H)$^+$.

Compound 114B: tert-butyl 4-(4-cyano-2-methylphenyl)piperazine-1-carboxylate To a solution of 3-methyl-4-(piperazin-1-yl)benzonitrile (2.533 g, 12.59 mmol) in THF (Ratio: 1.000, Volume: 25 mL) and MeOH (Ratio: 1.000, Volume: 25 mL) was added Di-tert-butyl dicarbonate (3.09 mL, 13.47 mmol) at 10° C. The reaction was stirred at 10° C. for 15 min warmed to 23° C. and stirred at for 18 hr. The resulting suspension was filtered, rinsed with THF (3×5 mL) and the filtrate was concentrated in vacuo. $^1$H NMR (400 MHz, DMSO-$d_6$) δ ppm 1.42 (s, 9H) 2.28 (s, 3H) 2.83-2.92 (m, 4H) 3.42-3.52 (m, 4H) 7.08-7.13 (m, 1H) 7.57-7.65 (m, 2H). ESI-MS: m/z 302.1 (M+H)$^+$.

Compound 114C: 4-(4-(tert-butoxycarbonyl)piperazin-1-yl)-3-methylbenzoic acid To a suspension of tert-butyl 4-(4-cyano-2-methylphenyl)piperazine-1-carboxylate (3.685 g, 12.23 mmol) in EtOH (Ratio: 1.000, Volume: 50 mL) and Water (Ratio: 1.000, Volume: 10 mL) was added Sodium hydroxide solution (8.48 mL, 162 mmol) at 23° C. Rinsed sodium hydroxide forward with Water (Ratio: 1.000, Volume: 2.5 mL) The reaction was stirred at 90° C. for 10 hr. The reaction mixture was cooled to 23° C., neutralized with 3N HCl (52 mL), filtered, rinsed with H2O (3×10 mL), and the resulting solid was dried in vacuo to provide 4-(4-(tert-butoxycarbonyl)piperazin-1-yl)-3-methylbenzoic acid (3.588 g, 11.20 mmol, 92% yield) as an off-white solid. $^1$H NMR (400 MHz, DMSO-$d_6$) δ ppm 1.42 (s, 9H) 2.29 (s, 3H) 2.81-2.90 (m, 4H) 3.42-3.53 (m, 4H) 7.05 (d, J=8.08 Hz, 1H) 7.70-7.77 (m, 2H) 12.61 (br. s., 1H). ESI-MS: m/z 321.2 (M+H)$^+$.

Compound 114D: tert-butyl 4-(4-(ethylcarbamoyl)-2-methylphenyl)piperazine-1-carboxylate 4-(4-(tert-butoxycarbonyl)piperazin-1-yl)-3-methylbenzoic acid (0.866 g, 2.70 mmol), ethanamine hydrochloride (0.264 g, 3.24 mmol), N1-((ethylimino)methylene)-N3,N3- dimethylpropane-1,3-diamine hydrochloride (0.777 g, 4.05 mmol) and 1H-benzo[d][1,2,3]triazol-1-ol hydrate (0.621 g, 4.05 mmol) were suspended in DMF (Volume: 3.68 ml) and 4-methylmorpholine (1.486 ml, 13.52 mmol) was added. The reaction mixture was stirred at ambient temperature for 2 h. It was diluted with water (50 mL) and extracted with ethyl acetate (3×75 mL). The combined organic extracts were washed with 1N HCl (aq., 25 mL), NaHCO3 (sat. aq., 25 mL), water (25 mL), brine (25 mL), dried (MgSO4), concentrated in vacuo and dried under vacuum to afford tert-butyl 4-(4-(ethylcarbamoyl)-2-methylphenyl)piperazine-1-carboxylate (0.9327 g, 2.68 mmol, 99% yield) as a white solid. $^1$H NMR (DMSO-d$_6$, 400 MHz): δ=8.24 (t, J=5.4 Hz, 1H), 7.66 (d, J=1.8 Hz, 2H), 7.03 (d, J=8.3 Hz, 1H), 3.42-3.52 (m, 4H), 3.20-3.27 (m, 2H), 2.78-2.87 (m, 4H), 2.28 (s, 3H), 1.43 (s, 9H), 1.10 ppm (t, J=7.2 Hz, 3H). ESI-MS: m/z 348.4 (M+H)$^+$.

Compound 114E:
N-ethyl-3-methyl-4-(piperazin-1-yl)benzamide

Tert-butyl 4-(4-(ethylcarbamoyl)-2-methylphenyl)piperazine-1-carboxylate (0.9323 g, 2.68 mmol) was diluted with 4.0M HCl in dioxane (8 mL) and stirred for 30 min. The thick white precipitate that formed was diluted with ethyl ether (10 mL) and stirred until a fine suspension resulted. The precipitate was filtered under nitrogen, washed with ether (5 mL) and dried in vacuum to afford N-ethyl-3-methyl-4-(piperazin-1-yl)benzamide hydrochloride (0.7528 g, 2.65 mmol, 99% yield) as a white solid. $_1$H NMR (400 MHz, DMSO-d$_6$) δ ppm 1.10 (t, J=7.20 Hz, 3H) 2.29 (s, 3H) 3.00-3.14 (m, 4H) 3.16-3.32 (m, 6H) 7.07 (d, J=8.34 Hz, 1H) 7.62-7.71 (m, 2H) 8.34 (t, J=5.43 Hz, 1H) 9.17 (br. s., 2H). ESI-MS: m/z 248.2 (M+H)$^+$.

Compound 114: (S)—N-ethyl-3-methyl-4-(4-((6-oxo-6,6a,7,8,9,10-hexahydro-5H-dipyrido[1,2-a:3', 2'-e]pyrazin-3-yl)methyl)piperazin-1-yl)benzamide (S)-3-(hydroxymethyl)-7,8,9,10-tetrahydro-5H-dipyrido[1,2-a:3',2'-e]pyrazin-6(6aH)-one (100 mg, 0.429 mmol), N-ethyl-3-methyl-4-(piperazin-1-yl)benzamide hydrochloride (133 mg, 0.469 mmol), (cyanomethyl)trimethylphosphonium iodide (167 mg, 0.686 mmol) and N,N-diisopropylethylamine (374 μl, 2.143 mmol) were suspended in Propiononitrile (Volume: 1287 μl) and heated in a closed vial at 90° C. for 4 h. The reaction mixture became a dark brown solution. It was cooled to room temperature and purified using HPLC(NH4HCO3 buffered, 20-70% ACN in water). The fractions were concentrated in vacuo and the resulting solid was slurried with hot MeCN (5 mL), cooled to ambient temperature, filtered off, washed with water (2 mL) and dried in vacuum to afford (S)—N-ethyl-3-methyl-4-(4-((6-oxo-6, 6a,7,8,9,10-hexahydro-5H-dipyrido[1,2-a:3',2'-e]pyrazin-3-yl)methyl)piperazin-1-yl)benzamide (70.3 mg, 0.152 mmol, 35.4% yield) as a light beige solid. $^1$H NMR (400 MHz, DMSO-d$_6$) δ ppm 1.09 (t, J=7.20 Hz, 3H) 1.33-1.57 (m, 3H) 1.64 (d, J=12.13 Hz, 1H) 1.85 (d, J=11.37 Hz, 1H) 2.04 (d, J=12.13 Hz, 1H) 2.26 (s, 3H) 2.52-2.70 (m, 5H) 2.87 (br. s., 4H) 3.19-3.29 (m, 2H) 3.37-3.43 (m, 2H) 3.84 (dd, J=11.49, 2.65 Hz, 1H) 4.50 (d, J=12.88 Hz, 1H) 6.98 (d, J=1.52 Hz, 1H) 7.01 (d, J=8.34 Hz, 1H) 7.62 (d, J=8.59 Hz, 1H) 7.65 (dd, J=9.35, 1.26 Hz, 2H) 8.26 (t, J=5.43 Hz, 1H) 10.49 (s, 1H); [M+H] calc'd for C$_{26}$H$_{34}$N$_6$O$_2$, 463; found, 463.

Compound 115: (S)—N-cyclopropyl-3-methyl-4-(4-((6-oxo-6,6a,7,8,9,10-hexahydro-5H-dipyrido[1,2-a: 3',2'-e]pyrazin-3-yl)methyl)piperazin-1-yl)benzamide

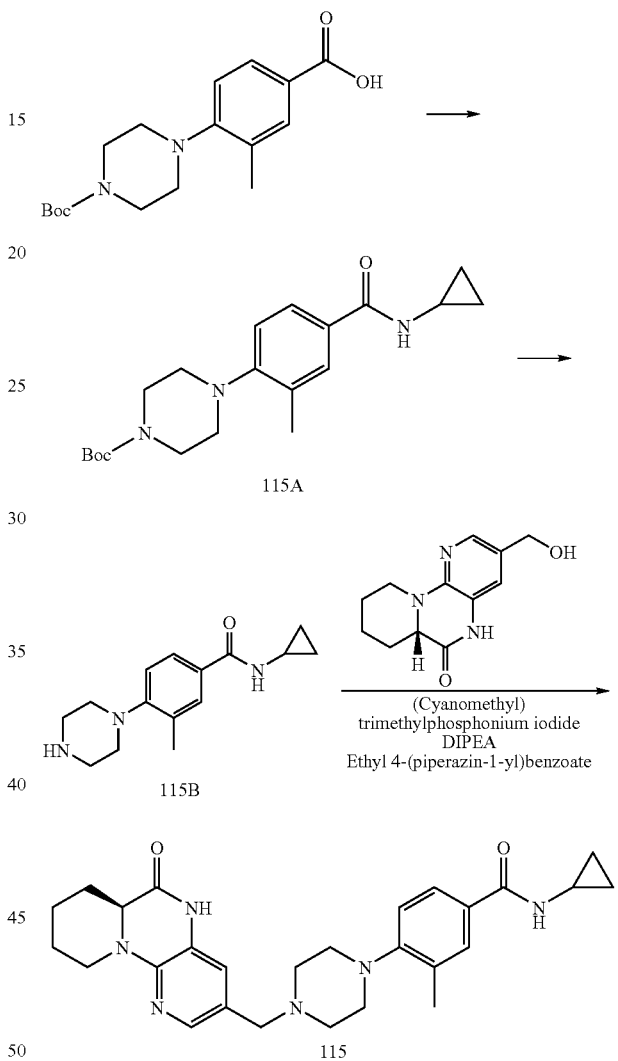

Compound 115A: tert-butyl 4-(4-(cyclopropylcarbamoyl)-2-methylphenyl)piperazine-1-carboxylate Cyclopropylamine (0.389 mL, 5.62 mmol), N1-((ethylimino)methylene)-N3,N3-dimethylpropane-1,3-diamine hydrochloride (1.346 g, 7.02 mmol), and 1H-benzo[d][1,2,3]triazol-1-ol hydrate (1.075 g, 7.02 mmol) in DMF (Volume: 6.4 mL) was added 4-methylmorpholine (2.57 mL, 23.41 mmol) at 23° C. The reaction was stirred at 23° C. for 2 hr. The reaction mixture was diluted with water (50 mL) and the product was extracted with EtOAc (3×50 mL). The organic extracts were combined, washed with 1N HCl (25 mL), saturated NaHCO3 (25 mL), H2O (25 mL), brine (25 mL), dried over MgSO4, filtered, rinsed with EtOAc, and dried in vacuo to provide tert-butyl 4-(4-(cyclopropylcarbamoyl)-2-methylphenyl)piperazine-1-carboxylate (1.53 g, 4.26 mmol, 91% yield) as a light yellow solid. $^1$H NMR (400 MHz, DMSO-$d_6$) δ ppm 0.51-0.60 (m, 2H) 0.60-0.70 (m, 2H) 1.42 (s, 9H) 2.28 (s, 3H) 2.77-2.87 (m, 5H) 3.41-3.53 (m, 4H) 7.02 (d, J=8.08 Hz, 1H) 7.61 (dd, J=8.21, 1.89 Hz, 1H) 7.64 (d, J=1.77 Hz, 1H) 8.25 (d, J=4.29 Hz, 1H). ESI-MS:m/z 360.3 (M+H)$^+$. mp=111.0-115.4° C.

Compound 115B:
N-cyclopropyl-3-methyl-4-(piperazin-1-yl)benzamide

To tert-butyl 4-(4-(cyclopropylcarbamoyl)-2-methylphenyl)piperazine-1-carboxylate (1.490 g, 4.15 mmol) was added Hydrochloric acid solution (8.72 mL, 34.9 mmol) in dioxane at 23° C. The reaction was stirred at 23° C. for 30 min. The resulting suspension was diluted with E2O (10 mL), filtered, rinsed with E2O (3×5 mL), and the resulting solid was dried in vacuo to provide N-cyclopropyl-3-methyl-4-(piperazin-1-yl)benzamide dihydrochloride (1.37 g, 4.15 mmol, 100% yield) as an off-white solid. $^1$H NMR (400 MHz, DMSO-$d_6$) δ ppm 0.51-0.61 (m, 2H) 0.61-0.70 (m, 2H) 2.28 (s, 3H) 2.82 (tq, J=7.41, 3.99 Hz, 1H) 3.02-3.13 (m, 4H) 3.14-3.29 (m, 4H) 7.05 (d, J=8.34 Hz, 1H) 7.62-7.69 (m, 2H) 8.32 (d, J=4.29 Hz, 1H) 9.38 (br. s., 2H). ESI-MS:m/z 260.2 (M+H)$^+$. mp=171.5-172.8° C.

Compound 115: (S)—N-cyclopropyl-3-methyl-4-(4-((6-oxo-6,6a,7,8,9,10-hexahydro-5H-dipyrido[1,2-a:3',2'-e]pyrazin-3-yl)methyl)piperazin-1-yl)benzamide (S)-3-(hydroxymethyl)-7,8,9,10-tetrahydro-5H-dipyrido[1,2-a:3',2'-e]pyrazin-6(6aH)-one (100 mg, 0.429 mmol), N-cyclopropyl-3-methyl-4-(piperazin-1-yl)benzamide dihydrochloride (143 mg, 0.430 mmol), (cyanomethyl)trimethylphosphonium iodide (167 mg, 0.686 mmol) and N,N-diisopropylethylamine (374 µl, 2.143 mmol) were suspended in Propiononitrile (Volume: 1287 µl) and heated in a closed vial at 90° C. for 4 h. The reaction mixture became a dark brown solution. It was cooled to room temperature and purified using HPLC(NH4HCO3 buffered, 20-70% ACN in water). The fractions were concentrated in vacuo and the resulting solid was recrystallized from MeCN (20 mL), filtered off, washed with water (2 mL) and dried in vacuum to afford (S)—N-cyclopropyl-3-methyl-4-(4-((6-oxo-6,6a,7,8,9,10-hexahydro-5H-dipyrido[1,2-a:3',2'-e]pyrazin-3-yl)methyl)piperazin-1-yl)benzamide (50.7 mg, 0.107 mmol, 24.92% yield) as a light brown solid. $^1$H NMR (400 MHz, DMSO-$d_6$) δ ppm 0.49-0.59 (m, 2H) 0.60-0.71 (m, 2H) 1.33-1.57 (m, 3H) 1.64 (d, J=12.88 Hz, 1H) 1.85 (d, J=12.63 Hz, 1H) 2.04 (d, J=12.88 Hz, 1H) 2.25 (s, 3H) 2.42-2.56 (m, 4H) 2.60 (td, J=12.63, 2.78 Hz, 1H) 2.76-2.93 (m, 5H) 3.38 (s, 2H) 3.84 (dd, J=11.37, 2.78 Hz, 1H) 4.50 (d, J=13.14 Hz, 1H) 6.98 (d, J=2.02 Hz, 1H) 7.00 (d, J=8.34 Hz, 1H) 7.56-7.63 (m, 2H) 7.66 (d, J=2.02 Hz, 1H) 8.22 (d, J=4.29 Hz, 1H) 10.49 (s, 1H); [M+H] calc'd for $C_{27}H_{34}N_6O_2$, 475; found, 475.

Compound 116: (S)—N-cyclopropyl-3-fluoro-4-(4-((6-oxo-6,6a,7,8,9,10-hexahydro-5H-dipyrido[1,2-a:3',2'-e]pyrazin-3-yl)methyl)piperazin-1-yl)benzamide

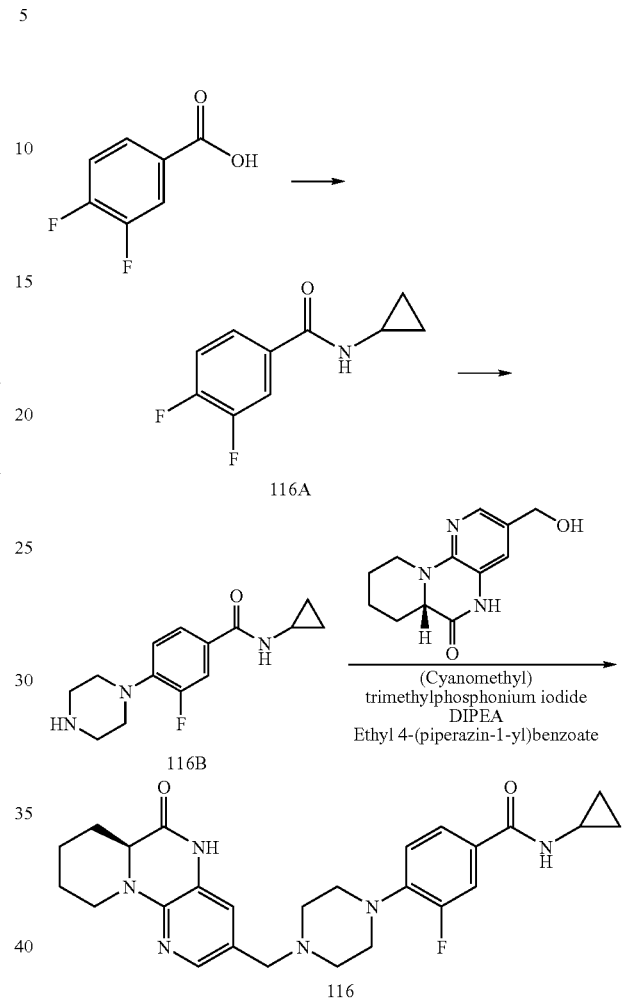

Compound 116A:
N-cyclopropyl-3,4-difluorobenzamide

Using cyclopropylamine and 3,4-difluorobenzoic acid in the general procedure for coupling of amines to carboxylic acids, the title compound was obtained (89% yield) as an off-white solid. $^1$H NMR (400 MHz, DMSO-$d_6$) δ ppm 0.52-0.63 (m, 2H) 0.63-0.74 (m, 2H) 2.83 (tq, J=7.42, 3.98 Hz, 1H) 7.52 (dt, J=10.55, 8.37 Hz, 1H) 7.66-7.75 (m, 1H) 7.85 (ddd, J=11.68, 7.89, 2.15 Hz, 1H) 8.42-8.60 (m, 1H). ESI-MS:m/z 198.1 (M+H)$^+$. mp=104.1-108.4° C.

Compound 116B:
N-cyclopropyl-3-fluoro-4-(piperazin-1-yl)benzamide

Using N-cyclopropyl-3,4-difluorobenzamide in the general procedure for nucleophilic aromatic substitution reactions, the title compound was obtained (33% yield) as white solid. $^1$H NMR (400 MHz, DMSO-$d_6$) δ ppm 0.51-0.61 (m, 2H) 0.61-0.71 (m, 2H) 2.55-2.68 (m, 1H) 2.71-2.91 (m, 5H)

2.92-3.09 (m, 4H) 6.97-7.09 (m, 1H) 7.51-7.65 (m, 2H) 8.27 (d, J=4.04 Hz, 1H). ESI-MS:m/z 264.2 (M+H)⁺. mp=140.9-143.1° C.

Compound 116: (S)—N-cyclopropyl-3-fluoro-4-(4-((6-oxo-6,6a,7,8,9,10-hexahydro-5H-dipyrido[1,2-a:3',2'-e]pyrazin-3-yl)methyl)piperazin-1-yl)benzamide (S)-3-(hydroxymethyl)-7,8,9,10-tetrahydro-5H-dipyrido[1,2-a:3',2'-e]pyrazin-6(6aH)-one (150 mg, 0.643 mmol), N-cyclopropyl-3-fluoro-4-(piperazin-1-yl)benzamide (203 mg, 0.772 mmol), (cyanomethyl)trimethylphosphonium iodide (250 mg, 1.029 mmol) and N,N-diisopropylethylamine (562 µl, 3.22 mmol) were suspended in Propiononitrile (Volume: 1931 µl) and heated in a closed vial at 100° C. for 4 h. The reaction mixture became a dark brown solution with precipitate. It was cooled to room temperature and the precipitate was filtered off, washed with MeCN (2 mL) and suspended in MeCN with heating and sonication. The suspension was cooled to ambient temperature, and the precipitate was filtered off, washed with MeCN (2 mL) and dried in vacuum to afford (S)—N-cyclopropyl-3-fluoro-4-(4-((6-oxo-6,6a,7,8,9,10-hexahydro-5H-dipyrido[1,2-a:3',2'-e]pyrazin-3-yl)methyl)piperazin-1-yl)benzamide (265 mg, 0.554 mmol, 86% yield) as a white solid. ¹H NMR (DMSO-d₆) δ 10.48 (s, 1H), 8.31 (d, J=4.3 Hz, 1H), 7.53-7.69 (m, 4H), 7.02 (t, J=8.8 Hz, 1H), 6.97 (d, J=2.0 Hz, 1H), 4.50 (br. d, J=12.9 Hz, 1H), 3.84 (dd, J=11.2, 2.7 Hz, 1H), 3.37 (s, 2H), 3.01-3.13 (m, 4H), 2.80 (tq, J=7.4, 3.9 Hz, 1H), 2.60 (td, J=12.6, 2.5 Hz, 1H), 2.44-2.51 (m, 4H), 2.04 (br. d, J=12.9 Hz, 1H), 1.85 (br. d, J=12.4 Hz, 1H), 1.64 (br. d, J=12.6 Hz, 1H), 1.33-1.56 (m, 3H), 0.61-0.71 (m, 2H), 0.50-0.60 (m, 2H); [M+H] calc'd for $C_{26}H_{31}FN_6O_2$, 479; found, 479.

Compound 117: (S)-3-chloro-N-cyclopropyl-4-(4-((6-oxo-6,6a,7,8,9,10-hexahydro-5H-dipyrido[1,2-a:3',2'-e]pyrazin-3-yl)methyl)piperazin-1-yl)benzamide

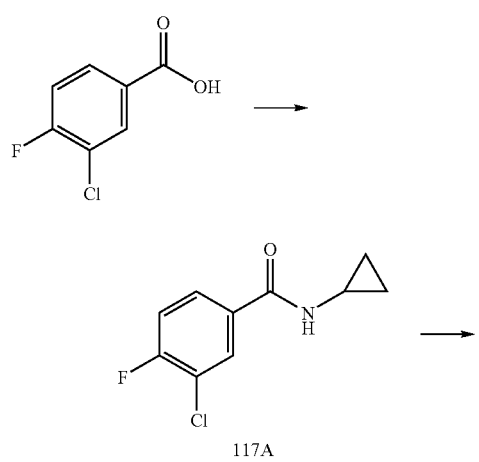

117A

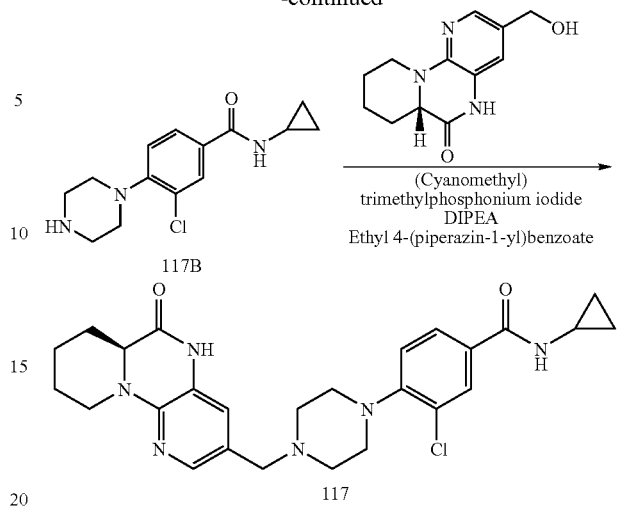

Compound 117A: 3-chloro-N-cyclopropyl-4-fluorobenzamide

Using cyclopropylamine and 3-chloro-4-fluorobenzoic acid in the general procedure for coupling of amines to carboxylic acids, the title compound was obtained (89% yield) as a white solid. ¹H NMR (DMSO-d₆, 400 MHz): δ=8.56 (d, J=3.5 Hz, 1H), 8.03 (dd, J=7.3, 2.3 Hz, 1H), 7.85 (ddd, J=8.6, 4.8, 2.3 Hz, 1H), 7.52 (t, J=9.0 Hz, 1H), 2.83 (tq, J=7.4, 3.9 Hz, 1H), 0.66-0.75 (m, 2H), 0.53-0.61 ppm (m, 2H). ESI-MS: m/z 214.0 (M+H)⁺.

Compound 117B: 3-chloro-N-cyclopropyl-4-(piperazin-1-yl)benzamide

Using 3-chloro-N-cyclopropyl-4-fluorobenzamide in the general procedure for nucleophilic aromatic substitution reactions, the title compound was obtained (77% yield) as a white solid. ESI-MS: m/z 280.2 (M+H)¹.

Compound 117: (S)-3-chloro-N-cyclopropyl-4-(4-((6-oxo-6,6a,7,8,9,10-hexahydro-5H-dipyrido[1,2-a:3',2'-e]pyrazin-3-yl)methyl)piperazin-1-yl)benzamide (S)-3-(hydroxymethyl)-7,8,9,10-tetrahydro-5H-dipyrido[1,2-a:3',2'-e]pyrazin-6(6aH)-one (150 mg, 0.643 mmol), 3-chloro-N-cyclopropyl-4-(piperazin-1-yl)benzamide (216 mg, 0.772 mmol), (cyanomethyl)trimethylphosphonium iodide (250 mg, 1.029 mmol) and N,N-diisopropylethylamine (562 µl, 3.22 mmol) were suspended in Propiononitrile (Volume: 1931 µl) and heated in a closed vial at 100° C. for 4 h. The reaction mixture became a dark brown solution with a precipitate. It was cooled to room temperature and the precipitate was filtered off, washed with MeCN (2 mL) and suspended in MeCN (15 mL) with heating and sonication. It was then cooled to ambient temperature, the precipitate was filtered off, washed with MeCN (2 mL) and dried in vacuum to afford (S)-3-chloro-N-cyclopropyl-4-(4-((6-oxo-6,6a,7,8,9,10-hexahydro-5H-dipyrido[1,2-a:3',2'-e]pyrazin-3-yl)methyl)piperazin-1-yl)benzamide (272.4 mg, 0.550 mmol, 86% yield) as a white solid. ¹H NMR (DMSO-d₆) δ 10.49 (s, 1H), 8.39 (d, J=4.3 Hz, 1H), 7.85 (d, J=2.0 Hz, 1H), 7.75 (dd, J=8.3, 2.0 Hz, 1H), 7.66 (s, 1H), 7.16 (d, J=8.6 Hz, 1H), 6.97

(d, J=1.8 Hz, 1H), 4.50 (d, J=12.9 Hz, 1H), 3.84 (dd, J=11.4, 2.8 Hz, 1H), 3.38 (s, 2H), 3.02 (br. s., 4H), 2.77-2.88 (m, J=0.8 Hz, 1H), 2.60 (td, J=12.6, 2.5 Hz, 1H), 2.49-2.55 (m, J=3.5, 1.8, 1.8 Hz, 4H), 2.04 (br. d, J=12.6 Hz, 1H), 1.86-1.87 (m, OH), 1.84 (br. s., 1H), 1.64 (br. d, J=12.6 Hz, 1H), 1.32-1.57 (m, 3H), 0.61-0.72 (m, 2H), 0.51-0.61 (m, 2H); [M+H] calc'd for $C_{26}H_{31}ClN_6O_2$, 495; found, 495.

Compound 118: (S)-3-methoxy-4-(4-((6-oxo-6,6a,7,8,9,10-hexahydro-5H-dipyrido[1,2-a:3',2'-e]pyrazin-3-yl)methyl)piperazin-1-yl)benzonitrile

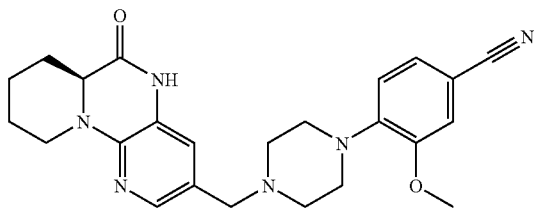

(S)-3-(hydroxymethyl)-7,8,9,10-tetrahydro-5H-dipyrido[1,2-a:3',2'-e]pyrazin-6(6aH)-one (150 mg, 0.643 mmol), 3-methoxy-4-(piperazin-1-yl)benzonitrile hydrochloride (163 mg, 0.643 mmol), (cyanomethyl)trimethylphosphonium iodide (250 mg, 1.029 mmol) and N,N-diisopropylethylamine (562 µl, 3.22 mmol) were suspended in Propiononitrile (Volume: 1931 µl) and heated in a closed vial at 100° C. for 2 h. The reaction mixture became a dark brown solution. It was diluted with MeCN (4 mL) and concentrated in vacuo to about 3 mL. The resulting precipitate was filtered, recrystallized from MeCN (5 mL) and dried in vacuum to afford (S)-3-methoxy-4-(4-((6-oxo-6,6a,7,8,9,10-hexahydro-5H-dipyrido[1,2-a:3',2'-e]pyrazin-3-yl)methyl)piperazin-1-yl)benzonitrile (125 mg, 0.289 mmol, 44.9% yield) as an off-white solid. $^1$H NMR (DMSO-$d_6$) δ 10.48 (s, 1H), 7.65 (d, J=2.0 Hz, 1H), 7.30-7.36 (m, 2H), 6.93-6.98 (m, 2H), 4.50 (d, J=12.9 Hz, 1H), 3.79-3.87 (m, 4H), 3.34-3.40 (m, 2H), 3.07 (br. s., 4H), 2.60 (td, J=12.7, 2.7 Hz, 1H), 2.47 (br. s., 4H), 2.02 (br. s., 1H), 1.85 (d, J=12.1 Hz, 1H), 1.64 (d, J=12.4 Hz, 1H), 1.32-1.57 (m, 3H); [M+H] calc'd for $C_{24}H_{28}N_6O_2$, 433; found, 433.

Compound 119: N-ethyl-4-(4-((6-oxo-6,6a,7,8,9,10-hexahydro-5H-dipyrido[1,2-a:3',2'-e]pyrazin-3-yl)methyl)piperazin-1-yl)benzamide

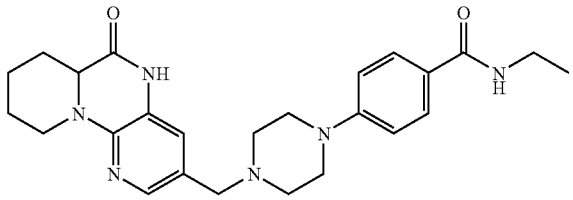

3-(hydroxymethyl)-7,8,9,10-tetrahydro-5H-dipyrido[1,2-a:3',2'-e]pyrazin-6(6aH)-one (50 mg, 0.214 mmol), N-ethyl-4-(piperazin-1-yl)benzamide (55.0 mg, 0.236 mmol), (cyanomethyl)trimethylphosphonium iodide (67.7 mg, 0.279 mmol) and N,N-diisopropylethylamine (187 µl, 1.072 mmol) were suspended in Propiononitrile (Volume: 644 µl) and heated in a closed vial at 90° C. for 1 h. It was cooled to ambient temperature, the resulting precipitate was filtered, washed with MeCN (5 mL) and dried in vacuum to afford N-ethyl-4-(4-((6-oxo-6,6a,7,8,9,10-hexahydro-5H-dipyrido[1,2-a:3',2'-e]pyrazin-3-yl)methyl)piperazin-1-yl)benzamide (56 mg, 0.125 mmol, 58.2% yield) as a white solid. $^1$H NMR (DMSO-$d_6$) δ 10.43 (s, 1H), 8.12 (t, J=5.6 Hz, 1H), 7.70 (d, J=9.1 Hz, 2H), 7.66 (d, J=2.0 Hz, 1H), 6.98 (d, J=2.0 Hz, 1H), 6.92 (d, J=9.1 Hz, 2H), 4.47-4.55 (m, 1H), 3.83 (dd, J=11.4, 2.8 Hz, 1H), 3.32-3.40 (m, 2H), 3.18-3.28 (m, 6H), 2.61 (td, J=12.6, 2.5 Hz, 1H), 2.43-2.49 (m, 4H), 2.04 (d, J=13.1 Hz, 1H), 1.80-1.91 (m, 2H), 1.64 (d, J=12.6 Hz, 2H), 1.33-1.58 (m, 3H), 1.09 (d, J=14.4 Hz, 3H); [M+H] calc'd for $C_{25}H_{32}N_6O_2$, 449; found, 449.

Compound 120: (6aS)-3-((2-methyl-4-(pyridin-2-yl)piperazin-1-yl)methyl)-6a,7,8,9-tetrahydropyrido[3,2-e]pyrrolo[1,2-a]pyrazin-6(5H)-one

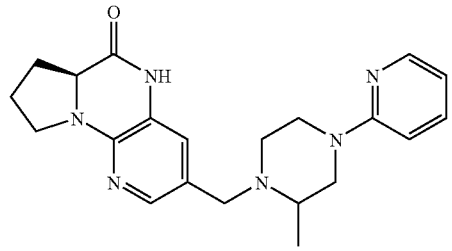

Compound 120 was prepared using a procedure analogous to that described in connection with compound 1, except that 3-methyl-1-(pyridin-2-yl)piperazine was used instead of 1-(4-chlorophenyl)piperazine hydrochloride. [M+H] calc'd for $C_{21}H_{26}N_6O$, 379; found, 379.

Compound 121: (S)-ethyl 6-(4-((6-oxo-5,6,6a,7,8,9-hexahydropyrido[3,2-e]pyrrolo[1,2-a]pyrazin-3-yl)methyl)piperazin-1-yl)nicotinate

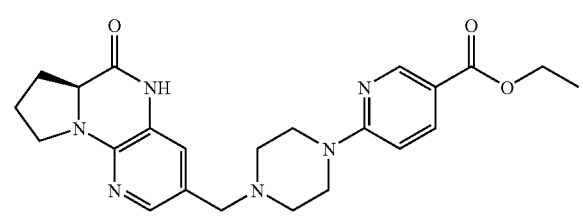

Compound 121 was prepared using a procedure analogous to that described in connection with compound 1, except that ethyl 6-(piperazin-1-yl)nicotinate was used instead of 1-(4- chlorophenyl)piperazine hydrochloride. [M+H] calc'd for $C_{23}H_{28}N_6O_3$, 437; found, 437.

Compound 122: (S)-3-((1-(4-chlorophenyl)piperidin-4-yl)methyl)-6a,7,8,9-tetrahydropyrido[3,2-e]pyrrolo[1,2-a]pyrazin-6(5H)-one

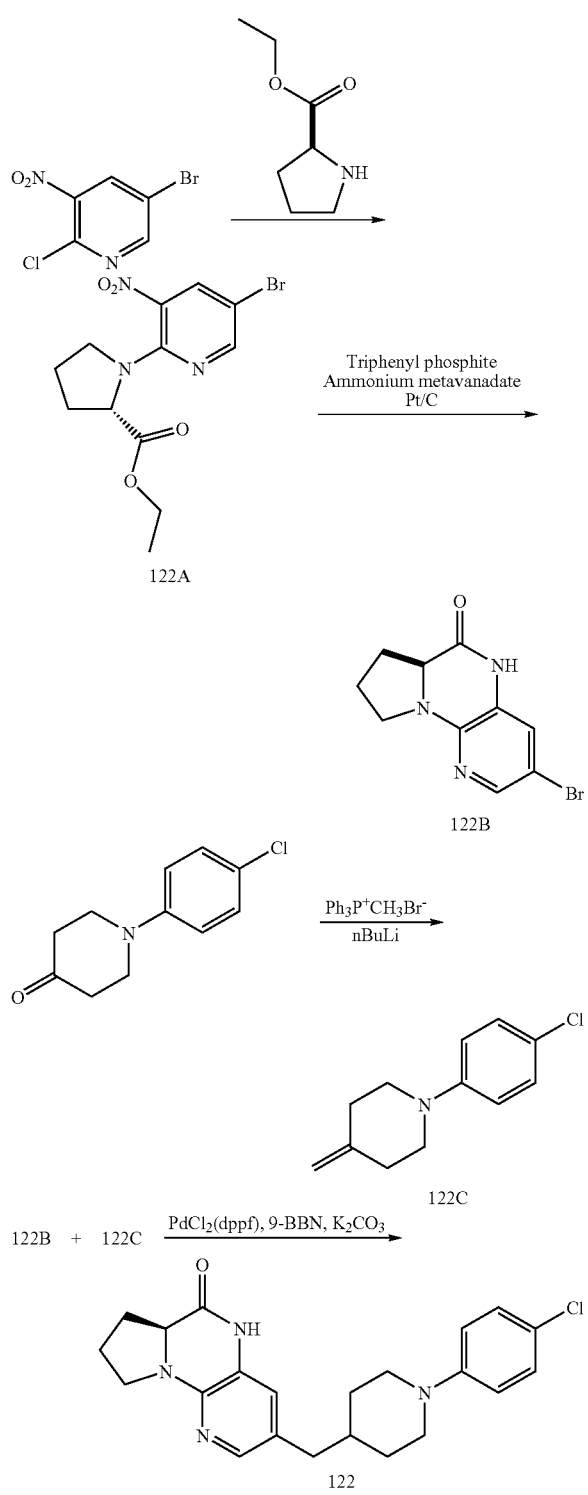

Compound 122A: (S)-ethyl 1-(5-bromo-3-nitropyridin-2-yl)pyrrolidine-2-carboxylate 5-bromo-2-chloro-3-nitropyridine (5.94 g, 25 mmol) and (S)-ethyl pyrrolidine-2-carboxylate (7.52 g, 52.5 mmol) were combined and stirred at 90° C. for 10 min in a closed vial. The crude material was purified by flash column chromatography (20-30% EtOAc in hexanes to afford (S)-ethyl 1-(5-bromo-3-nitropyridin-2-yl)pyrrolidine-2-carboxylate (8.43 g, 24.49 mmol, 98% yield) as a yellow viscous oil. [M+H] calc'd for $C_{12}H_{14}BrN_3O_4$, 344; found, 344.

Compound 122B: (S)-3-bromo-6a,7,8,9-tetrahydropyrido[3,2-e]pyrrolo[1,2-a]pyrazin-6(5H)-one (S)-ethyl 1-(5-bromo-3-nitropyridin-2-yl)pyrrolidine-2-carboxylate (8.6 g, 24.99 mmol) was dissolved in dichloromethane (Volume: 125 ml) and to this solution was added triphenyl phosphite (0.078 g, 0.250 mmol), ammonium metavanadate (0.175 g, 1.499 mmol) and Pt/C (5% wt.) (0.975 g, 0.250 mmol). The reaction mixture was hydrogenated at 80 psi at 25° C. for 4 h. The reaction mixture was filtered through celite using DCM and MeOH to complete the transfer and wash the celite plug. The combined filtrates and washes were concentrated in vacuo and crystallized with ethyl ether (75 mL). The precipitate was filtered and dried in vacuum to afford (S)-3-bromo-6a,7,8,9-tetrahydropyrido[3,2-e]pyrrolo[1,2-a]pyrazin-6(5H)-one (2.87 g, 10.70 mmol, 42.8% yield) as a pale beige solid. $^1$H NMR (400 MHz, DMSO-d6) δ ppm 1.82-2.03 (m, 3H) 2.11-2.26 (m, 1H) 3.27-3.47 (m, 1H) 3.49-3.63 (m, 1H) 4.01-4.11 (m, 1H) 7.06 (d, J=2.27 Hz, 1H) 7.77 (d, J=2.02 Hz, 1H) 10.57 (s, 1H). [M+H] calc'd for $C_{10}H_{10}BrN_3O$, 268; found, 268.

Compound 122C: 1-(4-chlorophenyl)-4-methylenepiperidine

Methyltriphenylphosphonium bromide (1.429 g, 4.00 mmol) was suspended in THF (Ratio: 1.667, Volume: 2.5 ml) and cooled to −78° C. n-butyllithium (0.960 ml, 2.400 mmol) was added dropwise over 3 min and the resulting yellow suspension was stirred at −78° C. for 10 min. A solution of 1-(4-chlorophenyl)piperidin-4-one (0.419 g, 2 mmol) in THF (Ratio: 1.000, Volume: 1.5 ml) was added dropwise over 3 min and the dark red suspension was stirred at −78° C. for 10 min and then allowed to slowly warm to 5° C. over 1 h. The reaction was stirred at 5° C. for 4 h and was quenched with water (4 mL). This was extracted with ethyl ether (2×5 mL) and the extracts were washed with water (4×5 mL). The combined water washes were back-extracted with ethyl ether (5 mL) and the combined organic extracts were washed with brine (5 ml), dried (MgSO4), filtered and concentrated in vacuo. Flash column chromatography (40 g SiO$_2$, hexanes: ethyl acetate 9:1) afforded 1-(4-chlorophenyl)-4-methylenepiperidine (0.196 g, 0.944 mmol, 47.2% yield) as a clear yellow oil. [M+H] calc'd for $C_{12}H_{14}Cl$, 208; found, 208.

Compound 122: (S)-3-((1-(4-chlorophenyl)piperidin-4-yl)methyl)-6a,7,8,9-tetrahydropyrido[3,2-e]pyrrolo[1,2-a]pyrazin-6(5H)-one 1-(4-chlorophenyl)-4-methylenepiperidine (70 mg, 0.337 mmol) was diluted with 0.5M THF solution of 9-BBN (0.674 mL, 0.337 mmol) under nitrogen and stirred at 75° C. for 1 h. The reaction mixture was then added to a suspension of (S)-3-bromo-6a,7,8,9-tetrahydropyrido[3,2-e]pyrrolo[1,2-a]pyrazin-6(5H)-one (90 mg, 0.337 mmol), PdCl2(dppf)-

CH2Cl2 adduct (8.26 mg, 10.11 μmol) and potassium carbonate (93 mg, 0.674 mmol) in DMF (1.0 mL) and water (0.1 mL) and stirred at 60° C. for 4 h.

The mixture was cooled, diluted with water (10 mL) and the resulting red material was separated off, washed with water, dissolved in ethyl acetate (10 mL), dried (MgSO4), filtered and concentrated in vacuo. Flash column chromatography (12 g SiO2, ethyl acetate) provided the desired product as a yellow solid. It was suspended in MeOH (5 mL) and the precipitate was filtered and dried in vacuo to give the product as a white solid (16 mg, 12% yield). $^1$H NMR (400 MHz, DMSO-d6) δ ppm 1.11-1.30 (m, 2H) 1.43-1.58 (m, 0H) 1.63 (d, J=12.13 Hz, 1H) 1.80-2.03 (m, 2H) 2.06-2.25 (m, 1H) 2.29-2.44 (m, 2H) 2.53-2.64 (m, 2H) 3.35-3.44 (m, 1H) 3.51-3.62 (m, 1H) 3.65 (d, J=12.13 Hz, 2H) 3.87-3.98 (m, 1H) 6.82 (d, J=1.77 Hz, 1H) 6.91 (d, J=9.09 Hz, 2H) 7.19 (d, J=9.09 Hz, 2H) 7.54 (d, J=1.77 Hz, 1H) 10.40 (s, 1H). [M+H] calc'd for $C_{22}H_{25}ClN_4O$, 397; found, 397.

Compound 123: (S)-5-(4-((6-oxo-5,6,6a,7,8,9-hexahydropyrido[3,2-e]pyrrolo[1,2-a]pyrazin-3-yl)methyl)piperazin-1-yl)picolinonitrile

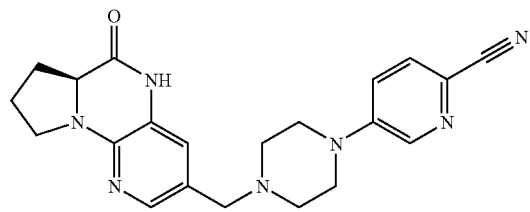

Compound 123 was prepared using a procedure analogous to that described in connection with compound 1, except that 5-(piperazin-1-yl)picolinonitrile was used instead of 1-(4-chlorophenyl)piperazine hydrochloride. $^1$H NMR (400 MHz, DMSO-d$_6$) δ ppm 1.84-2.02 (m, 3H) 2.09-2.24 (m, 1H) 2.39-2.48 (m, 4H) 3.34-3.43 (m, 7H) 3.53-3.64 (m, 1H) 3.94-4.03 (m, 1H) 6.97 (d, J=1.77 Hz, 1H) 7.34 (dd, J=8.97, 2.91 Hz, 1H) 7.61 (d, J=1.52 Hz, 1H) 7.74 (d, J=8.84 Hz, 1H) 8.40 (d, J=2.78 Hz, 1H) 10.44 (s, 1H). [M+H] calc'd for $C_{21}H_{23}N_7O$, 390; found, 390.

Compound 124: (S)—N-ethyl-2,5-difluoro-4-(4-((6-oxo-5,6,6a,7,8,9-hexahydropyrido[3,2-e]pyrrolo[1,2-a]pyrazin-3-yl)methyl)piperazin-1-yl)benzamide

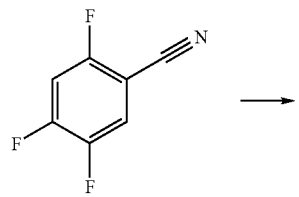

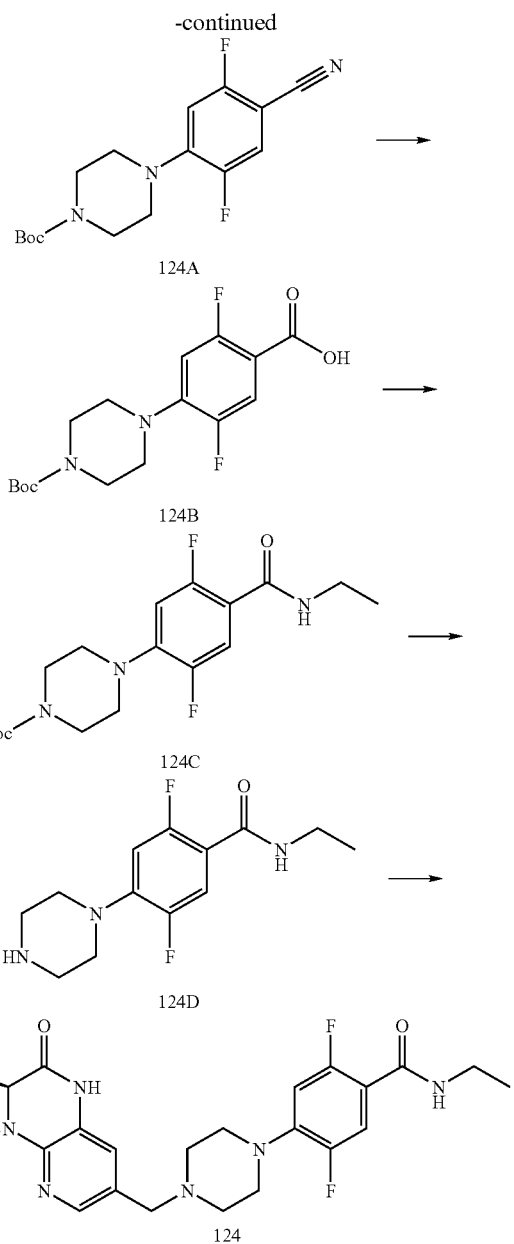

Compound 124A: tert-butyl 4-(4-cyano-2,5-difluorophenyl)piperazine-1-carboxylate Tert-butyl piperazine-1-carboxylate (0.931 g, 5 mmol) and 2,4,6-trifluorobenzonitrile (0.785 g, 5.00 mmol) were combined, potassium carbonate (0.898 g, 6.50 mmol) was added and the reaction mixture was stirred at 90° C. for 1d. The mixture was triturated with ethyl acetate (3×5 mL) and the combined organic extracts were filtered. This was concentrated down to about 5-10 mL and subjected to flash column chromatography on silica gel (120 g SiO$_2$, hexanes:ethyl acetate 1:0 to 4:1) to afford tert-butyl 4-(4-cyano-2,5-difluorophenyl)piperazine-1-carboxylate (1.363 g, 4.22 mmol, 84% yield) as a white solid. $^1$H NMR (400 MHz, DMSO-d6) δ ppm 1.41 (s, 9H) 3.12-3.27 (m, 4H) 3.45 (d, J=4.80 Hz, 4H) 7.12 (dd, J=11.87, 7.07 Hz, 1H) 7.80 (dd, J=12.88, 6.32 Hz, 1H).

Compound 124B: 4-(4-(tert-butoxycarbonyl)piperazin-1-yl)-2,5-difluorobenzoic acid Tert-butyl 4-(4-cyano-2,5-difluorophenyl)piperazine-1-carboxylate (20 mg, 0.062 mmol) was dissolved in ethanol (1 mL) and treated with water (0.2 mL) and 50% NaOH (0.2 mL, 2.500 mmol). The reaction mixture was stirred at 90° C. for 1 h, diluted with water (2 mL) and acidified with 1N HCl to pH<4. The solid was filtered, washed with water and dried in vacuum to afford 4-(4-(tert-butoxycarbonyl)piperazin-1-yl)-2,5-difluorobenzoic acid (21.0 mg, 0.061 mmol, 99% yield) as a white solid. ESI-MS:m/z 343 (M+H)$^+$.

Compound 124C: tert-butyl 4-(4-(ethylcarbamoyl)-2,5-difluorophenyl)piperazine-1-carboxylate 4-(4-(tert-butoxycarbonyl)piperazin-1-yl)-2,5-difluorobenzoic acid (0.021 g, 0.061 mmol) and ethylamine hydrochloride (7.50 mg, 0.092 mmol) were suspended in DMF (Volume: 0.7 mL) and treated with DIPEA (0.054 mL, 0.307 mmol) and 2-(3H-[1,2,3]triazolo[4,5-b]pyridin-3-yl)-1,1,3,3-tetramethylisouronium hexafluorophosphate(V) (0.047 g, 0.123 mmol). The reaction mixture was stirred at room temperature for 15 min and diluted with water. The precipitate was filtered, washed with water and dried in vacuum to afford tert-butyl 4-(4-(ethylcarbamoyl)-2,5-difluorophenyl)piperazine-1-carboxylate (20.1 mg, 0.054 mmol, 89% yield). ESI-MS:m/z 370 (M+H)$^+$.

Compound 124D: N-ethyl-2,5-difluoro-4-(piperazin-1-yl)benzamide tert-butyl 4-(4-(ethylcarbamoyl)-2,5-difluorophenyl)piperazine-1-carboxylate (0.020 g, 0.054 mmol) was diluted with 4.0M HCl in dioxane (3 mL) and stirred for 30 min. The thick white precipitate that formed was diluted with ethyl ether (10 mL) and stirred until a fine suspension resulted. The precipitate was filtered under nitrogen and dried in vacuum to afford N-ethyl-2,5-difluoro-4-(piperazin-1-yl)benzamide hydrochloride (16.2 mg, 0.053 mmol, 98% yield) as a white solid. ESI-MS:m/z 270 (M+H)$^+$.

Compound 124: (S)—N-ethyl-2,5-difluoro-4-(4-((6-oxo-5,6,6a,7,8,9-hexahydropyrido[3,2-e]pyrrolo[1,2-a]pyrazin-3-yl)methyl)piperazin-1-yl)benzamide (S)-3-(hydroxymethyl)-6a,7,8,9-tetrahydropyrido[3,2-e]pyrrolo[1,2-a]pyrazin-6(5H)-one (10.76 mg, 0.049 mmol), N-ethyl-2,5-difluoro-4-(piperazin-1-yl)benzamide hydrochloride (15 mg, 0.049 mmol), (cyanomethyl)trimethylphosphonium iodide (17.88 mg, 0.074 mmol) and N,N-diisopropylethylamine (0.043 mL, 0.245 mmol) were suspended in propiononitrile (Volume: 0.2 mL) and heated in a closed vial at 90° C. for 2 h. The reaction mixture became a dark brown solution. It was cooled to room temperature, diluted with dichloromethane (2 mL) and methanol (0.3 mL), and purified using flash column chromatography on silica gel (12 g SiO$_2$, dichloromethane-methanol 100:0-90:10). The resulting solid was suspended in ether (1 mL), stirred until a fine suspension resulted, filtered and the solid was recrystallized from MeOH-water (1:7, 4 mL) and dried in vacuum to afford (S)—N-ethyl-2,5-difluoro-4-(4-((6-oxo-5,6,6a,7,8,9-hexahydropyrido[3,2-e]pyrrolo[1,2-a]pyrazin-3-yl)methyl)piperazin-1-yl)benzamide (8.5 mg, 0.018 mmol, 36.8% yield) as an off-white solid. $^1$H NMR (400 MHz, DMSO-d$_6$) δ ppm 1.02 (t, J=7.20 Hz, 3H) 1.76-1.97 (m, 3H) 2.11 (m, J=6.44, 4.17 Hz, 1H) 2.36-2.42 (m, 4H) 3.03 (br. s., 4H) 3.12-3.22 (m, 2H) 3.28-3.37 (m, 3H) 3.46-3.59 (m, 1H) 3.86-3.97 (m, 1H) 6.81 (dd, J=12.63, 7.07 Hz, 1H) 6.91 (d, J=1.77 Hz, 1H) 7.30 (dd, J=13.64, 6.82 Hz, 1H) 7.55 (d, J=1.52 Hz, 1H) 7.95-8.04 (m, 1H) 10.38 (s, 1H). [M+H] calc'd for C$_{24}$H$_{28}$F$_2$N$_6$O$_2$, 471; found, 471.

Compound 125: (S)—N-ethyl-2-fluoro-4-(4-((6-oxo-5,6,6a,7,8,9-hexahydropyrido[3,2-e]pyrrolo[1,2-a]pyrazin-3-yl)methyl)piperazin-1-yl)benzamide

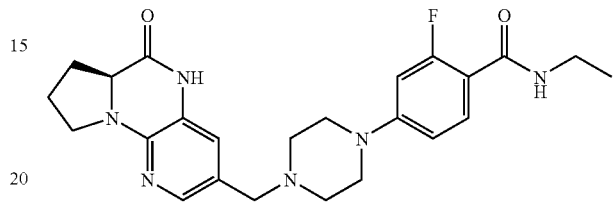

(S)-3-(hydroxymethyl)-6a,7,8,9-tetrahydropyrido[3,2-e]pyrrolo[1,2-a]pyrazin-6(5H)-one (76 mg, 0.348 mmol), N-ethyl-2-fluoro-4-(piperazin-1-yl)benzamide hydrochloride (100 mg, 0.348 mmol), (cyanomethyl)trimethylphosphonium iodide (127 mg, 0.521 mmol) and N,N-diisopropylethylamine (0.303 ml, 1.738 mmol) were suspended in propiononitrile (Volume: 1.370 ml) and heated in a closed vial at 120° C. for 3 h. The reaction mixture became a dark brown suspension. It was cooled to room temperature, concentrated in vacuo, dissolved in DMSO (2 mL) and purified using HPLC (basic, 10-95% ACN in water). The fractions were concentrated in vacuo and the resulting solid was recrystallized from water-methanol (5:1, 6 mL) and dried in vacuum to afford (S)—N-ethyl-2-fluoro-4-(4-((6-oxo-5,6,6a,7,8,9-hexahydropyrido[3,2-e]pyrrolo[1,2-a]pyrazin-3-yl)methyl)piperazin-1-yl)benzamide (28.5 mg, 0.063 mmol, 18.12% yield) as a brownish solid. $^1$H NMR (400 MHz, DMSO-d6) δ ppm 1.13 (t, J=7.20 Hz, 3H) 1.83-2.02 (m, 3H) 2.18 (dd, J=6.44, 4.17 Hz, 1H) 2.44-2.49 (m, 4H) 2.81-3.01 (m, 4H) 3.23-3.32 (m, 2H) 3.34-3.44 (m, 3H) 3.52-3.64 (m, 1H) 3.93-4.01 (m, 1H) 6.91 (td, J=8.21, 2.53 Hz, 1H) 6.97 (d, J=1.77 Hz, 1H) 7.00 (dd, J=11.37, 2.53 Hz, 1H) 7.62 (d, J=1.52 Hz, 1H) 7.67 (dd, J=8.46, 7.20 Hz, 1H) 8.86 (t, J=5.43 Hz, 1H) 10.45 (s, 1H). [M+H] calc'd for C$_{24}$H$_{29}$FN$_6$O$_2$, 453; found, 453.

Compound 126: (S)—N-ethyl-3-fluoro-4-(4-((6-oxo-5,6,6a,7,8,9-hexahydropyrido[3,2-e]pyrrolo[1,2-a]pyrazin-3-yl)methyl)piperazin-1-yl)benzamide

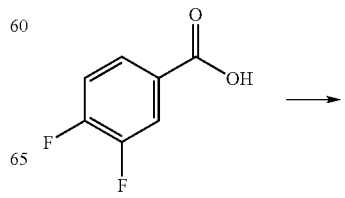

-continued

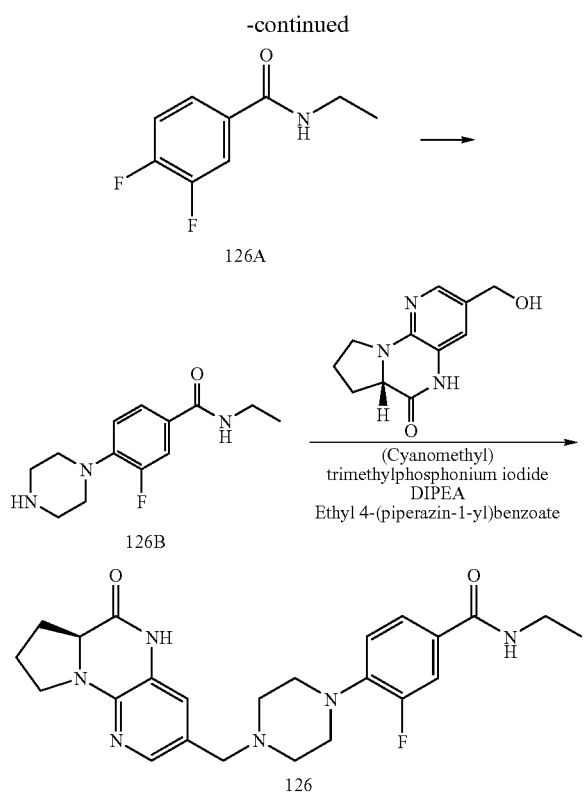

Compound 126A: 3,4-difluoro-N-ethylbenzamide

Using ethanamine hydrochloride and 3,4-difluorobenzoic acid in the general procedure for coupling of amines to carboxylic acids, the title compound was obtained (56% yield) as an off-white solid. $^1$H NMR (400 MHz, DMSO-d$_6$) δ ppm 1.12 (t, J=7.20 Hz, 3H) 3.28 (qd, J=7.24, 5.56 Hz, 2H) 7.55 (dt, J=10.48, 8.40 Hz, 1H) 7.73 (m, J=7.33, 4.74, 2.08, 1.14, 1.14 Hz, 1H) 7.88 (ddd, J=11.75, 7.83, 2.15 Hz, 1H) 8.58 (t, J=4.93 Hz, 1H). ESI-MS: m/z 186.1 (M+H)$^+$. mp=94.1-96.2° C.

Compound 126B: 3-fluoro-N-ethyl-4-(piperazin-1-yl)benzamide

Using 3,4-difluoro-N-ethylbenzamide in the general procedure for nucleophilic aromatic substitution reactions, the title compound was obtained (80% yield) as white solid. $^1$H NMR (400 MHz, DMSO-d$_6$) δ ppm 1.10 (t, J=7.20 Hz, 3H) 2.31 (br. s., 1H) 2.79-2.87 (m, 4H) 2.95-3.03 (m, 4H) 3.26 (qd, J=7.20, 5.68 Hz, 2H) 7.03 (t, J=8.59 Hz, 1H) 7.55-7.65 (m, 2H) 8.35 (t, J=5.43 Hz, 1H). ESI-MS: m/z 252.2 (M+H)$^+$. mp=142.4-144.9° C.

Compound 126: (S)—N-ethyl-3-fluoro-4-(4-((6-oxo-5,6,6a,7,8,9-hexahydropyrido[3,2-e]pyrrolo[1,2-a]pyrazin-3-yl)methyl)piperazin-1-yl)benzamide (126)

(S)-3-(hydroxymethyl)-6a,7,8,9-tetrahydropyrido[3,2-e]pyrrolo[1,2-a]pyrazin-6(5H)-one (100 mg, 0.456 mmol), N-ethyl-3-fluoro-4-(piperazin-1-yl)benzamide hydrochloride (131 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90° C. for 4 h. The reaction mixture became a dark brown solution. It was cooled to room temperature, concentrated in vacuo, dissolved in DMSO (2 mL) and purified using HPLC (basic, 10-95% ACN in water). The fractions were concentrated in vacuo and the resulting solid was recrystallized from water-methanol (5:1, 6 mL) and dried in vacuum to afford (S)—N-ethyl-3-fluoro-4-(4-((6-oxo-5,6,6a,7,8,9-hexahydropyrido[3,2-e]pyrrolo[1,2-a]pyrazin-3-yl)methyl)piperazin-1-yl)benzamide (82.3 mg, 0.182 mmol, 39.9% yield) as a yellow-green solid. $^1$H NMR (400 MHz, DMSO-d6) δ ppm 0.98-1.08 (m, 3H) 1.77-1.96 (m, 3H) 2.04-2.18 (m, 1H) 2.35-2.43 (m, 4H) 2.93-3.07 (m, 4H) 3.13-3.23 (m, 2H) 3.28-3.38 (m, 3H) 3.47-3.57 (m, 1H) 3.88-3.95 (m, 1H) 6.92 (d, J=2.02 Hz, 1H) 6.97 (t, J=8.84 Hz, 1H) 7.47-7.57 (m, 3H) 8.28 (t, J=5.56 Hz, 1H) 10.37 (s, 1H). [M+H] calc'd for $C_{24}H_{29}FN_6O_2$, 453; found, 453.

Compound 127: (S)-3-chloro-N-ethyl-4-(4-((6-oxo-5,6,6a,7,8,9-hexahydropyrido[3,2-e]pyrrolo[1,2-a]pyrazin-3-yl)methyl)piperazin-1-yl)benzamide

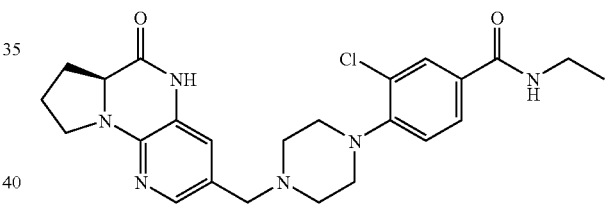

(S)-3-(hydroxymethyl)-6a,7,8,9-tetrahydropyrido[3,2-e]pyrrolo[1,2-a]pyrazin-6(5H)-one (100 mg, 0.456 mmol), 3-chloro-N-ethyl-4-(piperazin-1-yl)benzamide hydrochloride (139 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 10-95% ACN in water). The fractions were concentrated in vacuo and the resulting solid was recrystallized from water-methanol (5:1, 6 mL) and dried in vacuum to afford (S)-3-chloro-N-ethyl-4-(44(6-oxo-5,6,6a,7,8,9-hexahydropyrido[3,2-e]pyrrolo[1,2-a]pyrazin-3-yl)methyl)piperazin-1-yl)benzamide (75.6 mg, 0.161 mmol, 35.3% yield) as a tan solid. $^1$H NMR (400 MHz, DMSO-d6) δ ppm 1.03 (t, J=7.20 Hz, 3H) 1.76-1.93 (m, 3H) 2.06-2.17 (m, 1H) 2.44-2.51 (m, 4H) 2.96 (br. s., 4H) 3.14-3.23 (m, 2H) 3.28-3.38 (m, 3H) 3.46-3.58 (m, 1H) 3.88-3.97 (m, 1H) 6.92 (d, J=2.02 Hz, 1H) 7.10 (d, J=8.34 Hz, 1H) 7.56 (d, J=1.77 Hz, 1H) 7.70 (dd, J=8.34, 2.02 Hz, 1H) 7.81 (d, J=2.27 Hz, 1H)

8.37 (t, J=5.43 Hz, 1H) 10.38 (s, 1H). [M+H] calc'd for $C_{24}H_{29}ClN_6O_2$, 469; found, 469.

Compound 128: (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzenesulfonamide

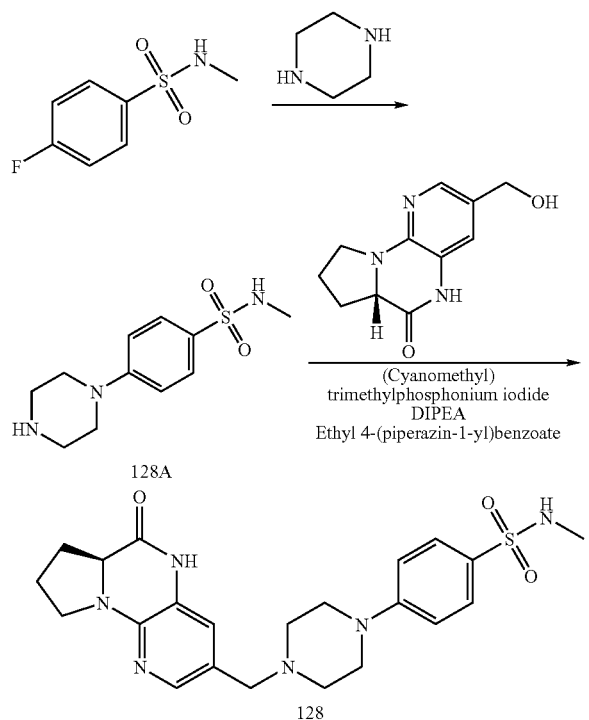

Compound 128A:
N-methyl-4-(piperazin-1-yl)benzenesulfonamide 4-fluoro-N-methylbenzenesulfonamide (189 mg, 0.999 mmol) and piperazine (430 mg, 4.99 mmol) were combined and the reaction mixture was stirred at 120° C. for 2 h. It was diluted with water (5 mL) and stirred until a fine suspension resulted. The precipitate was filtered, washed with water (5×3 mL) and dried in vacuum to afford N-methyl-4-(piperazin-1-yl)benzenesulfonamide (222 mg, 0.869 mmol, 87% yield) as a white solid. ESI-MS:m/z 256 (M+H)+.

Compound 128: (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzenesulfonamide (S)-3-(hydroxymethyl)-6a,7,8,9-tetrahydropyrido[3,2-e]pyrrolo[1,2-a]pyrazin-6(5H)-one (100 mg, 0.456 mmol), N-methyl-4-(piperazin-1-yl)benzenesulfonamide (116 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 10-95% ACN in water). The fractions were concentrated in vacuo and the resulting solid was recrystallized from water-methanol (2:1, 6 mL) and dried in vacuum to afford (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzenesulfonamide (110 mg, 0.241 mmol, 52.8% yield) as a tan solid. $^1$H NMR (400 MHz, DMSO-d$_6$) δ ppm 1.88-2.04 (m, 3H) 2.15-2.27 (m, 1H) 2.38 (d, J=4.80 Hz, 3H) 2.51 (d, J=4.29 Hz, 4H) 3.32 (br. s., 4H) 3.38-3.49 (m, 3H) 3.57-3.69 (m, 1H) 3.97-4.07 (m, 1H) 7.02 (d, J=1.52 Hz, 1H) 7.07 (d, J=9.09 Hz, 2H) 7.15 (q, J=4.72 Hz, 1H) 7.59 (d, J=8.84 Hz, 2H) 7.66 (d, J=1.77 Hz, 1H) 10.48 (s, 1H). [M+H] calc'd for $C_{24}H_{29}ClN_6O_2$, 457; found, 457.

Compound 129: (S)-3-methyl-4-(4-((6-oxo-5,6,6a,7,8,9-hexahydropyrido[3,2-e]pyrrolo[1,2-a]pyrazin-3-yl)methyl)piperazin-1-yl)benzonitrile

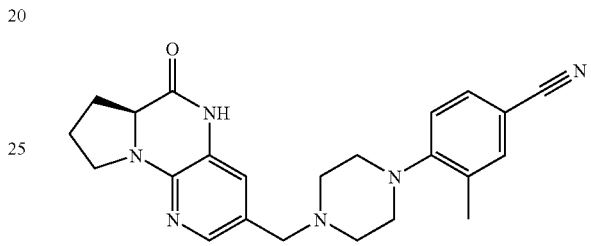

(S)-3-(hydroxymethyl)-6a,7,8,9-tetrahydropyrido[3,2-e]pyrrolo[1,2-a]pyrazin-6(5H)-one (100 mg, 0.456 mmol), 3-methyl-4-(piperazin-1-yl)benzonitrile (92 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 10-95% ACN in water). The fractions were concentrated in vacuo and the resulting solid was recrystallized from water (6 mL) and dried in vacuum to afford (S)-3-methyl-4-(4-((6-oxo-5,6,6a,7,8,9-hexahydropyrido[3,2-e]pyrrolo[1,2-a]pyrazin-3-yl)methyl)piperazin-1-yl)benzonitrile (90.1 mg, 0.224 mmol, 49.1% yield) as an off-white solid. $^1$H NMR (400 MHz, DMSO-d6) δ ppm 1.85-2.01 (m, 3H) 2.12-2.21 (m, 1H) 2.24 (s, 3H) 2.43-2.55 (m, 4H) 2.85-2.97 (m, 4H) 3.35-3.44 (m, 3H) 3.53-3.63 (m, 1H) 3.95-4.03 (m, 1H) 6.98 (d, J=2.02 Hz, 1H) 7.05-7.12 (m, 1H) 7.54-7.60 (m, 2H) 7.62 (d, J=1.77 Hz, 1H) 10.44 (s, 1H). [M+H] calc'd for $C_{23}H_{26}N_6O$, 403; found, 403.

Compound 130: (S)-3-((4-(4-fluoro-2-methylphenyl)piperazin-1-yl)methyl)-6a,7,8,9-tetrahydropyrido[3,2-e]pyrrolo[1,2-a]pyrazin-6(5H)-one

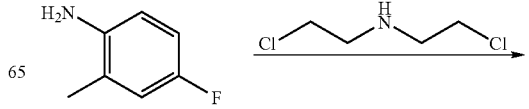

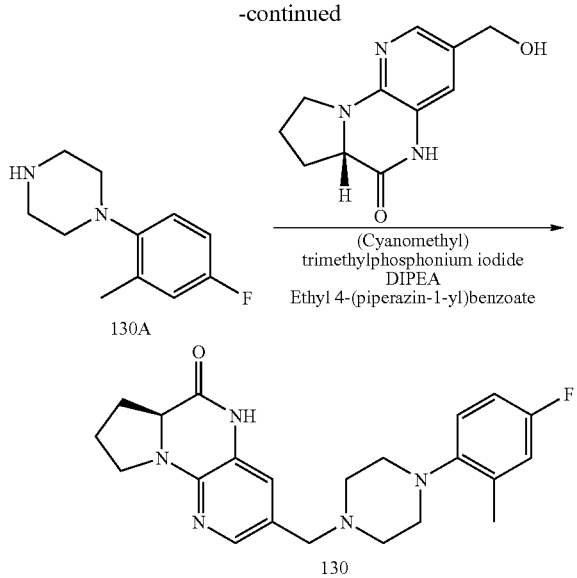

ompound 130A: 1-(4-fluoro-2-methylphenyl)piperazine

Bis(2-chloroethyl)amine hydrochloride (1.79 g, 10.03 mmol) and 4-fluoro-2-methylaniline (1.26 g, 10.07 mmol) were dissolved in 2-propanol (Volume: 10 mL) and stirred in a closed vial at 100° C. overnight. The reaction mixture was diluted with i-PrOH (10 mL) and cooled to 10° C. The resulting precipitate was filtered and purified using HPLC (10-80% ACN in water, TFA-buffered). The fractions were concentrated in vacuo, suspended in ether (3 mL) and treated with 4N HCl in dioxane (1 mL). The precipitate was filtered and dried in vacuum to afford 1-(4-fluoro-2-methylphenyl)piperazine dihydrochloride (150 mg, 0.561 mmol, 5.60% yield). ESI-MS:m/z 195 (M+H)$^+$.

Compound 130: (S)-3-((4-(4-fluoro-2-methylphenyl) piperazin-1-yl)methyl)-6a,7,8,9-tetrahydropyrido[3,2-e]pyrrolo[1,2-a]pyrazin-6(5H)-one (S)-3-(hydroxymethyl)-6a,7,8,9-tetrahydropyrido[3,2-e]pyrrolo[1,2-a]pyrazin-6(5H)-one (100 mg, 0.456 mmol), 1-(4-fluoro-2-methylphenyl)piperazine dihydrochloride (122 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 45-95% ACN in water, basic). The fractions were concentrated in vacuo and the resulting solid was recrystallized from water-MeOH (2:1, 6 mL) and dried in vacuum to afford (S)-3-((4-(4-fluoro-2-methylphenyl)piperazin-1-yl)methyl)-6a,7,8,9-tetrahydropyrido[3,2-e]pyrrolo[1,2-a]pyrazin-6(5H)-one (102.3 mg, 0.259 mmol, 56.7% yield) as an off-white solid. $^1$H NMR (400 MHz, DMSO-d$_6$) δ ppm 1.80-2.02 (m, 3H) 2.09-2.20 (m, 1H) 2.23 (s, 3H) 2.37-2.49 (m, 4H) 2.77 (br. s., 4H) 3.34-3.44 (m, 3H) 3.52-3.65 (m, 1H) 3.93-4.03 (m, 1H) 6.88-7.07 (m, 4H) 7.62 (s, 1H) 10.44 (s, 1H). [M+H] calc'd for C$_{22}$H$_{26}$FN$_5$O, 396; found, 396.

Compound 131: (S)-3-fluoro-N-methyl-4-(4-((6-oxo-5,6,6a,7,8,9-hexahydropyrido[3,2-e]pyrrolo[1,2-a]pyrazin-3-yl)methyl)piperazin-1-yl)benzamide

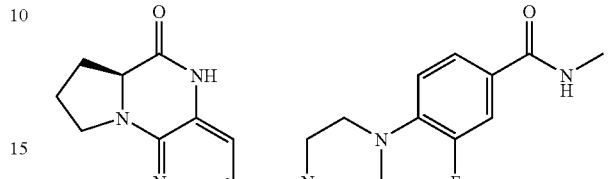

(S)-3-(hydroxymethyl)-6a,7,8,9-tetrahydropyrido[3,2-e]pyrrolo[1,2-a]pyrazin-6(5H)-one (100 mg, 0.456 mmol), 3-fluoro-N-methyl-4-(piperazin-1-yl)benzamide hydrochloride (125 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 45-95% ACN in water, basic). The fractions were concentrated in vacuo and the resulting solid was recrystallized from water-MeOH (2:1, 6 mL) and dried in vacuum to afford (S)-3-fluoro-N-methyl-4-(4-((6-oxo-5,6,6a,7,8,9-hexahydropyrido[3,2-e]pyrrolo[1,2-a]pyrazin-3-yl)methyl)piperazin-1-yl)benzamide (128.5 mg, 0.293 mmol, 64.2% yield) as an off-white solid. $^1$H NMR (400 MHz, DMSO-d$_6$) δ ppm 1.83-2.03 (m, 3H) 2.09-2.25 (m, 1H) 2.50 (m, 4H) 2.75 (d, J=4.29 Hz, 3H) 2.96-3.14 (m, 4H) 3.35-3.45 (m, 3H) 3.53-3.65 (m, 1H) 3.93-4.05 (m, 1H) 6.98 (d, J=1.77 Hz, 1H) 7.04 (t, J=8.59 Hz, 1H) 7.51-7.67 (m, 3H) 8.27-8.38 (m, 1H) 10.44 (s, 1H). [M+H] calc'd for C$_{23}$H$_{27}$FN$_6$O$_2$, 439; found, 439.

Compound 132: (S)—N-cyclopropyl-3-fluoro-4-(4-((6-oxo-5,6,6a,7,8,9-hexahydropyrido[3,2-e]pyrrolo[1,2-a]pyrazin-3-yl)methyl)piperazin-1-yl)benzamide

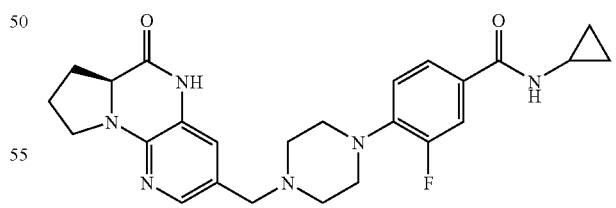

(S)-3-(hydroxymethyl)-6a,7,8,9-tetrahydropyrido[3,2-e]pyrrolo[1,2-a]pyrazin-6(5H)-one (100 mg, 0.456 mmol), N-cyclopropyl-3-fluoro-4-(piperazin-1-yl)benzamide hydrochloride (137 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 45-95% ACN in water, basic). The fractions were concentrated in vacuo and the resulting solid was recrystallized from water-MeOH (2:1, 6 mL) and dried in vacuum to afford (S)—N-cyclopropyl-3-fluoro-4-(4-((6-oxo-5,6,6a,7,8,9-hexahydropyrido[3,2-e]pyrrolo[1,2-a]pyrazin-3-yl)methyl)piperazin-1-yl)benzamide (85.3 mg, 0.184 mmol, 40.3% yield) as an off-white solid. $^1$H NMR (400 MHz, DMSO-$d_6$) δ ppm 0.45-0.61 (m, 2H) 0.61-0.76 (m, 2H) 1.83-2.05 (m, 3H) 2.08-2.25 (m, 1H) 2.44-2.49 (m, 4H) 2.80 (td, J=7.33, 3.79 Hz, 1H) 3.08 (br. s., 4H) 3.54-3.66 (m, 1H) 3.91-4.06 (m, 1H) 6.98 (d, J=1.77 Hz, 1H) 7.02 (t, J=8.84 Hz, 1H) 7.49-7.69 (m, 3H) 8.31 (d, J=4.04 Hz, 1H) 10.44 (s, 1H). [M+H] calc'd for $C_{25}H_{29}FN_6O_2$, 465; found, 465.

Compound 133: (S)-3-fluoro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide

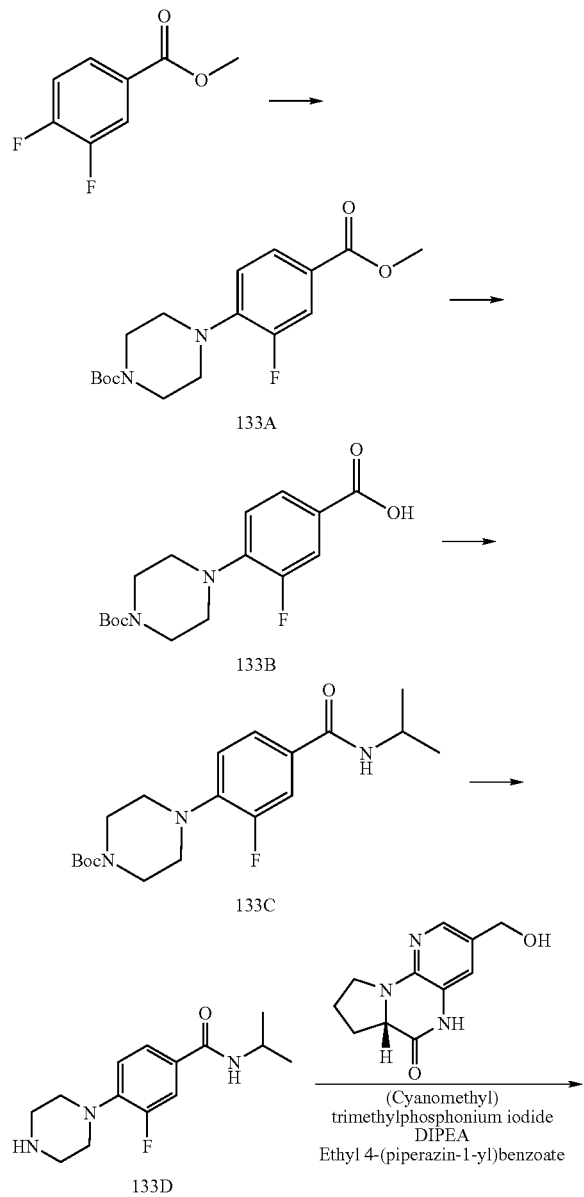

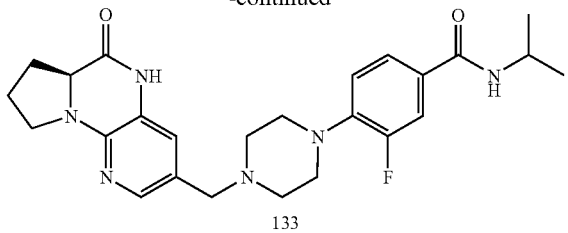

133

Compound 133A: tert-butyl 4-(2-fluoro-4-(methoxycarbonyl)phenyl)piperazine-1-carboxylate Potassium carbonate (5.56 g, 40.3 mmol) and tert-butyl piperazine-1-carboxylate (6.92 g, 37.2 mmol) were combined, methyl 3,4-difluorobenzoate (5.33 g, 31.0 mmol) was added and the reaction mixture was stirred at 90° C. for 1d. The mixture was triturated with ethyl acetate (3×5 mL) and the combined organic extracts were filtered. This was concentrated down to about 5-10 mL and subjected to flash column chromatography on silica gel (120 g SiO2, hexanes: ethyl acetate 1:0 to 4:1) to afford tert-butyl 4-(2-fluoro-4-(methoxycarbonyl)phenyl)piperazine-1-carboxylate (4.702 g, 13.90 mmol, 44.9% yield) as a white solid. ESI-MS:m/z 339 (M+H)$^+$.

Compound 133B: 4-(4-(tert-butoxycarbonyl)piperazin-1-yl)-3-fluorobenzoic acid

Tert-butyl 4-(2-fluoro-4-(methoxycarbonyl)phenyl)piperazine-1-carboxylate (4.6 g, 13.59 mmol) was suspended in 1,4-Dioxane (Volume: 68.0 ml) and treated with 1N LiOH (68.0 ml, 68.0 mmol). The reaction mixture was stirred at room temperature for 23 h. The reaction mixture was concentrated in vacuo until most of the dioxane was gone and acidified with HCl (4.5 N) until a thick precipitate resulted. It was filtered off, washed with water and dried in vacuum to afford 4-(4-(tert-butoxycarbonyl)piperazin-1-yl)-3-fluorobenzoic acid (4.40 g, 13.57 mmol, 100% yield) as a brown solid. ESI-MS:m/z 325 (M+H)$^+$.

Compound 133C: tert-butyl 4-(2-fluoro-4-(isopropylcarbamoyl)phenyl)piperazine-1-carboxylate 4-(4-(tert-butoxycarbonyl)piperazin-1-yl)-3-fluorobenzoic acid (1.1 g, 3.39 mmol), propan-2-amine (0.241 g, 4.07 mmol), N1-((ethylimino)methylene)-N3,N3-dimethylpropane-1,3-diamine hydrochloride (0.975 g, 5.09 mmol) and 1H-benzo[d][1,2,3]triazol-1-ol hydrate (0.779 g, 5.09 mmol) were suspended in DMF (Volume: 13.57 ml) and 4-methylmorpholine (1.864 ml, 16.96 mmol) was added. The reaction mixture was stirred at ambient temperature for 2 h. It was diluted with water (50 mL) and extracted with ethyl acetate (3×100 mL). The combined organic extracts were washed with brine (3×50 mL), dried (MgSO4) and concentrated in vacuo to afford tert-butyl 4-(2-fluoro-4-(isopropylcarbamoyl)phenyl)piperazine-1-carboxylate (1.11 g, 3.04 mmol, 89% yield) as an off-white solid. ESI-MS:m/z 366 (M+H)$^+$.

Compound 133D: 3-fluoro-N-isopropyl-4-(piperazin-1-yl)benzamide (133D)

Tert-butyl 4-(2-fluoro-4-(isopropylcarbamoyl)phenyl)piperazine-1-carboxylate (1.10 g, 3.01 mmol) was diluted with 4.0M HCl in dioxane (3 mL) and stirred for 30 min. The thick white precipitate that formed was diluted with ethyl ether (10 mL) and stirred until a fine suspension resulted. The precipitate was filtered under nitrogen and dried in vacuum to afford 3-fluoro-N-isopropyl-4-(piperazin-1-yl)benzamide hydrochloride as a white solid. ESI-MS:m/z 302 (M+H)$^+$.

Compound 133: (S)-3-fluoro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide (S)-3-(hydroxymethyl)-6a,7,8,9-tetrahydropyrido[3,2-e]pyrrolo[1,2-a]pyrazin-6(5H)-one (100 mg, 0.456 mmol), 3-fluoro-N-isopropyl-4-(piperazin-1-yl)benzamide hydrochloride (138 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 45-95% ACN in water, basic). The fractions were concentrated in vacuo and the resulting solid was recrystallized from water-MeOH (2:1, 6 mL) and dried in vacuum to afford (S)-3-fluoro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide (71.4 mg, 0.153 mmol, 33.6% yield) as a light yellow solid. $^1$H NMR (400 MHz, DMSO-d$_6$) δ ppm 1.14 (d, J=6.57 Hz, 6H) 1.82-2.01 (m, 3H) 2.12-2.24 (m, 1H) 2.46-2.50 (m, 4H) 2.98-3.15 (m, 4H) 3.35-3.44 (m, 3H) 3.54-3.64 (m, 2H) 3.92-4.14 (m, 2H) 6.98 (d, J=1.77 Hz, 1H) 7.03 (t, J=8.84 Hz, 1H) 7.56-7.66 (m, 3H) 8.09 (d, J=7.83 Hz, 1H) 10.45 (s, 1H). [M+H] calc'd for C$_{25}$H$_{31}$FN$_6$O$_2$, 467; found, 467.

Compound 134: (S)-3-chloro-N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide

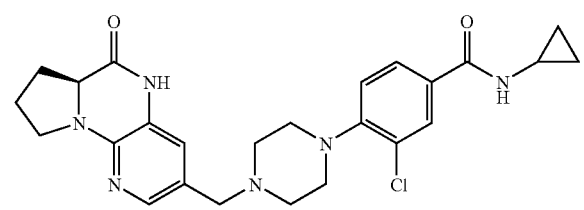

(S)-3-(hydroxymethyl)-6a,7,8,9-tetrahydropyrido[3,2-e]pyrrolo[1,2-a]pyrazin-6(5H)-one (100 mg, 0.456 mmol), 3-chloro-N-cyclopropyl-4-(piperazin-1-yl)benzamide (128 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 25-95% ACN in water, basic). The fractions were concentrated in vacuo and the resulting solid was recrystallized from water-MeOH (2:1, 15 mL) and dried in vacuum to afford(S)-3-chloro-N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide (120.4 mg, 0.250 mmol, 54.9% yield) as an off-white solid. $^1$H NMR (400 MHz, DMSO-d$_6$) δ ppm 0.50-0.60 (m, 2H) 0.61-0.72 (m, 2H) 1.84-2.01 (m, 3H) 2.12-2.23 (m, 1H) 2.51-2.57 (m, 4H) 2.77-2.86 (m, 1H) 3.02 (br. s., 4H) 3.35-3.46 (m, 3H) 3.54-3.64 (m, 1H) 3.95-4.03 (m, 1H) 6.98 (d, J=1.77 Hz, 1H) 7.16 (d, J=8.34 Hz, 1H) 7.63 (d, J=1.77 Hz, 1H) 7.75 (dd, J=8.34, 2.02 Hz, 1H) 7.85 (d, J=2.02 Hz, 1H) 8.39 (d, J=4.04 Hz, 1H) 10.45 (s, 1H). [M+H] calc'd for C$_{25}$H$_{29}$ClN$_6$O$_2$, 481; found, 481.

Compound 135: (S)-3-chloro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide

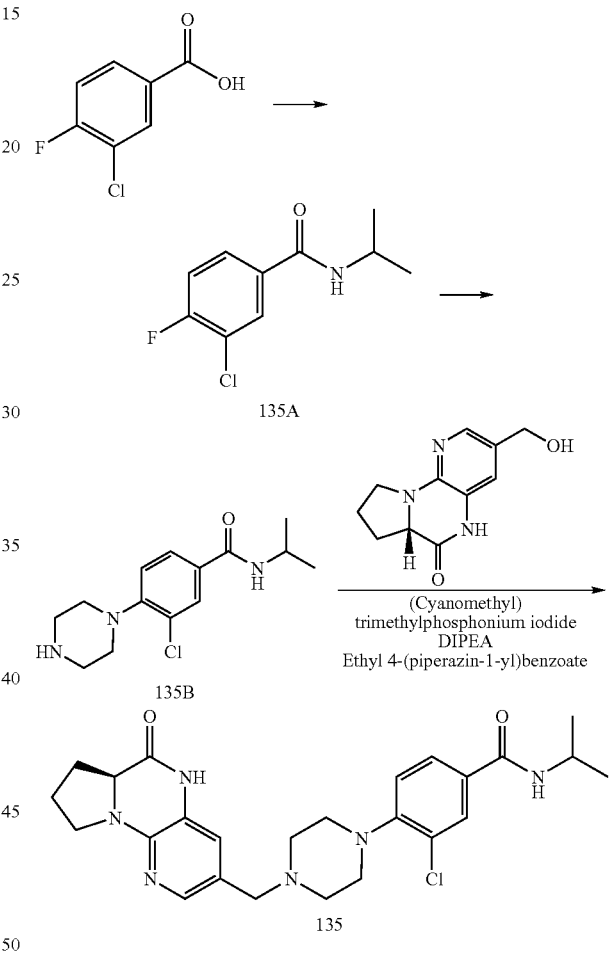

Compound 135A:
3-chloro-4-fluoro-N-isopropylbenzamide

Using isopropylamine hydrochloride and 3-chloro-4-fluorobenzoic acid in the general procedure for coupling of amines to carboxylic acids, the title compound was obtained (81% yield) as a white solid. ESI-MS: m/z 216 (M+H)$^+$.

Compound 135B:
3-chloro-N-isopropyl-4-(piperazin-1-yl)benzamide

Using 3-chloro-4-fluoro-N-isopropylbenzamide in the general procedure for nucleophilic aromatic substitution reactions, the title compound was obtained (51% yield) as an off-white solid. ESI-MS: m/z 282.2 (M+H)$^+$.

Compound 135: (S)-3-chloro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide (S)-3-(hydroxymethyl)-6a,7,8,9-tetrahydropyrido[3,2-e]pyrrolo[1,2-a]pyrazin-6(5H)-one (100 mg, 0.456 mmol), 3-chloro-N-isopropyl-4-(piperazin-1-yl)benzamide (129 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 25-95% ACN in water, basic). The fractions were concentrated in vacuo and the resulting solid was recrystallized from water-MeOH (2:1, 15 mL) and dried in vacuum to afford (S)-3-chloro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide (122.1 mg, 0.253 mmol, 55.4% yield) as a light tan solid. $^1$H NMR (400 MHz, DMSO-$d_6$) δ ppm 1.14 (d, J=6.57 Hz, 6H) 1.84-2.03 (m, 3H) 2.12-2.25 (m, 1H) 2.50-2.59 (m, 4H) 3.02 (br. s., 4H) 3.35-3.45 (m, 3H) 3.53-3.64 (m, 1H) 3.94-4.09 (m, 2H) 6.98 (d, J=1.52 Hz, 1H) 7.17 (d, J=8.59 Hz, 1H) 7.63 (d, J=1.77 Hz, 1H) 7.77 (dd, J=8.34, 2.02 Hz, 1H) 7.89 (d, J=2.02 Hz, 1H) 8.18 (d, J=7.58 Hz, 1H) 10.45 (s, 1H). [M+H] calc'd for $C_{25}H_{31}ClN_6O_2$, 483; found, 483.

Compound 136: (S)-3-chloro-N-methyl-4-(4-((6-oxo-5,6,6a,7,8,9-hexahydropyrido[3,2-e]pyrrolo[1,2-a]pyrazin-3-yl)methyl)piperazin-1-yl)benzamide

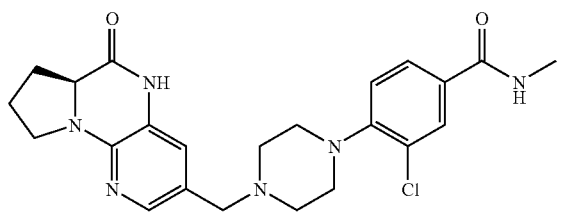

(S)-3-(hydroxymethyl)-6a,7,8,9-tetrahydropyrido[3,2-e]pyrrolo[1,2-a]pyrazin-6(5H)-one (100 mg, 0.456 mmol), 3-chloro-N-methyl-4-(piperazin-1-yl)benzamide hydrochloride (132 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 45-95% ACN in water, basic). The fractions were concentrated in vacuo and the resulting solid was recrystallized from water-MeOH (2:1, 6 mL) and dried in vacuum to afford (S)-3-chloro-N-methyl-4-(4-((6-oxo-5,6,6a,7,8,9-hexahydropyrido[3,2-e]pyrrolo[1,2-a]pyrazin-3-yl)methyl)piperazin-1-yl)benzamide (53.1 mg, 0.117 mmol, 25.6% yield) as an off-white solid. $^1$H NMR (400 MHz, DMSO-$d_6$) δ ppm 1.83-2.02 (m, 3H) 2.10-2.24 (m, 1H) 2.51 (br. s., 4H) 2.75 (d, J=4.55 Hz, 3H) 3.03 (br. s., 4H) 3.36-3.45 (m, 3H) 3.52-3.65 (m, 1H) 3.93-4.03 (m, 1H) 6.98 (d, J=1.77 Hz, 1H) 7.17 (d, J=8.34 Hz, 1H) 7.63 (d, J=1.77 Hz, 1H) 7.75 (dd, J=8.34, 2.02 Hz, 1H) 7.86 (d, J=2.02 Hz, 1H) 8.41 (q, J=4.13 Hz, 1H) 10.45 (s, 1H). [M+H] calc'd for $C_{23}H_{27}ClN_6O_2$, 455; found, 455.

Compound 137: (S)—N-ethyl-3-methyl-4-(4-((6-oxo-5,6,6a,7,8,9-hexahydropyrido[3,2-e]pyrrolo[1,2-a]pyrazin-3-yl)methyl)piperazin-1-yl)benzamide

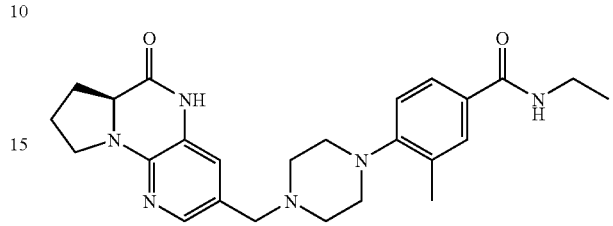

(S)-3-(hydroxymethyl)-6a,7,8,9-tetrahydropyrido[3,2-e]pyrrolo[1,2-a]pyrazin-6(5H)-one (100 mg, 0.456 mmol), N-ethyl-3-methyl-4-(piperazin-1-yl)benzamide hydrochloride (129 mg, 0.456 mmol), (cyanomethyl)trimethylphosphonium iodide (166 mg, 0.684 mmol) and N,N-diisopropylethylamine (0.398 ml, 2.281 mmol) were suspended in propiononitrile (Volume: 1.370 ml) and heated in a closed vial at 90-120° C. for 4 h. The reaction mixture became a dark brown solution. It was cooled to room temperature, concentrated in vacuo, dissolved in DMSO (2 mL) and purified using HPLC (basic, 45-95% ACN in water, basic). The fractions were concentrated in vacuo and the resulting solid was recrystallized from water-MeOH (2:1, 6 mL) and dried in vacuum to afford (S)—N-ethyl-3-methyl-4-(4-((6-oxo-5,6,6a,7,8,9-hexahydropyrido[3,2-e]pyrrolo[1,2-a]pyrazin-3-yl)methyl)piperazin-1-yl)benzamide (128.5 mg, 0.286 mmol, 62.8% yield) as an off-white solid. $^1$H NMR (400 MHz, DMSO-$d_6$) δ ppm 1.83-2.03 (m, 3H) 2.09-2.25 (m, 1H) 2.50 (m, 4H) 2.75 (d, J=4.29 Hz, 3H) 2.96-3.14 (m, 4H) 3.35-3.45 (m, 3H) 3.53-3.65 (m, 1H) 3.93-4.05 (m, 1H) 6.98 (d, J=1.77 Hz, 1H) 7.04 (t, J=8.59 Hz, 1H) 7.51-7.67 (m, 3H) 8.27-8.38 (m, 1H) 10.44 (s, 1H). [M+H] calc'd for $C_{25}H_{32}N_6O_2$, 449; found, 449.

Compound 138: (S)-3-((4-(4-(pyrrolidine-1-carbonyl)phenyl)piperazin-1-yl)methyl)-6a,7,8,9-tetrahydropyrido[3,2-e]pyrrolo[1,2-a]pyrazin-6(5H)-one

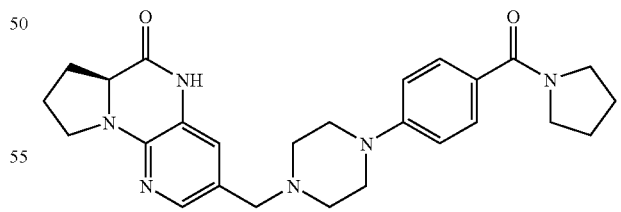

In a 1 dram vial, (S)-4-(4-((6-oxo-5,6,6a,7,8,9-hexahydropyrido[3,2-e]pyrrolo[1,2-a]pyrazin-3-yl)methyl)piperazin-1-yl)benzoic acid (100 mg, 0.245 mmol) was suspended in DMF (Volume: 1.227 mL) then added pyrrolidine (0.024 mL, 0.295 mmol), HATU (140 mg, 0.368 mmol) and N-methylmorpholine (0.108 mL, 0.982 mmol). The rxn was stirred at RT overnight. The mixture was purified by prep HPLC-MS (acidic mode, 15-35%). The pH of the combined fractions was adjusted to pH=8-9 and extracted with EtOAc (3×30 ml), washed with brine, dried with MgSO₄, filtered and concentrated to dryness. The residue was taken up with water/ACN (1:1), and concentrated in vacuo to provide the title compound as a fluffy white solid (29 mg, 26% yield). m.p.=121.3° C. ¹H NMR (400 MHz, DMSO-d6) δ ppm 1.73-1.87 (m, 4H) 1.87-2.01 (m, 3H) 2.14-2.21 (m, 1H) 2.43-2.49 (m, 4H) 3.15-3.23 (m, 4H) 3.35 (br. s., 2H) 3.37-3.49 (m, 5H) 3.54-3.65 (m, 1H) 3.95-4.04 (m, 1H) 6.91 (d, J=9.09 Hz, 2H) 6.99 (d, J=2.02 Hz, 1H) 7.42 (d, J=8.84 Hz, 2H) 7.62 (d, J=1.77 Hz, 1H) 10.44 (s, 1H). [M+H] calc'd for $C_{26}H_{32}N_6O_2$, 461; found, 461.

Compound 139: (S)—N,N-dimethyl-4-(4-((6-oxo-5,6,6a,7,8,9-hexahydropyrido[3,2-e]pyrrolo[1,2-a]pyrazin-3-yl)methyl)piperazin-1-yl)benzamide

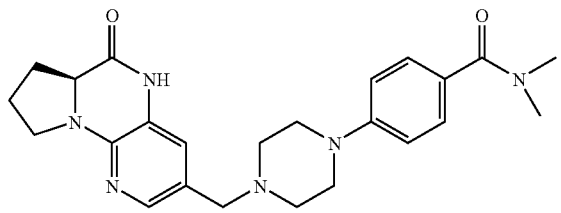

In a 1 dram vial, (S)-4-(4-((6-oxo-5,6,6a,7,8,9-hexahydropyrido[3,2-e]pyrrolo[1,2-a]pyrazin-3-yl)methyl)piperazin-1-yl)benzoic acid (100 mg, 0.245 mmol) was suspended in DMF (Volume: 1.227 mL) then added dimethylamine hydrochloride (24.02 mg, 0.295 mmol), HATU (140 mg, 0.368 mmol) and N-methylmorpholine (0.108 mL, 0.982 mmol). The reaction was stirred at RT overnight. The mixture was purified by prep HPLC-MS (acidic mode, 15-35%). The pH of the combined fractions was adjusted to pH=8-9 and extracted with EtOAc (3×30 ml), washed with brine, dried with MgSO₄, filtered and concentrated to dryness. The residue was taken up with water/ACN (1:1), and concentrated in vacuo to provide the title compound as a fluffy white solid (21 mg, 19% yield). m.p.=99.2° C. ¹H NMR (400 MHz, DMSO-d6) δ ppm 1.85-2.04 (m, 3H) 2.12-2.21 (m, 1H) 2.43-2.49 (m, 4H) 2.94 (s, 6H) 3.14-3.23 (m, 4H) 3.35-3.43 (m, 3H) 3.54-3.64 (m, 1H) 3.94-4.03 (m, 1H) 6.92 (d, J=9.09 Hz, 2H) 6.99 (d, J=1.77 Hz, 1H) 7.29 (d, J=8.84 Hz, 2H) 7.62 (d, J=1.52 Hz, 1H) 10.44 (s, 1H). [M+H] calc'd for $C_{24}H_{30}N_6O_2$, 435; found, 435.

Compound 140: (S)—N-ethyl-N-methyl-4-(4-((6-oxo-5,6,6a,7,8,9-hexahydropyrido[3,2-e]pyrrolo[1,2-a]pyrazin-3-yl)methyl)piperazin-1-yl)benzamide

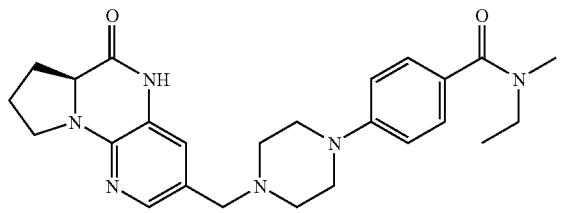

In a 1 dram vial, (S)-4-(4-((6-oxo-5,6,6a,7,8,9-hexahydropyrido[3,2-e]pyrrolo[1,2-a]pyrazin-3-yl)methyl)piperazin-1-yl)benzoic acid (100 mg, 0.245 mmol) was suspended in DMF (Volume: 1.227 mL) then added N-methylethanamine (0.025 mL, 0.295 mmol), HATU (140 mg, 0.368 mmol) and N-methylmorpholine (0.108 mL, 0.982 mmol). The reaction was stirred at RT overnight. The mixture was purified by prep HPLC-MS (acidic mode, 15-35%). The pH of the combined fractions was adjusted to pH=8-9 and extracted with EtOAc (3×30 ml), washed with brine, dried with MgSO₄, filtered and concentrated to dryness. The residue was taken up with water/ACN (1:1), and concentrated in vacuo to provide the title compound as a fluffy white solid (18 mg, 17% yield). m.p.=91.9° C. ¹H NMR (400 MHz, DMSO-d6) δ ppm 1.09 (t, J=7.07 Hz, 3H) 1.24 (br. s., 3H) 1.85-2.04 (m, 3H) 2.13-2.21 (m, 1H) 2.43-2.48 (m, 3H) 2.90 (s, 3H) 3.14-3.22 (m, 4H) 3.34-3.43 (m, 3H) 3.54-3.64 (m, 1H) 3.95-4.02 (m, 1H) 6.92 (d, J=8.84 Hz, 2H) 6.99 (d, J=2.02 Hz, 1H) 7.25 (d, J=8.59 Hz, 2H) 7.62 (d, J=1.77 Hz, 1H) 10.44 (s, 1H). [M+H] calc'd for $C_{25}H_{32}N_6O_2$, 449; found, 449.

Compound 141: (S)—N,3-dimethyl-4-(4-((6-oxo-5,6,6a,7,8,9-hexahydropyrido[3,2-e]pyrrolo[1,2-a]pyrazin-3-yl)methyl)piperazin-1-yl)benzamide

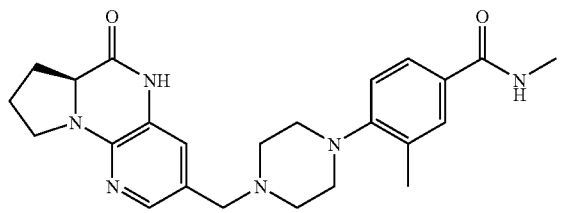

(S)-3-(hydroxymethyl)-6a,7,8,9-tetrahydropyrido[3,2-e]pyrrolo[1,2-a]pyrazin-6(5H)-one (300 mg, 1.368 mmol), [Reactants], (cyanomethyl)trimethylphosphonium iodide (499 mg, 2.053 mmol) and N,N-diisopropylethylamine (1195 µl, 6.84 mmol) were suspended in propiononitrile (Volume: 4109 µl) and heated in a closed vial at 120° C. for 2 h. The reaction mixture became a dark brown solution. It was cooled to room temperature, concentrated in vacuo, dissolved in DMSO (2 mL) and purified using HPLC(NH₄HCO₃ buffered, 20-70% ACN in water). The fractions were concentrated in vacuo and the resulting solid was recrystallized from water-MeOH (1:1, 5 mL), and then from ACN (30 mL), and dried in vacuum to afford (S)—N,3-dimethyl-4-(4-((6-oxo-5,6,6a,7,8,9-hexahydropyrido[3,2-e]pyrrolo[1,2-a]pyrazin-3-yl)methyl)piperazin-1-yl)benzamide (232.7 mg, 0.536 mmol, 39.1% yield) as a light tan solid. ¹H NMR (DMSO-d₆) δ: 10.40 (s, 1H), 8.19 (q, J=4.0 Hz, 1H), 7.57-7.66 (m, 3H), 6.95-7.04 (m, 2H), 3.93-4.02 (m, 1H), 3.54-3.64 (m, 1H), 3.38 (s, 3H), 2.87 (br. s., 4H), 2.74 (d, J=4.5 Hz, 3H), 2.49-2.55 (m, 4H), 2.25 (s, 3H), 2.11-2.22 (m, 1H), 1.80-2.02 (m, 3H). [M+H] calc'd for $C_{24}H_{30}N_6O_2$, 435; found, 435.

219

Compound 142: (S)—N-cyclopropyl-3-methyl-4-(4-((6-oxo-5,6,6a,7,8,9-hexahydropyrido[3,2-e]pyrrolo[1,2-a]pyrazin-3-yl)methyl)piperazin-1-yl)benzamide

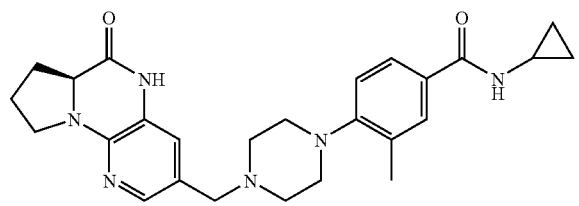

To a suspension of (S)-3-(hydroxymethyl)-6a,7,8,9-tetrahydropyrido[3,2-e]pyrrolo[1,2-a]pyrazin-6(5H)-one (0.1 g, 0.456 mmol), N-cyclopropyl-3-methyl-4-(piperazin-1-yl)benzamide dihydrochloride (0.179 g, 0.538 mmol), and (cyanomethyl)trimethylphosphonium iodide (0.188 g, 0.775 mmol) in Propiononitrile (Volume: 2.0 mL) was added N-ethyl-N-isopropylpropan-2-amine (0.556 mL, 3.19 mmol) at 23° C. The reaction was stirred at 90° C. for 8 hr. The reaction mixture was cooled to room temperature, filtered, and rinsed with propiononitrile (3×1 mL). The resulting solid was reconstituted in DMSO (Volume: 3.0 mL) and purified via preparative mass trigger LCMS using a gradient eluant of 25-65% ACN:10 mM $NH_4HCO_3$ (aq). The collected fractions were combined and the ACN was removed via rotary evaporation to furnish a suspension. The suspension was filtered, rinsed with H2O (3×10 mL), and the resulting solid was dried in vacuo to provide (S)—N-cyclopropyl-3-methyl-4-(4-((6-oxo-5,6,6a,7,8,9-hexahydropyrido[3,2-e]pyrrolo[1,2-a]pyrazin-3-yl)methyl)piperazin-1-yl)benzamide (0.0624 g, 0.135 mmol, 29.7% yield) as an off-white solid. $^1$H NMR (400 MHz, DMSO-$d_6$) δ ppm 0.50-0.59 (m, 2H) 0.60-0.70 (m, 2H) 1.86-2.00 (m, 3H) 2.14-2.20 (m, 1H) 2.25 (s, 3H) 2.47-2.50 (m, 4H) 2.76-2.93 (m, 5H) 3.34-3.44 (m, 3H) 3.55-3.63 (m, 1H) 3.93-4.02 (m, 1H) 6.96-7.04 (m, 2H) 7.56-7.67 (m, 3H) 8.22 (d, J=4.29 Hz, 1H) 10.45 (s, 1H). ESI-MS:m/z 461.4 (M+H)$^+$. mp=226.7-233.5° C.

Compound 143: N-ethyl-4-(4-((6-oxo-5,6-dihydropyrido[3,2-e]pyrrolo[1,2-a]pyrazin-3-yl)methyl)piperazin-1-yl)benzamide

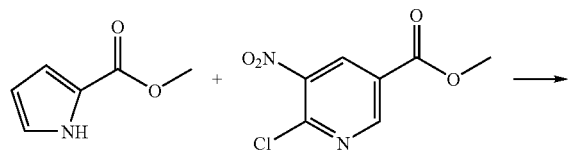

220

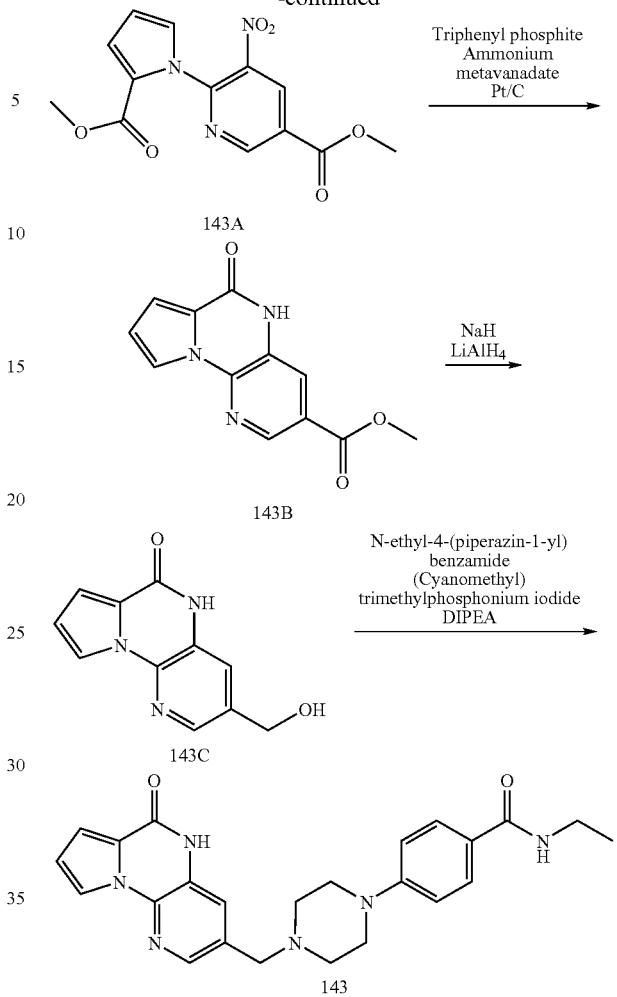

Compound 143A: Methyl 6-(2-(methoxycarbonyl)-1H-pyrrol-1-yl)-5-nitronicotinate Methyl 1H-pyrrole-2-carboxylate (5.78 g, 46.2 mmol) was dissolved in DMSO and cooled to 10° C. NaH was added in two portions over 5 min. The reaction mixture was stirred at 10° C. for 10 min and methyl 6-chloro-5-nitronicotinate (5 g, 23.09 mmol) in DMSO (10 mL) was added slowly over 3 min. The red reaction mixture was allowed to warm to room temperature and stirred overnight. It was cooled to 0° C. and quenched with water (12 mL) and diluted with brine (50 mL). The mixture was washed with EtOAc (2×25 mL) and the aqueous layer was acidified to pH=2 with 4.5 N HCl. It was extracted with EtOAc (1×100 mL) and the organic layer was dried ($Na_2SO_4$), filtered and concentrated in vacuo to afford a yellow solid, which was dissolved in MeOH (100 mL) and cooled to 0° C. Thionyl chloride (45 mL, 617 mmol) was added slowly over 5 min. The reaction mixture was stirred at 0° C. for 1 h and then at room temperature overnight. It was concentrated in vacuo and the resulting solid was triturated with ethyl acetate (300 mL). The solid was filtered off and the filtrate was concentrated in vacuo. then washed with ethyl ether to afford methyl 6-(2-(methoxycarbonyl)-1H-pyrrol-1-yl)-5-nitronicotinate (5.04 g, 16.51 mmol, 92% yield) as a yellow solid, [M+H] calc'd for $C_{13}H_{11}N_3O_6$, 306; found, 306.

Compound 143B: Methyl 6-oxo-5,6-dihydropyrido[3,2-e]pyrrolo[1,2-a]pyrazine-3-carboxylate Methyl 6-(2-(methoxycarbonyl)-1H-pyrrol-1-yl)-5-nitronicotinate (5.00 g, 16.38 mmol) was dissolved in dichloromethane (Volume: 82 ml) and to this solution was added triphenyl phosphite (0.051 g, 0.164 mmol), ammonium metavanadate (0.115 g, 0.983 mmol) and Pt/C (5% wt.) (0.639 g, 0.164 mmol). The reaction mixture was hydrogenated at 100 psi at 25° C. for 36 h. The reaction mixture was filtered through a short plug of celite and the plug and precipitate were washed well with methanol (100 mL) and then MeOH:DCM (100 mL, 1:1). The solids (celite and Pt/—C) were continuously extracted with MeOH/DCM mixture (1:1) in a Soxlet extractor for 2d. The extracts were combined with the earlier filtrates, concentrated in vacuo, crystallized with MeOH (100 mL) and the resulting solid was filtered off and suspended in ethyl ether (200 mL). The solid were filtered off and dried in vacuum to afford methyl 6-oxo-5,6-dihydropyrido[3,2-e]pyrrolo[1,2-a]pyrazine-3-carboxylate (2.15 g, 8.84 mmol, 54.0% yield) as a grey solid. $^1$H NMR (DMSO-$d_6$) δ 11.49 (s, 1H), 8.69 (s, 1H), 8.15 (br. s., 1H), 8.11 (s, 1H), 7.16 (d, J=2.5 Hz, 1H), 6.78 (t, J=3.0 Hz, 1H), 3.91 (s, 3H). [M+H] calc'd for $C_{12}H_9N_3O_3$, 244; found, 244.

Compound 143C: 3-(hydroxymethyl)pyrido[3,2-e]pyrrolo[1,2-a]pyrazin-6(5H)-one Methyl 6-oxo-5,6-dihydropyrido[3,2-e]pyrrolo[1,2-a]pyrazine-3-carboxylate (2.0 g, 8.22 mmol) was suspended in THF (Volume: 27.4 ml) under nitrogen atmosphere and cooled to 0° C. Sodium hydride (0.658 g, 16.45 mmol) was added in several portions over 7 min. The reaction mixture was stirred at 0° C. for 10 min, at room temperature for 20 min and cooled to below −50° C. Lithium aluminum hydride (7.40 ml, 14.80 mmol) was added over the period of 5 min and the reaction was kept at a temperature between −30 and −20° C. for 1 h. The mixture was cooled to below −40° C. and MeOH (6 mL) was added. Water (5 mL) was added and then more MeOH (50 mL). The reaction mixture was stirred at rt for 10 min. The resulting precipitate was filtered, suspended in MeOH (100 mL) and filtered again. The solid was suspended with heating overnight in MeOH:DCM (1:1, 200 mL) and filtered hot. This solid was dissolved in MeOH/DCM (100 mL, 3:1) and loaded onto silica gel (12 g) then purified by flash column chromatography on silica gel (220 g SiO2, gradient DCM:MeOH 100:1-85:15) to give 3-(hydroxymethyl)pyrido[3,2-e]pyrrolo[1,2-a]pyrazin-6(5H)-one (854 mg, 3.97 mmol, 48.3% yield) as a white solid. $^1$H NMR (DMSO-d6) δ 11.36 (br. s., 1H), 8.14 (d, J=1.8 Hz, 1H), 8.10 (dd, J=2.8, 1.5 Hz, 1H), 7.61-7.66 (m, 1H), 7.09 (dd, J=3.8, 1.5 Hz, 1H), 6.71 (dd, J=3.7, 2.9 Hz, 1H), 5.42 (br. s., 1H), 4.53-4.64 (m, 2H). [M+H] calc'd for $C_{11}H_9N_3O_2$, 216; found, 216.

Compound 143: N-ethyl-4-(4-((6-oxo-5,6-dihydropyrido[3,2-e]pyrrolo[1,2-a]pyrazin-3-yl)methyl)piperazin-1-yl)benzamide 3-(hydroxymethyl)pyrido[3,2-e]pyrrolo[1,2-a]pyrazin-6(5H)-one (100 mg, 0.465 mmol), N-ethyl-4-(piperazin-1-yl)benzamide (119 mg, 0.511 mmol), (cyanomethyl)trimethylphosphonium iodide (158 mg, 0.651 mmol) and N,N-diisopropylethylamine (406 μl, 2.323 mmol) were suspended in propiononitrile (Volume: 1395 μl) and heated in a small closed vial for 7 h at 90-120° C. (the temperature was increased by 10° C. after 4, 5 and 6 h. An additional portion of (cyanomethyl)trimethylphosphonium iodide (43.3 mg) was added after 4 h. The reaction mixture was cooled to rt, filtered and the precipitate was washed with MeCN (5 mL) to give an off-white solid (168.4 mg). The solid was heated to reflux in EtOH (15 mL) for 5 min and allowed to cool to ambient temperature. It was filtered and dried in vacuum to afford N-ethyl-4-(4-((6-oxo-5,6-dihydropyrido[3,2-e]pyrrolo[1,2-a]pyrazin-3-yl)methyl)piperazin-1-yl)benzamide (112.5 mg, 0.261 mmol, 56.2% yield) as a while solid. $^1$H NMR (DMSO-$d_6$) δ: 11.31 (s, 1H), 8.08-8.17 (m, 3H), 7.71 (d, J=8.8 Hz, 2H), 7.66 (d, J=1.8 Hz, 1H), 7.09 (dd, J=3.7, 1.6 Hz, 1H), 6.93 (d, J=8.8 Hz, 2H), 6.72 (dd, J=3.7, 2.9 Hz, 1H), 3.62 (s, 2H), 3.20-3.28 (m, 6H), 2.52-2.59 (m, 4H), 1.09 (t, J=7.2 Hz, 3H). [M+H] calc'd for $C_{24}H_{26}N_6O_2$, 431; found, 431.

Compound 144: (S)-3-((4-(4-(2-methoxypyridin-4-yl)phenyl)piperazin-1-yl)methyl)-7,8,9,10-tetrahydro-5H-dipyrido[1,2-a:3',2'-e]pyrazin-6(6aH)-one

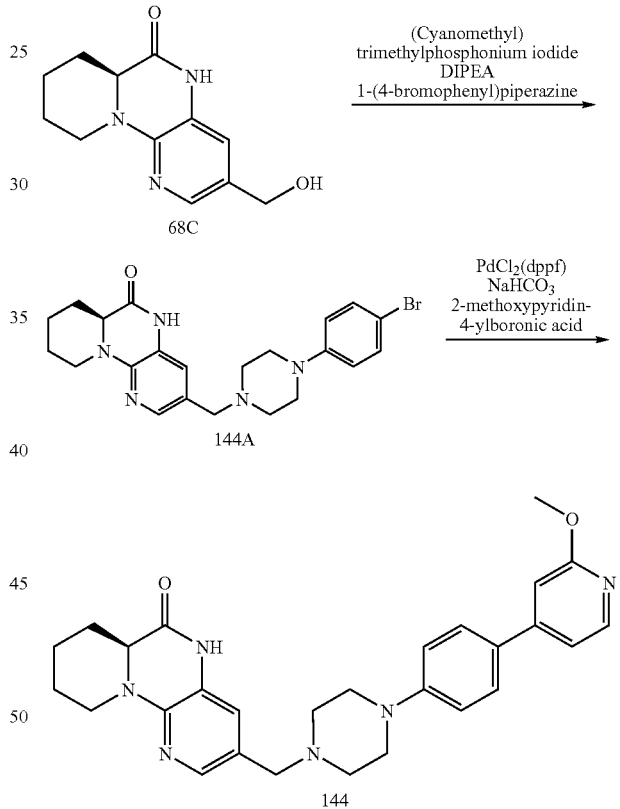

Compound 144A: (S)-3-((4-(4-bromophenyl)piperazin-1-yl)methyl)-7,8,9,10-tetrahydro-5H-dipyrido[1,2-a:3',2'-e]pyrazin-6(6aH)-one Compound 144 was prepared using a procedure analogous to that described in connection with compound 68, except that 1-(4-bromophenyl)piperazine was used instead of 4-(4-chlorophenyl)-1,2,3,6-tetrahydropyridine hydrochloride to give a white solid: [M+H] calc'd for $C_{22}H_{26}BrN_5O$, 456; found, 456.

Compound 144: (S)-3-((4-(4-(2-methoxypyridin-4-yl)phenyl)piperazin-1-yl)methyl)-7,8,9,10-tetrahydro-5H-dipyrido[1,2-a:3',2'-e]pyrazin-6(6aH)-one (S)-3-((4-(4-bromophenyl)piperazin-1-yl)methyl)-7,8,9,10-tetrahydro-5H-dipyrido[1,2-a:3',2'-e]pyrazin-6(6aH)-one (0.04 mmol), 2-methoxypyridin-4-ylboronic acid (0.060 mmol), PdCl2(dppf)-CH$_2$Cl$_2$ Adduct (3.27 mg, 4.00 µmol), sodium bicarbonate (0.500 ml, 0.500 mmol), dioxane (Volume: 1 ml) and a stir bar were sealed in a 5 mL microwave vial. The vial was heated to 135° C. for 30 minutes. The aqueous layer was removed from the vial and reaction mixture the filtered into a 1.8 mL HPLC submission vial. The reaction mixture was purified by LCMS to give a yellow solid: [M+H] calc'd for C$_{28}$H$_{32}$N$_6$O$_2$, 485; found, 485.

Compound 145: (S)-3-((4-(4-(6-aminopyridin-2-yl)phenyl)piperazin-1-yl)methyl)-7,8,9,10-tetrahydro-5H-dipyrido[1,2-a:3',2'-e]pyrazin-6(6aH)-one

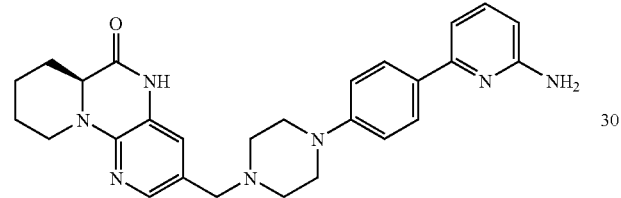

Compound 145 was prepared using a procedure analogous to that described in connection with compound 144, except that 6-(4,4,5,5-tetramethyl-1,3,2-dioxaborolan-2-yl)pyridin-2-amine was used instead of 2-methoxypyridin-4-ylboronic acid to give a white solid as the TFA salt after purification by HPLC-MS: [M+H] calc'd for C$_{27}$H$_{31}$N$_7$O, 470; found, 470.

Compound 146: (S)-3-((4-(4-(thiophen-3-yl)phenyl)piperazin-1-yl)methyl)-7,8,9,10-tetrahydro-5H-dipyrido[1,2-a:3',2'-e]pyrazin-6(6aH)-one

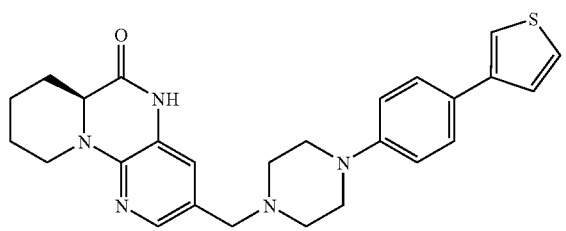

Compound 146 was prepared using a procedure analogous to that described in connection with compound 144, except that thiophen-3-ylboronic acid was used instead of 2-methoxypyridin-4-ylboronic acid to give a white solid as the TFA salt after purification by HPLC-MS: [M+H] calc'd for C$_{26}$H$_{29}$N$_5$OS, 460; found, 460.

Compound 147: (S)-3-((4-(4-(thiophen-2-yl)phenyl)piperazin-1-yl)methyl)-7,8,9,10-tetrahydro-5H-dipyrido[1,2-a:3',2'-e]pyrazin-6(6aH)-one

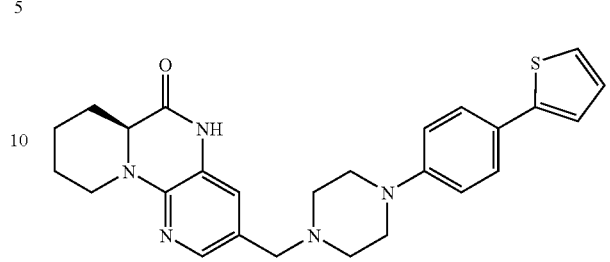

Compound 147 was prepared using a procedure analogous to that described in connection with compound 144, except that thiophen-2-ylboronic acid was used instead of 2-methoxypyridin-4-ylboronic acid to give a brown solid as the TFA salt after purification by HPLC-MS: [M+H] calc'd for C$_{26}$H$_{29}$N$_5$OS, 460; found, 460.

Compound 148: (S)-3-((4-(4-(pyridin-4-yl)phenyl)piperazin-1-yl)methyl)-7,8,9,10-tetrahydro-5H-dipyrido[1,2-a:3',2'-e]pyrazin-6(6aH)-one

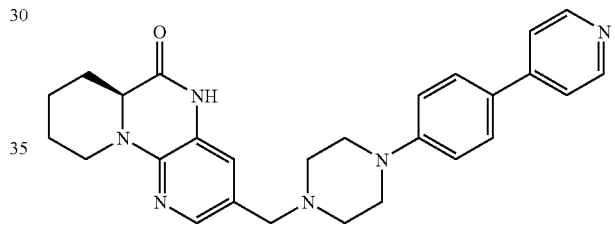

Compound 148 was prepared using a procedure analogous to that described in connection with compound 144, except that pyridin-4-ylboronic acid was used instead of 2-methoxypyridin-4-ylboronic acid to give a brown solid as the TFA salt after purification by HPLC-MS: [M+H] calc'd for C$_{27}$H$_{30}$N$_6$O, 455; found, 455.

Compound 149: (S)-3-((4-(biphenyl-4-yl)piperazin-1-yl)methyl)-7,8,9,10-tetrahydro-5H-dipyrido[1,2-a:3',2'-e]pyrazin-6(6aH)-one

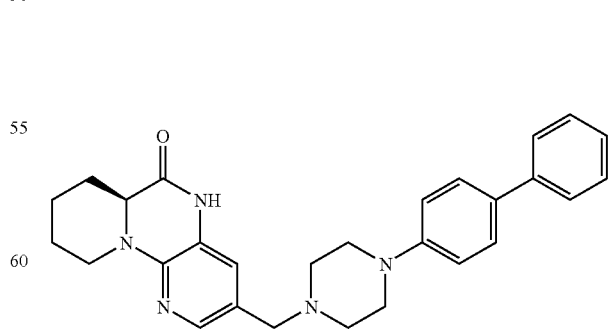

Compound 149 was prepared using a procedure analogous to that described in connection with compound 144, except that phenylboronic acid was used instead of 2-methoxypyridin-4-ylboronic acid to give a brown solid as the TFA salt after purification by HPLC-MS: [M+H] calc'd for $C_{28}H_{31}N_5O$, 454; found, 454.

Compound 150: (S)-3-((4-(4-(6-methoxypyridin-3-yl)phenyl)piperazin-1-yl)methyl)-7,8,9,10-tetrahydro-5H-dipyrido[1,2-a:3',2'-e]pyrazin-6(6aH)-one

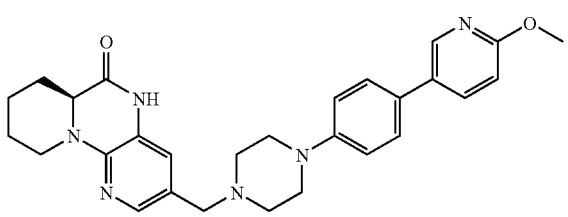

Compound 150 was prepared using a procedure analogous to that described in connection with compound 144, except that 6-methoxypyridin-3-ylboronic acid was used instead of 2-methoxypyridin-4-ylboronic acid to give a white solid as the TFA salt after purification by HPLC-MS: [M+H] calc'd for $C_{28}H_{32}N_6O_2$, 485; found, 485.

Compound 151: (S)-3-((4-(4-(pyrimidin-5-yl)phenyl)piperazin-1-yl)methyl)-7,8,9,10-tetrahydro-5H-dipyrido[1,2-a:3',2'-e]pyrazin-6(6aH)-one

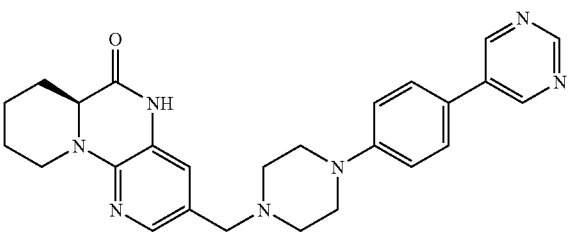

Compound 151 was prepared using a procedure analogous to that described in connection with compound 144, except that pyrimidin-5-ylboronic acid was used instead of 2-methoxypyridin-4-ylboronic acid to give a white solid as the TFA salt after purification by HPLC-MS: [M+H] calc'd for $C_{26}H_{29}N_7O$, 456; found, 456.

Compound 152: (S)-3-((4-(4-(2-methoxypyrimidin-5-yl)phenyl)piperazin-1-yl)methyl)-7,8,9,10-tetrahydro-5H-dipyrido[1,2-a:3',2'-e]pyrazin-6(6aH)-one

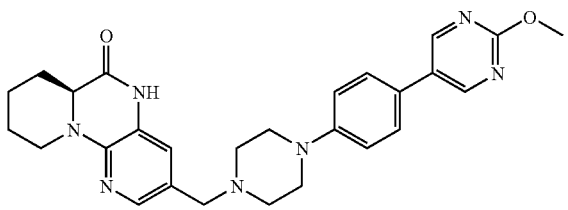

Compound 152 was prepared using a procedure analogous to that described in connection with compound 144, except that 2-methoxypyrimidin-5-ylboronic acid was used instead of 2-methoxypyridin-4-ylboronic acid to give a green solid as the TFA salt after purification by HPLC-MS: [M+H] calc'd for $C_{27}H_{31}N_7O_2$, 486; found, 486.

Compound 153: (S)-3-((4-(4-(3-methoxypyridin-4-yl)phenyl)piperazin-1-yl)methyl)-7,8,9,10-tetrahydro-5H-dipyrido[1,2-a:3',2'-e]pyrazin-6(6aH)-one

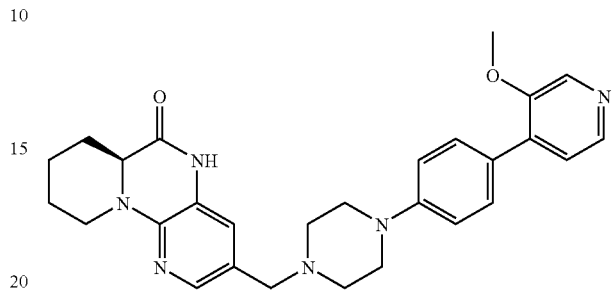

Compound 153 was prepared using a procedure analogous to that described in connection with compound 144, except that 3-methoxypyridin-4-ylboronic acid was used instead of 2-methoxypyridin-4-ylboronic acid to give a brown solid as the TFA salt after purification by HPLC-MS: [M+H] calc'd for $C_{28}H_{32}N_6O_2$, 485; found, 485.

Compound 154: (S)-3-((4-(2'-methylbiphenyl-4-yl)piperazin-1-yl)methyl)-7,8,9,10-tetrahydro-5H-dipyrido[1,2-a:3',2'-e]pyrazin-6(6aH)-one

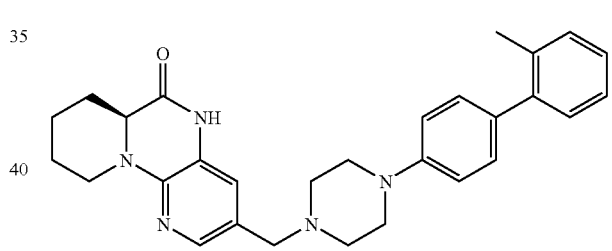

Compound 154 was prepared using a procedure analogous to that described in connection with compound 144, except that o-tolylboronic acid was used instead of 2-methoxypyridin-4-ylboronic acid to give a gray solid as the TFA salt after purification by HPLC-MS: [M+H] calc'd for $C_{29}H_{33}N_5O$, 468; found, 468.

Compound 155: (S)-3-((4-(4-(3-methylpyridin-4-yl)phenyl)piperazin-1-yl)methyl)-7,8,9,10-tetrahydro-5H-dipyrido[1,2-a:3',2'-e]pyrazin-6(6aH)-one

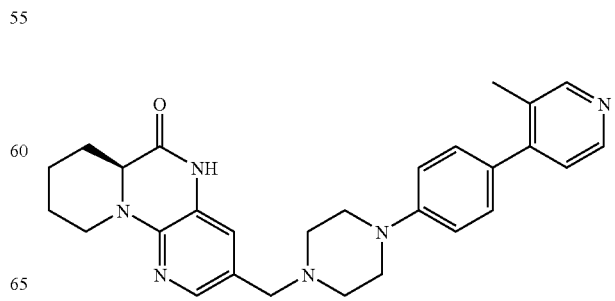

Compound 155 was prepared using a procedure analogous to that described in connection with compound 144, except that 3-methylpyridin-4-ylboronic acid was used instead of 2-methoxypyridin-4-ylboronic acid to give a brown solid as the TFA salt after purification by HPLC-MS: [M+H] calc'd for $C_{28}H_{32}N_6O$, 469; found, 469.

Compound 156: (S)-3-((4-(4-(6-methoxypyridin-2-yl)phenyl)piperazin-1-yl)methyl)-7,8,9,10-tetrahydro-5H-dipyrido[1,2-a:3',2'-e]pyrazin-6(6aH)-one

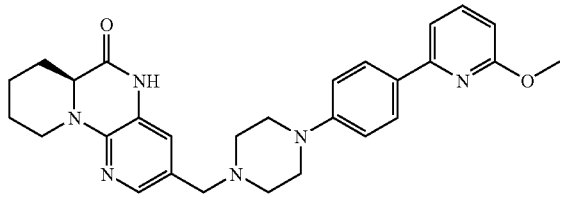

Compound 156 was prepared using a procedure analogous to that described in connection with compound 144, except that 2-methoxy-6-(4,4,5,5-tetramethyl-1,3,2-dioxaborolan-2-yl)pyridine was used instead of 2-methoxypyridin-4-ylboronic acid to give a brown solid as the TFA salt after purification by HPLC-MS: [M+H] calc'd for $C_{28}H_{32}N_6O_2$, 485; found, 485.

Compound 157: (S)-3-((4-(4-(pyridin-2-yl)phenyl)piperazin-1-yl)methyl)-7,8,9,10-tetrahydro-5H-dipyrido[1,2-a:3',2'-e]pyrazin-6(6aH)-one

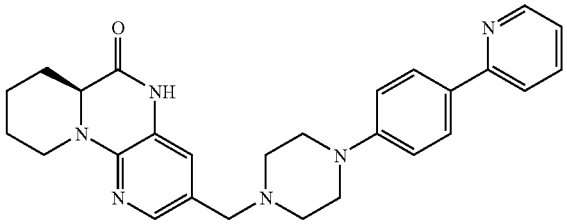

Compound 157 was prepared using a procedure analogous to that described in connection with compound 144, except that 2-(4,4,5,5-tetramethyl-1,3,2-dioxaborolan-2-yl)pyridine was used instead of 2-methoxypyridin-4-ylboronic acid to give a yellow solid as the TFA salt after purification by HPLC-MS: [M+H] calc'd for $C_{27}H_{30}N_6O$, 455; found, 455.

Compound 158: (S)-3-((4-(4-(pyridin-3-yl)phenyl)piperazin-1-yl)methyl)-7,8,9,10-tetrahydro-5H-dipyrido[1,2-a:3',2'-e]pyrazin-6(6aH)-one

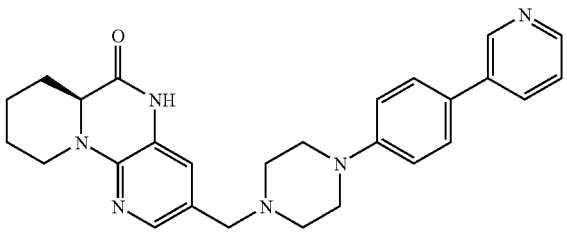

Compound 158 was prepared using a procedure analogous to that described in connection with compound 144, except that pyridin-3-ylboronic acid was used instead of 2-methoxypyridin-4-ylboronic acid to give a brown solid as the TFA salt after purification by HPLC-MS: [M+H] calc'd for $C_{27}H_{30}N_6O$, 455; found, 455.

Compound 159: (S)-3-((4-(4-(5-methylthiophen-2-yl)phenyl)piperazin-1-yl)methyl)-7,8,9,10-tetrahydro-5H-dipyrido[1,2-a:3',2'-e]pyrazin-6(6aH)-one

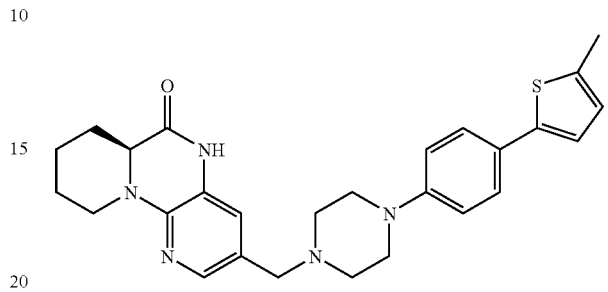

Compound 159 was prepared using a procedure analogous to that described in connection with compound 144, except that 5-methylthiophen-2-ylboronic acid was used instead of 2-methoxypyridin-4-ylboronic acid to give a brown solid as the TFA salt after purification by HPLC-MS: [M+H] calc'd for $C_{27}H_{31}N_5OS$, 474; found, 474.

Compound 160: (S)-3-((4-(2'-(hydroxymethyl)biphenyl-4-yl)piperazin-1-yl)methyl)-7,8,9,10-tetrahydro-5H-dipyrido[1,2-a:3',2'-e]pyrazin-6(6aH)-one

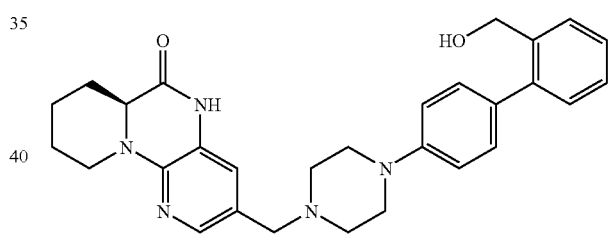

Compound 160 was prepared using a procedure analogous to that described in connection with compound 144, except that benzo[c][1,2]oxaborol-1(3H)-ol was used instead of 2-methoxypyridin-4-ylboronic acid to give a gray solid as the TFA salt after purification by HPLC-MS: [M+H] calc'd for $C_{29}H_{33}N_5O_2$, 484; found, 484.

Compound 161: (S)-3-((4-(4-(4-methylthiophen-3-yl)phenyl)piperazin-1-yl)methyl)-7,8,9,10-tetrahydro-5H-dipyrido[1,2-a:3',2'-e]pyrazin-6(6aH)-one

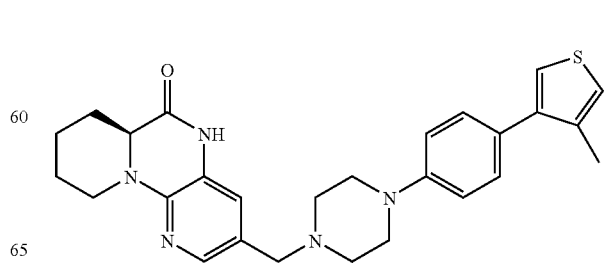

Compound 161 was prepared using a procedure analogous to that described in connection with compound 144, except that 4-methylthiophen-3-ylboronic acid was used instead of 2-methoxypyridin-4-ylboronic acid to give a white solid as the TFA salt after purification by HPLC-MS: [M+H] calc'd for $C_{27}H_{31}N_5OS$, 474; found, 474.

Compound 162: (S)-3-((4-(4-(3-methylthiophen-2-yl)phenyl)piperazin-1-yl)methyl)-7,8,9,10-tetrahydro-5H-dipyrido[1,2-a:3',2'-e]pyrazin-6(6aH)-one

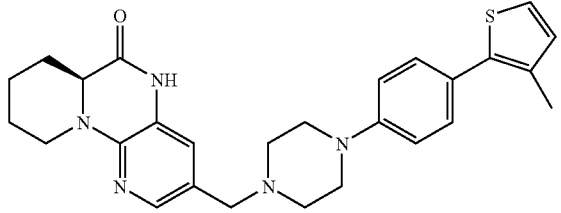

Compound 162 was prepared using a procedure analogous to that described in connection with compound 144, except that 3-methylthiophen-2-ylboronic acid was used instead of 2-methoxypyridin-4-ylboronic acid to give a yellow solid as the TFA salt after purification by HPLC-MS: [M+H] calc'd for $C_{27}H_{31}N_5OS$, 474; found, 474.

Compound 163: (S)-3-((4-(4-(5-oxocyclopent-1-enyl)phenyl)piperazin-1-yl)methyl)-7,8,9,10-tetrahydro-5H-dipyrido[1,2-a:3',2'-e]pyrazin-6(6aH)-one

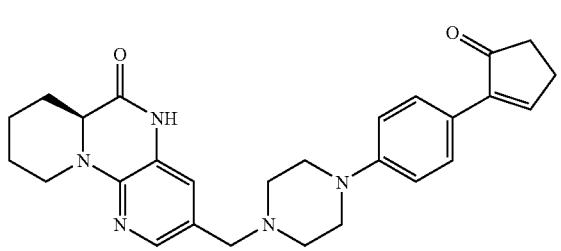

Compound 163 was prepared using a procedure analogous to that described in connection with compound 144, except that 5-oxocyclopent-1-enylboronic acid was used instead of 2-methoxypyridin-4-ylboronic acid to give a brown solid as the TFA salt after purification by HPLC-MS: [M+H] calc'd for $C_{27}H_{31}N_5O_2$, 458; found, 458.

Compound 164: (S)-3-((4-(4-(6-methylpyridin-3-yl)phenyl)piperazin-1-yl)methyl)-7,8,9,10-tetrahydro-5H-dipyrido[1,2-a:3',2'-e]pyrazin-6(6aH)-one

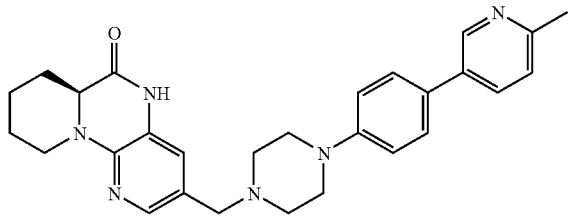

Compound 164 was prepared using a procedure analogous to that described in connection with compound 144, except that 6-methylpyridin-3-ylboronic acid was used instead of 2-methoxypyridin-4-ylboronic acid to give a black solid as the TFA salt after purification by HPLC-MS: [M+H] calc'd for $C_{28}H_{32}N_6O$, 469; found, 469.

Compound 165: (S)-3-((4-(4-(1-methyl-1H-pyrazol-4-yl)phenyl)piperazin-1-yl)methyl)-7,8,9,10-tetrahydro-5H-dipyrido[1,2-a:3',2'-e]pyrazin-6(6aH)-one

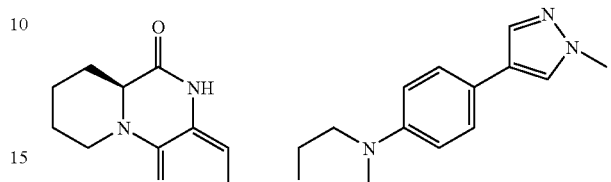

Compound 165 was prepared using a procedure analogous to that described in connection with compound 144, except that 1-methyl-1H-pyrazol-4-ylboronic acid was used instead of 2-methoxypyridin-4-ylboronic acid to give a white solid as the TFA salt after purification by HPLC-MS: [M+H] calc'd for $C_{26}H_{31}N_7O$, 458; found, 458.

Compound 166: (S)-3-((4-(4-(4-methylpyridin-2-yl)phenyl)piperazin-1-yl)methyl)-7,8,9,10-tetrahydro-5H-dipyrido[1,2-a:3',2'-e]pyrazin-6(6aH)-one

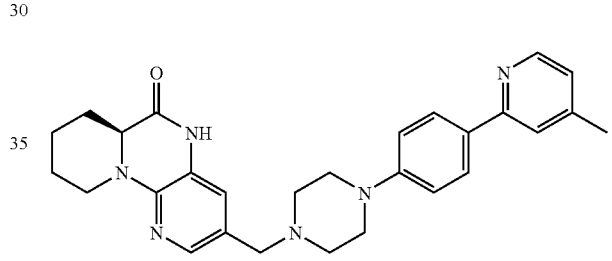

Compound 166 was prepared using a procedure analogous to that described in connection with compound 144, except that 4-methyl-2-(4,4,5,5-tetramethyl-1,3,2-dioxaborolan-2-yl)pyridine was used instead of 2-methoxypyridin-4-ylboronic acid to give a brown solid as the TFA salt after purification by HPLC-MS: [M+H] calc'd for $C_{28}H_{32}N_6O$, 469; found, 469.

Compound 167: (S)-3-((4-(4-(2-methylpyridin-4-yl)phenyl)piperazin-1-yl)methyl)-7,8,9,10-tetrahydro-5H-dipyrido[1,2-a:3',2'-e]pyrazin-6(6aH)-one

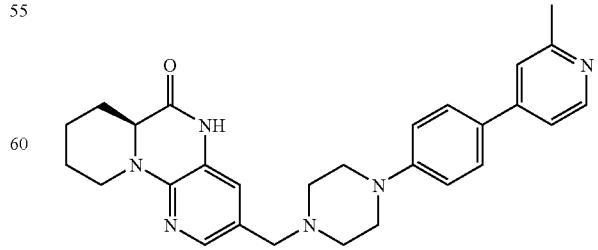

Compound 167 was prepared using a procedure analogous to that described in connection with compound 144, except that 2-methylpyridin-4-ylboronic acid was used instead of 2-methoxypyridin-4-ylboronic acid to give a yellow solid as the TFA salt after purification by HPLC-MS: [M+H] calc'd for $C_{28}H_{32}N_6O$, 469; found, 469.

Compound 168: (S)-3-((4-(4-(pyrazin-2-yl)phenyl)piperazin-1-yl)methyl)-7,8,9,10-tetrahydro-5H-dipyrido[1,2-a:3',2'-e]pyrazin-6(6aH)-one

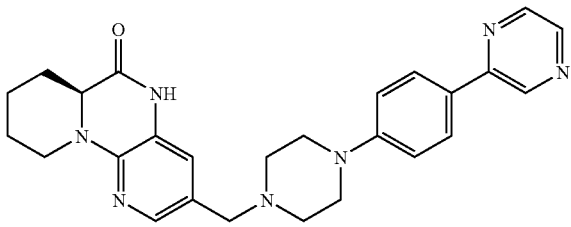

Compound 168 was prepared using a procedure analogous to that described in connection with compound 144, except that pyrazin-2-ylboronic acid was used instead of 2-methoxypyridin-4-ylboronic acid to give a tan solid as the TFA salt after purification by HPLC-MS: [M+H] calc'd for $C_{26}H_{29}N_7O$, 456; found, 456.

Compound 169: (S)-3-((4-(4-(2-methoxypyridin-3-yl)phenyl)piperazin-1-yl)methyl)-7,8,9,10-tetrahydro-5H-dipyrido[1,2-a:3',2'-e]pyrazin-6(6aH)-one

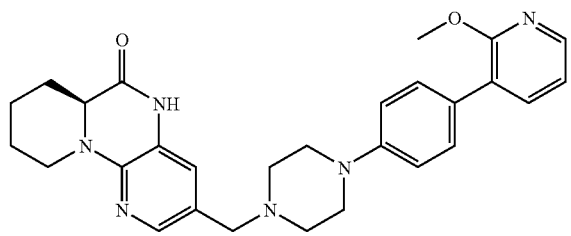

Compound 169 was prepared using a procedure analogous to that described in connection with compound 144, except that 2-methoxypyridin-3-ylboronic acid was used instead of 2-methoxypyridin-4-ylboronic acid to give a green solid as the TFA salt after purification by HPLC-MS: [M+H] calc'd for $C_{28}H_{32}N_6O_2$, 485; found, 485.

Biological Testing

The activity of compounds as PARP inhibitors may be assayed in vitro, in vivo or in a cell line. Provided below are descriptions of an in vitro enzymatic PARP activity assay for activity against PARP and a PARP cellular chemopotentiation assay.

Enzymatic PARP Assay

Dissociation Constant ($K_D$) from Surface Plasmon Resonance

Enzyme Preparation

The catalytic domain of Human PARP was cloned and prepared as described in Kinoshita, T.; Nakanishi, I.; Warizaya, M.; Iwashita, A.; Kido, Y.; Hattori, K. and Fujii, T. 2006 FEBS Letters 556, 43-46. Purified enzyme was stored at −80° C. in 25 mM Tris(hydroxymethyl)aminomethane (Tris) pH 7.4, 150 mM NaCl, 2 mM dithiothreitol (DTT) at a concentration of 6 mg/ml.

Biacore Assays

Biacore affinity assays for test compounds were conducted on a Biacore T100 (GE Healthcare) as follows. A Series S Sensor Chip CM5 (part number BR-1006-68, GE Healthcare) was activated for amide coupling with an Amine Coupling Kit (part number BR-1000-50, GE Healthcare) as described by the manufacturer. The mobile phase buffer consisted of Biacore buffer HBS-P (part number BR-1003-68, GE Healthcare) supplemented with 1% v/v dimethylsulfoxide (DMSO), 0.5 mM Tris(2-carboxyethyl)phosphine hydrochloride (TCEP), and 5 mM $MgCl_2$. Enzyme samples (2 µl/6 mg/ml) stored at −80° C. were diluted to 0.080 mg/ml with 10 mM 4-morpholinoethanesulfonic acid (MES) pH 6.5 and then mounted on the activated Biacore CM5 chip at a flow rate of 10 µl/min for 240 seconds. When successfully mounted, a signal of approximately 8,000 reflective units was observed. Test compounds were diluted 9 times 2-fold serially in mobile phase buffer (listed above) at 1% v/v DMSO final to generate a concentration gradient bracketing their anticipated $K_D$s. Biacore mounted PARP was given a 1 minute exposure (association phase) to various concentrations of test compounds to observe a steady state equilibrium or an on rate. The exposure was followed with a dissociation phase of 5 minutes. The association and dissociation phases were at a flow rate of 50 µl/min and a temperature of 25° C.

Biacore Binding Analysis

Rapid equilibrium model: If the test compound binding displayed rapid equilibrium, a plot of steady state response versus concentration was generated and the equation Rmax*[compound]/([compound]+$K_D$) was fit to the profile. Parameters Rmax (response at saturation) and $K_D$ (binding constant) were calculated through a nonlinear least squares fitting of the equation to the data by use of the Biacore T100 analysis software.

Slow binding model: If the binding of the test compound did not achieve equilibrium within the 1 minute exposure, the association rate constant and the dissociation rate constant for the test compound were calculated through the simultaneous analysis of the family of progress curves obtained from the concentration gradient experiment. Parameter optimization was through a nonlinear least squares analysis of the association phase Response=Rmax*(1-exp(−($k_{on}$[cmpd]+$k_{off}$)*t)) and dissociation phase Response=Rmax*exp(−($k_{on}$[cmpd]+$k_{off}$)*t) by use of the Biacore T100 analysis software. The binding constant $K_D$ was calculated from the definition $K_D = k_{off}/k_{on}$ Inhibition Constant ($IC_{50}$) from PARP ELISA Inhibition of PARP catalytic activity was determined by use of an ELISA-based colorimetric PARP/Apoptosis Assay kit (part number 4684-096-K HT, Trevigen). To each histone coated well in the 96-well plate supplied by the manufacturer (part number 4677-096-P) is added 39 µl of PARP buffer (part number 4671-096-02) and 1 µl of test compound dissolved in DMSO (diluted serially 3-fold 11 times). After mixing, 5 µl of 0.1 nM PARP (part number 4684-096-01) is added and the solution allowed to stand at ambient temperature for 10 minutes. PARP catalysis is initiated with the addition of 5 µl of 100 uM β-nicotinamide adenine dinucleotide (NAD+) (part number 4684-096-02) with activated DNA (part number 4671-096-06). After 10 minutes of catalysis the reaction is quenched by solvent aspiration followed by irrigation of the assay wells 4 times with phosphate buffered saline (PBS)

containing 0.1% t-Octylphenoxypolyethoxyethanol (Triton® X-100). Mouse Anti-poly ADP ribose (PAR) monoclonal antibody, goat antimouse immunoglobulin G (IgG)-horse radish peroxidase (HRP) conjugate and HRP substrate are added according to the manufacture's specifications to generate a colorimetric signal proportional to PARP catalytic activity. An $IC_{50}$ for the test compound is calculated from the equation Absorbance=(Amax−background)/(1+([cmpd]/$IC_{50}$)^n)+background fit to the 12 point test compound concentration gradient via nonlinear least squares.

Potentiation Factor ($PF_{50}$) Determination From PARP Cellular Chemopotentiation Assay Jurkat cell line was maintained according to the supplier (American Type Culture Collection (Rockville, Md.)). Cells were seeded in 96-well tissue culture microplates at 10,000 cells per well and cultured for 24 hours prior to addition of compounds, TMZ (Temozolomide) or DMSO (dimethylsulfoxide) vehicle. After 96 hours of treatment, the conversion of MTS ([3-(4,5-dimethylthiazol-2-yl)-5-(3-carboxymethoxyphenyl)-2-(4-sulfophenyl)-2H-tetrazolium, inner salt], Promega, Madison, Wis.) by metabolically active cells was determined through measuring the $OD_{490\,nm}$ with a Spectramax microplate reader (Molecular Devices, San Diego, Calif.). To generate concentration-response curves, cells were treated in duplicate with a range of serial compound dilutions (final DMSO concentration was 0.5%) in the absence or presence of 100 μM TMZ chemoreagent. The percentage of viable cells per well was calculated by correction for background and normalizing against DMSO-treated cells. $EC_{50}$ values for inhibition of cell viability were calculated using XLfit4 MicroSoft Excel curve-fitting software. Chemopotentiation factor $PF_{50}$ was calculated as the ratio of $EC_{50}$ values of cells co-treated without and with TMZ, respectively.

It should be noted that a variety of other expression systems and hosts are also suitable for the expression of PARP, as would be readily appreciated by one of skill in the art.

TABLE 1 lists $pK_D$, $pIC_{50}$ and $PF_{50}$ values for select compounds of the present invention. Here, $pIC_{50}=-\log(IC_{50})$ and $pK_D=-\log(K_D)$ where $IC_{50}$ and $K_D$ are expressed in molar concentration.

TABLE 1

$pK_D$, $pIC_{50}$ and $PF_{50}$ Values of Exemplified Compounds Against PARP

| COMPOUND | $pK_D$ | $pIC_{50}$ | $PF_{50}$ |
|---|---|---|---|
| 1 | | | >500 |
| 2 | >7.5 | | >2000 |
| 3 | 6.1-7.5 | | >10 |
| 4 | | 7.4-7.8 | >2000 |
| 5 | >7.5 | 7.4-7.8 | >5000 |
| 6A | | | ≧0 |
| 6 | | ≧7.9 | >10 |
| 7 | | | >10 |
| 8 | | | >10 |
| 9 | | | ≧0 |
| 10 | >7.5 | ≧7.9 | >5000 |
| 11 | | 7.4-7.8 | >10 |
| 12 | | 7.4-7.8 | >10 |
| 13 | | 7.4-7.8 | >5000 |
| 14 | | | >500 |
| 15 | | | >500 |
| 16 | | | >500 |
| 17 | | | >2000 |
| 18 | | | >10 |
| 19 | | | ≧0 |
| 20 | | | ≧0 |
| 21 | | | >2000 |
| 22 | | | >10 |
| 23 | | | ≧0 |
| 24 | | 7.4-7.8 | >5000 |
| 25 | | | ≧0 |
| 26 | | | >10 |
| 28 | | | ≧0 |
| 29 | | ≦7.3 | >500 |
| 31 | | | ≧0 |
| 32 | | | ≧0 |
| 34 | | | ≧0 |
| 35 | | | ≧0 |
| 36 | | | ≧0 |
| 37 | | ≦7.3 | >2000 |
| 38 | | | ≧0 |
| 39 | | | ≧0 |
| 40 | | | >10 |
| 41 | | | ≧0 |
| 42 | | ≦7.3 | >500 |
| 45 | | 7.4-7.8 | >10 |
| 46 | | | ≧0 |
| 47 | | ≦7.3 | >10 |
| 48 | | | ≧0 |
| 49 | | | ≧0 |
| 50 | | | ≧0 |
| 51 | | | ≧0 |
| 52 | >7.5 | | ≧0 |
| 53 | 6.1-7.5 | ≦7.3 | ≧0 |
| 54 | ≦6 | | |
| 56 | >7.5 | | ≧0 |
| 57 | >7.5 | | ≧0 |
| 58 | ≦6 | | |
| 59 | >7.5 | | ≧0 |
| 60 | ≦6 | | |
| 61 | ≦6 | | |
| 63 | 6.1-7.5 | | ≧0 |
| 64 | >7.5 | | ≧0 |
| 65 | ≦6 | ≧7.9 | >10 |
| 66 | ≦6 | 7.4-7.8 | >10 |
| 67 | >7.5 | 7.4-7.8 | ≧0 |
| 68 | | ≧7.9 | >5000 |
| 69 | | ≧7.9 | >10 |
| 70 | | ≦7.3 | ≧0 |
| 71 | | ≧7.9 | >500 |
| 72 | | ≧7.9 | >500 |
| 73 | | ≧7.9 | >2000 |
| 74 | | ≧7.9 | >10 |
| 75 | | 7.4-7.8 | >500 |
| 76 | | | ≧0 |
| 77 | | 7.4-7.8 | >10 |
| 78 | | | >10 |
| 79 | | | >10 |
| 80 | >7.5 | ≦7.3 | ≧0 |
| 81 | 6.1-7.5 | ≦7.3 | ≧0 |
| 82 | 6.1-7.5 | ≦7.3 | ≧0 |
| 83 | ≦6 | 7.4-7.8 | ≧0 |
| 84 | 6.1-7.5 | ≧7.9 | ≧0 |
| 85 | 6.1-7.5 | 7.4-7.8 | ≧0 |
| 86 | >7.5 | 7.4-7.8 | >500 |
| 87 | | 7.4-7.8 | >10 |
| 88 | >7.5 | ≧7.9 | ≧0 |
| 89 | | | >10 |
| 90 | | ≧7.9 | >10 |
| 91 | | | >2000 |
| 92 | | | >5000 |
| 93 | | | ≧0 |
| 94 | | ≦7.3 | ≧0 |
| 95 | | ≦7.3 | ≧0 |
| 96 | | ≦7.3 | |
| 97 | | | ≧0 |
| 98 | | | >5000 |
| 99 | | | >5000 |
| 100 | | | >10 |
| 101 | | ≦7.3 | >10 |

TABLE 1-continued pK$_D$, pIC$_{50}$ and PF$_{50}$ Values of Exemplified Compounds Against PARP

| COMPOUND | pK$_D$ | pIC$_{50}$ | PF$_{50}$ |
|---|---|---|---|
| 102 | | 7.4-7.8 | ≧0 |
| 103 | | 7.4-7.8 | ≧0 |
| 104 | | ≦7.3 | ≧0 |
| 105 | | 7.4-7.8 | >10 |
| 106 | | ≧7.9 | >5000 |
| 107 | | 7.4-7.8 | >2000 |
| 108 | | ≧7.9 | >500 |
| 109 | | 7.4-7.8 | >2000 |
| 110 | | 7.4-7.8 | >5000 |
| 111 | | 7.4-7.8 | >5000 |
| 112 | | ≧7.9 | >10 |
| 113 | | ≦7.3 | >2000 |
| 114 | | ≦7.3 | >2000 |
| 115 | | 7.4-7.8 | >2000 |
| 116 | | ≧7.9 | >5000 |
| 117 | | 7.4-7.8 | >5000 |
| 118 | | ≧7.9 | >5000 |
| 120 | | ≦7.3 | ≧0 |
| 121 | | 7.4-7.8 | ≧0 |
| 122 | | ≦7.3 | ≧0 |
| 123 | | 7.4-7.8 | >10 |
| 124 | | ≦7.3 | ≧0 |
| 125 | | ≦7.3 | ≧0 |
| 126 | | 7.4-7.8 | >5000 |
| 127 | | 7.4-7.8 | >500 |
| 128 | | ≦7.3 | ≧0 |
| 129 | | 7.4-7.8 | >500 |
| 130 | | 7.4-7.8 | >2000 |
| 131 | | ≧7.9 | >500 |
| 132 | | ≧7.9 | >2000 |
| 133 | | 7.4-7.8 | >2000 |
| 134 | | 7.4-7.8 | >5000 |
| 135 | | 7.4-7.8 | >5000 |
| 136 | | ≧7.9 | >5000 |
| 137 | | ≧7.9 | >5000 |
| 138 | | ≦7.3 | ≧0 |
| 139 | | ≦7.3 | ≧0 |
| 140 | | ≦7.3 | ≧0 |
| 141 | | ≧7.9 | >500 |
| 142 | | ≧7.9 | >2000 |
| 144 | | ≦7.3 | |
| 145 | | ≦7.3 | |
| 146 | | 7.4-7.8 | |
| 147 | | ≦7.3 | |
| 148 | | 7.4-7.8 | |
| 149 | | ≦7.3 | |
| 150 | | ≦7.3 | |
| 151 | | ≦7.3 | |
| 152 | | 7.4-7.8 | |
| 153 | | ≦7.3 | |
| 154 | | ≦7.3 | |
| 155 | | ≦7.3 | |
| 156 | | ≦7.3 | |
| 157 | | ≦7.3 | |
| 158 | | ≦7.3 | |
| 159 | | ≦7.3 | |
| 160 | | ≦7.3 | |
| 161 | | ≦7.3 | |
| 162 | | ≦7.3 | |
| 163 | | ≦7.3 | |
| 164 | | 7.4-7.8 | |
| 165 | | 7.4-7.8 | |
| 166 | | 7.4-7.8 | |
| 167 | | 7.4-7.8 | |
| 168 | | 7.4-7.8 | |
| 169 | | ≦7.3 | |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound having the formula:

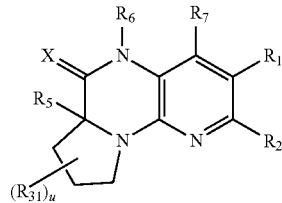

or a tautomer thereof or a pharmaceutically acceptable salt of the compound or tautomer, wherein X is selected from the group consisting of O, S and NR$_8$;

R$_1$ is -L$_1$-R$_{13}$;

L$_1$ is —(CR$_{14}$R$_{15}$)$_r$—;

r is selected from the group consisting of 1, 2 and 3;

R$_2$ is selected from the group consisting of hydrogen, halo, nitro, cyano, hydroxy, (C$_{4-12}$)aryloxy, hetero(C$_{1-10}$)aryloxy, amino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl;

R$_5$ is independently selected from the group consisting of hydrogen, halo, nitro, cyano, hydroxy, (C$_{4-12}$)aryloxy, hetero(C$_{1-10}$)aryloxy, amino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl;

R$_6$ is selected from the group consisting of hydrogen, amino, (C$_{1-10}$)alkyl, halo(C$_{1-10}$)alkyl, hydroxy(C$_{1-10}$)alkyl, aza(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl;

R$_7$ is selected from the group consisting of hydrogen, halo, nitro, cyano, hydroxy, (C$_{4-12}$)aryloxy, hetero(C$_{1-10}$)aryloxy, amino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, (C$_{1-10}$)oxoalkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{4-10}$)aryl, (C$_{9-12}$)bicycloaryl and hetero(C$_{4-12}$)bicycloaryl;

$R_8$ is selected from the group consisting of hydrogen, hydroxy, $(C_{1-10})$alkoxy, $(C_{4-12})$aryloxy, hetero$(C_{1-10})$aryloxy, amino, $(C_{1-10})$alkyl, halo$(C_{1-10})$alkyl, hydroxy$(C_{1-10})$alkyl, aza$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl;

$R_{13}$ is selected from the group consisting of:

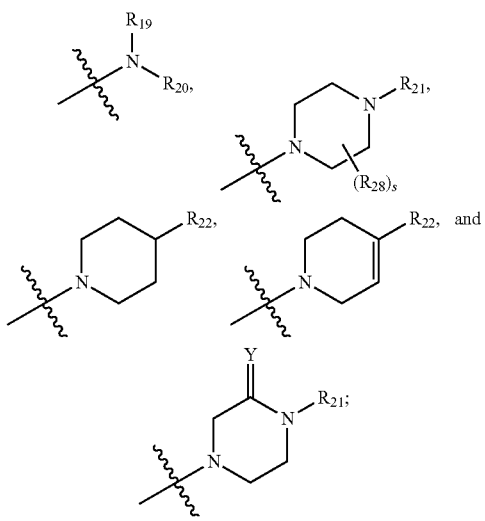

each $R_{14}$ and $R_{15}$ is independently selected from the group consisting of hydrogen, halo, and $(C_{1-3})$alkyl;

$R_{19}$ and $R_{20}$ are each independently selected from the group consisting of hydrogen and $(C_{1-3})$alkyl optionally substituted with one or more substituents independently selected from halo, nitro, cyano, hydroxy, $(C_{1-10})$alkoxy, $(C_{4-12})$aryloxy, hetero$(C_{1-10})$aryloxy, amino, $(C_{1-10})$alkyl, halo$(C_{1-10})$alkyl, hydroxy$(C_{1-10})$alkyl, $(C_{1-10})$azaalkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl;

s is selected from the group consisting of 0, 1, 2, 3, 4, 5, 6, 7 and 8;

Y is selected from the group consisting of O and S;

$R_{21}$ and $R_{22}$ are each independently selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, wherein the $(C_{4-12})$aryl and hetero$(C_{1-10})$aryl substituents are each optionally substituted with one or more substituents independently selected from halo, nitro, cyano, amino, hydroxy, $(C_{1-10})$alkoxy, carbonyl, sulfonyl, $(C_{1-10})$alkyl, halo$(C_{1-10})$alkyl, hydroxy$(C_{1-10})$alkyl, $(C_{1-10})$azaalkyl, $(C_{3-12})$cycloalkyl, hetero$(C_{3-12})$cycloalkyl, $(C_{4-12})$aryl, and hetero$(C_{1-10})$aryl; the optional carbonyl substituent is substituted with hydrogen, hydroxy, $(C_{1-10})$alkoxy, $(C_{1-10})$alkyl, $(C_{3-12})$cycloalkyl, hetero$(C_{3-12})$cycloalkyl, $(C_{1-10})$alkylamino or amino optionally substituted with $(C_{3-12})$cycloalkyl; the optional sulfonyl substituent is substituted with $(C_{1-10})$alkyl or $(C_{1-10})$alkylamino; the optional $(C_{3-12})$cycloalkyl and hetero$(C_{3-12})$cycloalkyl substituents are each optionally substituted with one or more substituents independently selected from cyano, oxo, hydroxy, $(C_{1-10})$alkoxy, amino, $(C_{1-10})$alkyl, halo$(C_{1-10})$alkyl, hydroxy$(C_{1-10})$alkyl, $(C_{3-12})$cycloalkyl, and hetero$(C_{3-12})$cycloalkyl; and the optional $(C_{4-12})$aryl and hetero$(C_{1-10})$aryl substituents are each optionally substituted with one or more substituents independently selected from halo, nitro, cyano, amino, hydroxy, $(C_{1-10})$alkoxy, $(C_{1-10})$alkyl, halo$(C_{1-10})$alkyl, hydroxy$(C_{1-10})$alkyl, and $(C_{1-10})$azaalkyl;

each $R_{28}$ is independently selected from the group consisting of hydrogen, halo, $(C_{1-3})$alkyl, $(C_{1-3})$alkoxy, amino, and thio;

u is selected from the group consisting of 0, 1, 2, 3, 4, 5 and 6; and each $R_{31}$ is independently selected from the group consisting of hydrogen, halo, and $(C_{1-3})$alkyl.

2. The compound, tautomer or pharmaceutically acceptable salt according to claim 1 having the formula:

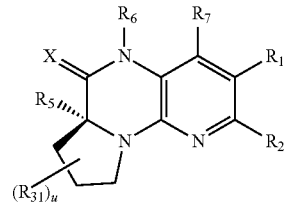

or a stereoisomer thereof, wherein $R_1$, $R_2$, $R_5$, $R_6$, $R_7$, $R_{31}$, u and X are as defined in claim 1.

3. The compound, tautomer or pharmaceutically acceptable salt according to claim 1, wherein $R_5$ is selected from hydrogen, halo, and $(C_{1-3})$alkyl.

4. The compound, tautomer or pharmaceutically acceptable salt according to claim 1, wherein X is O.

5. The compound, tautomer or pharmaceutically acceptable salt according to claim 1, wherein X is $NR_8$, and $R_8$ is selected from the group consisting of hydrogen and $(C_{1-3})$alkyl.

6. The compound, tautomer or pharmaceutically acceptable salt according to claim 1, wherein $L_1$ is —$CH_2$—.

7. The compound, tautomer or pharmaceutically acceptable salt according to claim 1, wherein $R_{21}$ or $R_{22}$ is selected from phenyl and pyridinyl, each optionally substituted with one or more substituents independently selected from halo, nitro, cyano, amino, hydroxy, $(C_{1-10})$alkoxy, carbonyl, sulfonyl, $(C_{1-10})$alkyl, halo$(C_{1-10})$alkyl, hydroxy$(C_{1-10})$alkyl, $(C_{1-10})$azaalkyl, $(C_{3-12})$cycloalkyl, hetero$(C_{3-12})$cycloalkyl, $(C_{4-12})$aryl, and hetero$(C_{1-10})$aryl; the optional carbonyl substituent is substituted with hydrogen, hydroxy, $(C_{1-10})$alkoxy, $(C_{1-10})$alkyl, $(C_{3-12})$cycloalkyl, hetero$(C_{3-12})$cycloalkyl, $(C_{1-10})$alkylamino or amino optionally substituted with $(C_{3-12})$cycloalkyl; the optional sulfonyl substituent is substituted with $(C_{1-10})$alkyl or $(C_{1-10})$alkylamino; the optional $(C_{3-12})$cycloalkyl and hetero$(C_{3-12})$cycloalkyl substituents are each optionally substituted with one or more substituents independently selected from cyano, oxo, hydroxy, $(C_{1-10})$alkoxy, amino, $(C_{1-10})$alkyl, halo$(C_{1-10})$alkyl, hydroxy$(C_{1-10})$alkyl, $(C_{3-12})$cycloalkyl, and hetero$(C_{3-12})$cycloalkyl; and the optional $(C_{4-12})$aryl and hetero$(C_{1-10})$aryl substituents are each optionally substituted with one or more substituents independently selected from halo, nitro, cyano, amino, hydroxy, (C$_{1-10}$)alkoxy, (C$_{1-10}$)alkyl, halo(C$_{1-10}$) alkyl, hydroxy(C$_{1-10}$)alkyl, and (C$_{1-10}$)azaalkyl.

8. The compound, tautomer or pharmaceutically acceptable salt according to claim 7, wherein R$_{21}$ or R$_{22}$ has the formula:

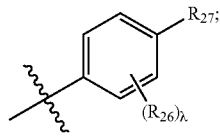

wherein
λ is selected from the group consisting of 0, 1, 2, 3 and 4; each R$_{26}$ is independently selected from the group consisting of hydrogen, halo, nitro, cyano, hydroxy, amino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, and (C$_{1-10}$)oxoalkyl; and
R$_{27}$ is selected from the group consisting of hydrogen, halo, nitro, cyano, hydroxy, (C$_{1-10}$)alkoxy, carbonyl, amino, sulfonyl, (C$_{1-10}$)alkyl, halo(C$_{1-10}$)alkyl, hydroxy(C$_{1-10}$)alkyl, aza(C$_{1-10}$)alkyl, (C$_{3-12}$)cycloalkyl, hetero(C$_{3-12}$)cycloalkyl, (C$_{4-12}$)aryl, and hetero(C$_{4-10}$)aryl; wherein the (C$_{3-12}$)cycloalkyl and hetero(C$_{3-12}$)cycloalkyl substituents are each optionally substituted with one or more substituents independently selected from cyano, oxo, hydroxy, (C$_{1-10}$)alkoxy, amino, (C$_{1-10}$) alkyl, halo(C$_{1-10}$)alkyl, hydroxy(C$_{1-10}$)alkyl, (C$_{3-12}$)cycloalkyl, and hetero(C$_{3-12}$)cycloalkyl; the (C$_{4-12}$)aryl and hetero(C$_{1-10}$)aryl substituents are each optionally substituted with one or more substituents independently selected from halo, nitro, cyano, amino, hydroxy, (C$_{1-10}$)alkoxy, (C$_{1-10}$)alkyl, halo(C$_{1-10}$)alkyl, hydroxy(C$_{1-10}$)alkyl, and (C$_{1-10}$)azaalkyl; the carbonyl substituent is substituted with hydrogen, hydroxy, (C$_{1-10}$) alkoxy, (C$_{1-10}$)alkyl, (C$_{3-12}$)cycloalkyl, hetero(C$_{3-12}$) cycloalkyl, (C$_{1-10}$)alkylamino or amino optionally substituted with (C$_{3-12}$)cycloalkyl; and the sulfonyl substituent is substituted with (C$_{1-10}$)alkyl or (C$_{1-10}$)alkylamino.

9. The compound, tautomer or pharmaceutically acceptable salt according to claim 8, wherein R$_{21}$ or R$_{22}$ is selected from:

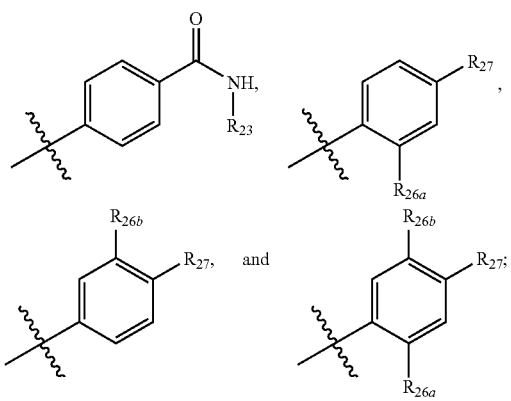

wherein
R$_{23}$ is selected from the group consisting of hydrogen, (C$_{1-10}$)alkyl, and (C$_{3-12}$)cycloalkyl;
R$_{26a}$ and R$_{26b}$ are each independently selected from the group consisting of halo, nitro, cyano, hydroxy, amino, (C$_{1-10}$)alkyl, halo(C$_{1-10}$)alkyl, hydroxy(C$_{1-10}$)alkyl, aza(C$_{1-10}$)alkyl, (C$_{1-10}$)oxaalkyl, and (C$_{1-10}$)oxoalkyl.

10. The compound, tautomer or pharmaceutically acceptable salt according to claim 9, wherein
R$_{23}$ is selected from hydrogen, (C$_{1-3}$)alkyl, and (C$_{3-6}$)cycloalkyl;
R$_{26a}$ and R$_{26b}$ are each independently selected from halo, (C$_{1-3}$)alkyl, and (C$_{1-3}$)alkoxy; and
R$_{27}$ is —CO—NH—R$_{23}$.

11. The compound, tautomer or pharmaceutically acceptable salt according to claim 1, wherein R$_1$ has the formula:

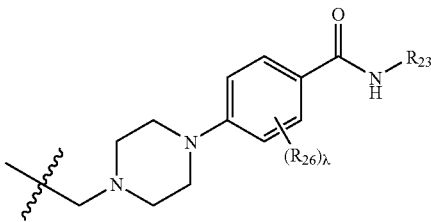

wherein
λ is selected from the group consisting of 0, 1 and 2;
R$_{23}$ is selected from the group consisting of (C$_{1-3}$)alkyl and (C$_{3-6}$)cycloalkyl; and
each R$_{26}$ is independently selected from the group consisting of hydrogen, halo, (C$_{1-3}$)alkyl and (C$_{1-3}$)alkoxy.

12. The compound, tautomer or pharmaceutically acceptable salt according to claim 1, wherein R$_2$ is selected from the group consisting of hydrogen, halo, and (C$_{1-3}$)alkyl.

13. The compound, tautomer or pharmaceutically acceptable salt according to claim 1, wherein R$_6$ and R$_7$ are each independently selected from the group consisting of hydrogen and (C$_{1-3}$)alkyl.

14. The compound, tautomer or pharmaceutically acceptable salt according to claim 1, wherein R$_6$ is hydrogen.

15. The compound according to claim 1, which is selected from:
(S)-3-((4-(4-chlorophenyl)piperazin-1-yl)methyl)-6a,7,8, 9-tetrahydropyrido[3,2-e]pyrrolo[1,2-a]pyrazin-6(5H)-one;
(S)-3-(4-(4-chlorophenyl)-5,6-dihydropyridin-1(2H)-yl) methyl)-6a,7,8,9-tetrahydropyrido[3,2-e]pyrrolo[1,2-a] pyrazin-6(5H)-one;
(S)-3-((4-(4-chlorophenyl)piperidin-1-yl)methyl)-6a,7,8, 9-tetrahydropyrido[3,2-e]pyrrolo[1,2-a]pyrazin-6(5H)-one;
(S)-4-(4-((6-oxo-5,6,6a,7,8,9-hexahydropyrido[3,2-e] pyrrolo[1,2-a]pyrazin-3-yl)methyl)piperazin-1-yl)benzonitrile;
(S)-6-(4-((6-oxo-5,6,6a,7,8,9-hexahydropyrido[3,2-e] pyrrolo[1,2-a]pyrazin-3-yl)methyl)piperazin-1-yl) nicotinonitrile;
(S)—N-methyl-6-(4-((6-oxo-5,6,6a,7,8,9-hexahydropyrido[3,2-e]pyrrolo[1,2-a]pyrazin-3-yl)methyl)piperazin-1-yl)nicotinamide;
(S)-ethyl 6-(4-((6-oxo-5,6,6a,7,8,9-hexahydropyrido[3,2-e]pyrrolo[1,2-a]pyrazin-3-yl)methyl)piperazin-1-yl) nicotinate;
(S)-6-(4-((6-oxo-5,6,6a,7,8,9-hexahydropyrido[3,2-e] pyrrolo[1,2-a]pyrazin-3-yl)methyl)piperazin-1-yl) nicotinic acid;
(S)—N-ethyl-6-(4-((6-oxo-5,6,6a,7,8,9-hexahydropyrido [3,2-e]pyrrolo[1,2-a]pyrazin-3-yl)methyl)piperazin-1-yl)nicotinamide;

(S)—N-cyclopropyl-6-(4-((6-oxo-5,6,6a,7,8,9-hexahydropyrido[3,2-e]pyrrolo[1,2-a]pyrazin-3-yl)methyl)piperazin-1-yl)nicotinamide;
(S)—N-isopropyl-6-(4-((6-oxo-5,6,6a,7,8,9-hexahydropyrido[3,2-e]pyrrolo[1,2-a]pyrazin-3-yl)methyl)piperazin-1-yl)nicotinamide;
(S)—N-ethyl-4-(4-((6-oxo-5,6,6a,7,8,9-hexahydropyrido[3,2-e]pyrrolo[1,2-a]pyrazin-3-yl)methyl)piperazin-1-yl)benzamide;
(S)-ethyl 4-(4-((6-oxo-5,6,6a,7,8,9-hexahydropyrido[3,2-e]pyrrolo[1,2-a]pyrazin-3-yl)methyl)piperazin-1-yl)benzoate;
(S)-4-(4-((6-oxo-5,6,6a,7,8,9-hexahydropyrido[3,2-e]pyrrolo[1,2-a]pyrazin-3-yl)methyl)piperazin-1-yl)benzoic acid;
(S)—N-methyl-4-(4-((6-oxo-5,6,6a,7,8,9-hexahydropyrido[3,2-e]pyrrolo[1,2-a]pyrazin-3-yl)methyl)piperazin-1-yl)benzamide;
(S)—N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide;
(S)—N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide;
(S)-3-fluoro-4-(4-((6-oxo-5,6,6a,7,8,9-hexahydropyrido[3,2-e]pyrrolo[1,2-a]pyrazin-3-yl)methyl)piperazin-1-yl)benzonitrile;
(S)-3-((4-(2,4-difluorophenyl)piperazin-1-yl)methyl)-6a,7,8,9-tetrahydropyrido[3,2-e]pyrrolo[1,2-a]pyrazin-6(5H)-one;
(S)-3-chloro-4-(4-((6-oxo-5,6,6a,7,8,9-hexahydropyrido[3,2-e]pyrrolo[1,2-a]pyrazin-3-yl)methyl)piperazin-1-yl)benzonitrile;
(S)-2,5-difluoro-4-(4-((6-oxo-5,6,6a,7,8,9-hexahydropyrido[3,2-e]pyrrolo[1,2-a]pyrazin-3-yl)methyl)piperazin-1-yl)benzonitrile;
(S)-2,3-difluoro-4-(4-((6-oxo-5,6,6a,7,8,9-hexahydropyrido[3,2-e]pyrrolo[1,2-a]pyrazin-3-yl)methyl)piperazin-1-yl)benzonitrile;
(S)-2,6-difluoro-4-(4-((6-oxo-5,6,6a,7,8,9-hexahydropyrido[3,2-e]pyrrolo[1,2-a]pyrazin-3-yl)methyl)piperazin-1-yl)benzonitrile;
(S)-3,5-difluoro-4-(4-((6-oxo-5,6,6a,7,8,9-hexahydropyrido[3,2-e]pyrrolo[1,2-a]pyrazin-3-yl)methyl)piperazin-1-yl)benzonitrile;
(S)-2-fluoro-4-(4-((6-oxo-5,6,6a,7,8,9-hexahydropyrido[3,2-e]pyrrolo[1,2-a]pyrazin-3-yl)methyl)piperazin-1-yl)benzonitrile;
(S)-3-fluoro-5-(4-((6-oxo-5,6,6a,7,8,9-hexahydropyrido[3,2-e]pyrrolo[1,2-a]pyrazin-3-yl)methyl)piperazin-1-yl)picolinonitrile;
(S)-3-((4-phenylpiperazin-1-yl)methyl)-6a,7,8,9-tetrahydropyrido[3,2-e]pyrrolo[1,2-a]pyrazin-6(5H)-one;
(S)-3-((4-(4-fluorophenyl)piperazin-1-yl)methyl)-6a,7,8,9-tetrahydropyrido[3,2-e]pyrrolo[1,2-a]pyrazin-6(5H)-one;
(S)-3-((4-(4-acetylphenyl)piperazin-1-yl)methyl)-6a,7,8,9-tetrahydropyrido[3,2-e]pyrrolo[1,2-a]pyrazin-6(5H)-one;
(S)-3-((4-(pyridin-2-yl)piperazin-1-yl)methyl)-6a,7,8,9-tetrahydropyrido[3,2-e]pyrrolo[1,2-a]pyrazin-6(5H)-one;
(S)-3-((benzyl(methyl)amino)methyl)-6a,7,8,9-tetrahydropyrido[3,2-e]pyrrolo[1,2-a]pyrazin-6(5H)-one;
(S)-3-((4-(3-methoxyphenyl)piperazin-1-yl)methyl)-6a,7,8,9-tetrahydropyrido[3,2-e]pyrrolo[1,2-a]pyrazin-6(5H)-one;
(S)-3-((4-m-tolylpiperazin-1-yl)methyl)-6a,7,8,9-tetrahydropyrido[3,2-e]pyrrolo[1,2-a]pyrazin-6(5H)-one;
(S)-3-((4-(3-methoxyphenyl)piperazin-1-yl)methyl)-6a,7,8,9-tetrahydropyrido[3,2-e]pyrrolo[1,2-a]pyrazin-6(5H)-one;
(S)-3-((4-(4-methoxyphenyl)piperazin-1-yl)methyl)-6a,7,8,9-tetrahydropyrido[3,2-e]pyrrolo[1,2-a]pyrazin-6(5H)-one;
(S)-3-((4-p-tolylpiperazin-1-yl)methyl)-6a,7,8,9-tetrahydropyrido[3,2-e]pyrrolo[1,2-a]pyrazin-6(5H)-one;
(S)-3-((4-(pyrimidin-2-yl)piperazin-1-yl)methyl)-6a,7,8,9-tetrahydropyrido[3,2-e]pyrrolo[1,2-a]pyrazin-6(5H)-one;
(S)-3-((4-(3-hydroxyphenyl)piperazin-1-yl)methyl)-6a,7,8,9-tetrahydropyrido[3,2-e]pyrrolo[1,2-a]pyrazin-6(5H)-one;
(S)-3-((4-(4-hydroxyphenyl)piperazin-1-yl)methyl)-6a,7,8,9-tetrahydropyrido[3,2-e]pyrrolo[1,2-a]pyrazin-6(5H)-one;
(S)-3-(4-(5-(trifluoromethyl)pyridin-2-yl)piperazin-1-yl)methyl)-6a,7,8,9-tetrahydropyrido[3,2-e]pyrrolo[1,2-a]pyrazin-6(5H)-one;
(S)-3-((4-(4-bromophenyl)piperazin-1-yl)methyl)-6a,7,8,9-tetrahydropyrido[3,2-e]pyrrolo[1,2-a]pyrazin-6(5H)-one;
(S)-3-((4-(3-fluorophenyl)piperazin-1-yl)methyl)-6a,7,8,9-tetrahydropyrido[3,2-e]pyrrolo[1,2-a]pyrazin-6(5H)-one;
(S)-3-((4-(1H-benzo[d]imidazol-2-yl)piperazin-1-yl)methyl)-6a,7,8,9-tetrahydropyrido[3,2-e]pyrrolo[1,2-a]pyrazin-6(5H)-one;
(S)-3-((4-(4-iodophenyl)piperazin-1-yl)methyl)-6a,7,8,9-tetrahydropyrido[3,2-e]pyrrolo[1,2-a]pyrazin-6(5H)-one;
(S)-3-((4-(benzo[d]oxazol-2-yl)piperazin-1-yl)methyl)-6a,7,8,9-tetrahydropyrido[3,2-e]pyrrolo[1,2-a]pyrazin-6(5H)-one;
(S)-3-(4-(5-chloropyridin-2-yl)piperazin-1-yl)methyl)-6a,7,8,9-tetrahydropyrido[3,2-e]pyrrolo[1,2-a]pyrazin-6(5H)-one;
(S)-3-(((4-methoxybenzyl)(methyl)amino)methyl)-6a,7,8,9-tetrahydropyrido[3,2-e]pyrrolo[1,2-a]pyrazin-6(5H)-one;
(S)-3-((4-(1,3,5-triazin-2-yl)piperazin-1-yl)methyl)-6a,7,8,9-tetrahydropyrido[3,2-e]pyrrolo[1,2-a]pyrazin-6(5H)-one;
(S)-methyl 4-(4-((6-oxo-5,6,6a,7,8,9-hexahydropyrido[3,2-e]pyrrolo[1,2-a]pyrazin-3-yl)methyl)piperazin-1-yl)benzoate;
(S)-3-((4-(3,5-difluorophenyl)piperazin-1-yl)methyl)-6a,7,8,9-tetrahydropyrido[3,2-e]pyrrolo[1,2-a]pyrazin-6(5H)-one;
(S)-3-((4-(4-chloro-3-fluorophenyl)piperazin-1-yl)methyl)-6a,7,8,9-tetrahydropyrido[3,2-e]pyrrolo[1,2-a]pyrazin-6(5H)-one;
(S)-3-((4-(4-(trifluoromethyl)phenyl)piperazin-1-yl)methyl)-6a,7,8,9-tetrahydropyrido[3,2-e]pyrrolo[1,2-a]pyrazin-6(5H)-one;
(R)-3-(4-(4-chlorophenyl)-5,6-dihydropyridin-1(2H)-yl)methyl)-6a,7,8,9-tetrahydropyrido[3,2-e]pyrrolo[1,2-a]pyrazin-6(5H)-one;
(R)-3-((4-(4-chlorophenyl)piperazin-1-yl)methyl)-6a,7,8,9-tetrahydropyrido[3,2-e]pyrrolo[1,2-a]pyrazin-6(5H)-one;
(R)-3-(4-(4-chlorophenyl)piperidin-1-yl)methyl)-6a,7,8,9-tetrahydropyrido[3,2-e]pyrrolo[1,2-a]pyrazin-6(5H)-one;

(6aS)-3-((2-methyl-4-(pyridin-2-yl)piperazin-1-yl)methyl)-6a,7,8,9-tetrahydropyrido[3,2-e]pyrrolo[1,2-a]pyrazin-6(5H)-one;

(S)-ethyl 6-(4-((6-oxo-5,6,6a,7,8,9-hexahydropyrido[3,2-e]pyrrolo[1,2-a]pyrazin-3-yl)methyl)piperazin-1-yl) nicotinate;

(S)-3-((1-(4-chlorophenyl)piperidin-4-yl)methyl)-6a,7,8,9-tetrahydropyrido[3,2-e]pyrrolo[1,2-a]pyrazin-6(5H)-one;

(S)-5-(4-((6-oxo-5,6,6a,7,8,9-hexahydropyrido[3,2-e]pyrrolo[1,2-a]pyrazin-3-yl)methyl)piperazin-1-yl)picolinonitrile;

(S)—N-ethyl-2,5-difluoro-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N-ethyl-2-fluoro-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N-ethyl-3-fluoro-4-(4-((6-oxo-5,6,6a,7,8,9-hexahydropyrido[3,2-e]pyrrolo[1,2-a]pyrazin-3-yl)methyl)piperazin-1-yl)benzamide;

(S)-3-chloro-N-ethyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N-methyl-4-(4-((6-oxo-5,6,6a,7,8,9-hexahydropyrido[3,2-e]pyrrolo[1,2-a]pyrazin-3-yl)methyl)piperazin-1-yl)benzenesulfonamide;

(S)-3-methyl-4-(4-((6-oxo-5,6,6a,7,8,9-hexahydropyrido[3,2-e]pyrrolo[1,2-a]pyrazin-3-yl)methyl)piperazin-1-yl)benzonitrile;

(S)-3-((4-(4-fluoro-2-methylphenyl)piperazin-1-yl)methyl)-6a,7,8,9-tetrahydropyrido[3,2-e]pyrrolo[1,2-a]pyrazin-6(5H)-one;

(S)-3-fluoro-N-methyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N-cyclopropyl-3-fluoro-4-(4-((6-oxo-5,6,6a,7,8,9-hexahydropyrido[3,2-e]pyrrolo[1,2-a]pyrazin-3-yl)methyl)piperazin-1-yl)benzamide;

(S)-3-fluoro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)-3-chloro-N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)-3-chloro-N-isopropyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)-3-chloro-N-methyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N-ethyl-3-methyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)-3-((4-(4-(pyrrolidine-1-carbonyl)phenyl)piperazin-1-yl)methyl)-6a,7,8,9-tetrahydropyrido[3,2-e]pyrrolo[1,2-a]pyrazin-6(5H)-one;

(S)—N,N-dimethyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N-ethyl-N-methyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N,3-dimethyl-4-(4-((6-oxo-5,6,6a,7,8,9-hexahydropyrido[3,2-e]pyrrolo[1,2-a]pyrazin-3-yl)methyl)piperazin-1-yl)benzamide;

(S)—N-cyclopropyl-3-methyl-4-(4-((6-oxo-5,6,6a,7,8,9-hexahydropyrido[3,2-e]pyrrolo[1,2-a]pyrazin-3-yl)methyl)piperazin-1-yl)benzamide;

stereoisomers of any of the aforementioned compounds;

tautomers of any of the aforementioned compounds or stereoisomers; and a pharmaceutically acceptable salt of any of the aforementioned compounds, stereoisomers or tautomers.

16. The compound according to claim 1, which is (S)—N-ethyl-4-(4-((6-oxo-5,6,6a,7,8,9-hexahydropyrido[3,2-e]pyrrolo[1,2-a]pyrazin-3-yl)methyl)piperazin-1yl)benzamide, a stereoisomer thereof, a tautomer of the compound or stereoisomer, or a pharmaceutically acceptable salt of the compound, stereoisomer or tautomer.

17. The compound according to claim 1, which is (S)—N-methyl-4-(4-((6-oxo-5,6,6a,7,8,9-hexahydropyrido[3,2-e]pyrrolo[1,2-a]pyrazin-3-yl)methyl)piperazin-1-yl)benzamide, a stereoisomer thereof, a tautomer of the compound or stereoisomer, or a pharmaceutically acceptable salt of the compound, stereoisomer or tautomer.

18. The compound according to claim 1, which is (S)—N-cyclopropyl-4-(4-((6-oxo-5,6,6a,7,8,9-hexahydropyrido[3,2-e]pyrrolo[1,2-a]pyrazin-3-yl)methyl)piperazin-1-yl)benzamide, a stereoisomer thereof, a tautomer of the compound or stereoisomer, or a pharmaceutically acceptable salt of the compound, stereoisomer or tautomer.

19. The compound according to claim 1, which is (S)—N-ethyl-3-fluoro-4-(4-((6-oxo-5,6,6a,7,8,9-hexahydropyrido[3,2-e]pyrrolo[1,2-a]pyrazin-3-yl)methyl)piperazin-1-yl) benzamide, a stereoisomer thereof, a tautomer of the compound or stereoisomer, or a pharmaceutically acceptable salt of the compound, stereoisomer or tautomer.

20. The compound according to claim 1, which is (S)-3-fluoro-N-methyl-4-(4-((6-oxo-5,6,6a,7,8,9-hexahydropyrido[3,2-e]pyrrolo[1,2-a]pyrazin-3-yl)methyl)piperazin-1-yl)benzamide, a stereoisomer thereof, a tautomer of the compound or stereoisomer, or a pharmaceutically acceptable salt of the compound, stereoisomer or tautomer.

21. A pharmaceutical composition comprising:
a compound, tautomer or pharmaceutically acceptable salt as defined in any one of claims 1, 2, 3, 5, 6, 7, 15, and 16-20; and
a pharmaceutically acceptable excipient.

* * * * *

UNITED STATES PATENT AND TRADEMARK OFFICE
CERTIFICATE OF CORRECTION

PATENT NO. : 7,928,105 B2
APPLICATION NO. : 12/691668
DATED : April 19, 2011
INVENTOR(S) : Anthony R. Gangloff et al.

Page 1 of 1

It is certified that error appears in the above-identified patent and that said Letters Patent is hereby corrected as shown below:

In the Claims

In Claim 21, Column 244, at lines 52 and 53:

"as defined in any one of claims 1, 2, 3, 5, 6, 7, 15, and 16-20; and"

should read -- as defined in any one of claims 1-20; and --

Signed and Sealed this
Eighteenth Day of March, 2014

Michelle K. Lee
*Deputy Director of the United States Patent and Trademark Office*